(12) United States Patent  
Becker et al.

(10) Patent No.: US 7,294,622 B2  
(45) Date of Patent: Nov. 13, 2007

(54) LACTAMS AND USES THEREOF

(75) Inventors: Christopher Becker, Wilmington, DE (US); Bruce Dembofsky, Wilmington, DE (US); Robert Jacobs, Wilmington, DE (US); James Kang, Wilmington, DE (US); Cyrus Ohnmacht, Wilmington, DE (US); James Rosamond, Wilmington, DE (US); Ashokkumar Bhikkappa Shenvi, Wilmington, DE (US); Thomas Simpson, Wilmington, DE (US); James Woods, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 129 days.

(21) Appl. No.: 10/528,640

(22) PCT Filed: Oct. 2, 2003

(86) PCT No.: PCT/SE03/01534

§ 371 (c)(1),  
(2), (4) Date: Mar. 22, 2005

(87) PCT Pub. No.: WO2004/031154

PCT Pub. Date: Apr. 15, 2004

(65) Prior Publication Data

US 2006/0089346 A1    Apr. 27, 2006

(30) Foreign Application Priority Data

Oct. 3, 2002 (SE) .................... 0202929  
Dec. 18, 2002 (SE) .................... 0203829

(51) Int. Cl.
C07D 223/16 (2006.01)  
C07D 267/14 (2006.01)  
C07D 281/06 (2006.01)  
A61K 31/55 (2006.01)  
A61P 25/28 (2006.01)

(52) U.S. Cl. .................... 514/211.03; 514/211.06; 514/212.03; 514/212.07; 540/488; 540/491; 540/523; 540/527

(58) Field of Classification Search ............. 540/488, 540/491, 523, 527; 514/211.03, 211.06, 514/212.03, 212.07  
See application file for complete search history.

(56) References Cited

FOREIGN PATENT DOCUMENTS

| WO | WO98/28268 | 7/1998 |
|----|------------|--------|
| WO | WO9967220  | 12/1999 |
| WO | WO 0172324 | 10/2001 |

OTHER PUBLICATIONS

Banzatti et al., "Synthesis of phenyl-substituted 2H-3,4-dihydro-3-aminomethyl-1,4-benzoxazines. Intermediates for 1H-2,3,3a,4-Tetrahydroimidazo-[5,1-c][1,4]benzoxizan-1-one derivatives. Part II," *J. Heterocyclic Chem.* (1983) 20:259-265.

Karim et al., "Synthese d'aminophosphinephosphinites chiraux. Utilisation en reduction asymetrique catalytique," *J. Organometallic Chem.* (1986) 317(1):93-104.

Lu et al., "Process development on the preparation of trans-(+)-2-methylaminocyclohexanol: a fascinating resolution example," *Org. Proc. R & D* (2001) 5:184-185.

Remington's Pharmaceutical Sciences, 17th ed., Mack Publishing Company, Easton, PA 1985, p. 1418-1419.

*Primary Examiner*—Bruck Kifle  
(74) *Attorney, Agent, or Firm*—Christine McComack; Pepper Hamilton LLP

(57) ABSTRACT

Compounds having the formula (I) pharmaceutical compositions containing them and their methods of use for the treatment of neurological disorders related to amyloid β protein production and neurological disorders such as Alzheimer's disease. These compounds inhibit γ secretase and thereby inhibit the production of amyloid β protein, thereby acting to prevent the formation of neurological deposits of amyloid protein.

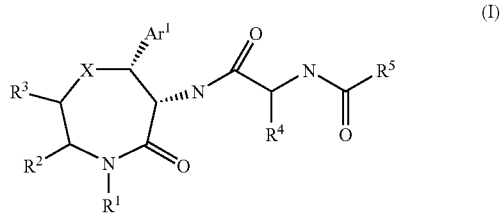

(I)

26 Claims, No Drawings

LACTAMS AND USES THEREOF

FIELD OF THE INVENTION

The present invention relates to novel lactams, their pharmaceutical compositions and methods of use. In addition, the present invention relates to therapeutic methods for the treatment and prevention of various diseases especially Alzheimer's disease and other diseases relating to the deposition of amyloid.

BACKGROUND OF THE INVENTION

Alzheimer's Disease (AD) is a progressive, neurodegenerative disease characterized clinically by progressive loss of memory, cognition, reasoning, judgment and emotionally stability. AD is a common cause of dementia in humans and a leading cause of death in the United States. AD has been observed in races and ethnic groups worldwide and presents a major public health problem throughout the world. No treatment that effectively prevents AD or reverses the clinical symptoms and underlying pathophysiology is currently available and the disease is currently considered among experts to be incurable.

The histopathological manifestations of AD are characteristic lesions known as amyloid (or senile) plaques and neurofibrillar tangles that are found in the regions of the brain associated with memory, reasoning and cognition. Similar alterations are observed in patients with Trisomy 21 (Down's syndrome) and hereditary cerebral hemorrhage with amyloidosis of the Dutch-type.

The major constituent of amyloid plaques is amyloid β protein. Amyloid β protein is derived from the proteolytic cleavage of amyloid precursor protein (APP). Processing of APP to amyloid β protein and other APP fragments is governed by a group of enzymes known as secretases. One type of secretase, γ-secretase, is responsible for the protein cleavage that produces amyloid β protein. Compounds that inhibit either β or γ secretase activity, either directly or indirectly would reduce the production of amyloid β protein resulting in the treatment or prevention of disorders associated with amyloid β protein. Thus there is a continuing need for compounds that inhibit amyloid β protein production. The present invention meets this and related needs by providing a family of novel compounds and related methods of use.

SUMMARY OF THE INVENTION

In accordance with the present invention, the applicants have hereby discovered novel compounds that inhibit γ secretase and thereby inhibit the production of amyloid β protein. Such compounds are as provided below:

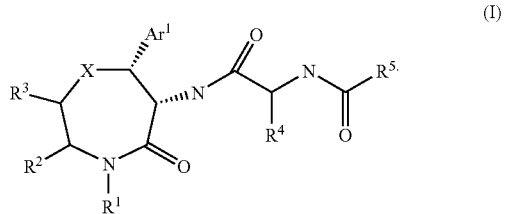

(I)

wherein:

X is C, O, $NR^1$, $SO_2$ or S;

$Ar^1$ is a 5- or 6-membered aromatic or heterocyclic ring optionally substituted with 0, 1, 2, or 3 $R^e$ moieties, said ring having 0, 1, 2 or 3 nitrogen, oxygen or sulfur atoms, but no more than 2 oxygen atoms or 2 sulfur atoms or 1 oxygen and 1 sulfur atom;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkyl$NR^aR^b$, $C_{1-4}$alkylC(=O)$R^d$; or $C_{1-3}$alkylphenyl substituted with 0, 1, 2 or 3 $R^e$;

$R^a$ and $R^b$ are at each occurrence independently selected from H, $C_{1-4}$alkyl or $C_{3-6}$cycloalkyl, or $R^a$ and $R^b$ and the N to which they are attached in combination form a 5 or 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^c$ is, at each occurrence independently selected from H, $C_{1-3}$alkyl, or substituted phenyl with 0, 1, 2, or 3 $R^e$;

$R^d$ is, at each occurrence independently selected from $C_{1-3}$alkyl, hydroxy, $C_{1-3}$alkoxy, or $NR^aR^b$;

$R^e$ is, at each occurrence independently selected from H, OH, F, Cl, Br, I, CN, $NO_2$, $CF_3$, $C_{1-6}$alkyl, or $C_{1-6}$alkoxy;

$R^2$ and $R^3$ are at each occurrence independently selected from H, $C_{1-6}$alkyl, $C_{4-6}$ cycloalkyl, aryl, or heteroaryl, or $R^2$ and $R^3$ in combination form a fused phenyl or cyclohexyl moiety that may be substituted with 0, 1 or 2 $R^f$ moieties, $R^f$ is $NO_2$, F, Cl, Br, I, $CF_3$, CN, $C_{1-6}$alkyl, or $C_{1-6}$alkoxy;

$R^4$ is H, $CHR^7R^8$, 5- or 6-membered cycloalkyl, 5- or 6-membered heterocyclic, 5 or 6-membered aromatic ring optionally substituted with 0, 1, or 2 $R^f$ moieties, said heterocyclic ring having 0, 1, 2 or 3 nitrogen, oxygen or sulfur atoms, but no more than 2 oxygen atoms or 2 sulfur atoms or 1 oxygen and 1 sulfur atom;

$R^5$ is $C_{1-3}$alkyl$R^9$ or $CH(OH)R^{10}$;

$R^7$ and $R^8$ are, at each occurrence are independently selected from H, $C_{1-4}$alkyl, OH, SH, $CH_2SCH_3$, $CONH_2$, $CH_2CONH_2$, $CO_2H$, $CH_2CO_2H$, $(CH_2)_3NHCH(NH_2)_2$, $C_{1-4}$alkylamine, indole, imidazole, phenyl or hydroxyphenyl or $R^7$ and $R^8$ in combination form a 6-membered aromatic or heterocyclic ring optionally substituted with 0, 1 or 2 $R^f$ moieties said heterocyclic ring having 0, 1, 2 or 3 nitrogen, oxygen or sulfur atoms, but no more than 2 oxygen atoms or 2 sulfur atoms or 1 oxygen and 1 sulfur atom;

$R^9$ is phenyl substituted with 0, 1, 2 or 3 $R^e$;

$R^{10}$ is alkyl or $R^9$;

or a pharmaceutically acceptable salt thereof.

The invention also includes pharmaceutically acceptable salts or prodrugs of such compounds. Also in accordance with the present invention applicants provide pharmaceutical compositions and a method to use invention compounds in the treatment of degenerative neurological disorders.

DETAILED DESCRIPTION OF THE INVENTION

Provided herein are novel compounds of formula (I):

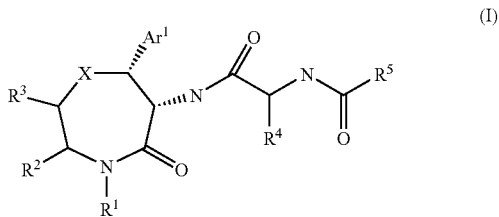

(I)

wherein:

X is C, O, $NR^1$, $SO_2$ or S;

$Ar^1$ is a 5- or 6-membered aromatic or heterocyclic ring optionally substituted with 0, 1, 2, or 3 $R^e$ moieties, said ring having 0, 1, 2 or 3 nitrogen, oxygen or sulfur atoms, but no more than 2 oxygen atoms or 2 sulfur atoms or 1 oxygen and 1 sulfur atom;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$, $C_{1-4}$alkylC(=O)R$^d$; or $C_{1-3}$alkylphenyl substituted with 0, 1, 2 or 3 R$^e$;

$R^a$ and $R^b$ are at each occurrence independently selected from H, $C_{1-4}$alkyl or $C_{3-6}$cycloalkyl, or $R^a$ and $R^b$ and the N to which they are attached in combination form a 5 or 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^c$ is, at each occurrence independently selected from H, $C_{1-3}$alkyl, or substituted phenyl with 0, 1, 2, or 3 R$^e$;

$R^d$ is, at each occurrence independently selected from $C_{1-3}$alkyl, hydroxy, $C_{1-3}$alkoxy, or NR$^a$R$^b$;

$R^e$ is, at each occurrence independently selected from H, OH, F, Cl, Br, I, CN, NO$_2$, CF$_3$, $C_{1-6}$alkyl, or $C_{1-6}$alkoxy;

$R^2$ and $R^3$ are at each occurrence independently selected from H, $C_{1-6}$alkyl, $C_{4-6}$ cycloalkyl, aryl, or heteroaryl, or $R^2$ and $R^3$ in combination form a fused phenyl or cyclohexyl moiety that may be substituted with 0, 1 or 2 R$^f$ moieties, $R^f$ is NO$_2$, F, Cl, Br, I, CF$_3$, CN, $C_{1-6}$alkyl, or $C_{1-6}$alkoxy, $R^4$ is H, CHR$^7$R$^8$, 5- or 6-membered cycloalkyl, 5- or 6-membered heterocyclic, 5 or 6-membered aromatic ring optionally substituted with 0, 1, or 2 R$^f$ moities, said heterocyclic ring having 0, 1, 2 or 3 nitrogen, oxygen or sulfur atoms, but no more than 2 oxygen atoms or 2 sulfur atoms or 1 oxygen and 1 sulfur atom;

$R^5$ is $C_{1-3}$alkylR$^9$ or CH(OH)R$^{10}$;

$R^7$ and $R^8$ are, at each occurrence are independently selected from H, $C_{1-4}$alkyl, OH, SH, CH$_2$SCH$_3$, CONH$_2$, CH$_2$CONH$_2$, CO$_2$H, CH$_2$CO$_2$H, (CH$_2$)$_3$NHCH(NH$_2$)$_2$, $C_{1-4}$alkylamine, indole, imidazole, phenyl or hydroxyphenyl or $R^7$ and $R^8$ in combination form a 6-membered aromatic or heterocyclic ring optionally substituted with 0, 1 or 2 R$^f$ moieties said heterocyclic ring having 0, 1, 2 or 3 nitrogen, oxygen or sulfur atoms, but no more than 2 oxygen atoms or 2 sulfur atoms or 1 oxygen and 1 sulfur atom;

$R^9$ is phenyl substituted with 0, 1, 2 or 3 R$^e$;

$R^{10}$ is alkyl or $R^9$;

or a pharmaceutically acceptable salt thereof.

Another embodiment of the invention occurs wherein a compound is selected from formula (I) wherein:

X is C, O, NR$^1$, SO$_2$ or S;

Ar$^1$ is a 5- or 6-membered aromatic or heterocyclic ring optionally substituted with 0, 1, 2, or 3 R$^e$ moieties, said ring having 0, 1, or 2 nitrogen, oxygen or sulfur atoms, but no more than 2 oxygen atoms or 1 oxygen and 1 sulfur atom;

$R^1$ is H, $C_{1-3}$alkyl$C_{3-6}$cycloalkyl, $C_{1-6}$alkyl, $C_{3-6}$alkenyl, $C_{3-6}$alkynyl, $C_{3-6}$cycloalkyl, $C_{2-4}$alkylNR$^a$R$^b$, $C_{1-4}$alkylC(=O)R$^d$; or $C_{1-3}$alkylphenyl substituted with 0, 1, 2 or 3 R$^e$;

$R^a$ and $R^b$ are, at each occurrence independently selected from H, $C_{1-4}$alkyl or $C_{3-6}$cycloalkyl, or $R^a$ and $R^b$ and the N to which they are attached in combination form a 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^c$ is, at each occurrence independently selected from H, $C_{1-3}$alkyl, or phenyl;

$R^d$ is, at each occurrence independently selected from $C_{1-3}$alkyl, or NR$^a$R$^b$;

$R^e$ is, at each occurrence independently selected from OH, F, Cl, Br, I, CN, NO$_2$, CF$_3$, $C_{1-3}$alkyl, or $C_{1-3}$alkoxy;

$R^2$ and $R^3$ are at each occurrence independently selected from H, $C_{1-6}$alkyl, $C_{4-6}$ cycloalkyl, or aryl, or $R^2$ and $R^3$ in combination form a fused phenyl moiety that may be substituted with 0, 1 or 2 R$^f$ moieties, $R^f$ is NO$_2$, F, Cl, Br, I, CF$_3$, CN, $C_1$-3alkyl, or $C_1$-3alkoxy;

$R^4$ is H, CHR$^7$R$^8$, 6-membered cycloalkyl, or 6-membered heterocyclic, or 6-membered aromatic ring optionally substituted with 0, 1, or 2 R$^f$ moities, said heterocyclic ring having 0, 1, 2 or 3 nitrogen, oxygen or sulfur atoms, but no more than 2 oxygen atoms or 2 sulfur atoms or 1 oxygen and 1 sulfur atom;

$R^5$ is $C_{1-3}$alkylR$^9$ or CH(OH)R$^{10}$;

$R^7$ and $R^8$ are, at each occurrence independently selected from H, $C_{1-4}$alkyl, OH, CONH$_2$, CH$_2$CONH$_2$, CO$_2$H, CH$_2$CO$_2$H, (CH$_2$)$_3$NHCH(NH$_2$)$_2$, $C_{1-4}$alkylamine, indole, imidazole, phenyl or hydroxyphenyl or $R^7$ and $R^8$ in combination form a 6-membered aromatic or heterocyclic ring optionally substituted with 0, 1 or 2 R$^f$ moieties said heterocyclic ring having 0, 1, 2 or 3 nitrogen, oxygen or sulfur atoms, but no more than 2 oxygen atoms or 2 sulfur atoms or 1 oxygen and 1 sulfur atom;

$R^9$ is phenyl substituted with 0, 1, or 2 R$^e$;

$R^{10}$ is alkyl or $R^9$;

Another embodiment of the invention occurs wherein a compound is selected from formula (I) wherein:

X is C, O, NR$^1$, SO$_2$ or S;

Ar$^1$ is a 5- or 6-membered aromatic or heterocyclic ring optionally substituted with 0, 1, 2, or 3 R$^e$ moieties, said ring having 0, 1, or 2 nitrogen, oxygen or sulfur atoms, but no more than 2 oxygen atoms or 1 oxygen and 1 sulfur atom;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$, $C_{1-4}$alkylC(=O)R$^d$; or $C_{1-3}$alkylphenyl substituted with 0, 1, or 2 R$^e$;

$R^a$ and $R^b$ are, at each occurrence independently selected from H, $C_{1-4}$alkyl or $C_{3-6}$cycloalkyl, or $R^a$ and $R^b$ and the N to which they are attached in combination form a 5-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^c$ is, at each occurrence independently selected from H, $C_{1-3}$alkyl, phenyl;

$R^d$ is, at each occurrence independently selected from $C_{1-3}$alkyl or NR$^a$R$^b$;

$R^e$ is, at each occurrence independently selected from H, OH, F, Cl, Br, I, CN, NO$_2$, CF$_3$, $C_{1-6}$alkyl, or $C_{1-6}$alkoxy;

$R^2$ and $R^3$ are at each occurrence independently selected from H, $C_{1-6}$alkyl, $C_{4-6}$ cycloalkyl or aryl or $R^2$ and $R^3$ in combination form a fused phenyl moiety that may be substituted with 0, 1 or 2 R$^f$ moieties, $R^f$ is H, NO$_2$, F, Cl, Br, I, CF$_3$, $C_{1-6}$alkyl, or $C_{1-6}$alkoxy;

$R^4$ is H, CHR$^7$R$^8$, or 6-membered heterocyclic, or 6-membered aromatic ring optionally substituted with 0, 1, or 2 R$^f$ moities, said heterocyclic ring having 0, 1, 2 or 3 nitrogen, oxygen or sulfur atoms, but no more than 2 oxygen atoms or 2 sulfur atoms or 1 oxygen and 1 sulfur atom;

$R^4$ is H or CHR$^7$R$^8$;

$R^5$ is $C_{1-3}$alkylR$^9$ or CH(OH)R$^{10}$;

n is 0, 1 or 2;

$R^7$ and $R^8$ are, at each occurrence independently selected from H, $C_{1-4}$alkyl, OH, CONH$_2$, CH$_2$CONH$_2$, CO$_2$H, CH$_2$CO$_2$H, (CH$_2$)$_3$NHCH(NH$_2$)$_2$, $C_{1-4}$alkylamine, indole, imidazole, phenyl or hydroxyphenyl or $R^7$ and $R^8$ in combination form a 6-membered aromatic or heterocyclic ring optionally substituted with 0, 1 or 2 R$^f$ moieties said heterocyclic ring having 0, 1, or 2 nitrogen; oxygen or sulfur atoms;

$R^9$ is phenyl substituted with 1, or 2 $R^e$;

$R^{10}$ is alkyl or phenyl substituted with 1, or 2 $R^e$;

Another embodiment of the invention occurs wherein a compound is selected from formula (I) wherein:

X is C, O, $NR^1$, $SO_2$ or S;

$Ar^1$ is a 5- or 6-membered aromatic or heterocyclic ring optionally substituted with 0, 1, 2, or 3 $R^e$ moieties, said ring having 0, 1, or 2 nitrogen, oxygen or sulfur atoms, but no more than 1 oxygen and 1 sulfur atom;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$, $C_{1-4}$alkylC(=O)R$^d$; or $C_{1-3}$alkylphenyl substituted with 0, or 1 $R^e$;

$R^a$ and $R^b$ are, at each occurrence independently selected from H, $C_{1-4}$alkyl or $C_{5-6}$cycloalkyl, or $R^a$ and $R^b$ and the N to which they are attached in combination form a 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^c$ is, at each occurrence independently selected from H, $C_{1-3}$alkyl;

$R^d$ is, at each occurrence independently selected from $C_{1-3}$alkyl;

$R^e$ is, at each occurrence independently selected from H, OH, F, Cl, Br, I, CN, $NO_2$, $CF_3$, $C_{1-6}$alkyl;

$R^2$ and $R^3$ are at each occurrence independently selected from H, $C_{1-6}$alkyl, or $R^2$ and $R^3$ in combination form a fused phenyl moiety that may be substituted with 0, 1 or 2 $R^f$ moieties, $R^f$ is H, F, Cl, Br, I, $CF_3$, $C_{1-6}$alkyl;

$R^4$ is H, CHR$^7$R$^8$, or 6- membered heterocyclic, or 6-membered aromatic ring optionally substituted with 0, 1, or 2 $R^f$ moities, said heterocyclic ring having 0, 1, or 2 nitrogen, oxygen or sulfur atoms;

$R^5$ is $C_{1-3}$alkylR$^9$ or CH(OH)R$^{10}$;

n is 0, 1 or 2;

$R^7$ and $R^8$ are, at each occurrence independently selected from H, $C_{1-4}$alkyl, OH, $CONH_2$, $CH_2CONH_2$, $CO_2H$, $CH_2CO_2H$, $(CH_2)_3NHCH(NH_2)_2$, $C_{1-4}$alkylamine, indole, imidazole, phenyl or hydroxyphenyl or $R^7$ and $R^8$ in combination form a 6-membered aromatic or heterocyclic ring optionally substituted with 0, 1 or 2 $R^f$ moieties said heterocyclic ring having 0, 1, or 2 nitrogen, or oxygen atoms;

$R^9$ is phenyl substituted with 1, or 2 $R^e$;

$R^{10}$ is alkyl or $R^9$;

Another embodiment of the invention occurs wherein a compound is selected from formula (I) wherein:

X is C, O, $SO_2$ or S;

$Ar^1$ is a 5- or 6-membered aromatic or heterocyclic ring optionally substituted with 0, 1, or 2 $R^e$ moieties, said ring having 0, 1, or 2 nitrogen, oxygen or sulfur atoms;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$, $C_{1-4}$alkylC(=O)R$^d$;

$R^a$ and $R^b$ are, at each occurrence independently selected from H, $C_{1-4}$alkyl or $C_{5-6}$cycloalkyl, or $R^a$ and $R^b$ and the N to which they are attached in combination form a 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^d$ is, at each occurrence independently selected from $C_{1-3}$alkyl;

$R^e$ is, at each occurrence independently selected from H, OH, F, Cl, Br, I, $NO_2$, $CF_3$, or $C_{1-6}$alkyl;

$R^2$ and $R^3$ are at each occurrence independently selected from $C_{1-6}$alkyl or $R^2$ and $R^3$ in combination form a fused phenyl moiety that may be substituted with 0, 1 or 2 $R^f$ moieties, $R^f$ is H, F, Cl, Br, I, $CF_3$;

$R^4$ is H, CHR$^7$R$^8$, or 6-membered heterocyclic, or 6-membered aromatic ring optionally substituted with 0, 1, or 2 $R^f$ moities, said heterocyclic ring having 0, 1, or 2 nitrogen, or oxygen atoms;

$R^5$ is $C_{1-3}$alkylR$^9$ or CH(OH)R$^{10}$;

$R^7$ and $R^8$ are, at each occurrence independently selected from H, $C_{1-4}$alkyl, OH, $CONH_2$, $CH_2CONH_2$, $CO_2H$, $C_{1-4}$alkylamine, phenyl or hydroxyphenyl or $R^7$ and $R^8$ in combination form a 6-membered aromatic or heterocyclic ring optionally substituted with 0, 1 or 2 $R^f$ moieties said heterocyclic ring having 0, 1, or 2 nitrogen, or oxygen atoms;

$R^9$ is phenyl substituted with 1 or 2 $R^e$;

$R^{10}$ is alkyl or $R^9$;

Another embodiment of the invention occurs wherein a compound is selected from formula (I) wherein:

X is C, O, $SO_2$ or S;

$Ar^1$ is a 6-membered aromatic or heterocyclic ring optionally substituted with 0, 1, or 2 $R^e$ moieties, said ring having 0, or 1 nitrogen, oxygen or sulfur atoms;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$, $C_{1-4}$alkylC(=O)R$^d$;

$R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen;

$R^d$ is, at each occurrence independently selected from $C_{1-3}$alkyl;

$R^e$ is, at each occurrence independently selected from H, OH, F, Cl, Br, I, $CF_3$;

$R^2$ and $R^3$ are combined to form a fused phenyl moiety substituted with 0, 1 or 2 $R^f$ moieties, $R^f$ is H, F, Cl, Br, I, or $CF_3$;

$R^4$ is H, CHR$^7$R$^8$, or 6-membered heterocyclic, or 6-membered aromatic ring optionally substituted with 0, 1, or 2 $R^f$ moities, said heterocyclic ring having 0, or 1, nitrogen, or oxygen atoms;

$R^5$ is $C_{1-3}$alkylR$^9$ or CH(OH)R$^{10}$;

$R^7$ and $R^8$ are, at each occurrence independently selected from H, OH, or $R^7$ and $R^8$ in combination form a 6-membered aromatic or heterocyclic ring optionally substituted with 0, 1 or 2 $R^f$ moieties said heterocyclic ring having 0, or 1, nitrogen, or oxygen atoms;

$R^9$ is phenyl substituted with 2 $R^e$;

$R^{10}$ is phenyl substituted with 2 $R^e$;

Another embodiment of the invention occurs wherein a compound is selected from formula (I) wherein:

X is C, O, or S;

$Ar^1$ is a 6-membered aromatic or heterocyclic ring optionally substituted with 0, 1, or 2 $R^e$ moieties, said ring having having 0, or 1 nitrogen, or oxygen atoms;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$;

$R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen;

$R^2$ and $R^3$ are combined to form a fused phenyl moiety substituted with 0, 1 or 2 $R^f$;

$R^e$ is, at each occurrence independently selected from H, OH, F, Cl, Br, I, $CF_3$;

$R^f$ is F or Cl;

$R^4$ is H, $CHR^7R^8$, or 6-membered aromatic ring optionally substituted with 0, 1, or 2 $R^f$ moieties;

$R^5$ is $C_{1-3}$alkyl$R^9$ or $CH(OH)R^{10}$;

$R^7$ and $R^8$ are, at each occurrence independently selected from H, OH, or $R^7$ and $R^8$ in combination form a 6-membered aromatic ring optionally substituted with 0, 1 or 2 $R^f$ moieties $R^7$ and $R^8$ are, at each occurrence independently selected from H or OH;

$R^9$ is phenyl substituted with 2 $R^e$;

$R^{10}$ is phenyl substituted with 2 $R^e$;

Another embodiment of the invention occurs wherein a compound is selected from formula (I) wherein:

X is O or C or S;

$Ar^1$ is a 6-membered aromatic or heterocyclic ring optionally substituted with 0, 1, or 2 $R^e$ moieties, said ring having having 0, or 1 nitrogen atom;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkyl$NR^aR^b$;

$R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen;

$R^2$ and $R^3$ are combined to form a fused phenyl moiety substituted with 0, 1 or 2 $R^f$ wherein $R^f$ is F or Cl;

$R^4$ is H, $CH_3$, or a 6-membered aromatic ring optionally substituted with 0, 1, or 2 $R^f$ moieties;

$R^5$ is $C_{1-3}$alkyl$R^9$;

$R^e$ is, at each occurrence independently selected from H, OH, F, Cl, Br, I, $CF_3$;

$R^9$ is phenyl substituted with 2 $R^e$.

Another embodiment of the invention occurs wherein:

X is O or C;

$Ar^1$ is a 6-membered aromatic ring optionally substituted with 0, 1, or 2 $R^e$ moieties;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkyl$NR^aR^b$;

$R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen;

$R^2$ and $R^3$ are combined to form a fused phenyl moiety substituted with 0, 1 or 2 $R^f$ wherein $R^f$ is F or Cl;

$R^4$ is H, $CH_3$, or a 6-membered aromatic ring optionally substituted with 0, 1, or 2 $R^f$ moieties;

$R^5$ is $C_{1-3}$alkyl$R^9$;

$R^e$ is, at each occurrence independently selected from H, OH, F, Cl, Br, I, $CF_3$;

$R^9$ is phenyl substituted with 2 $R^e$.

Another embodiment of the invention occurs wherein a compound is selected from formula (I) wherein:

X is O;

$Ar^1$ is a 6-membered aromatic ring optionally substituted with 0, 1, or 2 $R^e$ moieties;

$R^1$ is $C_{1-3}$alkyl$C_{3-6}$cycloalkyl, $C_{1-6}$alkyl, $C_{3-6}$alkenyl, $C_{3-6}$alkynyl;

$R^2$ and $R^3$ are combined to form a fused phenyl moiety substituted with 0, 1 or 2 $R^f$ wherein $R^f$ is F or Cl;

$R^4$ is H, $CH_3$, or a 6-membered aromatic ring optionally substituted with 0, 1, or 2 $R^f$ moieties;

$R^5$ is $C_{1-3}$alkyl$R^9$;

$R^e$ is, at each occurrence independently selected from H, OH, F, Cl, Br, I, $CF_3$;

$R^9$ is phenyl substituted with 2 $R^e$.

Another embodiment of the invention occurs wherein a compound is selected from formula (I) wherein X is C, O, $SO_2$ or S.

Another embodiment of the invention occurs wherein a compound is selected from formula (I) wherein $Ar^1$ is a 5-or 6-membered aromatic or heterocyclic ring optionally substituted with 0 or 1 $R^e$.

Another embodiment of the invention occurs wherein a compound is selected from formula (I) wherein $R^1$ is $C_{1-3}$alkyl$C_{3-6}$cycloalkyl, $C_{1-6}$alkyl, $C_{3-6}$alkenyl, $C_{3-6}$alkynyl.

Another embodiment of the invention occurs wherein a compound is selected from formula (I) wherein $R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen.

Another embodiment of the invention occurs wherein a compound is selected from formula (I) wherein $R^2$ and $R^3$ are combined to form a fused phenyl moiety substituted with 0, 1 or 2 $R^f$.

Another embodiment of the invention occurs wherein a compound is selected from formula (I) wherein $R^e$ is, at each occurrence independently selected from F or Cl.

Another embodiment of the invention occurs wherein a compound is selected from formula (I) wherein, wherein $R^f$ is F or Cl.

Another embodiment of the invention occurs wherein a compound is selected from formula (I) wherein $R^4$ is H or $CHR^7R^8$ or a 6-membered aromatic ring optionally substituted with 0, 1, or 2 $R^f$ moieties wherein $R^7$ and $R^8$ are, at each occurrence independently selected from H or OH.

Another embodiment of the invention occurs wherein a compound is selected from formula (I) wherein $R^4$ is a 6-membered aromatic ring optionally substituted with 0, 1, or 2 $R^f$ moieties wherein $R^f$ is halo.

Another embodiment of the invention occurs wherein a compound is selected from formula (I) wherein $R^5$ is $C_{1-3}$alkyl$R^9$ or $CH(OH)R^{10}$.

Another embodiment of the invention occurs wherein a compound is selected from formula (I) wherein $R^7$ and $R^8$ are, at each occurrence independently selected from H or OH.

Another embodiment of the invention occurs wherein a compound is selected from formula (I) wherein $R^9$ is phenyl substituted with 2 $R^e$.

Another embodiment of the invention occurs wherein a compound is selected from formula (I) wherein $R^{10}$ is phenyl substituted with 2 $R^e$.

Another embodiment of the invention occurs wherein a compound is selected from the following:

$N^2$-[(3,5-difluorophenyl)acetyl]-$N^1$-[(2R,3R)-2-(2,5-difluorophenyl)-4-oxo-2,3,4,5-tetrahydro-1,5-benzothiazepin-3-yl]-L-alaninamide;

$N^1$-[(2R,3R)-5-cyclohexyl-2-(2,5-difluorophenyl)-4-oxo-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-{(2R,3R)-2-(2,5-difluorophenyl)-5-[2-(dimethylamino)ethyl]-4-oxo-2,3,4,5-tetrahydro-1,5-benzothiazepin-3-yl}-L-alaninamide;

N²-[(3,5-difluorophenyl)acetyl]-N¹-[(2R,3R)-2-(2,5-difluorophenyl)-4-oxo-2,3,4,5-tetrahydro-1,5-benzothiazepin-3-yl]-L-serinamide;

N²-[(3,5-difluorophenyl)acetyl]-N¹-[(2R,3R)-2-(2,5-difluorophenyl)-5-methyl-4-oxo-2,3,4,5-tetrahydro-1,5-benzothiazepin-3-yl]-L-alaninamide;

N²-[(3,5-difluorophenyl)acetyl]-N¹-[(2R,3S)-4-oxo-2-phenyl-2,3,4,5-tetrahydro-1,5-benzoxazepin-3-yl]-L-alaninamide;

N²-[(3,5-difluorophenyl)acetyl]-N¹-[(6R,7R)-5-oxo-7-phenyl-1,4-thiazepan-6-yl]-L-alaninamide;

N²-[(3,5-difluorophenyl)acetyl]-N¹-[(3S,4R)-8-fluoro-2-oxo-4-phenyl-2,3,4,5-tetrahydro-1H-1-benzazepin-3-yl]-L-alaninamide;

N²-[(3,5-difluorophenyl)acetyl]-N¹-[(2R,3R)-4-oxo-2-phenyl-2,3,4,5-tetrahydro-1,5-benzothiazepin-3-yl]-L-alaninamide;

N¹-[(2R,3R)-2-(3,4-dichlorophenyl)-4-oxo-2,3,4,5-tetrahydro-1,5-benzothiazepin-3-yl]-N²-[(3,5-difluorophenyl)acetyl]-L-alaninamide;

N¹-[(2R,3R)-2-(4-chlorophenyl)-4-oxo-2,3,4,5-tetrahydro-1,5-benzothiazepin-3-yl]-N²-[(3,5-difluorophenyl)acetyl]-L-alaninamide;

N²-[(3,5-difluorophenyl)acetyl]-N¹-[(2R,3R)-2-(4-methylphenyl)-4-oxo-2,3,4,5-tetrahydro-1,5-benzothiazepin-3-yl]-L-alaninamide;

N¹-[(2R,3R)-7-chloro-4-oxo-2-phenyl-2,3,4,5-tetrahydro-1,5-benzothiazepin-3-yl]-N²-[(3,5-difluorophenyl)acetyl]-L-alaninamide;

N¹-{(2R,3R)-7-chloro-5-[2-(dimethylamino)ethyl]-4-oxo-2-phenyl-2,3,4,5-tetrahydro-1,5-benzothiazepin-3-yl}-N²-[(3,5-difluorophenyl)acetyl]-L-alaninamide;

N¹-[(2R,3R)-2-(3-chlorophenyl)-4-oxo-2,3,4,5-tetrahydro-1,5-benzothiazepin-3-yl]-N²-[(3,5-difluorophenyl)acetyl]-L-alaninamide;

N²-[(3,5-difluorophenyl)acetyl]-N¹-[(2R,3R)-2-(3,5-difluorophenyl)-4-oxo-2,3,4,5-tetrahydro-1,5-benzothiazepin-3-yl]-L-alaninamide;

N²-[(3,5-difluorophenyl)acetyl]-N¹-[(2R,3R)-2-(3,5-difluorophenyl)-5-methyl-4-oxo-2,3,4,5-tetrahydro-1,5-benzothiazepin-3-yl]-L-alaninamide;

N²-[(3,5-difluorophenyl)acetyl]-N¹-[(2R,3R)-2-(2-fluorophenyl)-5-methyl-4-oxo-2,3,4,5-tetrahydro-1,5-benzothiazepin-3-yl]-L-alaninamide;

N¹-{(2R,3R)-2-(3-chlorophenyl)-5-[2-(dimethylamino)ethyl]-4-oxo-2,3,4,5-tetrahydro-1,5-benzothiazepin-3-yl}-N²-[(3,5-difluorophenyl)acetyl]-L-alaninamide;

N²-[(3,5-difluorophenyl)acetyl]-N¹-[(2R,3R)-2-(2,5-difluorophenyl)-4-oxo-2,3,4,5-tetrahydro-1,5-benzothiazepin-3-yl]-D-serinamide;

N¹-[(2R,3R)-2-(3-chlorophenyl)-5-methyl-4-oxo-2,3,4,5-tetrahydro-1,5-benzothiazepin-3-yl]-N²-[(3,5-difluorophenyl)acetyl]-L-alaninamide;

N²-[(3,5-difluorophenyl)acetyl]-N¹-[(2R,3R)-5-methyl-4-oxo-2-phenyl-2,3,4,5-tetrahydro-1,5-benzothiazepin-3-yl]-L-alaninamide;

N¹-[(2R,3R)-5-cyclohexyl-4-oxo-2-phenyl-2,3,4,5-tetrahydro-1,5-benzothiazepin-3-yl]-N²-[(3,5-difluorophenyl)acetyl]-L-alaninamide;

N¹-[(2R,3R)-7-chloro-5-cyclohexyl-4-oxo-2-phenyl-2,3,4,5-tetrahydro-1,5-benzothiazepin-3-yl]-N²-[(3,5-difluorophenyl)acetyl]-L-alaninamide;

N²-[(3,5-difluorophenyl)acetyl]-N¹-[(6R,7R)-7-(1-naphthyl)-5-oxo-1,4-thiazepan-6-yl]-L-alaninamide;

(2S)-2-{[(3,5-difluorophenyl)acetyl]amino}-N-[(6R,7R)-7-(1-naphthyl)-5-oxo-1,4-thiazepan-6-yl]-2-phenylacetamide;

(2S)-2-hydroxy-4-methyl-N-((1S)-2-{[(6R,7R)-7-(1-naphthyl)-5-oxo-1,4-thiazepan-6-yl]amino}-2-oxo-1-phenylethyl)pentanamide;

(2S)-2-hydroxy-4-methyl-N-((1S)-2-oxo-2-{[(2R,3S)-4-oxo-2-phenyl-2,3,4,5-tetrahydro-1,5-benzoxazepin-3-yl]amino}-1-phenylethyl)pentanamide;

N²-[(2S)-2-hydroxy-4-methylpentanoyl]-N¹-[(2R,3S)-4-oxo-2-phenyl-2,3,4,5-tetrahydro-1,5-benzoxazepin-3-yl]-L-leucinamide;

N²-[(3,5-difluorophenyl)acetyl]-N¹-[(6S,7R)-4-methyl-5-oxo-7-phenyl-1,4-oxazepan-6-yl]-L-alaninamide;

N²-[(3,5-difluorophenyl)acetyl]-N¹-[(2S,6S,7R)-4-methyl-5-oxo-2,7-diphenyl-1,4-oxazepan-6-yl]-L-alaninamide;

N²-[(3,5-difluorophenyl)acetyl]-N¹-[(6R,7R)-4-methyl-5-oxo-7-phenyl-1,4-thiazepan-6-yl]-L-alaninamide;

N²-[(3,5-difluorophenyl)acetyl]-N¹-[(3R,6S,7R)-4-methyl-5-oxo-3,7-diphenyl-1,4-oxazepan-6-yl]-L-alaninamide;

(2S)-2-hydroxy-4-methyl-N-((1S)-2-{[(6S,7R)-4-methyl-5-oxo-7-phenyl-1,4-oxazepan-6-yl]amino}-2-oxo-1-phenylethyl)pentanamide;

(2S)-2-{[(3,5-difluorophenyl)acetyl]amino}-N-[(6S,7R)-4-methyl-5-oxo-7-phenyl-1,4-oxazepan-6-yl]-2-phenylacetamide;

(2S)-2-cyclohexyl-2-{[(3,5-difluorophenyl)acetyl]amino}-N-[(3R,6S,7R)-4-methyl-5-oxo-3,7-diphenyl-1,4-oxazepan-6-yl]acetamide;

(2S)-2-{[(3,5-difluorophenyl)acetyl]amino}-N-[(3R,6S,7R)-4-methyl-5-oxo-3,7-diphenyl-1,4-oxazepan-6-yl]-2-phenylacetamide;

N²-[(3,5-difluorophenyl)acetyl]-N¹-[(6S,7R)-4-(4-methoxybenzyl)-5-oxo-7-phenyl-1,4-oxazepan-6-yl]-L-alaninamide;

N²-[(3,5-difluorophenyl)acetyl]-N¹-[(2R,3S,5aR,9aR)-5-methyl-4-oxo-2-phenyldecahydro-1,5-benzoxazepin-3-yl]-L-alaninamide;

(2S)-2-{[(3,5-difluorophenyl)acetyl]amino}-N-[(6S,7R)-4-(4-methoxybenzyl)-5-oxo-7-phenyl-1,4-oxazepan-6-yl]-2-phenylacetamide;

N²-[(3,5-difluorophenyl)acetyl]-N¹-[(2R,3R)-2-(4-methoxyphenyl)-4-oxo-2,3,4,5-tetrahydro-1,5-benzothiazepin-3-yl]-L-alaninamide;

N¹-[(2R,3R)-7-chloro-2-(2,5-difluorophenyl)-4-oxo-2,3,4,5-tetrahydro-1,5-benzothiazepin-3-yl]-N²-[(2S)-2-(3,5-difluorophenyl)-2-hydroxyacetyl]-L-alaninamide;

N²-[(2S)-2-hydroxy-4-methyl-1-oxopentyl]-N¹-[(2R,3S)-4-oxo-2-phenyl-2,3,4,5-tetrahydro-1,5-benzoxazepin-3-yl]-L-alaninamide;

N²-[(3,5-difluorophenyl)acetyl]-N¹-[(2R,3S)-5-methyl-4-oxo-2-phenyl-2,3,4,5-tetrahydro-1,5-benzoxazepin-3-yl]-L-alaninamide;

N¹-[(2R,3R)-7-chloro-2-(2,5-difluorophenyl)-5-methyl-4-oxo-2,3,4,5-tetrahydro-1,5-benzothiazepin-3-yl]-N²-[(3,5-difluorophenyl)acetyl]-L-alaninamide;

N²-[(3,5-difluorophenyl)acetyl]-N¹-{(2R,3S)-5-[2-(dimethylamino)ethyl]-4-oxo-2-phenyl-2,3,4,5-tetrahydro-1,5-benzoxazepin-3-yl}-L-alaninamide;

N¹-[(2R,3R)-7-chloro-2-(2,5-difluorophenyl)-4-oxo-5-phenyl-2,3,4,5-tetrahydro-1,5-benzothiazepin-3-yl]-N²-[(3,5-difluorophenyl)acetyl]-L-alaninamide;

N²-[(3,5-difluorophenyl)acetyl]-N¹-[(6R,7R)-5-oxo-7-phenyl-1,4-thiazepan-6-yl]-L-phenylalaninamide;

N²-[(2S)-2-hydroxy-4-methylpentanoyl]-N¹-[(6R,7R)-5-oxo-7-phenyl-1,4-thiazepan-6-yl]-L-phenylalaninamide;

(2S)-2-{[(3,5-difluorophenyl)acetyl]amino}-N-[(6R,7R)-5-oxo-7-phenyl-1,4-thiazepan-6-yl]-2-phenylacetamide;

(2S)-2-hydroxy-4-methyl-N-((1S)-2-oxo-2-{[(6R,7R)-5-oxo-7-phenyl-1,4-thiazepan-6-yl]amino}-1-phenylethyl)pentanamide;

N²-[(3,5-difluorophenyl)acetyl]-N¹-[(6R,7R)-5-oxo-7-phenyl-1,4-thiazepan-6-yl]-L-leucinamide;

N²-[(2S)-2-hydroxy-4-methylpentanoyl]-N¹-[(6R,7R)-5-oxo-7-phenyl-1,4-thiazepan-6-yl]-L-leucinamide;

N²-[(3,5-difluorophenyl)acetyl]-N¹-[(6R,7R)-5-oxo-7-phenyl-1,4-thiazepan-6-yl]-L-valinamide;

N²-[(2S)-2-hydroxy-4-methylpentanoyl]-N¹-[(6R,7R)-5-oxo-7-phenyl-1,4-thiazepan-6-yl]-L-valinamide;

N¹-[(2R,3S)-7-chloro-4-oxo-2-phenyl-2,3,4,5-tetrahydro-1,5-benzoxazepin-3-yl]-N²-[(3,5-difluorophenyl)acetyl]-L-alaninamide;

(2S)-N-((1S)-2-{[(2R,3S)-7chloro-4-oxo-2-phenyl-2,3,4,5-tetrahydro-1,5-benzoxazepin-3-yl]amino}-2-oxo-1-phenylethyl)-2-hydroxy-4-methylpentanamide;

(2S)-2-{[(3,5-difluorophenyl)acetyl]amino}-N-[(2R,3S)-4-oxo-2-phenyl-2,3,4,5-tetrahydro-1,5-benzoxazepin-3-yl]-2-phenylacetamide;

N²-[(3,5-difluorophenyl)acetyl]-N¹-[(2R,3S)-4-oxo-2-phenyl-2,3,4,5-tetrahydro-1,5-benzoxazepin-3-yl]-L-serinamide;

(2S)-2-cyclohexyl-2-{[(3,5-difluorophenyl)acetyl]amino}-N-[(2R,3S)-4-oxo-2-phenyl-2,3,4,5-tetrahydro-1,5-benzoxazepin-3-yl]acetamide;

(2S)-N-((1S)-1-cyclohexyl-2-oxo-2-{[(2R,3S)-4-oxo-2-phenyl-2,3,4,5-tetrahydro-1,5-benzoxazepin-3-yl]amino}ethyl)-2-hydroxy-4-methylpentanamide;

3-cyclohexyl-N²-[(3,5-difluorophenyl)acetyl]-N¹-[(6R,7R)-5-oxo-7-phenyl-1,4-thiazepan-6-yl]-L-alaninamide;

N²-[(3,5-difluorophenyl)acetyl]-N¹-[(2R,3S)-5-(2-morpholin-4-ylethyl)-4-oxo-2-phenyl-2,3,4,5-tetrahydro-1,5-benzoxazepin-3-yl]-L-alaninamide;

N²-[(3,5-difluorophenyl)acetyl]-N¹-[(2R,3)-4-oxo-2-phenyl-2,3,4,5-tetrahydro-1,5-benzoxazepin-3-yl]-L-leucinamide;

(2S)-2-{[(3,5-difluorophenyl)acetyl]amino}-2-(4-fluorophenyl)-N-[(2R,3S)-4-oxo-2-phenyl-2,3,4,5-tetrahydro-1,5-benzoxazepin-3-yl]acetamide;

(2S)-2-[(cyclohexylacetyl)amino]-2-(4-fluorophenyl)-N-[(2R,3S)-4-oxo-2-phenyl-2,3,4,5-tetrahydro-1,5-benzoxazepin-3-yl]acetamide;

N²-[(3,5-difluorophenyl)acetyl]-N¹-[(2R,3S)-4-oxo-2-phenyl-5-prop-2-yn-1-yl-2,3,4,5-tetrahydro-1,5-benzoxazepin-3-yl]-L-alaninamide;

N²-[(3,5-difluorophenyl)acetyl]-N¹-[(2R,3S)-7-methoxy-4-oxo-2-phenyl-2,3,4,5-tetrahydro-1,5-benzoxazepin-3-yl]-L-alaninamide;

N²-[(3,5-difluorophenyl)acetyl]-N¹-[(2R,3S)-5-isopropyl-4-oxo-2-phenyl-2,3,4,5-tetrahydro-1,5-benzoxazepin-3-yl]-L-alaninamide;

methyl [(2R,³S)-3-({N-[(3,5-difluorophenyl)acetyl]-L-alanyl}amino)-4-oxo-2-phenyl-3,4-dihydro-1,5-benzoxazepin-5(2H)-yl]acetate;

[(2R,3S)-3-({N-[(3,5-difluorophenyl)acetyl]-L-alanyl}amino)-4-oxo-2-phenyl-3,4-dihydro-1,5-benzoxazepin-5(2H)-yl]acetic acid;

N¹-[(2R,3S)-5-(cyclopropylmethyl)-4-oxo-2-phenyl-2,3,4,5-tetrahydro-1,5-benzoxazepin-3-yl]-N²-[(3,5-difluorophenyl)acetyl]-L-alaninamide;

N¹-[(2R,3S)-5-(cyclopropylmethyl)-7-methoxy-4-oxo-2-phenyl-2,3,4,5-tetrahydro-1,5 -benzoxazepin-3-yl]-N²-[(3,5-difluorophenyl)acetyl]-L-alaninamide;

N¹-[(2R,3S)-5-(2-azetidin-1-yl-2-oxoethyl)-4-oxo-2-phenyl-2,3,4,5-tetrahydro-1,5-benzoxazepin-3-yl]-N²-[(3,5-difluorophenyl)acetyl]-L-alaninamide;

N²-[(3,5-difluorophenyl)acetyl]-N¹-[(2R,3S)-7-fluoro-4-oxo-2-phenyl-2,3,4,5-tetrahydro-1,5-benzoxazepin-3-yl]-L-alaninamide;

(2S)-N-((1S)-2-{[(2R,3S)-7-fluoro-4-oxo-2-phenyl-2,3,4,5-tetrahydro-1,5-benzoxazepin-3-yl]amino}-2-oxo-1-phenylethyl)-2-hydroxy-4-methylpentanamide;

N²-[(2R)-2-(3,5-difluorophenyl)-2-hydroxyacetyl]-N¹-[(2R,3S)-4-oxo-2-phenyl-2,3,4,5-tetrahydro-1,5-benzoxazepin-3-yl]-L-alaninamide;

N²-[(2S-2-(3,5-difluorophenyl)-2-hydroxyacetyl]-N¹-[(2R,3S)-4-oxo-2-phenyl-2,3,4,5-tetrahydro-1,5-benzoxazepin-3-yl]-L-alaninamide;

N²-[(3,5-difluorophenyl)acetyl]-N¹-[(3S,4R)-2-oxo-4-phenyl-2,3,4,5-tetrahydro-1H-1-benzazepin-3-yl]-L-alaninamide;

N²-[(3,5-difluorophenyl)acetyl]-N¹-[(3S,4R)-8-fluoro-1-methyl-2-oxo-4-phenyl-2,3,4,5-tetrahydro-1H-1-benzazepin-3-yl]-L-alaninamide;

(2S)-N-((1S)-2-{[(3S,4R)-8-fluoro-2-oxo-4-phenyl-2,3,4,5-tetrahydro-1H-1-benzazepin-3-yl]amino}-2-oxo-1-phenylethyl)-2-hydroxy-4-methylpentanamide;

(2S)-2-hydroxy-4-methyl-N-((1S)-2-oxo-2-{[(3S,4R)-2-oxo-4-phenyl-2,3,4,5-tetrahydro-1H-1-benzazepin-3-yl]amino}-1-phenylethyl)pentanamide;

N²-[(3,5-difluorophenyl)acetyl]-N¹-[(3S,4R)-2-oxo-4-phenyl-1-prop-2-yn-1-yl-2,3,4,5-tetrahydro-1H-1-benzazepin-3-yl]-L-alaninamide;

N¹-[(3S,4R)-1-(cyclopropylmethyl)-2-oxo-4-phenyl-2,3,4,5-tetrahydro-1H-1-benzazepin-3-yl]-N²-[(3,5-difluorophenyl)acetyl]-L-alaninamide;

N²-[(3,5-difluorophenyl)acetyl]-N¹-[(3S,4R)-1-isopropyl-2-oxo-4-phenyl-2,3,4,5-tetrahydro-1H-1-benzazepin-3-yl]-L-alaninamide;

N²-[(2S)-2-hydroxy-4-methyl-1-oxopentyl]-N¹-[(2R,3R)-2-(4-methoxyphenyl)-4-oxo-2,3,4,5-tetrahydro-1,5-benzothiazepin-3-yl]-L-alaninamide;

N¹-[(2R,3R)-2-(2-chlorophenyl)-4-oxo-2,3,4,5-tetrahydro-1,5-benzothiazepin-3-yl]-N²-[(2S)-2-hydroxy-4-methyl-1-oxopentyl]-L-alaninamide;

N¹-[(2R,3R)-2-(2-chlorophenyl)-4-oxo-2,3,4,5-tetrahydro-1,5-benzothiazepin-3-yl]-N²-[(3,5-difluorophenyl)acetyl]-L-alaninamide;

N¹-[(2R,3R)-7-chloro-5-methyl-4-oxo-2-phenyl-2,3,4,5-tetrahydro-1,5-benzothiazepin-3-yl]-N²-[(3,5-difluorophenyl)acetyl]-L-alaninamide;

N²-[(3,5-difluorophenyl)acetyl]-N¹-[(2R,3R)-2-(2-fluorophenyl)-4-oxo-2,3,4,5-tetrahydro-1,5-benzothiazepin-3-yl]-L-alaninamide;

N²-[(3,5-difluorophenyl)acetyl]-N¹-[(2R,3R)-2-(4-fluorophenyl)-4oxo-2,3,4,5-tetrahydro-1,5-benzothiazepin-3-yl]-L-alaninamide;

N¹-[(2R,3R)-7-chloro-2-(2,5-difluorophenyl)-4-oxo-2,3,4,5-tetrahydro-1,5-benzothiazepin-3-yl]-N²-[(3,5-difluorophenyl)acetyl]-L-alaninamide;

N²-[(2S)-2-hydroxy-4-methyl-1-oxopentyl]-N¹-[(6R,7R)-5-oxo-7-phenyl-1,4-thiazepan-6-yl]-L-alaninamide;

N²-[(3,5-difluorophenyl)acetyl]-N¹-[(2S,3R)-2-(3-methyl-2-thienyl)-4-oxo-2,3,4,5-tetrahydro-1,5-benzothiazepin-3-yl]-L-alaninamide;

N²-[(3,5-difluorophenyl)acetyl]-N¹-[(2S,3R)-2-(4-methyl-2-thienyl)-4-oxo-2,3,4,5-tetrahydro-1,5-benzothiazepin-3-yl]-L-alaninamide;

Methyl 5-[(2S,3R)-3-({N-[(3,5-difluorophenyl)acetyl]-L-alanyl}amino)-4-oxo-2,3,4,5-tetrahydro-1,5-benzothiazepin-2-yl]thiophene-3-carboxylate;

N¹-[(2R,3R)-4-oxo-2-phenyl-2,3,4,5-tetrahydro-1,5-benzothiazepin-3-yl]-N²-(phenylacetyl)-L-alaninamide;

N¹-[(2R,3R)-4-oxo-2-phenyl-2,3,4,5-tetrahydro-1,5-benzothiazepin-3-yl]-N²-(2-phenylethyl)-L-alaninamide;

N²-[(3,5-difluorophenyl)acetyl]-N¹-[(2S,3R)-4-oxo-2-(2-thienyl)-2,3,4,5-tetrahydro-1,5-benzothiazepin-3-yl]-L-alaninamide;

N²-[(3,5-difluorophenyl)acetyl]-N¹-[(2R,3R)-4-oxo-2-(3-thienyl)-2,3,4,5-tetrahydro-1,5-benzothiazepin-3-yl]-L-alaninamide;

N²-[(3,5-difluorophenyl)acetyl]-N¹-[(2S,3R)-2-(2-furyl)-4-oxo-2,3,4,5-tetrahydro-1,5-benzothiazepin-3-yl]-L-alaninamide;

N²-[(3,5-difluorophenyl)acetyl]-N¹-[(2R,3R)-2-(3-furyl)-4-oxo-2,3,4,5-tetrahydro-1,5-benzothiazepin-3-yl]-L-alaninamide;

N¹-[(2S,3R)-2-(5-bromo-2-thienyl)-4-oxo-2,3,4,5-tetrahydro-1,5-benzothiazepin -3-yl]-N²-[(3,5-difluorophenyl)acetyl]-L-alaninamide;

N¹-[(2S,3R)-2-(4-bromo-2-thienyl)-4-oxo-2,3,4,5-tetrahydro-1,5-benzothiazepin -3-yl]-N²-[(3,5-difluorophenyl)acetyl]-L-alaninamide;

N-[(3,5-difluorophenyl)acetyl]-N-[(2R,3R)-4-oxo-2-phenyl-2,3,4,5-tetrahydro-1,5-benzothiazepin-3-yl]-L-phenylalaninamide;

N²-[(3,5-difluorophenyl)acetyl]-N¹-[(2R,3R)-4-oxo-2-phenyl-2,3,4,5-tetrahydro -1,5-benzothiazepin-3-yl]glycinamide;

N²-[(3,5-difluorophenyl)acetyl]-N¹-[(2R,3R)-4-oxo-2-phenyl-2,3,4,5-tetrahydro -1,5-benzothiazepin-3-yl]-L-valinamide;

N²-[(3,5-difluorophenyl)acetyl]-N¹-[(2R,3R)-4-oxo-2-phenyl-2,3,4,5-tetrahydro -1,5-benzothiazepin-3-yl]-L-leucinamide;

N²-[(3,5-difluorophenyl)acetyl]-N¹-[(2R,3R)-4-oxo-2-phenyl-2,3,4,5-tetrahydro -1,5-benzothiazepin-3-yl]-L-methioninamide;

N²-[(3,5-difluorophenyl)acetyl]-3-(1H-indol-2-yl)-N¹-[(2R,3R)-4-oxo-2-phenyl-2,3,4,5-tetrahydro-1,5-benzothiazepin-3-yl]-L-alaninamide;

N²-[(3,5-difluorophenyl)acetyl]-N¹-[(2R,3R)-4-oxo-2-phenyl-2,3,4,5-tetrahydro -1,5-benzothiazepin-3-yl]-L-a-asparagine;

N²-[(3,5-difluorophenyl)acetyl]-N¹-[(2R,3R)-4-oxo-2-phenyl-2,3,4,5-tetrahydro -1,5-benzothiazepin-3-yl]-L-a-glutamine;

N¹-[(2R,3S)-4-oxo-2-phenyl-2,3,4,5-tetrahydro-1,5-benzoxazepin-3-yl]-N²-(phenylacetyl)-L-alaninamide;

N²-[(2-fluorophenyl)acetyl]-N¹-[(2R,3S)-4-oxo-2-phenyl-2,3,4,5-tetrahydro-1,5-benzoxazepin-3-yl]-L-alaninamide;

N²-[(3-fluorophenyl)acetyl]-N¹-[(2R,3S)-4-oxo-2-phenyl-2,3,4,5-tetrahydro-1,5-benzoxazepin-3-yl]-L-alaninamide;

N²-[(4-fluorophenyl)acetyl]-N¹-[(2R,3S)-4-oxo-2-phenyl-2,3,4,5-tetrahydro-1,5-benzoxazepin-3-yl]-L-alaninamide;

N¹-[(2R,3S,5aS,9aS)-5-(cyclopropylmethyl)-4-oxo-2-phenyldecahydro-1,5-benzoxazepin-3-yl]-N²-[(3,5-difluorophenyl)acetyl]-L-alaninamide.

or a pharmaceutical acceptable salt thereof.

In another aspect the invention encompasses the use of a compound as defined herein, in the manufacture of a medicament for the treatment or prophylaxis of disorders associated with β-amyloid production, Alzheimer's disease, or Down's Syndrome.

In another aspect the invention encompasses a method for the treatment of neurological disorders associated with β-amyloid production comprising administering to a host in need of such treatment a therapeutically effective amount of a compound as defined herein.

In another embodiment the invention encompasses a method for inhibiting γ-secretase activity comprising administering to a host in need of such inhibition a therapeutically effective amount of a compound as defined herein that inhibits γ-secretase activity.

In another embodiment the invention encompasses a method for the treatment or prophylaxis of Alzheimer's disease, or Down's Syndrome comprising adminstering a therapeutically effective amount of a compound of formula (I) or a pharmaceutically acceptable salt thereof.

Yet another aspect of the invention encompasses a pharmaceutical composition comprisisng a compound of formula (I), as defined herein, together with at least one pharmaceutically acceptable carrier, diluent or excipient.

DEFINITIONS

The definitions set forth in this section are intended to clarify terms used throughout this application. The term "herein" means the entire application.

As used in this application, the term "substituted," as used herein, means that any number of hydrogens on the designated atom is replaced with a selection from the indicated group, provided that the designated atom's normal valency is not exceeded, and that the substitution results in a stable compound. For example when a substituent is keto (i.e., =O), then 2 hydrogens on the atom are replaced.

When any variable (e.g., $R^1$, $R^7$, $R^a$, $R^e$ etc.) occurs more than one time in any constituent or formula for a compound, its definition at each occurrence is independent of its definition at every other occurrence. Thus, for example, if a group is shown to be substituted with 0-3 $R^1$, then said group may optionally be substituted with 0, 1, 2 or 3 $R^1$ groups and $R^e$ at each occurrence is selected independently from the definition of $R^e$. Also, combinations of substituents and/or variables are permissible only if such combinations result in stable compounds.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein "acyl" refers to radicals of the of the general formula —C(=O)—R, wherein R is hydrogen, hydrocarbyl radical, amino or alkoxy. Acyl groups include, for example, acetyl, propionyl, benzoyl, phenyl acetyl, carboethoxy, and dimethylcarbamoyl.

As used herein "aromatic" refers to hydrocarbyl radicals having one or more polyunsaturated carbon rings having aromatic character, (e.g., 4n+2 delocalized electrons) and comprising up to about 14 carbon atoms.

As used herein, "alkyl" or "alkylene" is intended to include both branched and straight-chain saturated aliphatic hydrocarbon groups having the specified number of carbon atoms. For example, "$C_{1-6}$alkyl" denotes alkyl having 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. As used herein, "$C_{1-3}$ alkyl", whether a terminal substituent or an alkylene group linking two substituents, is understood to specifically include both branched and straight-chain methyl, ethyl, and propyl.

As used herein, "alkylcycloalkyl is intended to include both an alkyl portion as defined herein and a cycloalkyl portion. For example $C_{1-3}$alkyl$C_{3-6}$cycloalkyl would include —CH$_2$—CH$_2$—CH$_2$-cyclopropyl.

As used herein, "alkenyl" or "alkenylene" is intended to include hydrocarbon chains of either a straight or branched configuration with one or more unsaturated carbon-carbon bonds that may occur at any stable point along the chain. Examples of "$C_{3-6}$alkenyl" include, but are not limited to, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration with one or more carbon-carbon triple bonds that may occur at any stable point along the chain, such as ethynyl, 1-propynyl, 2-propynyl, 1-butynyl, 2-butynyl, 3-butynyl, and the like.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" represent an alkyl group as defined above with the indicated number of carbon atoms attached through a sulphur bridge.

As used herein, the term "aryl" is intended to mean aromatic radicals including both monocyclic aromatic radicals comprising 6 carbon atoms and polycyclic aromatic radicals comprising up to about 14 carbon atoms.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, bicyclooctane, bicyclononane, bicyclodecane (decalin), bicyclooctane, fluorenyl, phenyl, naphthyl, indanyl, adamantyl, or tetrahydronaphthyl (tetralin).

As used herein "cycloalkyl" is intended to include saturated ring groups, having the specified number of carbon atoms. For example, "$C_{3-6}$ cycloalkyl" denotes such groups as cyclopropyl, cyclobutyl, cyclopentyl, or cyclohexyl.

As used herein "cycloalkenyl refers to ring-containing radicals having at least one carbon-carbon double bond in the ring, and having in the range about 3 up to 12 carbons atoms.

As used herein "cycloalkynyl" refers to ring-containing radicals having at least one carbon-carbon triple bond in the ring, and having in the range about 3 up to 12 carbons atoms.

As used herein, "halo" or "halogen" refers to fluoro, chloro, bromo, and iodo. "Counterion" is used to represent a small, negatively charged species such as chloride, bromide, hydroxide, acetate, sulfate, and the like. "Haloalkyl" is intended to include both branched and straight-chain saturated aliphatic hydrocarbon groups having the specified number of carbon atoms, substituted with 1 or more halogen (for example —C$_v$F$_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

As used herein, the term "heterocycle" or "heterocyclic" refers to a ring-containing monovalent and divalent radicals having one or more heteroatoms, independently selected from N, O and S, as part of the ring structure and comprising at least 3 and up to about 20 atoms in the rings. Heterocyclic groups may be saturated or unsaturated, containing one or more double bonds, and heterocyclic groups may contain more that one ring. The heterocyclic rings described herein may be substituted on carbon or on a nitrogen atom if the resulting compound is stable. If specifically noted, nitrogen in the heterocycle may optionally be quaternized. It is understood that when the total number of S and O atoms in the heterocycle exceeds 1, then these heteroatoms are not adjacent to one another.

Examples of heterocycles include, but are not limited to, 1H-indazole, 2-pyrrolidonyl, 2H, 6H-1, 5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azetidine, aziridine, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dioxolane, furyl, 2,3-dihydrofuran, 2,5-dihydrofuran, dihydrofuro[2,3-b]tetrahydrofuran, furanyl, furazanyl, homopiperidinyl, imidazolidine, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxirane, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, purinyl, pyranyl, pyrrolidine, pyrroline, pyrrolidine, pyrazinyl, pyrazolidinyl, pyrazolinyl, pyrazolyl, pyridazinyl, pyridooxazole, pyridoimidazole, pyridothiazole, pyridinyl, N-oxide-pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, thiophane, thiotetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl thienooxazolyl, thienoimidazolyl, thiophenyl, thiirane, triazinyl, 1,2,3-triazolyl, 1,2,4-triazolyl, 1,2,5-triazolyl, 1,3,4-triazolyl, xanthenyl.

As used herein, "5-membered ring" refers to a group having a ring that contains 5 ring atoms.

As used herein "6-membered ring" refers to a group having a ring that contains 6 ring atoms.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

"Prodrugs" are intended to include any covalently bonded carriers that release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Formulation

Compounds of formula I according to the present invention may be administered orally, sublingually, intramuscularly, subcutaneously, topically, intranasally, intraperitoneally, intrathoracially, intravenously, epidurally, intrathecally, intracerebroventricularly and by injection into the joints.

Preferred routes of administration are orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

An effective amount of a compound of formula I of the present invention for use in therapy of Alzheimer's Disease is an amount sufficient to symptomatically relieve in a warm-blooded animal, particularly a human the cognitive symptoms, to slow the progression of worsening cognitive symptoms, or to reduce in patients with cognitive symptoms the risk of getting worse (progressing to dementia or worsening the present degree of dementia).

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Salts include, but are not limited to, pharmaceutically acceptable salts. Examples of pharmaceutically acceptable salts of compounds of the present invention include: acetate, bicarbonate, carbonate, hydrobromide, hydrochloride, phosphate/diphosphate, sulfate, choline, diethanolamine, ethylenediamine, meglumine, aluminum, calcium, magnesium, potassium and sodium.

The term composition is intended to include the formulation of the active component with encapsulating material as a carrier providing a capsule in which the active component (with or without other carriers) is surrounded by a carrier which is thus in association with it. Similarly, cachets are included. Tablets, powders, cachets, and capsules can be used as solid dosage forms suitable for oral administration.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds of this invention may be prepared using the reactions and techniques described in this application. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Examples of such processes are illustrated herein.

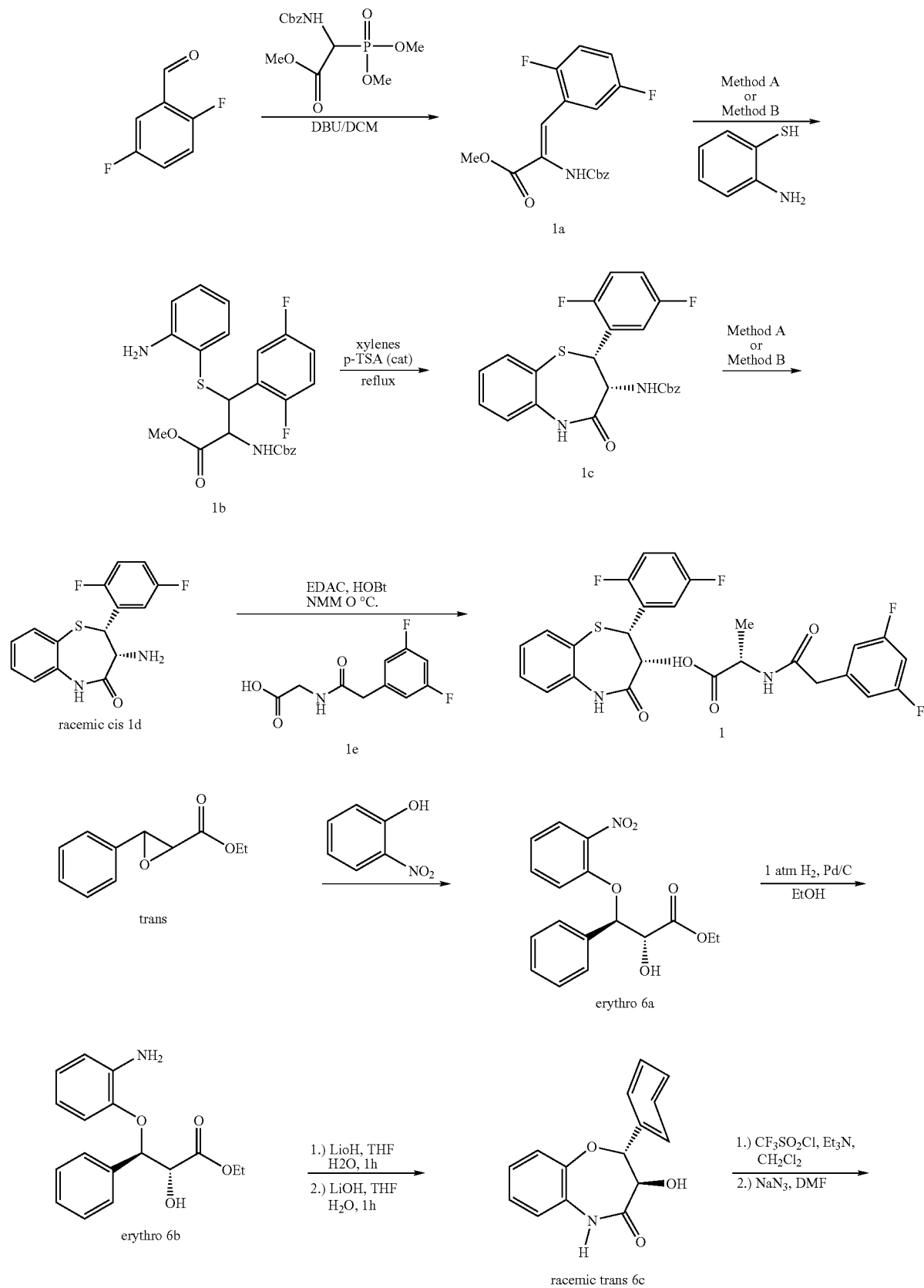

-continued
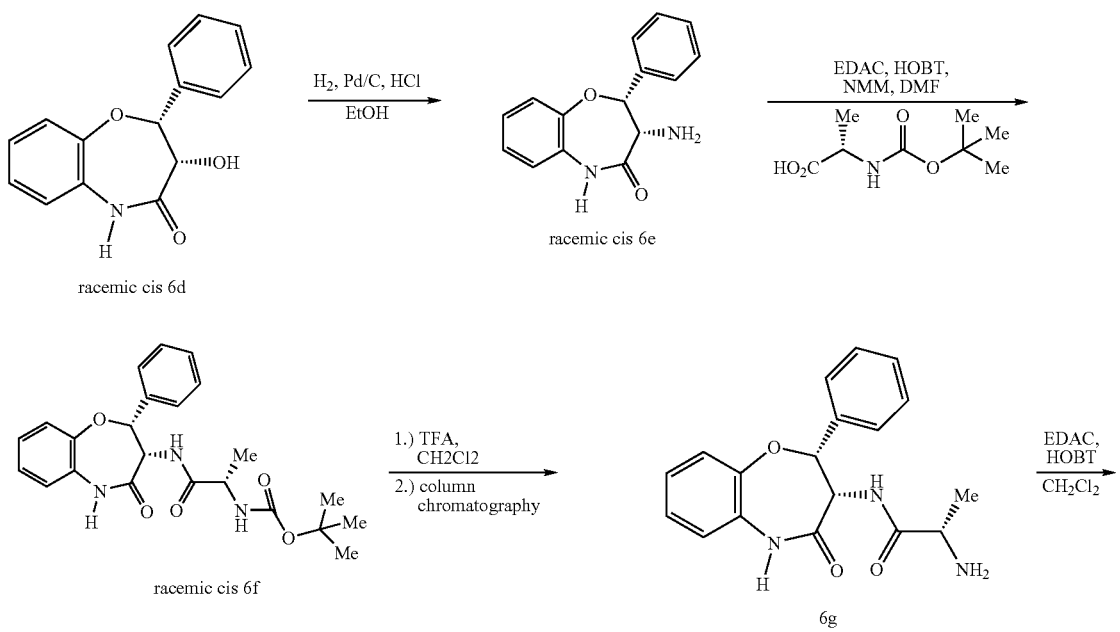
racemic cis 6d
racemic cis 6e
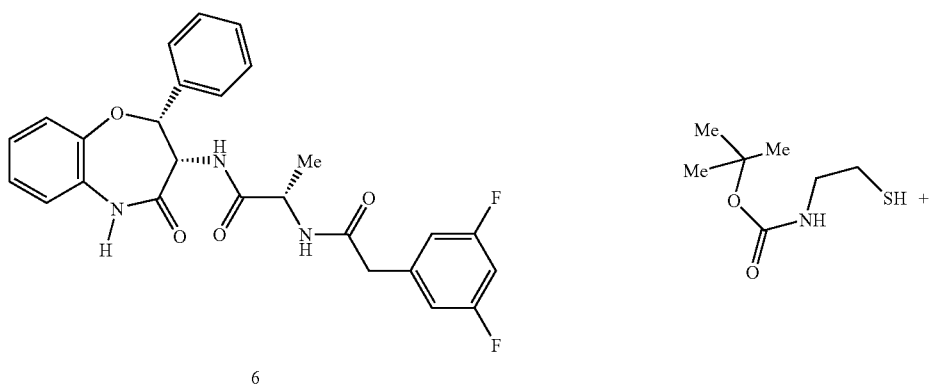
racemic cis 6f
6g
6
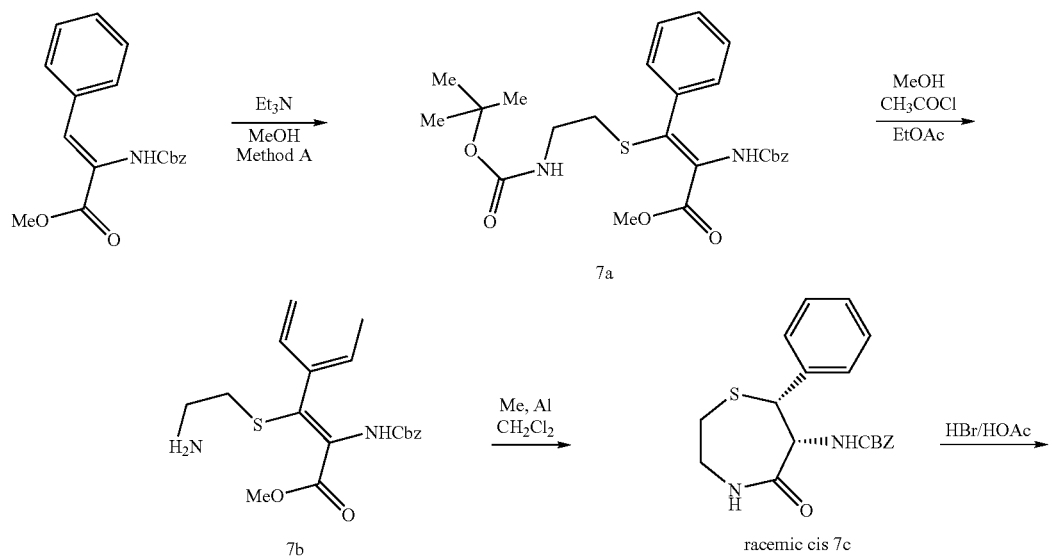
7a
7b
racemic cis 7c

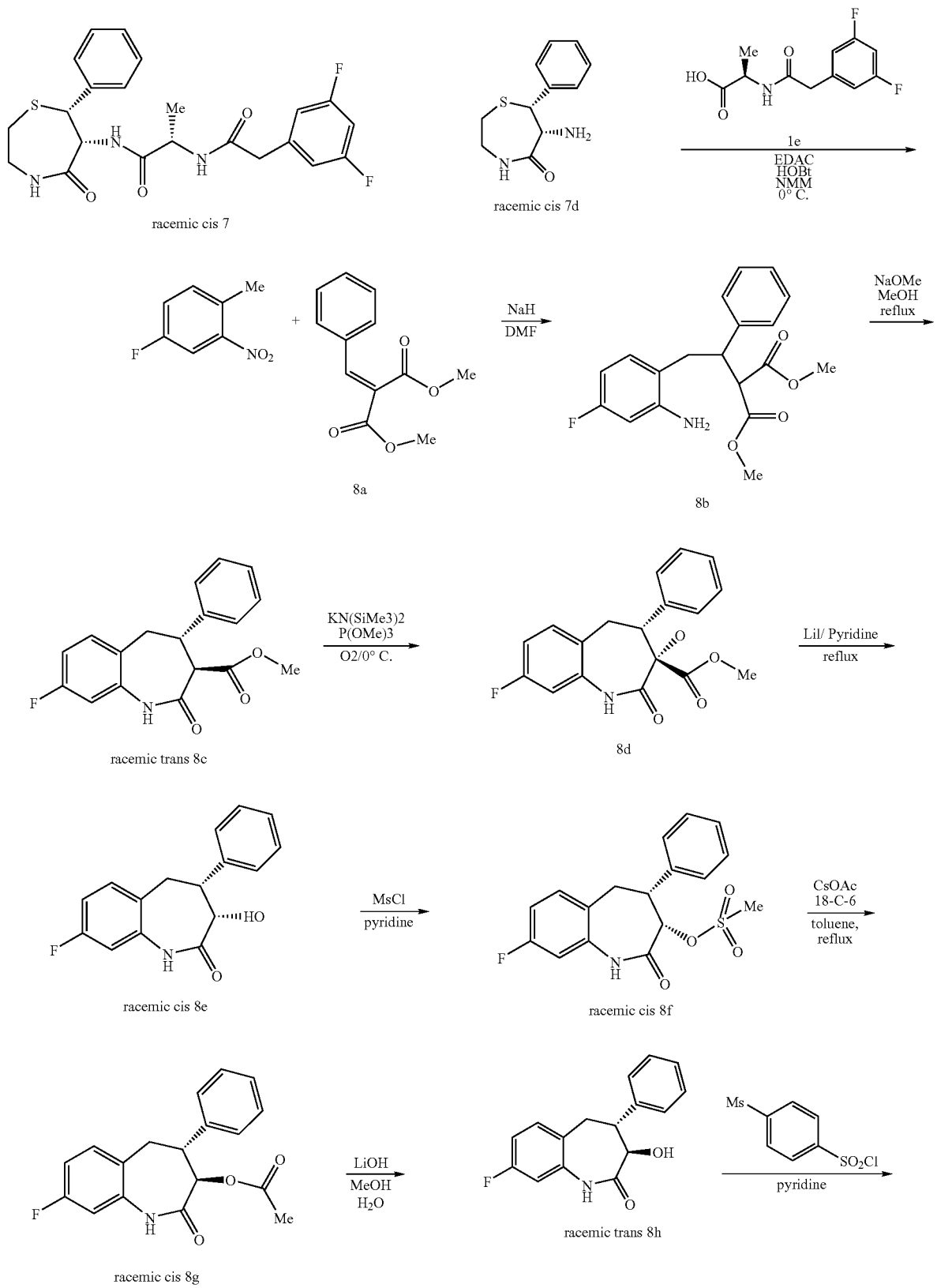

-continued
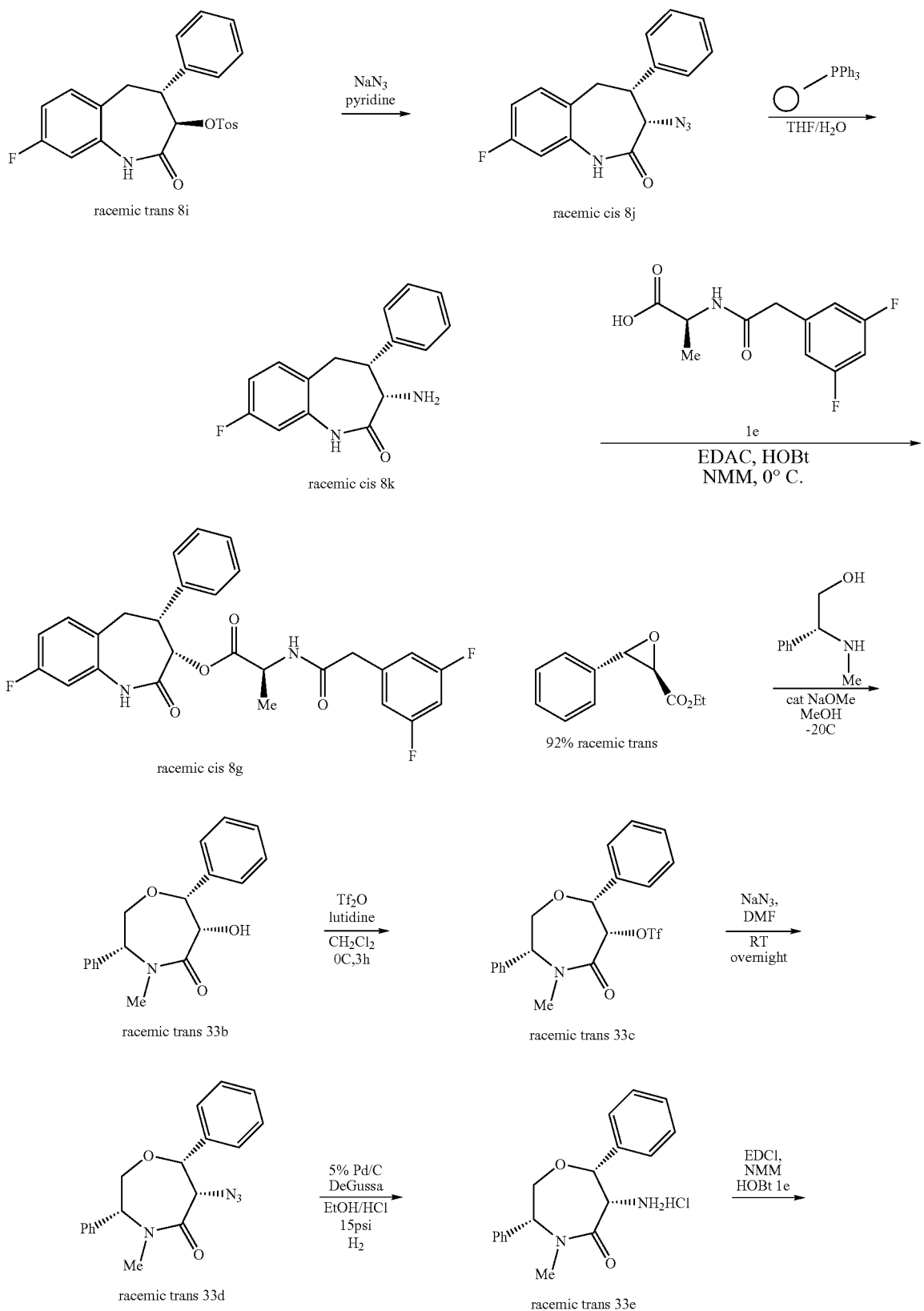

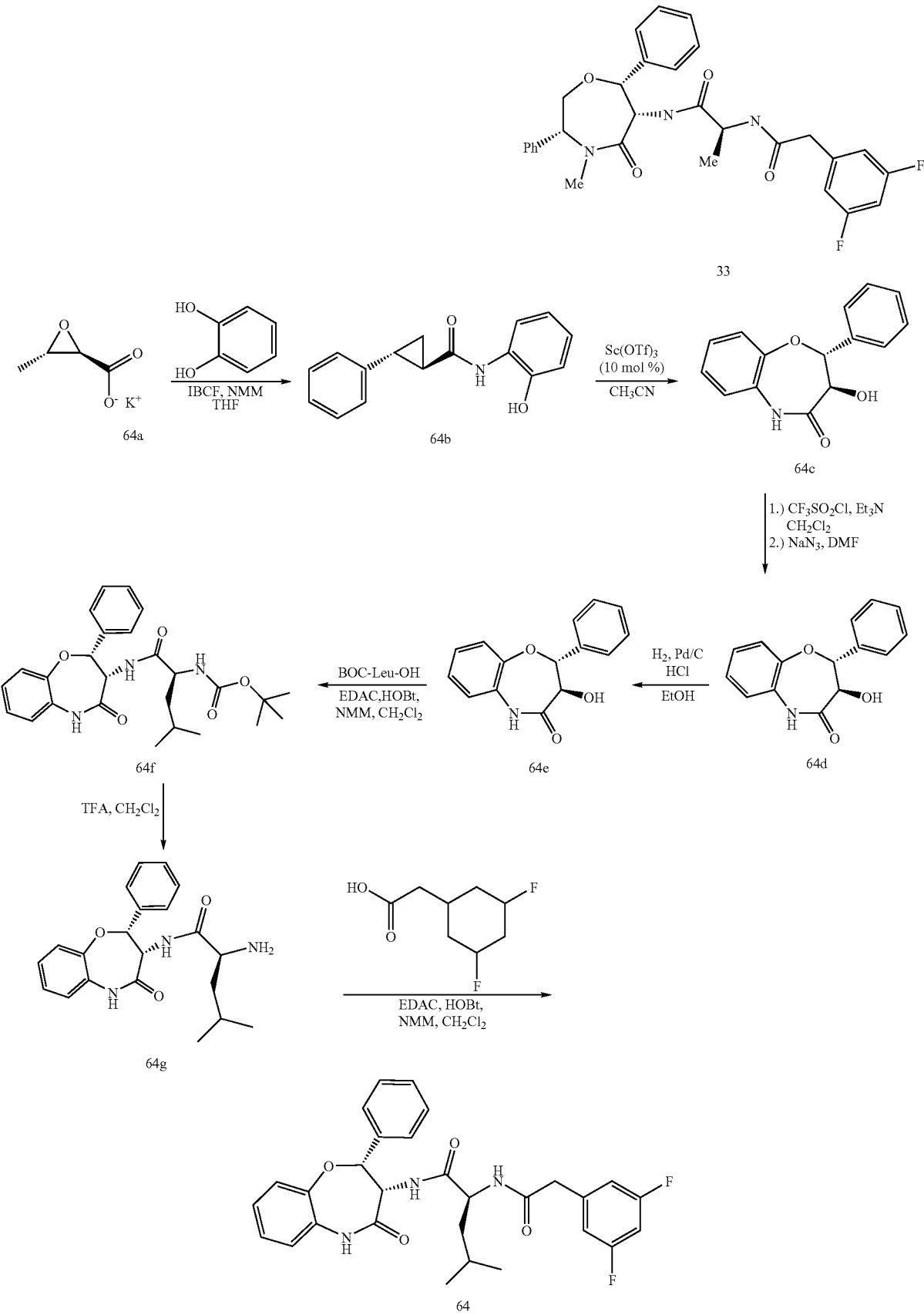

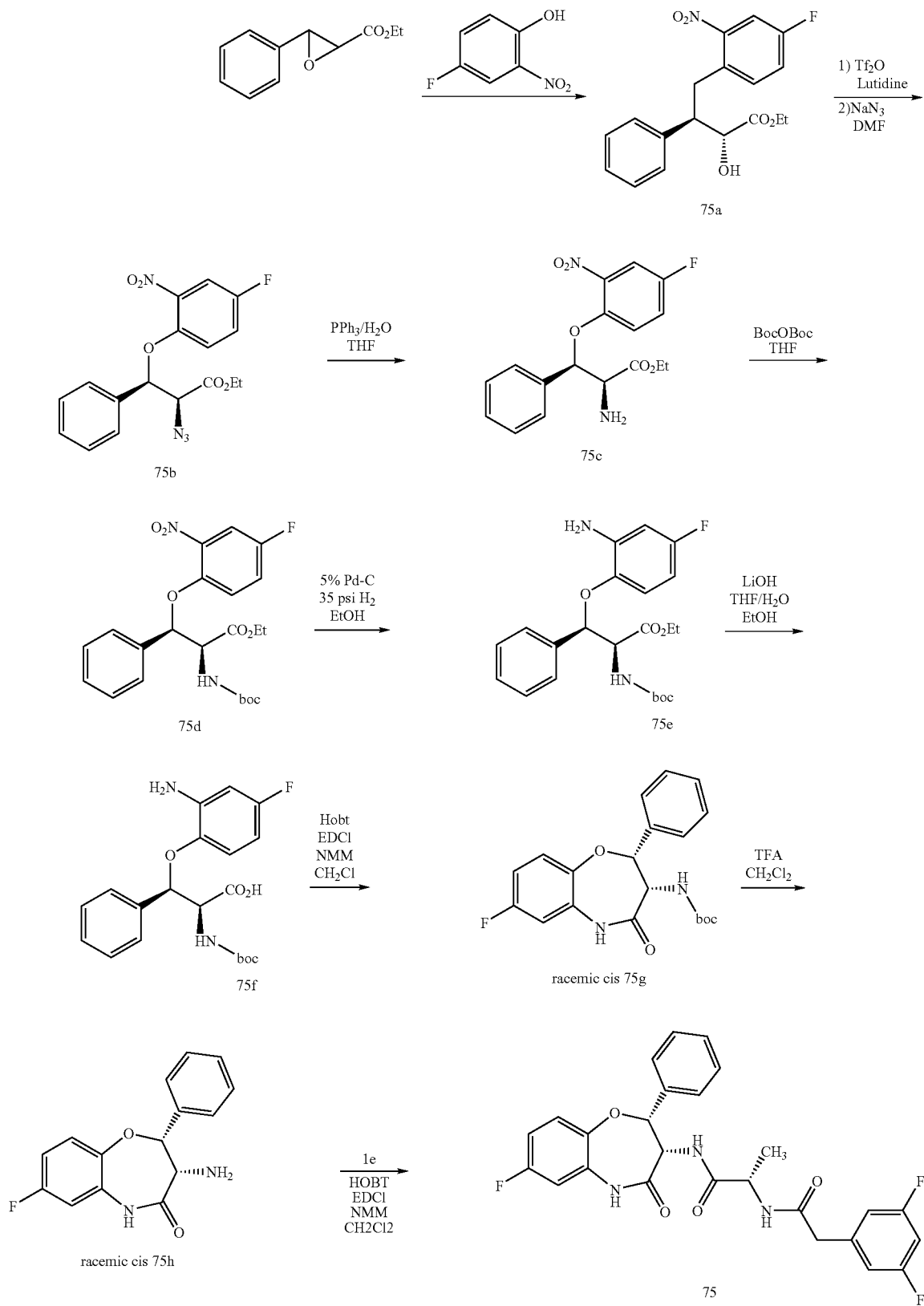

-continued

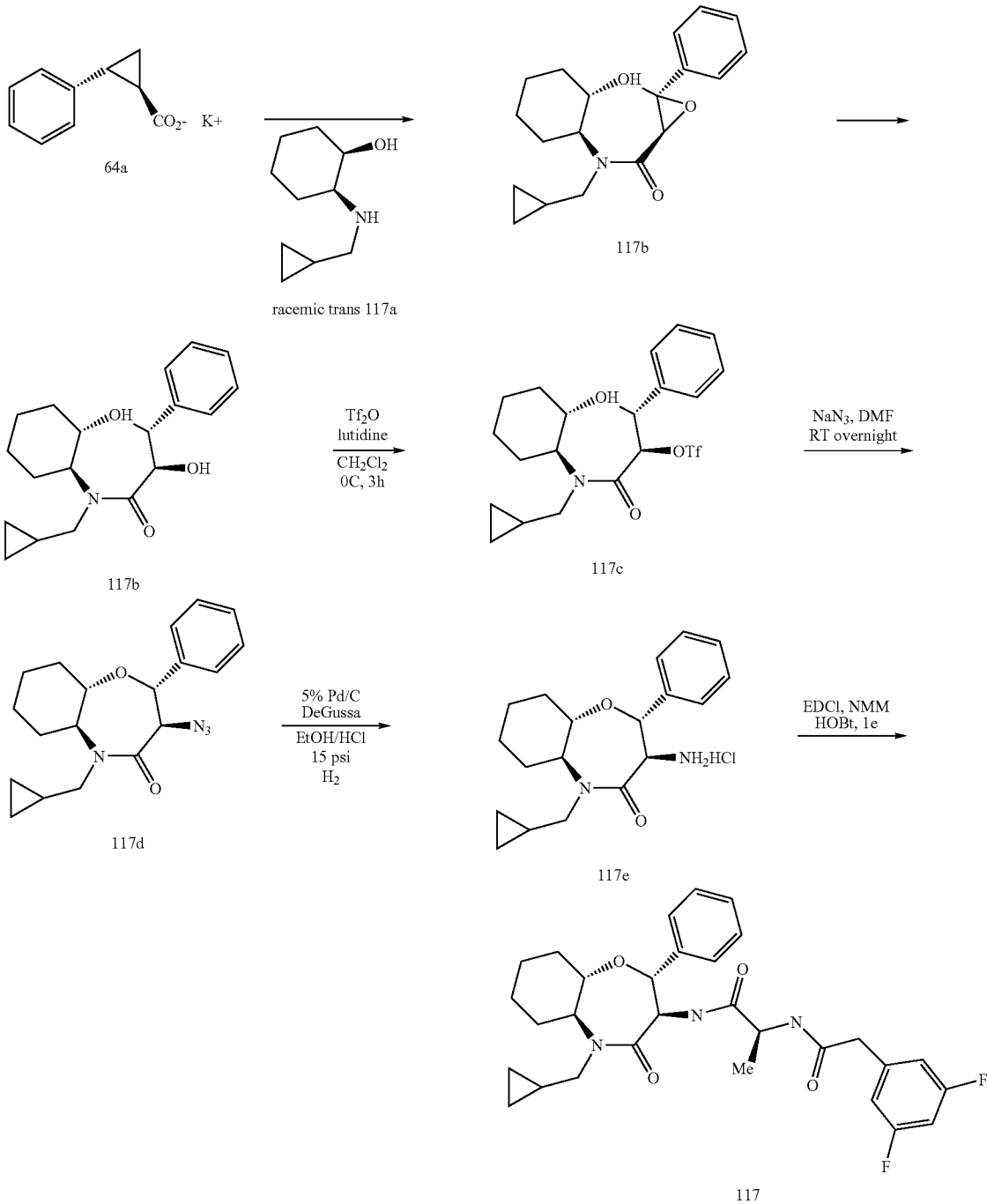

EXAMPLES

Chemical abbreviations used in the Examples are defined as follows: "BOC" denotes N-tert-butoxycarbonyl, "CBZ" denotes carbobenzyloxy; "DBU" denotes 1,8-diazabicyclo[5.4.0]undec-7-ene; "DIEA" denotes N,N-diisopropylethylamine, "DMF" denotes N,N-dimethylformamide; "EDAC-HCl" denotes 1-Ethyl-3-(dimethylaminopropyl) carbodiimide hydrochloride; "HOBt" denotes hydroxybenzotriazole; "NMM" denotes N-methylmorpholine; "p-TSA" denotes p-toluenesulfonic acid "TBAB" denotes tetrabutylammonium bromide; "THF" denotes tetrahydrofuran, "ether" denotes ethyl ether, Tos-Cl denotes p-toluenesulfonyl chloride, "min." denotes minutes; "h" denotes hours; "RT" denotes room temperature. Unless otherwise noted, organic solutions were "dried" over anhydrous sodium sulfate.

HPLC Method A: Phenomenex Luna 3 μ C18(2), 4.6×75 mm column. Solvents: A=$H_2O$ with 0.1% TFA, B=Acetonitrile with 0.1% TFA. Flow rate 2.0 mL/min. 20% B until 0.5 min then a linear gradient to 95% B at 3 min. Maintain at 95% B until 6 min HPLC Method B: Phenomenex Luna 3 μ C18(2), 4.6×75 mm column. Solvents: A=H2O with 0.1% TFA, B=Acetonitrile with 0.1% TFA. Flow rate 2.0 mL/min. Linear gradient from 10% to 95% B at 5 min. Maintain at 95% B until 7 min.

HPLC Method C: 5μ SB-C8 column 2.1 mm×5 cm. Solvents: A=$H_2O$ with 0.05% TFA, B=10% $H_2O$, 90% Acetonitrile, 0.05% TFA. Flow rate 1.4 mL/min. Gradient: (5-90% B over 5 min., 90% B hold for 2 min.).

HPLC Method D: Agilent Zorbax 5μ SB-C8 column 2.1 mm×5 cm. Solvents: A=H2O with 0.1% TFA, B=Acetonitrile with 0.1% TFA. Flow rate 1.4 mL/min. Linear gradient from 9% to 81% B at 3 min. then linear gradient to 95% B at 4 min. Maintain 95% B until 4.5 min.

HPLC Method E: Agilent Zorbax 5μ SB-C8 column 2.1 mm×5 cm. Solvents: A=H2O with 0.05% TFA, B=90% Acetonitrile, 10% water, 0.05% TFA. Flow rate 1.4 mL/min. Linear gradient from 15% to 90% B in 12 min.

LC/MS:HPLC method: Agilent Zorbax 5μ SB-C8 column 2.1 mm×5 cm. Solvents: A=$H_2O$ with 0.05% TFA, B=10% $H_2O$, 90% Acetonitrile, 0.05% TFA. Gradient: 10 to 90% B over 3 min., 90% B hold thru 4 min., 10% B at 5 min. and hold at 10% B until 6 min).

Example 1

$N^2$-[(3,5-Difluorophenyl)acetyl]-$N^1$-[(2R,3R)-2-(2,5-difluorophenyl)-4-oxo-2,3,4,5-tetrahydro-1,5-benzothiazepin-3-yl]-L-alaninamide (1)

To a solution of racemic 2,3-cis-3-amino-2-(2,5-difluorophenyl)-2,3-dihydro-1,5-benzothiazepin-4(5H)-one (1d) (300 mg) in dichloromethane (40 mL) at 0° C. under nitrogen was added N-[(3,5-difluorophenyl)acetyl]-L-alanine (1e) (238 mg), HOBt-hydrate (330 mg), EDAC-HCl (282 mg) and NMM (165 mg). The reaction mixture was stirred 1 h at 0° C., concentrated in vacuo and partitioned between water (100 mL) and ethyl acetate (125 mL). The organic phase was collected and consecutively washed with water, saturated aqueous sodium bicarbonate, and brine, dried, filtered and evaporated to yield a mixture of the title compound and $N^2$-[(3,5-difluorophenyl)acetyl]-$N^1$-[(2S,3S)-2-(2,5-difluorophenyl)-4-oxo-2,3,4,5-tetrahydro-1,5-benzothiazepin-3-yl]-L-alaninamide. The crude product (500 mg) was purified by flash chromatography (50% ethyl acetate/hexanes) to afford the title compound (180 mg, 69%) as an off-white solid. $^1$H NMR (300 MHz, CDCl$_3$) δ1.22 (d, 3H), 3.48 (s, 2H), 4.29 (m, 1H), 4.93 (t, 1H), 5.68 (d, 1H), 6.01 (d, 1H), 6.50 (d, 1H), 6.73-6.80 (m, 3H), 6.93-7.02 (m, 2H), 7.15 (d, 1H), 7.30 (t, 1H), 7.43 (t, 1H),7.5-7.6 (m, 1H), 7.73 (d, 1H), 7.74 (s, 1H). MS APCI, m/z=532 (M+1). LC/MS: 2.53 min.

The starting amine, racemic 2,3-cis-3-amino-2-(2,5-difluorophenyl)-2,3-dihydro-1,5-benzothiazepin-4(5H)-one (1d), was prepared in the following manner:

a. Methyl (2Z)-2-{[(benzyloxy)carbonyl]amino}-3-(2,5-difluorophenyl)prop-2-enoate (1a)

A stirred solution of N-(benzyloxycarbonyl)-α-phosphonoglycine trimethyl ester (6.1 g) and 2,5-difluorobenzaldehyde (2.0 g) in dry dichloromethane (60 mL), was treated dropwise with a solution of DBU (2.5 mL) in dichloromethane (20 mL). The mixture was stirred at room temperature for 2 h, then was concentrated to approximately 20 mL and partitioned between ethyl acetate (150 mL) and 1N hydrochloric acid (50 mL). The organic extract was collected, consecutively washed with 1N hydrochloric acid, water, saturated aqueous sodium bicarbonate, and brine, dried (sodium sulfate), filtered and evaporated. The crude product (6.5 g) was purified by flash chromatography (20% ethyl acetate/hexanes) to yield the title compound (4.0 g, 82%). $^1$H NMR (300 MHz, CDCl$_3$) δ 3.85 (s, 3H), 5.10, (s, 2H), 6.60 (bs, 1H), 6.9-7.1 (m, 2H), 7.21 (m, 1H), 7.2-7.3 (m, 6H). MS APCI, m/z=348 (M+1). LC/MS: 2.53 min.

b. Methyl β-[(2-aminophenyl)thio]-N-[(benzyloxy)carbonyl]-2,5-difluorophenylalaninate (1b)

Method A

To an ice-cooled solution of sodium methoxide (760 mg) in anhydrous methanol (20 mL) under nitrogen (vacuum degassed 3× with nitrogen) was added 2-aminothiophenol (1.7 g). The reaction mixture stirred at 0° C. for 10 min and then a solution of methyl (2Z)-2-{[(benzyloxy)carbonyl]amino}-3-(2,5-difluorophenyl)prop-2-enoate (2.32 g) in methanol (10 mL) was added. The reaction mixture was heated to reflux for 2 h and then was cooled to room temperature and stirred overnight. The reaction mixture was concentrated to ca. 10 mL, then was partitioned between cold 1N hydrochloric acid (75 mL) and ethyl acetate (125 mL). The organic phase was separated and consecutively washed with 1N hydrochloric acid (4×), dilute aqueous sodium bicarbonate and brine, dried, filtered and evaporated. The title compound was isolated as the hydrochloride salt. (3.0 g, 88%, 2:1 Z:E). $^1$H NMR (300 MHz, d6-DMSO) δ3.4 (s, 2H),3.7 (s, 1H), 4.6-5.1 (m, 7H), 6.3 (t, 0.67H), 6.4 (t, 0.33H), 6.7-7.4 (m, 10H), 8.1 (d, 0.33H), 8.4 (d, 0.67H). MS APCI, m/z=473(M+1). LC/MS: 2.78 min.

Method B

To an ice-cooled solution of 2-aminothiophenol (8.7 g) in anhydrous methanol under nitrogen (vacuum degassed 3× with nitrogen) was added methyl (2Z)-2-{[(benzyloxy)carbonyl]amino}-3-(2,5-difluorophenyl)prop-2-enoate (3.46 g) followed by triethylamine (975 uL). The reaction mixture was stirred at room temperature for 4 days, then was reduced in vacuo to near dryness. The mixture was partitioned between cold 1N hydrochloric acid (75 mL) and ethyl acetate (125 mL). The organic phase was separated and consecutively washed with 1N hydrochloric acid (4×), dilute aqueous sodium bicarbonate and brine, dried, filtered and evaporated to yield 5.8 g of an oil. Purification by flash chromatography (25% ethyl acetate/hexanes) afforded the title compound (4.3 g, 65%) Z:E ratio of 82:18. $^1$HNMR (300 MHz, CDCl$_3$) δ3.48 (s, 2.4H), 3.71 (s, 0.6H), 4.28 (s, 1.6H), 4.72 (s, 0.4H), 4.8-5.1 (m, 4H), 5.43 (d, 0.2H), 5.86 (d, 0.8H), 6.58 (t, 0.8H), 6.68 (d, 0.8H), 6.9-7.4 (m, 8H). MS APCI, m/z=473 (M+1). LC/MS: 2.78 min.

c. Benzyl cis-2-(2,5-difluorophenyl)-4-oxo-2,3,4,5-tetrahydro-1,5-benzothiazepin-3-ylcarbamate (1c)

A suspension of methyl β-[(2-aminophenyl)thio]-N-[(benzyloxy)carbonyl]-2,5-difluorophenylalaninate (4:1, Z:E) (4.3 g) and p-toluenesulfonic acid (catalytic) in xylenes (100 mL) was heated to reflux for 2 h, using a Dean-Stark apparatus to remove water. The mixture was then cooled, resulting in precipitation of the crude product as a white solid (3.3 g, 4:1, cis:trans). This was recrystallized from ethyl acetate/ether to afford the title compound (2.4 g, 60%). $^1$H NMR (300 MHz, d6-DMSO) δ 4.63 (t, 1H), 4.96 (s, 2H), 5.47 (d, 1H), 7.00 (d, 1H), 7.23-7.34 (m, 9H), 7.49-7.53 (m, 2H), 7.70 (d, 1H), 10.57(s, 1H). MS APCI, m/z=441 (M+1). LC/MS: 2.74 min.

d. cis-3-Amino-2-(2,5-difluorophenyl)-2,3-dihydro-1,5-benzothiazepin-4(5H)-one (1d)

Method C

A mixture of benzyl cis-2-(2,5-difluorophenyl)-4-oxo-2,3,4,5-tetrahydro-1,5-benzothiazepin-3-ylcarbamate (1.7 g) and 10% palladium on carbon (1.7 g, DeGussa type 50% wt water) in glacial acetic acid (80 mL) was hydrogenated at 50 psi $H_2$ for 3 h. The reaction mixture was filtered through diatomaceous earth and concentrated in vacuo. The crude oil was triturated with ether to yield a white solid (1.3 g). The solid was partitioned between ethyl acetate and dilute ammonium hydroxide. The organic phase was separated and consecutively washed with dilute ammonium hydroxide and brine, dried and evaporated. The residue was treated with saturated HCl(g) in ethyl aceate/ether to provide the hydrochloride salt of the title compound as a white solid (1.1 g, 90%). $^1$H NMR (300 MHz, d6-DMSO) δ 4.33 (d, 1H, J=7 Hz), 5.60 (d, 1H, J=7 Hz), 7.13-7.38 (m, 4H), 7.48-7.60 (m, 2H), 7.72, (d, 1H), 8.4 (bs, 3H), 11.0 (s, 1H). MS APCI, m/z=307 (M+1). LC/MS: 1.65min.

Method D

To benzyl cis-2-(2,5-difluorophenyl)-4-oxo-2,3,4,5-tetrahydro-1,5-benzothiazepin-3-ylcarbamate (0.9 g) was added 30% HBr/HOAc (5 mL). The stirred suspension became a homogeneous solution over 20 min. The reaction stirred at room temperature for an additional 50 min, then was diluted with ether to afford the hydrobromide salt of the title compound (0.75 g, 95%). The solid was partitioned between ethyl acetate and saturated aqueous sodium bicarbonate. The organic phase was separatated and consecutively washed with dilute aqueous sodium bicarbonate and brine, dried, filtered and evaporated. The resulting oil was treated with saturated HCl(g) in ethyl aceate/ether to provide the hydrochloride salt of the title compound as a white solid (0.60 g, 85%). This material was indistinguishable from that obtained by Method C.

e. N-[(3,5-Difluorophenyl)acetyl]-L-alanine (1e)

To a stirred solution of 3,5-difluorophenylacetic acid (6.02 g, 34.97 mmol), L-alanine methyl ester hydrochloride (4.88 g, 34.96 mmol) and HOBt (5.20 g, 38.48 mmol) in dichloromethane (200 mL) under nitrogen at 0° C. was added NMM (8.84 g, 87.39 mmol) and EDAC-HCl (7.38 g, 38.49 mmol). The mixture was allowed to warm gradually to ambient temperature and stir overnight. The reaction was diluted with ethyl acetate and extracted sequentially with aqueous sodium bicarbonate, 1N aqueous HCl and brine. The organic phase was dried, filtered and evaporated. The residue was purified by flash chromatography on silica gel eluting with 1:1 (v/v) hexanes: ethyl acetate to afford N-[(3,5-difluorophenyl)acetyl]-L-alanine methyl ester (7.91 g, 88% yield) as a white solid. $^1$H NMR (300 MHz, CDCl$_3$) δ 1.39 (d, 3H, J=7.0 Hz), 3.54 (s, 2H), 3.75 (s, 3H), 4.59 (m, 1H), 6.02 (br 1H), 6.67-6.87 (m, 3H). MS APCI, m/z=258 (M+1). LC/MS: 1.68 Lithium hydroxide (1.40 g, 33.33 mmol) in water (60 mL) was added dropwise to a solution of N-[(3,5-difluorophenyl)acetyl]-L-alanine methyl ester (7.79 g, 30.28 mmol) in 1,4-dioxane (150 mL). After 2 h the solvent was evaporated. The residue was dissolved in water and the solution extracted with diethyl ether. The aqueous phase was acidified with 1N aqueous HCl and extracted with ethyl acetate three times. The combined ethyl acetate extracts were dried, filtered and evaporated to afford the title compound (7.16 g, 97% yield) as a white solid. $^1$H NMR (300 MHz, d6-DMSO) δ 1.28 (d, 3H, J=7.4 Hz), 3.51 (s, 2H), 4.20 (m, 1H), 6.93-7.12 (m, 3H), 8.44 (d, 1H, J=7.0 Hz), 12.46 (br, 1H). HPLC Method A: 2.12 min.

Example 2

N$^1$-[(2,3-cis)-5-Cyclohexyl-2-(2.5-difluorophenyl)-4-oxo-2,3,4,5-tetrahydro-1,5-benzothiazepin-3-yl]-N$^2$-[(3,5-difluorophenyl)acetyl]-L-alaninamide (2)

Using a procedure similar to that described in Example 1, except using (2,3-cis)-3-amino-5-cyclohexyl-2-(2,5-difluorophenyl)-2,3-dihydro-1,5-benzothiazepin-4(5H)-one (2b) (85 mg) as the amine component, the title compound (2) was obtained as a white solid (20 mg, 30%). $^1$H NMR (300 MHz, CDCl$_3$) δ 1.0-2.1 (m, 13H), 3.47 (s, 2H), 4.20 (m, 1H), 4.45 (m, 1H), 4.64 (t, 1H), 5.44 (d, 1H), 5.95 (d, 1H), 6.40 (d, 1H), 6.73-6.80 (m, 3H), 6.85-6.95 (m, 2H), 7.35-7.49 (m, 4H), 7.75 (d, 1H). MS APCI, m/z =614(M+1). LC/MS: 3.44 min.

The amine component, (2,3-cis)-3-amino-5-cyclohexyl-2-(2,5-difluorophenyl)-2,3-dihydro-1,5-benzothiazepin-4(5H)-one (2b) was prepared in the following manner:

a. Benzyl (2,3-cis)-5-(2-cyclohexen-1-yl)-2-(2,5-difluorophenyl)-4-oxo-2,3,4,5-tetrahydro-1,5-benzothiazepin-3-ylcarbamate (2a)

To a solution of benzyl cis-2-(2,5-difluorophenyl)-4-oxo-2,3,4,5-tetrahydro-1,5-benzothiazepin-3-ylcarbamate (1c) (150 mg,) in THF (10 mL) under nitrogen was added powdered potassium hydroxide (25 mg), tetrabutylammonium bromide (11 mg) and 1-bromo-2-cyclohexene (40 μl). The reaction mixture was stirred at RT overnight, then was partitioned between water and ethyl acetate. The organic phase was separated and consecutively washed with water and brine, dried, filtered and evaporated to yield the title compound 2a (175 mg, 98%). This material was used without further purification. $^1$H NMR (300 MHz, CDCl$_3$) δ1.5-2.3 (m, 6H), 4.6 (t, 1H), 5.0 (d, 2H), 5.2-5.5 (m, 3H), 5.7 (m, 1H), 5.9 (m, 1H), 6.9 (m, 2H), 7.2-7.3 (m, 6H), 7.4 (m, 3H), 7.73 (d, 1H). MS APCI, m/z=521 (M+1). LC/MS: 3.63 min b. (2,3-cis)-3-Amino-5-cyclohexyl-2-(2,5difluorophenyl)-2,3-dihydro-1,5-benzothiazepin-4(5H)-one (2b)

Using a method similar to that described in Example 1, part d (Method C), benzyl (2,3-cis)-5-(2-cyclohexen-1-yl)-2-(2,5-difluorophenyl)-4-oxo-2,3,4,5-tetrahydro-1,5-benzothiazepin-3-ylcarbamate 2a (90 mg) was converted to crude 2b. The crude product purified by flash chromatography (2% Methanol, 1% NH$_4$OH/CHCl$_3$) to yield 2b (45 mg, 67%), converted to HCl salt (EtOH/ether/HCl). $^1$H NMR (300 MHz, d6-DMSO) δ1.0-2.1 (m, 10H), 4.11 (d, 1H), 4.35 (m, 1H), 5.38 (d, 1H), 7.35 (t, 2H), 7.4-7.5 (m, 2H), 7.6-7.7 (m, 2H), 7.81, (d, 1H), 8.29 (bs, 3H). MS APCI, m/z=389 (M+1). LC/MS: 2.57 min.

Example 3

N²-[(3,5-Difluorophenyl)acetyl]-N¹-{(2R,3R)-2-(2,5-difluorophenyl)-5-[2-(dimethylamino)ethyl]-4-oxo-2,3,4,5-tetrahydro-1,5-benzothiazepin-3-yl}-L-alaninamide (3)

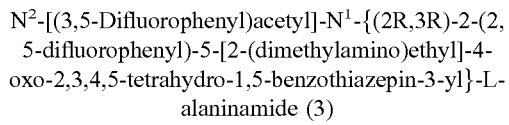

Using a procedure similar to that described in Example 1, except using racemic (2,3-cis)-3-amino-2-(2,5-difluorophenyl)-5-(2-dimethylamino)ethyl)-2,3-dihydro-1,5-benzothiazepin-4(5H)-one (3b) (100 mg) as the amine component, the title compound (3) was obtained as a white solid (37 mg, 46%). ¹H NMR (300 MHz, d6-DMSO) δ1.2 (3H), 2.3 (s, 6H), 2.35 (m, 1H), 2.6, (m, 1H), 3.48 (s, 2H), ), 3.55 (m, 1H), ), 4.22 (m, 1H), ), 4.65 (m, 1H), 4.77 (t, 1H), ), 5.35 (d, 1H), 5.95 (d, 1H), 6.36 (d, 1), 6.7-7.0 (m, 5H), 7.27-7.35 (t, 1H), 7.38 (d, 1H), 7.48, (t, 1H), 7.71 (d, 1H), 7.9 (m, 1H),. MS APCI, m/z =603 (M+1). LC/MS: 2.13 min.

The amine component, (2,3-cis)-3-amino-5-(2-dimethylamino)ethyl-2-(2,5-difluorophenyl)-2,3-dihydro-1,5-benzothiazepin-4(5H)-one (3b) was prepared in the following manner:

a. Benzyl (2,3-cis)-5-(2-dimethylaminoethyl)-2-(2,5-difluorophenyl)-4-oxo-2,3,4,5-tetrahydro-1,5-benzothiazepin-3-ylcarbamate (3a)

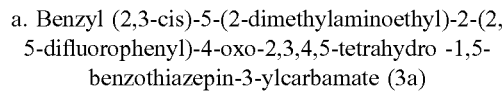

To a solution of benzyl cis-2-(2,5-difluorophenyl)-4-oxo-2,3,4,5-tetrahydro-1,5-benzothiazepin-3-ylcarbamate 1c (530 mg), prepared as described in Example 1, part c, in methyl isobutyl ketone (14 mL) was added 10N NaOH (0.6 mL) followed by water (2.3 mL) and N,N-dimethylaminoethylchloride hydrochloride (260 mg). The reaction mixture was heated to 95° C. for 4 H. (HPLC indicated 3:1 3a:1c), allowed to cool to RT and diluted with ethyl acetate. The organic phase was collected and consecutively washed with water (3×), brine, dried, filtered and the solvent removed in vacuo to yield crude oil. The crude oil was purified by flash chromatography (5% Methanol/CHCl₃) to afford pure title compound (400 mg, 60%). ¹H NMR (300 MHz, d6-DMSO) δ2.2 (d, 6H), 2.3 (m, 1H), 2.4 (m, 1H), 3.27 (m, 1H), 3.6 (d of t, 1H), 4.4 (t, 1H), 4.5 (t, 1H), 4.9 (s, 2H), 5.3 (d, 2H), 6.8 (d, 1H), 7.2-7.3 (m, 6H), 7.4 (t, 1H), 7.6-7.7 (m, 2H), 7.76, (d, 1), 7.86(m, 1H). MS APCI, m/z=512 (M+1). LC/MS: 2.23 min.

b. (2,3-cis)-3-Amino-5-(2-dimethylaminoethyl)-2-(2,5-difluorophenyl)-2,3-dihydro-1,5-benzothiazepin-4(5R)-one (3b)

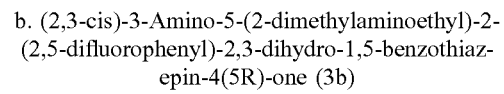

Using a method similar to that described in Example 1, part d (Method C), benzyl (2,3-cis)-5-(2-dimethylamino)ethyl)-2-(2,5-difluorophenyl)-4-oxo-2,3,4,5-tetrahydro-1,5-benzothiazepin-3-ylcarbamate, 3a (90 mg) was converted overnight to crude 3b. The crude product was purified by flash chromatography (5% Methanol, 1% NH₄OH/CHCl₃) to afford pure title compound (125 mg, 57%). ¹H NMR (300 MHz, d6-DMSO) δ2.29 (s, 6H), 2.39, (m, 1H), 2.64, (m, 1H), 3.62 (m, 1H), 3.79 (d, 1H), 4.56 (dt, 1H), 5.27 (d, 2H), 6.95-7.05 (m, 2H), 7.28 (m, 1H), 7.40 (d, 1H), 7.72, (d, 1H), 7.78 (m, 1H). MS APCI, m/z=378 (M+1). LC/MS: 1.23 min.

Example 4

(2S)-2-{[(3,5-Difluorophenyl)acetyl]amino}-N-[(2R,3R)-2-(2,5-difluorophenyl)-4-oxo-2,3,4,5-tetrahydro-1,5-benzothiazepin-3-yl]-3-hydroxypropanamide (4)

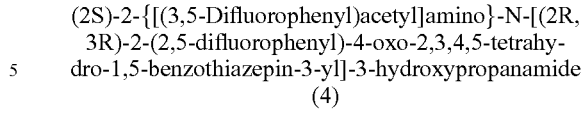

To a solution N-[(3,5-difluorophenyl)acetyl]-L-serine (4b) (75 mg) in dichloromethane (15 mL) at 0° C. under N₂, was added racemic 2,3-cis-3-amino-2-(2,5-difluorophenyl)-2,3-dihydro-1,5-benzothiazepin-4(5H)-one-HCl (1d) (100 mg) followed by the HOBt-hydrate (97 mg) and NMM (32 μL). Reaction stirred for 5 min. and then added EDAC-HCl (84 mg) and NMM (50 μL). The reaction mixture was stirred 2 H at 0° C. under N₂, concentrated in vacuo and partitioned between water (100 mL) and ethyl acetate (125 mL). The organic phase was collected and consecutively washed with water, saturated aqueous sodium bicarbonate, brine, dried, filtered and evaporated to yield a mixture of the title compound and (2S)-2-{[(3,5-difluorophenyl)acetyl]amino}-N-[(2S,3S)-2-(2,5-difluorophenyl)-4-oxo-2,3,4,5-tetrahydro-1,5-benzothiazepin-3-yl]-3-hydroxypropanamide. The crude product (165 mg) was purified by flash chromatography (80% ethyl acetate/hexanes) to afford the title compound (60 mg, 73%) as a white solid. ¹H NMR (300 MHz, d6-DMSO) δ(d, 3H), 3.48 (s, 2H), 4.21 (q, 1H), 4.74, (t, 1H), 4.85 (bs, 1H), 5.50 (d, 1H), 6.93 (d, 2H), 7.09 (m, 1H), 7.18-7.35 (m, 4H), 7.45-7.55 (m, 2H), 7.71 (t, 2H), 8.17(d, 1H), 10.68 (s, 1H). MS APCI, m/z=548 (M+1). LC/MS: 2.34 min.

The starting acid, N-[(3,5-difluorophenyl)acetyl]-L-serine (4b), was prepared in the following manner:

a. N-[(3,5-Difluorophenyl)acetyl]-L-serine methyl ester (4a)

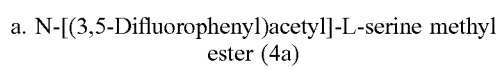

To an ice cooled solution of 3,5-difluorophenylacetic acid (2.16 g) in anhydrous dichloromethane (100 mL) under nitrogen was added HOBt-hydrate (4.23 g), EDAC-HCl (3.6 g), and NMM (2.2 mL). The reaction mixture was stirred at 0° C. under nitrogen for 15 min and L-serine methyl ester-HCl (1.96 g) was added followed by NMM (1.38 mL). The reaction was stirred at 0° C. for 1 H and RT for 2 H. The reaction mixture was concentrated in vacuo and partitioned between water (100 mL) and ethyl acetate (125 mL). The organic phase was collected and consecutively washed with water, dilute aqueous sodium bicarbonate, brine, dried, filtered and the solvent removed in vacuo to yield a white solid. Trituration with CHCl₃ afforded pure title compound (1.8 g). The impure filtrate was subjected to flash chromatography (20% acetone/CHCl₃) to afford additional title compound (800 mg, total yield 76%). ¹H NMR (300 MHz, d6-DMSO) δ3.57 (d, 2H), 3.62(s, 3H), 3.7 (m, 1H), 4.35, (m, 1H), 5.1 (bs, 1H), 7.00 (d, 2H), 7.09 (t, 1H), 8.53, (d, 1H). MS APCI, m/z=274 (M+1). LC/MS: 1.34 min.

b. N-[(3,5-Difluorophenyl)acetyl]-L-serine (4b)

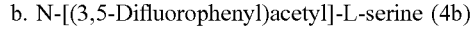

To a stirred solution of N-[(3,5-difluorophenyl)acetyl]-L-serine methyl ester (4a) in THF (13 mL) was added 1M aqueous lithium hydroxide (13.2 mL) and the mixture stirred at RT for 40 H. Brine (50 mL) was added, the aqueous layer made acidic to pH 1 with 1N hydrochloric acid (~15 mL), and the aqueous layer extracted with 10% Methanol/CHCl₃ (2×). The organic phase was collected, dried, filtered and the solvent removed in vacuo to afford the title compound (112 mg, 54%). This material was used without further purification. ¹H NMR (300 MHz, d6-DMSO) δ3.57 (d, 2H), 3.7 (m, 1H), 4.27, (m, 1H), 5.03 (bs, 1H), 7.00 (d, 2H), 7.09 (t, 1H), 8.38, (d, 1H). 12.6, (bs, 1H). MS APCI, m/z=274 (M+1). LC/MS: 1.0 min.

Example 5

N²-[(3,5-Difluorophenyl)acetyl]-N¹-[(2R,3R)-2-(2, 5difluorophenyl)-5-methyl-4-oxo-2,3,4,5-tetrahydro-1,5-benzothiazepin-3-yl]-L-alaninamide (5)

Using a procedure similar to that described in Example 1, except using racemic (2,3-cis)-3-amino-5-methyl-2-(2,5-difluorophenyl)-2,3-dihydro-1,5-benzothiazepin-4(5H)-one (5b) (170 mg) as the amine component, the title compound (5) was obtained as a white solid (85 mg, 59%) $^1$H NMR (300 MHz, CDCl$_3$) δ1.19 (d, 3H), 3.48 (s, 2H),3.50 (s, 3H), 4.22 (m, 1H), 4.83, (t, 1H), 5.56 (d, 1H), 5.92 (d, 1H), 6.37 (d, 1H), 6.80-6.90(m, 3H), 6.90-7.00(m, 2H), 7.32 (d, 1H), 7.40-7.50 (m, 2H), 7.72 (d, 1H). MS APCI, m/z=546 (M+). LC/MS: 2.67 min.

The amine component (2,3-cis)-3-amino-5-methyl-2-(2, 5-difluorophenyl)-2,3-dihydro-1,5-benzothiazepin-4(5H)-one (5b) was prepared in the following manner:

a. Benzyl (2,3-cis)-5-(methyl)-2-(2,5-difluorophenyl)-4-oxo-2,3,4,5-tetrahydro-1,5-benzothiazepin-3-ylcarbamate (5a)

To a round bottom flask charged with powdered KOH (182 mg) under nitrogen was added a solution of benzyl cis-2-(2,5-difluorophenyl)-4-oxo-2,3,4,5-tetrahydro-1,5-benzothiazepin-3-ylcarbamate (1c) (1.1 g) prepared as described in Example 1, part c, in THF (15 mL). To the suspension was added tetrabutylammonium bromide (80 mg) followed by addition of methyl iodide (156 μl) via syringe. The mixture stirred at RT over the weekend. The reaction mixture was partitioned between water and ethyl acetate. The organic phase was collected and consecutively washed with water and brine, dried, filtered and the solvent removed in vacuo to afford the crude product (1.15 g). Recrystallization from ethyl acetate (10 mL) yielded pure title compound 5a (660 mg, 58%). $^1$H NMR (300 Mdz, d6-DMSO) δ3.42 (s, 3H), 4.60 (t, 1H), 4.93 (s, 2H), 5.34 (d, 1H), 7.01 (d, 1H), 7.22-7.34 (m, 7H), 7.42 (q, 2H), 7.62 (s, 1H), 7.63 (d, 1H), 7.76 (d, 1H). MS APCI, m/z=455 (M+1). LC/MS: 2.93 min.

b. (2,3-cis)-3-Amino-5-methyl-2-(2,5-difluorophenyl)-2,3-dihydro-1,5-benzothiazepin-4(5H)-one (5b)

Using a method similar to that described in Example 1, part d (Method D), benzyl (2,3-cis)-5-(methyl)-2-(2,5-difluorophenyl)-4-oxo-2,3,4,5-tetrahydro-1,5-benzothiazepin-3-ylcarbamate 5a (600 mg) was converted to nearly pure 5b (350 mg, 83%). Recrystallization (ether/hexanes) afforded the pure title compound (162 mg). $^1$H NMR (300 MHz, d6DMSO) δ1.6-2.5 (bs, 2H), 3.41 (s, 3H), 3.50 (s, 3H), 3.76 (d, 1H), 5.17 (d, 1H), 7.25-7.38 (m, 4H), 7.58 (s, 1H), 7.59 (d, 1H), 7.72 (d, 1H). MS APCI, m/z=321 (M+1). LC/MS: 1.76min.

Example 6

N²-[(3,5-Difluorophenylacetyl]-N¹-[(2R,3S)-4-oxo-2-phenyl-2,3,4,5-tetrahydro-1,5-benzoxazepin-3-yl]-L-alaninamide (6)

To a stirred solution of N¹-[(2R,3S)-4-oxo-2-phenyl-2,3, 4,5-tetrahydro-1,5-benzoxazepin-3-yl]-L-alaninamide (6 g) (765 mg, 2.351 mmol) in dichloromethane (10 mL) was added 3,5-difluorophenylacetic acid (450 mg, 2.614 mmol), HOBt (441 mg, 3.265 mmol), NMM (330 mg, 3.267 mmol) and EDAC-HCl (626 mg, 3.265 mmol). The mixture was stirred at ambient temperature under nitrogen overnight. The solvent was evaporated and the residue partitioned between ethyl acetate and saturated aqueous sodium bicarbonate. The organic phase was separated and then washed in succession with 1N aqueous HCl and brine. The organic solution was dried, filtered and evaporated. The residue was purified by flash chromatography on silica gel eluting with 2:1 (v/v) ethyl acetate:hexanes to afford the title compound (968 mg, 86%) as a white solid. TLC R$_f$=0.30 (2:1 ethyl acetate: hexanes). $^1$H NMR (300 MHz, DMSO-d6) δ1.11 (d, 3H, J=7.0 Hz), 3.46 (q AB, 2H, J=14.4 Hz), 4.24 (m, 1H), 4.95 (m, 1H), 5.61 (d, 1H, J=6.6 Hz), 6.94 (m, 2H), 7.02-7.29 (m,5H), 7.32-7.40, (m, 6H), 8.32 (m, 1H), 10.29 (br, 1H). MS APCI, m/z=480 (M+1). LC/MS: 2.31min.

The precursor N¹-[(2R,3S)-4-oxo-2-phenyl-2,3,4,5-tetrahydro-1,5-benzoxazepin-3-yl]-L-alaninamide (6 g) was prepared as follows:

a. erythro Ethyl 2-hydroxy-3-(2-nitrophenoxy)-3-phenylpropanoate (6a)

The title compound was prepared according to the published procedure of Carlo Banzatti, Franco Heidempergher, and Piero Melloni; J. Heterocyclic Chem. 20, 259 (1983).

b. erythro Ethyl 3-(2-aminophenoxy)-2-hydroxy-3-phenylpropanoate (6b)

To a solution of erythro ethyl 2-hydroxy-3-(2-nitrophenoxy)-3-phenylpropanoate (6a) (3.956 g, 11.940 mmol) in ethanol (150 mL) was added 5% palladium on carbon (500 mg) and the mixture was hydrogenated at 35 psi on a Parr shaker for 30 min. The reaction mixture was filtered through diatomaceous earth and the resulting solution concentrated in-vacuo. The residue was purified by flash chromatography on silica gel eluting with ethyl acetate to afford the title compound (3.585 g, 99%) as a red oil. $^1$H NMR (300 MHz, CDCl$_3$) δ1.18 (t, 3H), 3.34 (m, 1H), 3.99 (br, 2H), 4.17 (m, 2H), 4.60 (m, 1H), 5.42 (d, 1H, J=3 Hz), 6.51-6.65 (m, 2H), 6.69-6.82 (m, 2H), 7.20-7.40 (m, 5H). MS APCI, m/z=324 (M+Na). LC/MS: 1.70min.

c. (2,3-trans)-3-Hydroxy-2-phenyl-2,3-dihydro-1,5-benzoxazepin-4(5H)-one (6c)

To a stirred solution of erythro ethyl 3-(2-aminophenoxy)-2-hydroxy-3-phenylpropanoate (6b) (3.585 g, 11.896 mmol) in THF (100 mL) cooled to 0° C. was added a solution of lithium hydroxide monohydrate (600 mg, 14.299 mmol) in water (25 mL) and methanol (2 mL). After 15 min the cooling bath was removed and the mixture stirred an additional 45 min warming to ambient temperature. The reaction was re-cooled to 0° C. and 1N aqueous hydrochloric acid (14.3 mL) was added. Solvent was then removed in-vacuo. The residue was dissolved in DMF (25 mL), HOBt (1.94 g, 14.40 mmol), NMM (3.34 g, 33.00 mmol), and EDAC (2.76 g, 14.40 mmol) were added and the mixture stirred overnight under nitrogen at ambient temperature. The reaction was diluted with water and extracted with ethyl acetate. The organic extracts were combined, dried, filtered and evaporated. The residue was purified by flash chromatography (2:1 (v/v) Hexane:ethyl acetate) to afford the title compound (1.05 g, 34%) as a white solid. $^1$H NMR (300 MHz, CDCl$_3$) δ3.70 (d, 1H, J=5 Hz), 4.63 (m, 1H), 5.28 (d, 1H, J=10 Hz), 6.89 (m, 1H), 7.02-7.16 (m, 3H), 7.35-7.47 (m 5H), 7.78 (br, 1H). MS APCI, m/z=256 (M+1). LC/MS: 1.84 min.

d. (2,3-cis)-3-Azido-2-phenyl-2,3-dihydro-1,5-benzoxazepin-4(5H)-one (6d)

Trifluoromethanesulfonyl chloride (770 mg, 4.57 mmol) was added via syringe to a stirred solution of (2,3-trans)-3-hydroxy-2-phenyl-2,3-dihydro-1,5-benzoxazepin-4(5H)-one (6c) (765 mg, 3.00 mmol) and triethylamine (508 mg, 5.00 mmol) in dichloromethane (20 mL) under nitrogen at 0° C. The mixture was kept at 0° C. overnight. Additional trifluoromethanesulfonyl chloride (770 mg, 4.57 mmol) and triethylamine (508 mg, 5.00 mmol) was added and the mixture kept at 0° C. for an additional 4 h. Additional trifluoromethanesulfonyl chloride (1540 mg, 9.14 mmol) and triethylamine (1016 mg, 10.00 mmol) was added and the mixture kept at 0° C. for an additional 3 h. The reaction was concentrated in vacuo without heating, and the resulting residue immediately dissolved in DMF (5 mL) at 0° C. under nitrogen. Sodium azide (650 mg, 10.00 mmol) was added to the solution and the mixture allowed to warm to ambient temperature over 30 min. After an additional 30 min. the reaction was diluted with water and extracted with ethyl acetate. The organic extracts were dried, filtered and evaporated. The residue was purified by flash chromatography on silica gel eluting with 3:1 (v/v) hexanes:ethyl acetate to afford the title compound (778 mg, 2.77 mmol, 92%) as a foamy white solid. TLC R$_f$=0.38 (3:1 hexanes:ethyl acetate). $^1$H NMR (300 MHz, CDCl$_3$) δ4.45 (d, 1H, J=6 Hz), 5.56 (d, 1H, J=6 Hz), 7.00-7.07 (m, 1H), 7.10-7.26 (m, 3H), 7.40-7.46 (m, 3H), 7.51-7.61 (m, 3H). MS APCI, m/z=253 (M+1−N$_2$). LC/MS: 2.25 min.

e. (2,3cis)-3-Amino-2-phenyl-2,3-dihydro-1,5-benzoxazepin-4(5H)-one hydrochloride (6e)

To a solution of (2,3-cis)-3-azido-2-phenyl-2,3-dihydro-1,5-benzoxazepin-4(5H)-one (6d) (610 mg, 2.176 mmol) in ethanol (40 mL) was added 5% palladium on carbon (65 mg) and 1N hydrochloric acid (2.4 mL). The mixture was stirred for 3 h under 1 atmosphere of hydrogen. The mixture was filtered through diatomaceous earth and the resulting solution was evaporated to afford the title compound (550 mg, 99%) as a tan solid $^1$H NMR (300 MHz, DMSO-d6) δ4.55 (d, 1H, J=7 Hz), 5.85 (d, 1H, J=7 Hz), 7.06-7.62 (m, 9H), 8.29 (br, 3H), 10.64 (s, 1H). MS APCI, m/z=255 (M+1). LC/MS: 1.29 min.

f. N$^2$-[tert-Butoxycarbonyl]-N$^1$-[(2,3-cis)-4-oxo-2-phenyl-2,3,4,5-tetrahydro-1,5-benzoxazepin-3-yl]-L-alaninamide (6f)

To a stirred solution of (2,3-cis)-3-amino-2-phenyl-2,3-dihydro-1,5-benzoxazepin-4(5H)-one hydrochloride (6e) (1.500 g, 5.90 mmol) in dry dichloromethane (50 mL) under nitrogen was added BOC-L-alanine (1.172 g, 6.190 mmol), HOBt (0.957 g, 7.083 mmol) and EDAC-HCl (1.357 g, 7.078 mmol). The mixture was stirred overnight at ambient temperature, then diluted with water and extracted with ethyl acetate three times. The combined organic extracts were washed in succession with saturated aqueous sodium bicarbonate, 1N aqueous HCl, and brine. The organic solution was dried, filtered and evaporated. The residue was purified by flash chromatography on silica gel eluting with diethyl ether to afford the title compound as a yellow solid (1.880 g, 75%). R$_f$=0.46 (Et$_2$O). $^1$H NMR (300 MHz, CDCl$_3$) δ1.14 (d, 1.5H, J=7.0 Hz), 1.21 (d, 1.5H, J=7.0 Hz), 1.38 (s, 4.5H), 1.41 (s, 4.5H), 2.86 (s, 1H), 2.92 (s, 1H), 4.05 (m, 1H), 4.63 (m, 0.5H), 4.75.(m, 0.5H), 5.17 (m, 1H), 5.79 (m,1H), 6.36 (m, 1H), 6.99-7.49 (m, 9H). MS APCI, m/z=448 (M+Na). LC/MS: 2.13 min.

g. N$^1$-[(2R,3S)-4Oxo-2-phenyl-2,3,4,5-tetrahydro-1,5-benzoxazepin-3-yl]-L-alaninamide (6 g)

N$^2$-[tert-butoxycarbonyl]-N$^1$-[(2,3-cis)-4-oxo-2-phenyl-2,3,4,5-tetrahydro-1,5-benzoxazepin-3-yl]-L-alaninamide (6f) (2.405 g, 5.652 mmol) was dissolved in 5:1 (v/v) dichloromethane:trifluoroacetic acid (50 mL) and kept at ambient temperature under nitrogen for 90 min. The solution was evaporated, the residue was dissolved in ethyl acetate and extracted with saturated aqueous sodium bicarbonate. The organic solution was dried and evaporated. The residue was purified by flash chromatography on silica gel (260 g) eluting with 100:5 (v/v) chloroform:methanol. The title compound (2R,3S diastereomer) eluted first (TLC R$_f$=0.28 in 100:5 chloroform:methanol) then the solvent was changed to 100:15 (v/v) chloroform:methanol to complete the elution of the 2S,3R diastereomer (TLC R$_f$=0.16 in 100:5 chloroform:methanol). Fractions containing the early eluting isomer were combined and evaporated to afford the title compound (765 mg, 2.351 mmol, 42%). $^1$H NMR (300 MHz, CDCl$_3$) δ1.20 (d, 3H, J=7.0 Hz), 1.38 (br, 2H), 3.36 (q, 1H, J=7.0 Hz), 5.20 (t, 1H, J=7.3 Hz), 5.79 (d, 1H, J=7.0 Hz), 7.06 (m, 1H), 7.15-7.31 (m, 3H), 7.34-7.56 (m, 7H). MS APCI, m/z=326 (M+1). LC/MS: 1.46 min.

Example 7

N$^2$-[(3,5-Difluorophenyl)acetyl]-N$^1$-[(6R,7R)-5-oxo-7-phenyl-1,4-thiazepan-6-yl]-L-alaninamide (7)

Using a procedure similar to that described in Example 1, except using (6,7-cis)-6-amino-7-phenyl-1,4-thiazepan-5-one (7d) (84.3 mg) as the amine component and isolation of title compound by Et$_2$O trituration of the crude material, the white solid title compound (7) was obtained as a 1:1 mixture with the 6S,7S diastereomer (99.8 mg, 59%), m.p. 128-133°. $^1$H NMR (300 MHz, CDCl$_3$) δ 1.11 (d, 1.5H, J=7.0 Hz), 1.28 (d, 1.5H, J=6.6 Hz), 2.80 (m, 1H), 3.06 (m, 1H), 3.48 (s, 1H), 3.49 (s, 1H), 3.76 (m, 2H), 4.32 (m, 1H), 4.47 (m, 1H), 5.25 (t, 0.5H), 5.33 (t, 0.5H), 6.09 (d, 0.5, exchangeable) 6.25 (m, 1H, exchangeable), 6.38 (t, 0.5H, exchangeable), 6.79 (m, 3H), 7.00 (d, 0.5H, exchangeable), 7.08 (d, 0.5H, exchangeable) 7.24 (m, 5H). MS APCI m/z=448(M+1). HPLC Method A: 2.62 min.

The starting amine (6,7-cis)-6-amino-7-phenyl-1,4-thiazepan-5-one (7d) was prepared in the following manner:

b. Methyl 2-{[(benzyloxy)carbonyl]amino}-3-({2-[(tert-butoxycarbonyl)amino]ethyl}thio)-3-phenyl-propanoate (7a)

Using a method similar to that described in Example 1, part b (Method B) a solution of tert-butyl N-(2-mercaptoethyl)carbamate (2.4 mL), methyl (2Z)-2-{[(benzyloxy)carbonyl]amino}-3-phenylprop-2-enoate (0.87 g), triethylamine (0.39 mL) and methanol (15 mL) was stirred at RT for 3 days. Removal of the solvent and chromatograpy of the resultant crude oil on silica gel (10% to 25% ethyl acetate/hexanes) returned the title compound as a viscous oil (1.22 g, 90%). The proton NMR displayed a mixture of diastereomers of approximate ratio 7:3; the major diastereomer is reported. $^1$HNMR (300 MHz, CDCl$_3$) δ 1.41 (s, 9H), 2.48 (t, 2H), 3.19 (br, 2H), 3.65 (s, 3H), 4.12 (q, 1H), 4.35 (t, 1H), 4.73 (t, 2H), 5.09 (d, 2H), 7.27-7.34 (m, 10H). MS APCI, m/z=389(M−t-BuOCO)$^+$. HPLC Method A: 3.47 min.

b. Methyl 3-[(2-aminoethyl)thio]-2-{[(benzyloxy)carbonyl]amino}-3-phenylpropanoate (7b)

To a stirred cooled (ice-bath) solution of methyl 2-{[(benzyloxy)carbonyl]amino}-3-({2-[(tert-butoxycarbonyl)amino]ethyl}thio)-3-phenylpropanoate (7a) (1.20 g) and methanol (0.284 mL) in ethyl acetate (2 mL) was added dropwise from a syringe acetyl chloride (0.43 mL) and the mixture stirred in the ice bath for an additional 10 min and then at RT for 50 min. Excess Et$_2$O was added and the white solid collected, dissolved in water, treated with an excess of sat. aqueous K$_2$CO$_3$ and extracted once with CH$_2$Cl$_2$ and twice with Et$_2$O. The dried organics (MgSO$_4$) were filtered and the solvent removed to yield the title compound as an oil (0.86 g, 90%). The proton NMR displayed a mixture of diastereomers of approximate ratio 7:3; the major diastereomer is reported. $^1$H NMR (300 MHz, CDCl$_3$) δ1.46 (s, 2H, exchangeable), 2.47 (t, 2H), 2.76 (t, 2H), 3.66 (s, 3H), 3.35 (d, 1H), 4.75 (t, 1H), 5.09 (m, 2H), 5.76 (d, 1H, exchangeable), 7.28-7.34 (m, 10H). MS APCI, m/z=389(M+1). HPLC Method A: 2.27 min.

c. Benzyl (6,7 cis)-5-oxo-7-phenyl-1,4-thiazepan-6-ylcarbamate (7c)

To a stirred solution of methyl 3-[(2-aminoethyl)thio]-2-{[(benzyloxy)carbonyl]amino}-3-phenylpropanoate (7b) (0.85 g) in CH$_2$Cl$_2$ (10 mL) was added 2.0 M (CH$_3$)$_3$Al in toluene (2.2 mL) and the mixture stirred overnight at RT. The reaction mixture was cautious treated with 0.5N hydrochloric acid (20 mL total) and extracted twice with CH$_2$Cl$_2$. The dried extracts (MgSO$_4$) yielded the title compound as a mixture with the 6,7-trans diastereomer; HPLC Method A: 2.96 and 3.22 min. Trituration with Et$_2$O returned pure title compound as a white solid (0.32 g, 41%). $^1$H NMR (300 MHz, CDCl$_3$) δ2.75-2.81 (m, 1H), 3.02-3.08 (m, 1H), 3.68-3.93 (M, 2H), 4.35 (d, 1H, J$_{6,7}$=3.8 Hz), 5.11 (2H), 5.23 (q, 1H, J$_{6,7}$=3.8 Hz), 6.02 (d, 1H, NH), 6.13 (br s, 1H, NH) 7.26-7.38 (m, 10H). MS APCI, m/z=357(M+1). HPLC Method A: 2.96 min.

d. (6,7 cis)-6-Amino-7-phenyl-1,4-thiazepan-5-one (7d)

To benzyl (6,7 cis)-5-oxo-7-phenyl-1,4-thiazepan-6-ylcarbamate (7c) (0.30 g) was added 30% HBr/HOAc (3 mL) and magnetic stirring initiated. After a few minutes the evolution of CO$_2$ was evident. After 45 min. the mixture was treated with excess Et$_2$O and the white solid collected by filtration, dissolved in water (~65 mL), treated with excess saturated aqueous sodium bicarbonate and extracted 10 times with CH$_2$Cl$_2$ (25 mL portions). The dried CH$_2$Cl$_2$ extracts (MgSO$_4$) yielded the title compound as a white solid (0.17 g, 91%). $^1$H NMR (300 MHz, CDCl$_3$) δ1.70 (br s, 2H, NH$_2$), 2.75-2.82 (m, 1H), 2.95-3.02 (m, 1H), 3.68-3.87 (m, 2H), 4.14 (d, 1H, J$_{6,7}$=3.1 Hz), 4.33 (d, 1H, J$_{6,7}$=3.1 Hz), 6.13 (br s, 1H, NH), 7.29-7.42 (m, 5H). MS APCI, m/z=223(M+1). HPLC Method A: 0.63 min.

Example 8

N$^2$-[(3,5-Difluorophenylacetyl]-N$^1$-[(3S,4R)-8-fluoro-2-oxo-4-phenyl-2,3,4,5-tetrahydro-1H-1-benzazepin-3-yl]-L-alaninamide (8)

To a solution of (3,4-cis)-3-amino-8-fluoro-4-phenyl-1,3,4,5-tetrahydro-2H-1-benzazepin-2-one (8k) (15 mg) in dichloromethane (6 mL) at 0° C. under nitrogen was added N-[3,5-difluorophenyl)acetyl]-L-alanine (8e) (14 mg), HOBt-hydrate (15 mg), EDAC·HCl (16 mg) and NMM (14 μL). The reaction mixture was stirred for 1 h at 0° C. and then for 2 h at RT. The mixture was concentrated in vacuo and then partitioned between water (10 mL) and ethyl acetate(12 mL). The organic phase was collected and consecutively washed with water, saturated aqueous sodium bicarbonate, and brine, dried, filtered and evaporated to yield the off-white solid title compound (14 mg, 52%) as a 1:1 mixture with the 3R,4S diastereomer. $^1$H NMR (400 MHz, CD$_3$OD) δ 0.86 (d 1.5H), 0.97 (d, 1.5H), 2.8 (m, 2H), 3.76 (s, 2H), 3.86 (m, 1H), 4.02 (m, 1H), 4.53 (t, 1H), 6.68-6.78 (m, 3H), 6.99 (m, 2H), 7.17-7.39 (m, 5H). MS APCI, m/z=496 (M+1), 518 (M+Na). LC/MS: 2.41 min.

The starting amine, (3,4-cis)-3-amino-8-fluoro-4-phenyl-1,3,4,5-tetrahydro-2H-1-benzazepin-2-one (8k), was prepared in the following manner:

a. Dimethyl [2-(4-fluoro-2-nitrophenyl)-1-phenylethyl]malonate (8a)

A solution of benzylidene malonate (14.2 g) in DMF (280 mL) was treated with sodium hydride (2.57 g, 95%). A solution of 4-fluoro-2-nitrotoluene in DMF (10 mL) was added over 1 H, and the reaction mixture was stirred at RT overnight and then quenched by the addition of glacial acetic acid (175 mL) at 0° C. A total of 500 mL of 70:30 water-methanol was added with stirring, and the organics were extracted with ethyl acetate. The organic extracts were combined and washed with saturated aqueous potassium carbonate solution (2×) and brine, dried over sodium sulfate, filtered, and concentrated in vacuo to give a dark brown oil. Flash chromatography on silica gel (75:25 hexane-ethyl acetate, then 50:50 hexane-ethyl acetate) provided 7.0 g (30%) of the title compound as a red-brown solid. $^1$H NMR (300 MHz, CDCl$_3$) δ 3.72 (d, 2H), 3.73 (d, 1H), 4.32 (m, 1H), 7.09-7.29 (m, 7H), 7.71 (m, 1H). MS APCI, m/z=398 (M+Na). LC/MS: 2.66 min.

b. Dimethyl [2-(2-amino-4-fluorophenyl)-1-phenylethyl]malonate (8b)

To a solution of dimethyl [2-(4-fluoro-2-nitrophenyl)-1-phenylethyl]malonate (8a) (5.0 g) in methanol (20 mL) was added ammonium chloride (1.5 g) and zinc dust (11.0 g).

The reaction mixture was then heated to reflux for 1 h. The reaction mixture was filtered through a diatomaceous earth pad, and the organic solvents were removed in vacuo. The resulting yellow oil was dissolved in ethyl acetate (100 mL) and washed with saturated aqueous potassium carbonate solution (2×), the organic layer was dried, filtered, and concentrated in vacuo to afford the title compound as a tan gum (4.1 g, 90%). MS APCI, m/z=346 (M+1). LC/MS: 2.51 min.

c. Methyl (3,4-trans)-8-fluoro-2-oxo-4-phenyl-2,3,4,5-tetrahydro-1H-1-benzazepine-3-carboxylate (8c)

A solution of dimethyl [2-(2-amino-4-fluorophenyl)-1-phenylethyl]malonate (8b) (4.3 g) in methanol (130 mL) was treated with sodium methoxide (1.73 g). The reaction mixture was heated to reflux for 5 h, cooled to RT, and acidified with 1N hydrochloric acid. The methanol was evaporated in vacuo, the residue was extracted with ethyl acetate, and the extract was washed with brine, 1N hydrochloric acid, and brine, dried, filtered, and concentrated in vacuo. The resulting crude product (4.0 g) was triturated with 1:1 diethyl ether:ethyl acetate to give the title compound as a colorless solid (3.87 g, 93%). $^1$H NMR (300 MHz, CDCl$_3$) δ 2.4 (m, 2H), 3.23 (m, 1H), 3.72 (s, 3H), 3.77 (m, 1H), 6.71-7.50 (m, 7H), 8.95 (s, 1H). MS APCI, m/z=336 (M+Na). LC/MS: 2.28 min.

d. Methyl (3,4-cis)-8-fluoro-3-hydroxyl-2-oxo-4-phenyl-2,3,4,5-tetrahydro-1H-1-benzazepine-3-carboxylate (8d)

A solution of methyl (3,4-trans)-8-fluoro-2-oxo-4-phenyl-2,3,4,5-tetrahydro-1H-1-benzazepine-3-carboxylate (8c) (156 mg) in THF (10 mL) was cooled to −78° C. under nitrogen. Potassium hexamethyldisilazide (0.5 M in toluene, 4.0 mL, 4 equiv) was added, and the reaction mixture was stirred for 1 h at −78° C. Trimethyl phosphite (0.24 mL, 4 equiv) was added, and bubbling with oxygen gas through the solution was started. Bubbling with oxygen gas was continued while the temperature was allowed to warm to 0° C. over approximately 30 min. The reaction was quenched with acetic acid (7 mL), the solvents were partially removed in vacuo, ethyl acetate was added, and the organic layer was washed with 1N hydrochloric acid (2×), saturated potassium carbonate (2×), and brine, dried, filtered, and concentrated in vacuo to provide the title compound as a light yellow solid (130 mg, 80%). MS APCI, m/z=330 (M+1). LC/MS: 2.22 min.

e. (3,4-cis)-8-Fluoro-3-hydroxyl-4-phenyl-1,3,4,5-tetrahydro-2H)-1-benzazepin-2-one (8e)

A solution of methyl (3,4-trans)-8-fluoro-3-hydroxyl-2-oxo-4-phenyl-2,3,4,5-tetrahydro-1H-1-benzazepine-3-carboxylate (8d) (1.4 g) and LiI (2.3 g, 4 equiv) in pyridine (35 ml) and water (0.35 mL) was heated to reflux for 3 h. Pyridine was removed in vacuo, ethyl acetate was added, and the ethyl acetate solution was washed with 1N hydrochloric acid (3×), saturated aqueous potassium carbonate solution, and brine, dried, and filtered. A small amount of insoluble material was collected from the separatory funnel. This material was washed several times with water and ether, and then used to seed the ethyl acetate solution. Refrigeration and filtration provided the title compound as an off-white solid (700 mg, 60%). $^1$H NMR (300 MHz, CDCl$_3$) δ 1.78-2.05 (m, 2H), 2.87 (m, 1H), 4.20 (m, 1H), 4.43 (d, 1H), 6.71-7.75 (m, 7H), 8.35 (s, 1H). MS APCI, m/z=272 (M+1). LC/MS: 1.95 min.

f. (3,4cis)-8-Fluoro-2-oxo-4-phenyl-2,3,4,5-tetrahydro-1H-1-benzazepin-3-yl methanesulfonate (8f)

To a solution of (3,4-cis)-8-fluoro-3-hydroxyl-4-phenyl-1,3,4,5-tetrahydro-2H-1-benzazepin-2-one (8e) (400 mg) in pyridine (3 mL) was added methylsulfonyl chloride (0.17 mL, 1.5 equiv) at 0° C. The reaction mixture was stirred for 3 h at 0° C., and then diluted with diethyl ether (50 mL), washed several times with water, 1N hydrochloric acid (3×), saturated aqueous sodium bicarbonate solution, and brine, dried, filtered and concentrated in vacuo to afford the title compound as a white solid (512 mg, 90.9%). MS APCI, m/z=350 (M+1). LC/MS: 2.58 min.

g. (3,4-trans)-8-Fluoro-2-oxo-4-phenyl-2,3,4,5-tetrahydro-1H-1-benzazepin-3-yl acetate (8 g)

To a solution of (3,4-cis)-8-fluoro-2-oxo-4-phenyl-2,3,4,5-tetrahydro-1H-1-benzazepin-3-yl methanesulfonate (8f) (512 mg) in toluene (10 mL) was added 18-crown-6 (391.2 mg) and cesium acetate (2.8 g) at RT under N$^2$. The reaction mixture was refluxed overnight and then washed consecutively with water (several times), brine, 1N hydrochloric acid (2×), saturated aqueous sodium bicarbonate solution, and brine, dried, filtered and concentrated in vacuo to afford light yellow solid (394 mg, 85%) as trans racemic. MS APCI, m/z=314 (M+1). LC/MS: 2.56 min.

h. (3,4-trans)-8-Fluoro-3-hydroxy-4-phenyl-1,3,4,5-tetrahydro-2H-1-benzazepin-2-one (8h)

To a solution of (3,4-trans)-8-fluoro-2-oxo-4-phenyl-2,3,4,5-tetrahydro-1H-1-benzazepin-3-yl acetate (8 g) (360 mg) in methanol (10 mL) with water (5 mL) was added lithium hydroxide (46 mg, 2 equiv). The reaction mixture was stirred at RT for 5 h, and it was then acidified to pH=1 with 1N hydrochloric acid. The mixture was extracted with ethyl acetate twice and the combined ethyl acetate layers were washed with water, and brine, dried, filtered and concentrated in vacuo. Flash chromatography (hexane:ethyl acetate=4:1) provided the title compound (218.20 mg, 70%). $^1$H NMR (300 MHz, CDCl$_3$) δ 1.8-2.15 (m, 2H), 2.9 (m, 1H), 4.30 (m, 1H), 4.53 (d, 1H), 6.71-7.5 (m, 7H), 7.95 (s, 1H). MS APCI, m/z=272 (M+1). LC/MS: 1.94 min.

i. (3,4-trans)-8-Fluoro-2-oxo-4-phenyl-2,3,4,5-tetrahydro-1H-1-benzazepin-3-yl 4-methylbenzensulfonate (8i)

To a solution of (3,4-trans)-8-fluoro-3-hydroxy-4-phenyl-1,3,4,5-tetrahydro-2H-1-benzazepin-2-one (8 h) (140.0 mg) in pyridine (4 mL) was added p-toluenesulfonyl chloride (170.0 mg, 2.3 equiv) at 0° C. The reaction mixture was stirred for 3 h at 0° C., and then for 24 h at RT. The reaction mixture was then diluted with dichloromethane (50 mL), and washed several times with water, saturated aqueous copper sulfate, and brine, dried, filtered and concentrated in vacuo to afford the title compound as a brown oil (153.7 mg, 70%). MS APCI, m/z=426 (M+1). LC/MS: 2.74.

j. (3,4-cis)-3-Azido-8-fluoro-4-phenyl-1,3,4,5-tetrahydro-2H-1-benzazepin-2-one (8j)

To a solution of (3,4-trans)-8-fluoro-2-oxo-4-phenyl-2,3,4,5-tetrahydro-1H-1-benzazepin-3-yl 4-methylbenzensulfonate (8i) (220.0 mg) in DMF (4 mL) was added sodium azide (135.2 mg, 4.0 equiv) at RT. The reaction mixture was heated to 90° C. for 24 h, cooled to RT, diluted with ethyl acetate (50 mL), and washed several times with water and brine, dried, filtered and concentrated in vacuo to provide a brown residue. Flash chromatography (hexane:ethyl acetate=4:1) provided the title compound (87.0 mg, 58.7%). MS APCI, m/z=297 (M+1). LC/MS: 2.46 min.

k. (3,4-cis)-3-Amino-8-fluoro-4-phenyl-1,3,4,5-tetrahydro-2H-1-benzazepin-2-one (8k)

To a solution of (3,4-cis)-3-azide-8-fluoro-4-phenyl-1,3,4,5-tetrahydro-2H-1-benzazepin-2-one (8j) (65.0 mg) in TEF (5 mL) was added PS-triphenylphosphine (1.0 g, 1.2 mmol/g, 5.5 equiv) at RT. The reaction mixture was stirred at RT for 24 h. The mixture was filtered, and the resin was extracted with THF (10 mL×2) and ethyl acetate (10 mL). The combined organic extracts were concentrated in vacuo to provide a brown residue. Flash chromatography (hexane:ethyl acetate=1: 1) provided the title compound (45.7 mg, 70.0%). $^1$H NMR (300 MHz, CDCl$_3$) δ 1.42-1.52 (m, 2H), 1.98 (s, 2H), 2.94 (m, 1H), 3.85 (d, 1H), 6.62-7.74 (m, 8H). $^{19}$F NMR (300 MHz, CDCl$_3$) δ −113.0. MS APCI, m/z=271 (M+1). LC/MS: 1.44 min.

Example 9

$N^2$-[(3,5-Difluorophenyl)acetyl]-$N^1$-[(2R,3R)-4-oxo-2-phenyl-2,3,4,5-tetrahydro-1,5-benzothiazepin-3-yl]-L-alaninamide (9)

To a suspension of (2,3-cis)-3-amino-2-phenyl-2,3-dihydro-1,5-benzothiazepin-4(5H)-one hydrobromide (9d) (100 mg, 0.28 mmol) in dichloromethane (20 ml) at 0° C. under nitrogen was added 1e (69 mg, 0.28 mmol) and NMM (31 μL, 0.28 mmol) until the solution cleared. To the solution was added HOBt-hydrate (96 mg, 0.63 mmol), EDAC.HCl (82 mg, 0.43 mmol) and NMM (50 μL, 0.43 mmol). The reaction mixture was stirred 2 h at 0° C., concentrated in vacuo and partitioned between H$_2$O (100 ml) and ethyl acetate (125 ml). The organic phase was collected and consecutively washed with HCl (2×), H$_2$O, saturated NaHCO$_3$, and brine, dried and the solvent removed in vacuo to yield the title compound (9) as a 1:1 mixture with the 2S,3S diastereomer (130 mg, 92%). The crude product was purified by isocratic flash chromatography (50% ethyl acetate/hexanes) to yield 9 as an 84:16 mixture with the 2S,3S diastereomer (50 mg, 60%). Recrystallization from chloroform—hexanes gave pure title compound (9) (15 mg, >98% de) as a white solid.

$^1$H NMR (300 MHz, CDCl$_3$) δ 1.16 (d, 3H), 3.43 (s, 2H), 4.18 (m, 1H), 4.87 (t, 1H), 5.25 (d, 1H), 5.77 (d, 1H), 6.30 (d, 1H), 6.75 (m, 2H), 7.15 (d, 1H), 7.35 (m, 8H), 7.64 (bs, 1H), 7.71 (d, 1H). MS APCI, m/z=496 (M+1). LC/MS: 2.41 min.

The starting amine, (2,3-cis)-3-amino-2-phenyl-2,3-dihydro-1,5-benzothiazepin-4(5H)-one hydrobromide (9d), was prepared in the following manner:

a. Methyl (2Z)-2-{[(benzyloxy)carbonyl]amino}-3-phenylacrylate (9a)

Using a procedure similar to that described in Example 1 part a, except using benzaldehyde (1.22 ml, 12.2 mmol) as the aldehyde component, the title compound (9a) was obtained as a 12:1 (Z:E) mixture of isomers as an oil (2.5 g, 66%). MS APCI, m/z=437 (M+1)

b. Methyl β-[(2-aminophenyl)thio]-N-[(benzyloxy)carbonyl]-2,5-difluorophenylalaninate (9b)

To a deoxygenated solution of methyl (2Z)-2-{[(benzyloxy)carbonyl]amino}-3-phenylacrylate (9a) (2.5 g, 8.0 mmol) in anhydrous methanol (250 ml) under nitrogen was added the 2-aminothiophenol (10.6 g, 84.7 mmol) followed by addition of triethylamine (560 μl, 4.02 mmol). After 5 days an additional portion of triethylamine (560 ul, 4.02 mmol) was added and the reaction stirred at ambient temperature for 2 days. The reaction mixture was concentrated to ~10 mL and partitioned between cold 1N hydrochloric acid (75 mL) and ethyl acetate (125 mL). The organic phase was separated and consecutively washed with 1N hydrochloric acid (4×), dilute aqueous sodium bicarbonate and brine, dried, filtered and evaporated. The title compound (9b) was isolated as the hydrochloride salt (1.5 g, 40%, contaminated with 10% polymer). A 500 mg sample was recrystallized from hot ethyl acetate (10 mL) to afford analytically pure title compound (180 mg). MS APCI, m/z=437 (M+1). LC/MS: 2.68 min.

c. Benzyl [(2,3-cis)-4-oxo-2-phenyl-2,3,4,5-tetrahydro-1,5-benzothiazepin-3-yl]carbamate (9c)

Using a procedure similar to that described in Example 1, part c, except using methyl β-[(2-aminophenyl)thio]-N-[(benzyloxy)carbonyl]phenylalaninate (9b) (850 mg, 1.9 mmol) as the anilino component, the title compound (9c) was obtained (730 mg, 92%) as a white solid. MS APCI, m/z=427 (M+Na), LC/MS: 2.67 min.

d. (2,3-cis)-3-Amino-2-phenyl-2,3-dihydro-1,5-benzothiazepin-4(5H)-one hydrobromide (9d)

Using a procedure similar to that described in Example 1, part d Method D, except using benzyl [(2,3-cis)-4-oxo-2-phenyl-2,3,4,5-tetrahydro-1,5-benzothiazepin-3-yl]carbamate (9c), (550 mg, 1.36 mmol) as the protected amine component, the title compound (9d) was obtained (414 mg, 86%) as a white solid. MS APCI, m/z=293 (M+Na), LC/MS: 1.54 min.

Example 10

$N^1$-[(2R,3R)-2-(3,4-Dichlorophenyl)-4-oxo-2,3,4,5-tetrahydro-1,5-benzothiazepin-3-yl]-$N^2$-[(3,5Difluorophenyl)acetyl]-L-alaninamide (10)

To a suspension of (2,3-cis)-3-amino-2-(3,4-dichlorophenyl)-2,3-dihydro-1,5-benzothiazepin-4(5H)-one hydrobromide (10d) (236 mg, 0.56 mmol) in dichloromethane (40 ml) at 0° C. under nitrogen was added the chiral acid (1e) (137 mg, 0.56 mmol) and NMM (62 μL, 0.56 mmol) until solution cleared. To the solution was added HOBt-hydrate (190 mg, 1.24 mmol), EDAC-HCl (162 mg, 0.85 mmol) and NMM (93 μL, 0.85 mmol). The reaction mixture was stirred 2 h at 0° C., then at RT for 30 min, concentrated in vacuo and partitioned between H₂O (100 ml) and ethyl acetate (125 ml). The organic phase was collected and consecutively washed with HCl (2×), H₂O, saturated NaHCO₃, and brine, dried and the solvent removed in vacuo to yield the title compound (10) as a 1:1 mixture with the 2S,3S diastereomer (130 mg, 92%). Crystallization from ether/hexanes gave 132 mg as a 3:1 mixture of predominantly the other 2S,3S diastereomer. The filtrate was evaporated and recrystallized from ethyl acetate/hexanes to give 65 mg of the title compound as a 6:1 mixture with the 2S,3S diastereomer as white solid.

$^1$H NMR (300 MHz, CDCl₃) δ 1.20 (d, 3H)[1.04 (d, 0.17H) 2S,3S], 3.45 (s, 2H), 4.23 (m, 1H), 4.82 (t, 1H), 5.25 (d, 1H), 5.76 (d, 1H), 6.53 (d, 1H), 6.6-6.8 (m, 3 H), 7.15 (d, 1H), 7.31 (m, 1H), 7.4-7.5, (m, 3H), 7.50 (d, 1H), 7.70 (m, 2H). MS APCI m/z=564 (M+1). LC/MS: 2.72 min.

The starting amine, (2,3-cis)-3-amino-2-(3,4-dichlorophenyl)-2,3-dihydro-1,5-benzothiazepin-4(5H)-one hydrobromide (10d), was prepared in the following manner:

a. Methyl (2Z)-2-{[(benzyloxycarbonyl]amino}-3-(3,4-dichlorophenyl)acrylate (10a)

Using a procedure similar to that described in Example 1 part a, except using 3,4-dichlorobenzaldehyde (1.05 g, 6.0 mmol) as the aldehyde component, the title compound (10a) was obtained as a 12:1 (Z:E) mixture of isomers as an oil (2.17 g, 92%)

b. Methyl β-[(2-aminophenyl)thio]-N-[(benzyloxy)carbonyl]-3,4-dichlorophenylalaninate (10b)

To a deoxygenated solution of methyl (2Z)-2-{[(benzyloxy)carbonyl]amino}-3-(3,4-dichlorophenyl)acrylate (10a) (2.17 g, 5.7 mmol) in anhydrous methanol (40 ml) (warmed to dissolve) under nitrogen was added the 2-aminothiophenol (3.1 ml, 28.5 mmol) followed by addition of triethylamine (400 ul, 2.85 mmol). The mixture stirred 3 days at ambient temperature, concentrated to ca. 10 mL, partitioned between cold 1N hydrochloric acid (75 mL) and ethyl acetate (100 mL). The organic phase was separated and consecutively washed with 1N hydrochloric acid (4×), dilute aqueous sodium bicarbonate and brine, dried, filtered and evaporated to give the title compound (10b) as an 4:1 mixture (erythro:threo) (2.8 g, 96%). A 100 mg sample was converted to the HCl salt to provide an analytically pure title compound (32 mg) as a (4:1) mixture. MS APCI, m/z=505 (M+1), 507 (M+3). LC/MS: 2.94 min.

c. Benzyl [(2,3-cis)-2-(3,4-dichlorophenyl)-4-oxo-2,3,4,5-tetrahydro-1,5-benzothiazepin-3-yl]carbamate (10c)

A suspension of methyl β-[(2-aminophenyl)thio]-N-[(benzyloxy)carbonyl]-3,4-dichlorophenylalaninate (10b) (4:1, 2.5 g, 4.9 mmol) and pTSA (catalytic) in xylenes (30 mL) was heated to reflux for 1 h, using a Dean-Stark apparatus. The mixture was then cooled, resulting in precipitation of the trans product as a white solid (300 mg, pure trans). The filtrate (1.6 g, 85% pure cis+15% SM) was taken up in 20 ml xylenes, cat p-TSA, refluxed additional 1 h, cooled, evaporated, purified by flash column chromatography eluting with 50% ether-hexanes to give pure title compound (10c) (900 mg, 39%) as a white solid. MS APCI, m/z=495 (M+Na) LC/MS: 2.96 min.

d. (2,3-cis)-3-Amino-2-phenyl-2,3-dihydro-1,5-benzothiazepin-4(5H)-one hydrobromide (10d)

Using a procedure similar to that described in Example 1, part d Method D, except using benzyl [(2,3-cis)-2-(3,4-dichlorophenyl)-4-oxo-2,3,4,5-tetrahydro-1,5-benzothiazepin-3-yl]carbamate (10c), (850 mg, 1.8 mmol) as the protected amine component, the title compound (10d) was obtained (750 mg, 99%) as a white solid. MS APCI, m/z=402 (M-NH₃), LC/MS: 1.88 min.

Example 11

N$^1$-[(2R,3R)-2-(4-chlorophenyl)-4-oxo-2,3,4,5-tetrahydro-1,5-benzothiazepin-3-yl]-N$^2$-[(3,5-Difluorophenyl)acetyl]-L-alaninamide (11)

To a suspension of (2,3-cis)-3-amino-2-phenyl-2,3-dihydro-1,5-benzothiazepin-4(5H)-one hydrobromide (11d) (112 mg, 0.29 mmol) in dichloromethane (25 ml) at 0° C. under nitrogen was added the chiral acid (1e) (71 mg, 0.29 mmol) and NMM (32 μL, 0.29 mmol) until solution cleared. To the solution was added HOBt-hydrate (98 mg, 0.64 mmol), EDAC.HCl (84 mg, 0.44 mmol) and NMM (51 μL, 0.44 mmol). The reaction mixture was stirred 2 h at 0° C., concentrated in vacuo and partitioned between H₂O (100 ml) and ethyl acetate (125 ml). The organic phase was collected and consecutively washed with HCl (2×), H₂O, saturated NaHCO₃, and brine, dried and the solvent removed in vacuo to yield the title compound (11) as a 1:1 mixture with the 2S,3S diastereomer (145 mg, 95%) as an off white solid.

$^1$H NMR (300 M , CDCl₃) δ0.99 (d, 1.5H), 1.18 (d, 1.5H), 3.43 (s, 1H), 3.45 (s, 1H), 4.28 (m, 0.5H), 4.63 (m, 0.5H), 4.83 (dt, 1H), 5.27 (dd, 1H), 5.87 (d, 0.5H), 6.18 (d, 0.5H), 6.55 (d, 0.5H), 6.74 (m, 3H), 6.85 (d, 0.5H), 7.05 (d, 0.5H), 7.16 (d, 0.5H), 7.34 (m, 6H), 7.63, (dd, 1H), 7.82 (s, 0.5H), 8.33 (s, 0.5H). MS APCI, m/z=530 (M+1), 552 (M+Na⁺). LC/MS: 2.58 min.

The starting amine, (2,3-cis)-3-amino-2-(4-chlorophenyl)-2,3-dihydro-1,5-benzothiazepin-4(5H)-one hydrobromide (11d), was prepared in the following manner:

a. Methyl (2Z)-2-{[(benzyloxy)carbonyl]amino}-3-(4-chlorophenyl)acrylate (11 a)

Using a procedure similar to tat described in Example 1 part a, except using 4-chlorobenzaldehyde (844 mg, 6.0 mmol) as the aldehyde component, the title compound (11 a) was obtained as white solid (2.0 g, 97%)

b. Methyl β-[(2-aminophenyl)thio]-N-[(benzyloxy)carbonyl]-4-chlorophenylalaninate (11 b)

Using a procedure similar to that described in Example 10, part b, except using methyl (2Z)-2-{[(benzyloxy)carbonyl]amino}-3-(4chlorophenyl)acrylate (11a) (1.9 g, 5.5 mmol), the product was obtained as a crude oil. Recrystallization from ether-hexanes afforded the title compound (11 b) (2.5 g, 97%) as white solid (95:5 mixture (erythro:threo)). MS APCI, m/z=471 (M+1). LC/MS: 2.82 min.

c. Benzyl [(2,3-cis)-2-(4-chlorophenyl)-4-oxo-2,3,4,5-tetrahydro-1,5-benzothiazepin-3-yl]carbamate (11c)

A suspension of methyl β-[(2-aminophenyl)thio]-N-[(benzyloxy)carbonyl]-4-chlorophenylalaninate (11b) (19:1, 2.4 g, 4.9 mmol) and pTSA (catalytic) in xylenes (30 mL) was heated to reflux for 2 h, using a Dean-Stark apparatus. The mixture was then cooled, resulting in precipitation of the trans product as a white solid (350 mg, pure trans). The filtrate (2.0 g) purified by flash column chromatography eluting with 30% ethyl acetate-hexanes to give pure title compound (11c) (1.6 g, 72%) as a white solid. $^1$H NMR (300 MHz, d6-DMSO) δ 4.54 (t, 1H, J=7.8 Hz), 4.95 (s, 2H), 5.19 (d, 1H, J=6.9 Hz), 6.41 (d, 1H), 7.23-7.34 (m, 6H), 7.42, (s, 5H), 7.51 (t, 1H, J=7.7 Hz), 7.67 (d, 1H, J=7.7 Hz), 10.50 (s, 1H). MS APCI, m/z=461 (M+Na). LC/MS: 2.83 min.

d. (2,3-cis)-3-Amino-2-phenyl-2,3-dihydro-1,5-benzothiazepin-4(5H)-one hydrobromide (11d)

To benzyl [(2,3-cis)-2-(4-chlorophenyl)-4-oxo-2,3,4,5-tetrahydro-1,5-benzothiazepin-3-yl]carbamate (11c) (1.5 g, 3.4 mmol) in 5 ml acetic acid was added 30% HBr/acetic acid (7 mL). The stirred suspension was heated to 60 C for 40 min, cooled and then was diluted with ether to afford the hydrobromide salt of the title compound (11d) (1.1 g, 84%) as a white solid. $^1$H NMR (300 MHz, d6-DMSO) δ 4.30 (d, 1H, J 6.6 Hz), 5.27 (d, 1H, J7.7 Hz), 6.41 (d, 1H), 7.29 (dd, 2H), 7.54 (m, 5H), 7.69 (d, 1H, J 7.9 Hz), 8.09 (bs, 3H), 10.88 (s, 1H). MS APCI, m/z=368 (M-NH$_3$). LC/MS: 1.73 min.

Example 12

N$^2$-[(3,5-Difluorophenyl)acetyl]-N$^1$-[(2R,3R)-2-(4-methylphenyl)-4-oxo-2,3,4,5-tetrahydro-1,5-benzothiazepin-3-yl]-L-alaninamide (12)

Using a procedure similar to that described in Example 11, except using (2,3-cis)-3-amino-2-(4-methylphenyl)-2,3-dihydro-1,5-benzothiazepin-4(5H)-one hydrobromide (12d) (100 mg, 0.27 mmol) as the amine component, the title compound (12) was obtained in a 1:1 mixture with the 2S,3S diastereomer (130 mg, 93%) as an off white solid. $^1$H NMR (300 MHz, d6-DMSO) δ0.93 (d, 1.5H), 1.01 (d, 1.5H), 2.29 (s, 1.5H), 2.30 (s, 1.5H), 3.38 (d, 2H), 4.17 (m, 1H), 4.68 (m, 1H), 5.08 (m, 1H), 6.90 (m, 2H), 7.26 (m, 7H), 7.49, (m, 2H), 7.67 (d, 1H), 8.17 (d, 0.5H), 8.28 (d, 0.5H), 10.47 (d, 1H). MS APCI, m/z=510 (M+Na). LC/MS: 2.53 min.

The starting amine, (2,3-cis)-3-amino-2-(4-methylphenyl)-2,3-dihydro-1,5-benzothiazepin-4(5H)-one hydrobromide (12d), was prepared in the following manner:

a. Methyl (2Z)-2-{[(benzyloxy)carbonyl]amino}-3-(4-methylphenyl)acrylate (12a)

Using a procedure similar to that described in Example 1 part a, except using 4-methylbenzaldehyde (1.56 g, 13.0 mmol) as the aldehyde component, the title compound (12a) was obtained as white solid (4.2 g, 98%). MS APCI, m/z=326 (M+1)

b. Methyl β-[(2-aminophenyl)thio]-N-[(benzyloxy)carbonyl]-4-methylphenylalaninate (12b)

Using a procedure similar to that described in Example 10, part b, except using methyl (2Z)-2-{[(benzyloxy)carbonyl]amino}-3-(4-chlorophenyl)acrylate (12a) (2.1 g, 6.45 mmol) (stirred for 4 weeks, very slow reaction ~85% complete) the title compound was obtained as a crude oil. Recrystallization from ethyl acetate-hexanes to afforded the title compound (12b) (1.2 g, 41%) as white solid (>98% erythro). MS APCI, m/z=451 (M+1). LC/MS: 2.79 min.

c. Benzyl [(2,3-cis)-2-(4-methylphenyl)-4-oxo-2,3,4,5-tetrahydro-1,5-benzothiazepin-3-yl]carbamate (12c)

A suspension of methyl β-[(2-aminophenyl)thio]-N-[(benzyloxy)carbonyl]-4-chlorophenylalaninate (12b) (1.1 g, 2.35 mmol) and pTSA (catalytic) in xylenes (30 mL) was heated to reflux for 2.5 h, using a Dean-Stark apparatus. The mixture was then cooled, evaporated to an oil, triturated with 10 ml methanol and filtered to yield the predominantly trans product as a white solid (50 mg, pure trans). The filtrate was evaporated and recrystallized from ether to afford pure title compound (12c) (750 mg, 76%) as a white solid.
$^1$H NMR (300 MHz, DMSO-d6) δ2.31 (s, 3H), 4.50 (m, 1H), 5.13 (d, 1H, J=7.0 Hz), 5.93 (br d, 1H, J=7.9 Hz), 7.12-7.37 (m, 11H), 7.50 (m, 1H), 7.67 (m, 1H), 10.49 (s, 1H). MS APCI, m/z=441 (M+Na). LC/MS: 2.78 min.

d. (2,3-cis)-3-Amino-2-(4-methylphenyl)-2,3-dihydro-1,5-benzothiazepin-4(5H)-one hydrobromide (12d)

To benzyl [(2,3-cis)-2-(4-methylphenyl)-4-oxo-2,3,4,5-tetrahydro-1,5-benzothiazepin-3-yl]carbamate (12c) (500 mg, 1.2 mmol) in 4 ml acetic acid was added 30% HBr/acetic acid (3 mL). The stirred suspension was heated to 60° C. for 30 min, cooled and then was diluted with ether to afford the hydrobromide salt of the title compound (12d) (410 mg, 94%) as a white solid. $^1$H NMR (300 MHz, d6-DMSO) δ2.34 (s, 3H), 4.24 (d, 1H, J=7.0 Hz), 5.20 (d, 1H, J=7.0 Hz), 7.24 (d, 3H), 7.30 (t, 1H, J=7.9 Hz), 7.42 (d, 2H, J=7.9 Hz), 7.54 (t, 1H, J=7.9 Hz), 7.68 (d, 1H, J=7.9 Hz), 8.00 (bs, 3H) 10.84 (s, 1H). MS APCI, m/z=268 (M+1-NH$_3$). LC/MS: 1.63 min.

Example 13

N$^1$-[(2R,3R)-7-Chloro-4-oxo-2-phenyl-2,3,4,5-tetrahydro-1,5-benzothiazepin-3-yl]-N$^2$-[(3,5-Difluorophenyl)acetyl]-L-alaninamide (13)

Using a procedure similar to that described in Example 11, except using (2,3-cis)-3-amino-7-chloro-2-phenyl-2,3-dihydro-1,5-benzothiazepin-4(5H)-one hydrobromide (13c) (100 mg, 0.26 mmol) as the amine component, the title compound (13) was obtained in a 1:1 mixture with the 2S,3S diastereomer (130 mg, 94%) as an off white solid. $^1$H NMR (300 MHz, CDCl$_3$) δ0.95 (d, 1.5H), 1.18 (d, 1.5H), 3.44 (s, 1H), 3.45 (s, 1H), 4.27 (m, 0.5H), 4.51 (m, 0.5H), 4.83 (dd, 1H), 5.24 (dd, 1H), 5.87 (d, 0.5H), 6.11 (d, 0.5H), 6.42 (d, 0.5H), 6.73 (m, 3.5H), 7.12 (d, 0.5H), 7.17 (d, 0.5H), 7.25 (m, 1H), 7.35 (m, 5H), 7.69 (dd, 1H, 7.89 (s, 0.5H), 8.57 (s, 0.5H). MS APCI, m/z=530 (M+1). LC/MS: 2.59 min.

The starting amine, (2,3-cis)-3-amino-7-chloro-2-phenyl-2,3-dihydro-1,5-benzothiazepin-4(5H)-one hydrobromide (13c), was prepared in the following manner:

a. Methyl β-[(2-amino-4-chlorophenyl)thio]-N-[(benzyloxy)carbonyl]phenylalaninate (13a)

Using a procedure similar to that described in Example 10, part b, except using methyl (2Z)-2-{[(benzyloxy)carbonyl]amino}-3-phenylacrylate (9a) (4.0 g, 12.9 mmol) as the olefin component, and 4-chloro-2-aminothiophenol (10 g, 62.7 mmol) as the thiol component (stirred for 6 days), the product was obtained as a crude oil. Flash column chromatography (5:1 hexanes:ethyl acetate) returned the title compound (1.7 g, 28%). Recrystallization from ethyl acetate-hexanes afforded the title compound (13a) (1.4 g) as a white solid (>98% erythro). MS APCI, m/z=471 (M+1). LC/MS: 2.90 min.

b. Benzyl [(2,3-cis)-7-chloro-4-oxo-2-phenyl-2,3,4,
5-tetrahydro-1,5-benzothiazepin-3-yl]carbamate
(13b)

A suspension of methyl β-[(2-amino-4-chlorophenyl)thio]-N-[(benzyloxy)carbonyl]phenylalaninate (13a) (2.2 g, 4.67 mmol) and pTSA (catalytic) in xylenes (30 mL) was heated to reflux for 1.5 h using a Dean-Stark apparatus. The solids were filtered off after cooling. Washing with ether afforded pure title compound (13b) (1.7 g, 83%) as a white solid. $^1$H NMR 300 MHz, d6-DMSO) δ4.56 (d, 1H, J=7.5 Hz), 4.96 (s, 2H), 5.19 (d, 1H, J=7.0 Hz), 6.12 (d, 1H), 7.2-7.4, (m, 12 H), 7.69 (d, 1H, J=8.3 Hz), 10.59 (s, 1H). MS APCI, m/z=439 (M+1). LC/MS: 2.85 min.

c. (2,3-cis)-3-Amino-7-chloro-2-phenyl-2,3-dihydro-
1,5-benzothiazepin-4(5H)-one hydrobromide (13c)

To benzyl [(2,3-cis)-7-chloro-4-oxo-2-phenyl-2,3,4,5-tetrahydro-1,5-benzothiazepin-3-yl]carbamate (13b) (490 mg, 1.1 mmol) in 5 ml acetic acid was added 30% HBr/acetic acid (4 mL). The stirred suspension was heated to 60° C. for 60 min, cooled and then was diluted with ether to afford the title compound (13c (280 mg, 65%) as a white solid. $^1$H NMR (300 MHz, DMSO-d6) δ4.40 (d, 1H, J=7.0 Hz), 5.24 (d, 1H, J=7.0 Hz), 7.30 (m, 1H), 7.35-7.57 (m, 6H), 7.70 (d, 1H, J=8.3 Hz), 8.07 (br s, 3H), 10.94 (s, 1H). MS APCI, m/z=305 (M+1). LC/MS: 1.68 min.

Example 14

$N^1$-(2R,3R)-7-chloro-5-[2-(dimethylamino)ethyl]-4-
oxo-2-phenyl-2,3,4,5-tetrahydro-1,5-benzothiazepin-
3-yl-$N^2$-[(3,5-Difluorophenyl)acetyl]-L-alaninamide
(14)

Using a procedure similar to that described in Example 1, except using (2,3-cis)-3-amino-7-chloro-5-[2-(dimethylamino)ethyl]-2-phenyl-2,3-dihydro-1,5-benzothiazepin-4(5H)-one (14b) (93 mg, 0.25 mmol) as the amine component, the title compound (14) was obtained as a 1:1 mixture with the 2S,3S diastereomer (94 mg, 62%) as a white solid. $^1$H NMR (300 MHz, CDCl$_3$) δ0.90 (d, 1.5H), 1.14 (d, 1.5H), 2.29 (s, 6H), 2.50 (m, 1H), 2.70 (m, 1H), 3.41 (s, 2H), 3.72 (m, 1H), 4.18 (m, 1H), 4.35 (m, 1H), 4.70 (td, 1H), 5.07 (d, 1H), 5.71 (d, 0.5H), 5.94 (d, 0.5H), 6.27 (t, 1H), 6.74 (m, 2.5H), 7.2-7.4 (m, 6.5H), 7.50 (m, 1H), 7.65 (d, 1H). MS APCI, m/z=601 (M+1). LC/MS: 2.18 min.

The starting amine, (2,3-cis)-3-amino-7-chloro-5-[2-(dimethylamino)ethyl]-2-phenyl-2,3-dihydro-1,5-benzothiazepin-4(5H)-one (14b), was prepared in the following manner:

a. Benzyl {(2,3-cis)-7-chloro-5-[2-(dimethylamino)ethyl]-4-oxo-2-phenyl-2,3,4,5-tetrahydro-1,5-benzothiazepin-3-yl}carbamate (14a)

To a solution of benzyl [(2,3-cis)-7-chloro-4-oxo-2-phenyl-2,3,4,5-tetrahydro-1,5-benzothiazepin-3-yl]carbamate (13b) (750 mg, 1.71 mmol) in methyl isobutyl ketone (20 mL) was added 10N NaOH (0.86 mL, 8.55 mmol) followed by H$_2$O (3.3 mL) and N,N-dimethylaminoethylchloride hydrochloride (370 mg, 2.57 mmol). The reaction mixture was heated to 95° C. for 2.5 h, allowed to cool to RT and diluted with ethyl acetate. The organic phase was collected and consecutively washed with H$_2$O (3×), brine, dried, filtered and the solvent removed in vacuo to yield crude oil (contained 10% 13b). The crude oil was dissolved in ethyl acetate made acidic to pH 1 with 4N dioxane, added ether to precipitate pure title compound (14a) (650 mg, 69%). MS APCI, m/z=510 (M+1). LC/MS: 2.37 min.

b. (2,3-cis)-3-Amino-7-chloro-5-[2-(dimethylamino)
ethyl]-2-phenyl-2,3-dihydro-1,5-benzothiazepin-4
(5H)-one dihydrobromide (14b)

To benzyl {(2,3-cis)-7-chloro-5-[2-(dimethylamino)ethyl]-4-oxo-2-phenyl-2,3,4,5-tetrahydro-1,5-benzothiazepin-3-yl}carbamate (14a) (270 mg, 0.49 mmol) in 1 ml acetic acid was added 30% HBr/acetiic acid (2 mL). The stirred suspension was heated to 60 C for 40 min, cooled and then was diluted with ether to afford the hydrobromide salt of the title compound (11d) (259 mg, 97%) as a grey solid.

Example 15

$N^1$-[(2R,3R)-2-(3-Chlorophenyl)-4-oxo-2,3,4,5-tetrahydro-1,5-benzothiazepin-3-yl]-$N^2$-[(3,5-Difluorophenyl)acetyl]-L-alaninamide (15)

Using a procedure similar to that described in Example 10 except using (2,3-cis)-3-amino-2-(3-chlorophenyl)-2,3-dihydro-1,5-benzothiazepin-4(5H)-one hydrobromide (15d) (115 mg, 0.3 mmol) as the amine component, the title compound (15) was obtained as a 1:1 mixture with the 2S,3S diastereomer (143 mg, 90%) as a off white semi-solid. This was crystallized from ethyl acetate-hexanes to give 62 mg of a 92:8 mixture of the 2S,3S diastereomer. The mother liquor was evaporated, washed with ether, dried in vacuo to yield the title compound (15) as a 87:13 mixture of diastereomers (50 mg) as a light yellow solid.
$^1$H NMR (300 MHz, CDCl$_3$) δ0.99 (d, 1.5H), 1.18 (d, 1.5H), 3.43 (s, 1H), 3.45 (s, 1H), 4.28 (m, 0.5H), 4.63 (m, 0.5H), 4.83 (dt, 1H), 5.27 (dd, 1H), 5.87 (d, 0.5H), 6.18 (d, 0.5H), 6.55 (d, 0.5H), 6.74 (m, 3H), 6.85 (d, 0.5H), 7.05 (d, 0.5H), 7.16 (d, 0.5H), 7.34 (m, 6H), 7.70 (dd, 1H), 7.89 (s, 0.5H), 8.57 (s, 0.5H). MS APCI, m/z=530 (N+1). LC/MS: 2.60 min.

The starting amine, (2,3-cis)-3-amino-2-(3-chlorophenyl)-2,3-dihydro-1,5-benzothiazepin-4(5H)-one hydrobromide (15d), was prepared in the following manner:

a. Methyl (2Z)-2-{[(benzyloxy)carbonyl]amino}-3-
(3-chlorophenyl)acrylate (15a)

Using a procedure similar to that described in Example 1 part a, except using 3-chlorobenzaldehyde (844 mg, 5.50 mmol) as the aldehyde component, the title compound (15a) with 15% of the (2E) isomer was obtained as a semi-solid (1.9 g, 97%).

b. Methyl β-[(2-aminophenyl)thio]-N-[(benzyloxy)
carbonyl]-3-chlorophenylalaninate (15b)

Using a procedure similar to that described in Example 10, part b, except using methyl (2Z)-2-{[(benzyloxy)carbonyl]amino}-3-(3-chlorophenyl)acrylate (15a) (1.9 g, 5.5 mmol), to afford the title compound (15b) as a 4:1 mix (erythro:threo) (2.5 g, 97%) as an oil. $^1$H NMR (300 MHz, CDCl$_3$) δ3.46 (s, 3H), 4.25 (br s, 2H), 4.59 (m, 1H), 4.79 (m, 1H), 5.10 (m, 2H), 5.85 (br, 1H), 6.59 (m, 1H), 6.68 (br d, 1H, J=7.9 Hz), 7.04-7.27 (m, 6H), 7.28-7.42 (m, 5H). MS APCI, m/z=471 (M+1). LC/MS: 2.82 min.

c. Benzyl [(2,3-cis)-2-(3-chlorophenyl)-4-oxo-2,3,4,5-tetrahydro-1,5-benzothiazepin-3-yl]carbamate (15c)

A suspension of methyl β-[(2-aminophenyl)thio]-N-[(benzyloxy)carbonyl]-4-chlorophenylalaninate (11b) (70:30 erythro:threo, 1.7 g, 4.9 mmol) and pTSA (catalytic) in xylenes (30 mL) was heated to reflux for 2 h, using a Dean-Stark apparatus. The mixture was then cooled, the solid filtered off and washed with ether to afford the title compound (12c) (1.45 g) as a 2:1 mixture with 2,3-trans product. Purification by flash column chromatography (20% ethyl acetate-hexanes) gave pure title compound (15c) (0.95 g, 60%) as a white solid. $^1$H NMR (300 MHz, d6-DMSO) δ4.56 (t, 1H, J=7.4 Hz), 4.96 (s, 2H), 5.19 (d, 1H, J=7.0 Hz), 6.53 (d, 1H), 7.23-7.41 (m, 10H), 7.52, (m, 2H), 7.67 (d, 1H, J=7.5 Hz), 10.53 (s, 1H). MS APCI, m/z=439 (M+1), 461 (M+Na). LC/MS: 2.88 min.

d. (2,3-cis)-3-Amino-2-(3-chlorophenyl-2,3-dihydro-1,5-benzothiazepin-4(5H)-one hydrobromide (15d)

To benzyl [(2,3-cis)-2-(3-chlorophenyl)-4-oxo-2,3,4,5-tetrahydro-1,5-benzothiazepin-3-yl]carbamate (15c) (230 mg, 0.52 mmol) in 5 ml acetic acid was added 30% HBr/acetic acid (1 mL). The stirred suspension was heated to 60° C. for 40 min, cooled and then was diluted with ether to afford the hydrobromide salt of the title compound (15d) (155 mg, 77%) as a white solid. $^1$H NMR (300 MHz, d6-DMSO) δ4.32 (d, 1H, J=7.0 Hz), 5.26 (d, 1H, J=7.0 Hz), 7.29 m, 2H), 7.53 (m, 5H), 7.69 (d, 1H, J=7.5 Hz), 8.09 (bs, 3H), 10.91 (s, 1H). MS APCI, m/z=304 (M+1), 288 (M-NH$_3$). LC/MS: 1.74 min.

Example 16

N$^2$-[(3,5-Difluorophenyl)acetyl]-N$^1$-[(2R,3R)-2-(3,5-difluorophenyl)-4-oxo-2,3,4,5-tetrahydro-1,5-benzothiazepin-3-yl]-L-alaninamide (16)

Using a procedure similar to that described in Example 11, except using (2,3-cis)-3-amino-2-(3,5-difluorophenyl)-2,3-dihydro-1,5-benzothiazepin-4(5H)-one (16d) (250 mg, 0.82 mmol) as the amine component, the title compound (16) was obtained in a 1:1 mixture with the 2S,3S diastereomer (430 mg, 98%) as a white solid. $^1$H NMR (300 MHz, CDCl$_3$) δ1.05 (d, 1.5H), 1.20 (d, 1.5H), 3.45 (s, 1H), 3.47 (s, 1H), 4.34 (m, 0.5H), 4.70 (m, 0.5H), 4.78 (m, 1H), 5.30 (dd, 1H), 5.88 (d, 0.5H), 6.15 (d, 0.5H), 6.65-6.85 (m, 4H), 6.97 (m, 3H), 7.05 (d, 0.5H), 7.16 (d, 0.5H), 7.2-7.3 (m, 1H), 7.43 (q, 1H), 7.69 (m, 1H), 7.86 (bs, 0.5H), 8.64 (bs, 0.5H). MS APCI, m/z=532 (M+1). LC/MS: 2.57 min.

The starting amine, (2,3-cis)-3-amino-2-(3,5-difluorophenyl-2,3-dihydro-1,5-benzothiazepin-4(5H)-one hydrobromide (16d), was prepared in the following manner:

a. Methyl (2Z)-2-{[(benzyloxy)carbonyl]amino}-3-(3,5-difluorophenyl)acrylate (16a)

Using a procedure similar to that described in Example 1 part a, except using 3,5-difluorobenzaldehyde (.61 ml, 5.50 mmol) as the aldehyde component, the crude product was obtained as an oil (2.7 g) (9:1 Z:E). After recrystallization from ethyl acetate-ether-hexanes (cold) the pure title compound (16a) was obtained (1.3 g, 71%) as a white solid. MS APCI, m/z=334 (M+1).

b. Methyl β-[(2-aminophenyl)thio]-N-[(benzyloxy)carbonyl]-3,5-difluorophenylalaninate (16b)

Using a procedure similar to that described in Example 9 part b, except using methyl (2Z)-2-{[(benzyloxy)carbonyl]amino}-3-(3,5-difluorophenyl)acrylate (16a) (1.2 g, 3.59 mmol) as the olefin component, the title compound (16b) (1.6 g, 97%) was obtained as a semi-solid.
$^1$H NMR (300 MHz, CDCl$_3$) δ3.50 (s, 3H), 4.27 (br s, 2H), 4.59 (m, 1H), 4.79 (m, 1H), 5.10 (m, 2H), 5.89 (br d, 1H, 9.2 Hz), 6.55-6.93 (m, 5H), 7.07-7.17 (m, 2H), 7.29-7.44 (m, 5H). MS APCI, m/z=473 (M+1).

c. Benzyl [(2,3-cis)-4-oxo-2-(3,5-difluorophenyl-2,3,4,5-tetrahydro-1,5benzothiazepin-3-yl]carbamate (16c)

Using a procedure similar to that described in Example 1, part c, except using methyl β-[(2-aminophenyl)thio]-N-[(benzyloxy)carbonyl](3,5-difluoro)phenylalaninate (9b) (850 mg, 1.9 mmol) as the anilino component, the title compound (9c) was obtained (730 mg, 92%) as a white solid. MS APCI, m/z=427 (M+Na), LC/MS: 2.67 min.

d. (2,3-cis)-3-Amino-2-(3,5-difluorophenyl)-2,3-dihydro-1,5-benzothiazepin-4(5H)-one hydrobromide (16d).

Using a procedure similar to that described in Example 1, part d method D, except using benzyl [(2,3-cis)-4-oxo-2-(3,5-difluoro)phenyl-2,3,4,5-tetrahydro-1,5-benzothiazepin-3-yl]carbamate (16c), (550 mg, 1.29 mmol) as the protected amine component, the title compound (16d) was obtained (433 mg, 86%) as a white solid. $^1$H NMR (300 MHz, DMSO-d6) δ4.38 (d, 1H, J=6.5 Hz), 5.30 (d, 1H, J=6.5 Hz), 7.17-7.44 (m, 5H), 7.57 (m, 1H), 7.71 (d, 1H), 8.18 (br, 3H), 10.97 (s, 1H). MS ES$^+$, m/z=307 (M+1), HPLC: 2.30 min (Method C).

Example 17

N$^2$-[(3,5-Difluorophenyl)acetyl]-N$^1$-[(2R,3R)-2-(3,5-difluorophenyl)-5-methyl-4-oxo-2,3,4,5-tetrahydro-1,5-benzothiazepin-3-yl]-L-alaninamide (17)

To a solution of N$^2$-[(3,5difluorophenyl)acetyl]-N$^1$-[(2R,3R)-2-(3,5-difluorophenyl)-4-oxo-2,3,4,5-tetrahydro-1,5-benzothiazepin-3-yl]-L-alaninamide (16) (85 mg, 0.16 mmol) in DMF (1 ml) was added a 60% suspension of NaH (6.6 mg, 0.165 mmol). The reaction was stirred at RT for 5 min and methyl iodide (23 mg, 0.16 mmol) was added via syringe. The reaction was stirred at RT for 3 h and was quenched with dropwise addition of 1N HCl, diluted with water and extracted with ethyl acetate. The organic phase was collected and washed with H$_2$O, dried, filtered and evaporated to yield a crude oil (85 mg). The crude product was purified by flash chromatography (50% ethyl acetate/hexanes) to afford the title compound (17) (70 mg, 80%) as a 1:1 mixture with the 2S,3S diastereomer as a white solid. $^1$H NMR (300 MHz, CDCl$_3$) δ0.99 (d, 1.5H), 1.17 (d, 1.5H), 3.44 (s, 1H), 3.46 (s, 1H), 3.50 (s, 3H), 4.24 (m, 1H), 4.70 (m, 1H), 5.15 (m, 1H), 5.77 (d, 0.5H), 5.91 (d, 0.5H), 6.46 (dd, 1H), 6.65-6.92 (m, 6H), 7.31 (m, 2H), 7.51 (m, 1H), 7.71 (m, 1H). MS APCI, m/z=546 (M+1). LC/MS: 2.80 min.

Example 18

N$^2$-[(3,5-Difluorophenyl)acetyl]-N$^1$-[(2R,3R)-2-(2-fluorophenyl)-5-methyl-4-oxo-2,3,4,5-tetrahydro-1,5-benzothiazepin-3-yl]-L-alaninamide (18)

Using a procedure similar to that described in Example 17, except using (2,3-cis)-3-amino-2-(2-fluorophenyl)-2,3-dihydro-1,5-benzothiazepin-4(5H)-one (90) (100 mg, 0.20 mmol) as the amine component, the title compound (18) was obtained in a 1:1 mixture with the 2S,3S diastereomer (70 mg, 68%) as a white solid. $^1$H NMR (300 MHz, CDCl$_3$) δ1.00 (d, 1.5H), 1.18 (d, 1.5H), 3.42 (s, 1H), 3.46 (s, 1H), 3.50 (s, 3H), 4.22 (m, 1H), 4.85 (m, 1H), 5.61 (m, 1H), 5.94 (m, 0.5H), 6.04 (m, 0.5H), 6.32 (m, 1H), 6.73 (m, 2H), 7.01 (m, 1H), 7.19-7.33 (m, 6H), 7.51 (m, 1H), 7.72 (m, 1H). MS APCI, m/z=550 (M+23). LC/MS: 2.78 min.

Example 19

N$^1$-(2R,3R)-2-(3-Chlorophenyl-5-[2-(dimethylamino)ethyl]-4-oxo-2,3,4,5-tetrahydro-1,5-benzothiazepin-3-yl-N$^2$-[(3,5-Difluorophenyl)acetyl]-L-alaninamide (19)

Using a procedure similar to that described in Example 1, part d, except using (2,3-cis)-3-amino-2-(3-chlorophenyl)-5-[2-(dimethylamino)ethyl]-2,3-dihydro-1,5-benzothiazepin-4(5H)-one (19b) (63 mg, 0.17 mmol) as the amine component, the title compound (19) was obtained as a 1:1 mixture with the 2S,3S diastereomer (45 mg, 45%) as a white solid. (flash column chromatography conditions: 5-10% methanol-dichloromethane). $^1$H NMR (300 MHz, CDCl$_3$) δ0.95 (d, 1.5H), 1.16 (d, 1.5H), 2.29 (s, 6H), 2.43 (m, 1H), 2.65 (m, 1H), 3.43 (s, 1H), 3.45 (s, 1H), 3.64 (m, 1H), 4.19 (m, 1H), 4.48 (m, 1H), 4.66 (td, 1H), 5.15 (d, 1H), 5.73 (d, 0.5H), 5.95 (d, 0.5H), 6.34 (d, 0.5H), 6.42 (d, 0.5H), 6.74 (m, 3H), 7.2-7.4 (m, 3H), 7.45 (m, 4H), 7.72 (d, 1H). MS APCI, m/z=601 (M+1). LC/MS: 2.03 min.

The starting amine, (2,3-cis)-3-amino-2-(3-chlorophenyl)-5-[2-(dimethylamino)ethyl]-2,3-dihydro-1,5-benzothiazepin-4(5H)-one (19b), was prepared in the following manner:

a. Benzyl {(2R,3R)-5-[2-(dimethylamino)ethyl]-4-oxo-2-phenyl-2,3,4,5-tetrahydro-1,5-benzothiazepin-3-yl}carbamate hydrochloride (19a)

Using a procedure similar to that described in Example 14, part a, except using benzyl [(2,3-cis)-4-oxo-2-(3-chlorophenyl-2,3,4,5-tetrahydro-1,5-benzothiazepin-3-yl]carbamate (15c) (311 mg, 0.71 mmol) as the amide component, the pure title compound (19a) (250 mg, 69%) was obtained as a white solid.

b. (2,3-cis)-3-Amino-5-[2-(dimethylamino)ethyl]-2-(3-chlorophenyl)-2,3-dihydro-1,5-benzothiazepin-4(5H)-one (19b)

Using a procedure similar to that described in Example 14, part b, substituting benzyl {(2,3-cis)-5-[2-(dimethylamino)ethyl]-4-oxo-2-(3-chlorophenyl)-2,3,4,5-tetrahydro-1,5-benzothiazepin-3-yl}carbamate (19a) (95 mg, 0.19 mmol) as the protected amine component, the crude product was isolated as the hydrobromide salt. Partitioned between ethyl acetate and saturated sodium bicarbonate, the organic layer washed with brine, dried, filtered and evaporated to afford slightly crude title compound (19b) (63 mg, 90%) as a white semi-solid.

Example 20

N$^2$-[(3,5-Difluorophenyl)acetyl]-N$^1$-[(2R,3R)-2-(2,5-difluorophenyl)-4-oxo-2,3,4,5-tetrahydro-1,5-benzothiazepin-3-yl]-D-serinamide (20)

Using a procedure similar to that described in Example 4, except using N-[(3,5-difluorophenyl)acetyl]-D-serine as the acid component, the title compound (20) was obtained as a 1:1 mixture with the 2S,3S diastereomer (150 mg, 73%) as a white solid. $^1$H NMR (300 MHz, DMSO) δ (d, 3H), 3.48 (s, 2H), 4.24 (m, 1H), 4.77 (m, 2H), 5.48 (dd, 1H), 6.93 (m, 2H), 7.05 (m, 1H), 7.18-7.35 (m, 5.5H), 7.45-7.55 (m, 2.5H), 7.64 (d, 0.5H), 7.72 (d, 1H), 7.79 (d, 0.5H), 8.13 (t, 1H), 10.64 (s, 1H). MS APCI, m/z=548 (M+1). LC/MS: 2.46 min.

a. N-[(3,5-Difluorophenyl)acetyl]-D-serine

Was prepared as in Example 4 except using methyl D-serinate as the reactant.

Example 21

N$^1$-[(2R,3R)-2-(3-Chlorophenyl)-5-methyl-4-oxo-2,3,4,5-tetrahydro-1,5-benzothiazepin-3-yl]-N$^2$-[(3,5-difluorophenyl)acetyl]-L-alaninamide (21)

Using a procedure similar to that described in Example 11, except using (2,3-cis)-3-amino-2-(3-chlorophenyl)-5-methyl-2,3-dihydro-1,5-benzothiazepin-4(5H)-one (21b) (72 mg, 0.18 mmol) as the amine component, the title compound (21) was obtained in a 1:1 mixture with the 2S,3S diastereomer (90 mg, 92%) as a white solid. $^1$H NMR (300 MHz, CDCl$_3$) δ0.95 (d, 1.5H), 1.16 (d, 1.5H), 3.43 (s, 1H), 3.45 (s, 1H), 3.50 (s, 3H), 4.21 (m, 1H), 4.72 (m, 1H), 5.13 (dd, 1H), 5.77 (m, 0.5H), 6.48 (m, 0.5H), 6.75 (m, 3H), 7.25-7.33 (m, 7H), 7.51 (t, 1H), 7.72 (d, 1H). MS APCI, m/z=544 (M+1). LC/MS: 2.84 min.

The starting amine, (2,3-cis)-3-amino-2-(3-chlorophenyl)-5-methyl-2,3-dihydro-1,5-benzothiazepin-4(5H)-one (21b) was prepared in the following manner:

a. Benzyl [(2,3-cis)-4-oxo-2-(3-chlorophenyl)-2,3,4,5-tetrahydro-1,5-benzothiazepin-3-yl]carbamate (21a)

Using a procedure similar to that described in Example 5, part a, substituting benzyl [(2,3-cis)-2-(3-chlorophenyl)-4-oxo-2,3,4,5-tetrahydro-1,5-benzothiazepin-3-yl]carbamate (15c) (170 mg, 0.39 mmol) as the amide component, the title compound (21a) was obtained in a 1:1 mixture with the 2S,3S diastereomer (101 mg, 58%) as a white solid. (flash column chromatography:ethyl acetate). MS APCI, m/z=476 (M+Na). LC/MS: 3.25 min.

b. (2,3-cis)-3-Amino-2-(3-chlorophenyl)-5-methyl-2,3-dihydro-1,5-benzothiazepin-4(5H)-one hydrobromide (21b)

Using a procedure similar to that described in Example 1, part d Method D, except using benzyl [(2,3-cis)-4-oxo-2-(3-chlorophenyl)-2,3,4,5-tetrahydro-1,5-benzothiazepin-3-yl]carbamate (21a), (98 mg, 0.22 mmol) as the protected amine component, the title compound (21b) was obtained (80 mg, 91%) as a white solid. 1H NMR (300 MHz, DMSO-d6) δ3.48 (s, 3H), 4.27 (d, 1H, J=7.0 Hz), 5.14 (d, 1H, J=7.0 Hz), 7.37-7.56 (m, 5H), 7.66 (m, 2H), 7.75 (m, 1H), 8.07 (br, 3H). MS APCI, m/z=319 (M+1), LC/MS: 2.47 min.

Example 22

$N^2$-[(3,5-Difluorophenyl)acetyl]-$N^1$-[(2R,3R)-5-methyl-4-oxo-2-phenyl-2,3,4,5-tetrahydro-1,5-benzothiazepin-3-yl]-L-alaninamide (22)

Using a procedure similar to that described in Example 11, except using (2,3-cis)-3-amino-5-methyl-2-phenyl-2,3-dihydro-1,5-benzothiazepin-4(5H)-one hydrobromide (22b) (99 mg, 0.27 mmol) as the amine component, the title compound (22) was obtained in a 1:1 mixture with the 2S,3S diastereomer (132 mg, 96%) as an off white solid. $^1$H NMR (300 MHz, CDCl$_3$) δ0.89 (d, 1.5H), 1.14 (d, 1.5H), 3.41 (s, 1H), 3.43 (s, 1H), 3.51 (s, 3H), 4.17 (m, 1H), 4.75 (dt, 1H), 5.14 (d, 1H), 5.75 (m, 0.5H), 5.97 (m, 0.5H), 6.33 (t, 1H), 6.73 (m, 3H), 7.30-7.33 (m, 7H), 7.51 (m, 1H), 7.72 (d, 1H). MS APCI, m/z=510(M+1). LC/MS: 2.41 min.

The starting amine, (2,3-cis)-3-amino-2-phenyl-5-methyl-2,3-dihydro-1,5-benzothiazepin-4(5H)-one (22b) was prepared in the following manner:

a. Benzyl [(2R,3R)-5-methyl-4-oxo-2-phenyl-2,3,4,5-tetrahydro-1,5-benzothiazepin-3-yl]carbamate (22a)

Using a procedure similar to that described in Example 5, part a, substituting benzyl [(2,3-cis)-4-oxo-2-phenyl-2,3,4,5-tetrahydro-1,5-benzothiazepin-3-yl]carbamate (9c) (300 mg, 0.74 mmol) as the amide component, the title compound (22a) was obtained in a 1:1 mixture with the 2S,3S diastereomer (285 mg, 91%) as a white solid. (recrystallized from ethyl acetate). MS APCI, m/z=441 (M+Na). LC/MS: 2.92 min.

b. (2,3-cis)-3-Amino-5-methyl-2-phenyl-2,3-dihydro-1,5-benzothiazepin-4(5H)-one hydrobromide (22b)

Using a procedure similar to that described in Example 1, part d Method D, except using benzyl [(2,3-cis)-4-oxo-2-phenyl-2,3,4,5-tetrahydro-1,5-benzothiazepin-3-yl]carbamate (22a), (260 mg, 0.622 mmol) as the protected amine component, the title compound (22b) was obtained (170 mg, 75%) as a white solid. $^1$H NMR (300 MHz, DMSO-d6) δ3.49 (s, 3H), 4.21 (d, 1H, J=7.0 Hz), 5.12 (d, 1H, J-7.0 Hz), 7.37-7.53 (m, 6H), 7.65 (m, 2H), 7.75 (d, 1H), 8.04 (br, 3H).MS APCI, m/z=353 (M+1). HPLC 2.25 min (Method C).

Example 23

$N^1$-[(2R,3R)-5-Cyclohexyl-4-oxo-2-phenyl-2,3,4,5-tetrahydro-1,5-benzothiazepin-3-yl]-$N^2$-[(3,5-Difluorophenyl)acetyl]-L-alaninamide (23)

Using a procedure similar to that described in Example 11, except using (2,3-cis)-3-amino-5-cyclohexyl-2-phenyl-2,3-dihydro-1,5-benzothiazepin-4(5H)-one (23b) 130 mg, 0.37 mmol) as the amine component, the title compound (23) was obtained in a 1:1 mixture with the 2S,3S diastereomer (210 mg, 98%) as an off white solid. $^1$H NMR (300 MHz, CDCl$_3$) δ0.84 (d, 1.5H), 1.10 (m, 2H), 1.13 (d, 1.5H), 1.2-1.9 (m, 7H), 2.19 (m, 1H), 3.41 (s, 2H), 4.15 (m, 1H), 4.55 (m, 2H), 5.03 (d, 1H), 5.69 (m, 0.5H), 5.99 (m, 0.5H), 6.35 (dd, 1H), 6.73 (d, 2.5H), 7.35 (m, 7H), 7.47 (m, 1.5H), 7.75 (d, 1H). MS APCI, m/z=578 (M+1). LC/MS: 3.35 min.

The starting amine, (2,3-cis)-3-amino-5-cyclohexyl-2-phenyl-2,3-dihydro-1,5-benzothiazepin-4(5H)-one (23b) was prepared in the following manner:

a. Benzyl [(2,3-cis)-5-cyclohex-2-en-1-yl-4-oxo-2-phenyl-2,3,4,5-tetrahydro-1,5-benzothiazepin-3-yl]carbamate (23a)

Using a procedure similar to that described in Example 2, part a, substituting benzyl [(2,3-cis)-4-oxo-2-phenyl-2,3,4,5-tetrahydro-1,5-benzothiazepin-3-yl]carbamate (9c) (500 mg, 1.24 mmol) as the amide component, the title compound (23a) was obtained in a 1:1 mixture with the 2S,3S diastereomer (400 mg, 67%) as a white solid. (recrystallized from ether). MS APCI, m/z=485 (M+1). LC/MS: 3.31.

b. (2,3-cis)-3-Amino-5-cyclohexyl-2-phenyl-2,3-dihydro-1,5-benzothiazepin-4(5H)-one (23b)

Using a procedure similar to that described in Example 1, part d Method C, except using benzyl [(2,3-cis)-5-cyclohex-2-en-1-yl-4-oxo-2-phenyl-2,3,4,5-tetrahydro-1,5-benzothiazepin-3-yl]carbamate (23a), (360 mg, 0.749 mmol) as the protected amine component, the title compound (23b) was obtained (247 mg, 94%) as a white semi-solid. $^1$H NMR (300 MHz, CDCl$_3$) δ1.31-1.89 (m, 12 h), 2.21 (m, 1H), 3.62 (d, 1H, J=7.0 Hz), 4.69 (d, 1H, J=7.0 Hz), 7.27-7.49 (m, 8H), 7.71 (m, 1H). MS APCI, m/z=353 (M+1). LC/MS: 2.45 min.

Example 24

$N^1$-[(2R,3R)-7-Chloro-5-cyclohexyl-4-oxo-2-phenyl-2,3,4,5-tetrahydro-1,5-benzothiazepin-3-yl]-$N^2$-[(3,5-difluorophenyl)acetyl]-L-alaninamide (24)

Using a procedure similar to that described in Example 11, except using (2,3-cis)-3-amino-7-chloro-5-methyl-2-phenyl-2,3-dihydro-1,5-benzothiazepin-4(5H)-one hydrobromide (24b) (91 mg, 0.194 mmol) as the amine component, the title compound (24) was obtained in a 1:1 mixture with the 2S,3S diastereomer (114 mg, 96%) as an off white solid. The diastereomers were separated by flash column chromatography (Rf=0.25 vs 0.30 for (2S,3S), 35% ethyl acetate-Hexanes) eluting with 25-50% ethyl acetate-hexanes to afford the pure title compound (35 mg) as a white solid. $^1$H NMR (300 MHz, CDCl$_3$) δ1.14 (d, 3H), 1.2-2.1 (m, 9H), 2.19 (m, 1H), 3.41 (s, 2H), 4.14 (m, 1H), 4.52 (m, 2H), 5.00 (d, 1H), 5.70 (d, 1H), 6.34 (d, 1H), 6.40 (d, 1H), 6.76 (m, 2.5H), 7.3-7.4 (m, 6.5H), 7.67 (d, 1H). MS APCI, m/z=612 (M+1). LC/MS: 3.28min.

The starting amine, (2,3-cis)-3-amino-7-chloro-5-cyclohexyl-2-phenyl-2,3-dihydro-1,5-benzothiazepin-4(5H)-one (24b) was prepared in the following manner:

a. Benzyl [(2,3-cis)-7-chloro-5-cyclohex-2-en-1-yl-4-oxo-2-phenyl-2,3,4,5-tetrahydro-1,5-benzothiazepin-3-yl]carbamate (24a)

Using a procedure similar to that described in Example 2, part a, substituting benzyl [(2,3-cis)-7-chloro-4-oxo-2-phenyl-2,3,4,5-tetrahydro-1,5-benzothiazepin-3-yl]carbamate (13b) (290 mg, 0.66 mmol) as the amide component, the title compound (24a) was obtained in a 1:1 mixture with the 2S,3S diastereomer (220 mg, 64%) as a white solid. (recrystallized from ether). MS APCI, m/z=519 (M+1). LC/MS: 3.51 min.

b. (2,3-cis)-3-Amino-7-chloro-5-cyclohexyl-2-phenyl-2,3-dihydro-1,5-benzothiazepin-4(5H)-one hydrobromide (24b)

A mixture of benzyl [(2,3-cis)-7-chloro-5-cyclohex-2-en-1-yl-4-oxo-2-phenyl-2,3,4,5-tetrahydro-1,5-benzothiazepin-3-yl]carbamate (24a), (200 mg, 0.622 mmol) and 10% Pd/C (200 mg, DeGussa type 50% wt $H_2O$) in glacial acetic acid (25 mL) was hydrogenated at 50 psi $H_2$ for overnight. The reaction mixture was filtered through diatomaceous earth and concentrated in vacuo. The crude oil (still contained unreduced CBZ) taken up in acetic acid (2 mL) added 30% HBr/acetic acid (2 mL) heated to 50° C. for 1 h, evaporated, recrystallized from ether to afford the title compound (with 10% des Cl product) as a white solid (115 mg, 64%). $^1$HNMR (300 MHz, d6-DMSO) δ1.03-2.14 (m, 11H), 4.13 (d, 1H, J=7.0 Hz), 4.96 (d, 1H, J=7.0 Hz), 7.45 (s, 5H), 7.53-7.63 (m, 2H), 7.79 (m, 1H), 7.93 (br 3H). MS APCI, M/z=387 (M+1). LC/MS: 2.55 min.

Example 25

$N^2$-[(3,5-Difluorophenyl)acetyl]-$N^1$-[(6R,7R)-7-(1-naphthyl)-5-oxo-1,4-thiazepan-6-yl]-L-alaninamide (25)

Using a procedure similar to that described in Example 11, except using (6,7-cis)-6-amino-7-(1-naphthyl)-1,4-thiazepan-5-one hydrobromide (25e) (110 mg, 0.30 mmol) as the amine component, the title compound (25) was obtained after recrystallization from ether in a 1:1 mixture with the 2S,3S diastereomer (82 mg, 55%) as a white solid. $^1$H NMR (300 MHz, CDCl$_3$) δ0.57 (d, 1.5H), 1.12 (d, 1.5H), 2.88-3.10 (m, 2H), 3.24 (s, 1H), 3.41 (s, 1H), 3.75-3.95 (m, 2H), 4.25 (m, 1H), 5.39 (m, 1H), 5.66 (d, 0.51), 6.09 (d, 0.5H), 6.35 (t, 1H), 6.6-6.8 (m, 2.5H), 6.76 (m, 2.5H), 6.86 (d, 0.5H), 7.03 (d, 0.5H), 7.3-7.5 (m, 3H), 7.61 (dd, 1H), 7.7-7.9 (m, 2 H), 7.96 (m, 1H). MS APCI, m/z=498 (M+1). LC/MS: 2.1 min.

The starting amine, (6,7-cis)-6-amino-7-(1-naphthyl)-1,4-thiazepan-5-one hydrobromide (25e), was prepared in the following manner:

a. Methyl (2Z)-2-{[(benzyloxy)carbonyl]amino}-3-(1-naphthyl)acrylate (25a)

Using a procedure similar to that described in Example 1 part a, except using 1-naphthylaldehyde (2.04 mL, 15.0 mmol) as the aldehyde component, the crude product was obtained as an oil (6.0 g). After recrystallization from ethyl acetate-ether-hexanes (cold) the pure title compound (25a) was obtained (3.9 g, 72%) as a white solid. MS APCI, m/z =362 (M+1), 2.77 min.

b. Methyl N-[(benzyloxy)carbonyl]-S2-{[(tert-butoxycarbonyl)amino]ethyl}-3-(1-naphthyl)cysteinate (25b)

Using a procedure similar to that described in Example 10 part b, substituting methyl (2Z)-2-{[(benzyloxy)carbonyl]amino}-3-(1-naphthyl)acrylate (25a) (2.8 g, 7.75 mmol) as the acrylate component and tert-butyl (2-mercaptoethyl)carbamate (5.3 g, 29.9 mmol) as the thio component (stirred 5 days), the title compound (25b) was obtained (3.3 g, 79%) as a semi-solid.

c. Methyl S-(2-aminoethyl)N-[(benzyloxy)carbonyl]-3-(1-naphthyl)cysteinate hydrochloride (25c)

To a stirred solution of methyl N-[(benzyloxy)carbonyl]-S-{2-[(tert-butoxycarbonyl)amino]ethyl}-3-(1-naphthyl)cysteinate (25b) (3.3 g, 6.13 mmol) in ethyl acetate (80 mL) at −30° C., was bubbled over HCl gas for 10 min, stirred at −30° C. for 15 min and then allowed to RT for 3 h. Evaporation to near dryness and precipitation from ether afforded pure title compound (25c) (2.6 g, 89%) as a white solid. MS APCI m/z=439 (M+1), 2.34 min.

d. Benzyl [(6,7-cis-7-(1-naphthyl)-5-oxo-1,4-thiazepan-6-yl]carbamate (25d)

To a stirred solution of methyl S-(2-aminoethyl)-N-[(benzyloxy)carbonyl]-3-(1-naphthyl)cysteinate hydrochloride (25c) (2.0 g, 4.2 mmol) in dichloromethane (35 mL) under nitrogen at 0 C was added via syringe a 2M solution of trimethyl aluminum (5 mL, 10.0 mmol), the reaction allowed to warm to RT and stirred overnight. The reaction was cooled to 0° C. and 1 N HCl added carefully until bubbling stopped, then 0.5 N HCl was added (20 mL). The aqueous layer was extracted with dichloromethane (2×20 mL), the organic layer dried (MgSO$_4$), filtered and evaporated to yield 2 g of crude product as a 3:1 mixture with the 6,7-trans product. Purification using flash column chromatography (1% methanol-dichloromethane) afforded the title compound (25d) (610 mg, 36%) as a white solid. MS APCI, m/z=407 (M+1), 2.37 min.

e. (6,7-cis)-6-Amino-7-(1-naphthyl)-1,4-thiazepan-5-one hydrobromide (25e)

Using a procedure similar to that described in Example 1, part d Method D, except using benzyl [(6,7-cis)-7-(1-naphthyl)-5-oxo-1,4-thiazepan-6-yl]carbamate (25d), (590 mg, 1.45 mmol) as the protected amine component, the title compound (25e) was obtained (500 mg, 88%) as a light yellow solid. $^1$H NMR (300 MHz, d6-DMSO) δ2.67-2.79 (m, 1H), 2.83-2.94 (m, 1H), 3.63-3.85 (m, 2H), 5.11 (m, 1H), 5.29 (d, 1H, J=4.0 Hz), 7.42-7.68 (m, 4H), 7.88-8.02 (m, 2H), 8.14 (d, 1H), 8.22 (br, 3H), 8.71 (br t, 1H). MS APCI, m/z=273 (M+Na), LC/MS: 1.23 min.

Example 26

(2S)-2-[(3,5-Difluorophenyl)acetyl]amino-N-[(6R, 7R)-7-(1-naphthyl)-5-oxo-1,4thiazepan-6-yl]-2-phenylacetamide (26)

To a solution of (2S)-2-amino-N-[(6,7-cis)-7-(1-naphthyl)-5-oxo-1,4-thiazepan-6-yl]-2-phenylacetamide hydrochloride (26b) (53 mg, 0.12 mmol) in dichloromethane (15 ml) at 0° C. under nitrogen was added 1 eq NMM (13 μl, 0.12 mmol), followed by the 3,5-difluorophenylacetic acid (21 mg, 0.12 mmol), HOBt-hydrate (40 mg, 0.264 mmol), EDAC.HCl (35 mg, 0.18 mmol) and NMM (34 μL, 0.18 mmol). The reaction mixture was stirred 2 h at 0° C., concentrated in vacuo and partitioned between $H_2O$ (100 ml) and ethyl acetate (125 ml). The organic phase was collected and consecutively washed with HCl (2×), $H_2O$, saturated $NaHCO_3$, and brine, dried and the solvent removed in vacuo to yield a crude semi-solid. This material was purified by flash column chromatography (5% methanol-$CHCl_3$) to afford the title compound (26) as a 1:1 mixture with the 2S,3S diastereomer (46 mg, 69%) as a white solid. $^1$H NMR (300 MHz, $CDCl_3$) δ2.77-2.96 (m, 2H), 3.47 (s, 2H), 3.57-3.78 (m, 2H), 5.25-5.40 (m, 2.5H), 5.49 (d, 0.5H), 6.31 (t, 0.5H), 6.54 (t, 0.5H), 6.66-6.86 (m, 6H), 6.95 (t, 1H), 7.06-7.25 (m, 4H), 7.32-7.49 (m, 3H), 7.54 (d, 0.5H), 7.62 (d, 0.5H), 7.79 (t, 1H), 6.86 (d, 0.5H), 7.95 (d, 0.5H). MS APCI, m/z=560 (M+1). LC/MS: 2.34 min.

The starting amine, (2S)-2-amino-N-[(6,7-cis)-7-(1-naphthyl)-5-oxo-1,4-thiazepan-6-yl]-2-phenylacetamide hydrochloride (26b), was prepared in the following manner:

a. tert-Butyl ((1S)-2-{[(6,7-cis)-7-(1-naphthyl)-5-oxo-1,4-thiazepan-6-yl]amino}-2-oxo-1-phenylethyl)carbamate (26a)

To a solution of (6,7-cis)-amino-7-(1-naphthyl)-1,4-thiazepan-5-one (25e) (162 mg, 0.545 mmol) in dichloromethane (15 ml) at 0° C. under nitrogen was added (2S)-[(tert-butoxycarbonyl)amino](phenyl)acetic acid (137 mg, 0.545 mmol) followed by HOBt-hydrate (190 mg, 1.24 mmol), EDAC.HCl (162 mg, 0.850 mmol) and NMM (93 μL, 0.850 mmol). The reaction mixture was stirred 1.5 h at 0° C. and for 30 min at RT, concentrated in vacuo and partitioned between $H_2O$ (25 ml) and ethyl acetate (25 ml). The organic phase was collected and consecutively washed with 0.5 N HCl (2×), $H_2O$, brine, dried and the solvent removed in vacuo to give the title compound (29a)(272 mg, 95%) as a light pink solid. MS APCI, m/z=528 (M+Na), LC/MS: 2.36 min.

b. (2S)-2-Amino-N-[(6,7cis)-7-(1-naphthyl)-5-oxo-1,4-thiazepan-6-yl]-2-phenylacetamide hydrochloride (26b)

Using a procedure similar to that described in Example 25, part c, except using tert-butyl ((1S)-2-{[(6,7-cis)-7-(1-naphthyl)-5-oxo-1,4-thiazepan-6-yl]amino}-2-oxo-1-phenylethyl)carbamate (26a) (130 mg, 0.257 mmol) as reactant, the title compound (26b) (114 mg, 99%) was obtained as a white solid. MS APCI, m/z=406 (M+Na), LC/MS: 1.55, 1.64 min.

Example 27

(2S)2-Hydroxy-4-methyl-N-((1S)-2-[(6R,7R)-7-(1-naphthyl)-5-oxo-1,4-thiazepan-6-yl]amino-2-oxo-1-phenylethyl)pentanamide (27)

Using a procedure similar to that described in example 28, except using (2S)-2-amino-N-[(6,7-cis)-7-(1-naphthyl)-5-oxo-1,4-thiazepan-6-yl]-2-phenylacetamide hydrochloride (26b) (50 mg, 0.113 mmol) as the amine component, the title compound (27) was obtained in a 1:1 mixture with the 6S,7S diastereomer (30 mg, 51%) as a white solid. $^1$H NMR (300 MHz, $CDCl_3$) δ0.82-0.88 (dd, 6H), 1.2-1.4 (m, 2H), 1.73 (m, 1H), 2.76-3.05 (m, 2H), 3.61 (m, 1.5H), 3.74-3.98 (m, 1.5H), 5.15-5.34 (m, 1.5H), 5.56 (q, 1H), 5.72 (d, 0.5H), 7.0-7.36 (m, 7H), 7.35-7.55 (t, 3H), 7.73 (dd, 1H), 7.8-8.0 (m, 3H), 8.13 (t, 1H), 8.32 (dd, 1H), MS APCI, m/z=520 (M+1). LC/MS: 2.29 min.

Example 28

(2S)-2-Hydroxy-4-methyl-N-((1S)-2-oxo-2-[(2R, 3S)-4-oxo-2-phenyl-2,3,4,5-tetrahydro-1,5-benzoxazepin-3-yl]amino-1-phenylethyl)pentanamide (28)

To a solution of (2S)-2-amino-N-[(2,3-cis)-4-oxo-2-phenyl-2,3,4,5-tetrahydro-1,5-benzoxazepin-3-yl]-2-phenylacetamide (58b) (110 mg,0.284 mmol) in dichloromethane (12 ml) at 0° C. under $N_2$ was added the (2S)-2-hydroxy-4-methylpentanoic acid (38 mg, 0.284 mmol) followed by addition of HOBt-hydrate (70 mg, 0.454 mmol), EDAC.HCl (65 mg, 0.341 mmol) and NMM (37 μL, 0.29 mmol). The reaction mixture was stirred 2 h at 0° C., concentrated in vacuo and partitioned between water (100 ml) and ethyl acetate (125 ml). The organic phase was collected and consecutively washed with HCl (2×), water, saturated $NaHCO_3$, and brine, dried and the solvent removed in vacuo to yield a crude semi-solid (140 mg). This material was purified by flash column chromatography eluting with 5% methanol-chloroform to afford the title compound (28) as a 1:1 mixture with the 2S,3R diastereomer (110 mg, 77%) as a white solid. $^1$H NMR (300 MHz, $CDCl_3$) δ0.77-0.88 (dd, 6H), 1.2-1.4 (m, 2H), 1.73 (m, 1H), 3.85 (m, 0.5H), 3.94 (m, 0.5H), 4.96 (t, 0.5H), 5.11 (t, 0.5H), 5.33 (t, 0.5H), 5.52-5.66 (m, 2.5H), 6.90 (d, 1H), 7.1-7.4 (m, 13H), 8.01 (dd, 1H), 8.19 (t, 1H), 10.23 (s, 0.5H), 10.29 (s, 0.5H). MS APCI, m/z=502(M+1). LC/MS: 2.36 and 2.44 min.

Example 29

$N^2$-[(2S)-2-Hydroxy-4-methylpentanoyl]-$N^1$-[(2R, 3s)-4-oxo-2-phenyl-2,3,4,5-tetrahydro-1,5-benzoxazepin-3-yl]-L-leucinamide (29)

Using a procedure similar to that described in example 28, except using $N^1$-[(2,3-cis)-4-oxo-2-phenyl-2,3,4,5-tetrahydro-1,5-benzoxazepin-3-yl]-L-leucinamide (29b) (80 mg,0.217 mmol) as the amine component, the title compound (29) was obtained in a 1:1 mixture with the 2S,3S diastereomer (90 mg, 86%) as an off white solid. $^1$H NMR (300 MHz, $CDCl_3$) δ0.73-0.88 (m, 12H), 1.2-1.5 (m, 6H), 1.73 (m, 1H), 3.81 (m, 1H), 4.33 (m, 1H), 4.96 (t, 0.5H), 5.03 (t, 0.5H), 5.33 (dd, 1H), 5.60 (dd, 1H), 7.11-7.27 (m, 4H), 7.28-7.38 (m, 5H), 7.53 (d, 0.5H), 7.61 (t, 1H), 7.77 (d, 0.5H), 10.28 (s, 0.5H), 10.30 (s, 0.5H). MS APCI, m/z=

The starting amine, $N^1$-[(2,3-cis)-4-oxo-2-phenyl-2,3,4,5-tetrahydro-1,5-benzoxazepin-3-yl]-L-leucinamide (29b), was prepared in the following manner:

a. N²-[tert-Butoxycarbonyl]-N¹-[(2,3-cis)-4-oxo-2-phenyl-2,3,4,5-tetrahydro-1,5-benzoxazepin-3-yl]-L-leucinamide (29a)

To a suspension of (2,3-cis)-3-amino-2-phenyl-2,3-dihydro-1,5-benzoxazepin-4(5H)-one hydrochloride (6e) (85 mg, 0.292 mmol) in dichloromethane (15 ml) at 0° C. under N₂ was added 1 eq NMM (32 ul, 0.292 mmol) and 4 drops DMF and the mixture stirred for 5 min. To the reaction mixture was added N-[(2,2-dimethylpropanoyl)oxy]-L-leucine (73 mg, 0.292 mmol), HOBt-hydrate (72 mg, 0.467 mmol), EDAC.HCl (67 mg, 0.35 1 mmol) and NMM (39 μL, 0.351 mmol). The reaction mixture was stirred 2 h at 0° C., concentrated in vacuo and partitioned between water (25 ml) and ethyl acetate (25 ml). The organic phase was collected and consecutively washed with water, brine, dried and the solvent removed in vacuo to give the title compound (29a) (135 mg, 98%) as a white solid.

b. N¹-[(2,3-cis)-4-Oxo-2-phenyl-2,3,4,5-tetrahydro-1,5benzoxazepin-3-yl]-L-leucinamide trifluoroacetate (29b)

To a solution of N²-[tert-butoxycarbonyl]-N¹-[(2,3-cis)-4-oxo-2-phenyl-2,3,4,5-tetrahydro-1,5-benzoxazepin-3-yl]-L-leucinamide (29a) in dichloromethane (1 ml) at 0° C. under N₂ was added a solution of 30% TFA in dichloromethane (2 ml). The reaction mixture stirred at 0° C. for 1 h and then at ambient temperature for 30 min., concentrated in vacuo to give the title compound (29b) as the TFA salt (105 mg, 88%) as a white solid. ¹H NMR (300 MHz, d6-DMSO) δ0.81 (m, 6H), 0.89 (m, 0.5 H), 1.30 (m, 1H), 1.45 (m, 1H), 1.56 (m, 0.5H), 4.45 (bm, 3H), 5.11 (q, 1H), 5.61 (t, 1H), 7.22 (m, 3H), 7.39 (m, 4H), 8.08 (m, 2H), 8.48 (d, 0.5H), 8.53 (d, 0.5H), 10.30 (s, 0.5H), 10.40 (s, 0.5H).

Example 30

N²-[(3,5-Difluorophenyl)acetyl]-N¹-[(6S,7R)-4-methyl-5-oxo-7-phenyl-1,4-oxazepan-6-yl]-L-alaninamide (30)

Using a procedure similar to that described in example 11, except using (6,7-cis)-6-amino-4-methyl-7-phenyl-1,4-oxazepan-5-one hydrochloride (30d) (100 mg, 0.389 mmol) as the amine component, to afford 150 mg crude product. After filtering thru a small plug of silica (chloroform) the title compound (30) was obtained in a 1:1 mixture with the 6R,7S diastereomer (122 mg, 70%) as a white foam. ¹H NMR (300 MHz, CDCl₃) δ0.81 (d, 1.5H), 1.18 (d, 1.5H), 3.11 (s, 3H), 3.40 (m, 1H), 3.45 (s, 1H), 3.46 (s, 1H), 3.73 (m, 1H), 3,92 (m, 2H), 4.25 (m, 1H), 4.97 (dd, 1H), 5.19 (q, 1H), 5.77 (d, 0.5H), 6.08 (d, 0.5H), 6.7-6.9 (m, 3H), 7.2-7.3 (m, 6H). MS APCI, m/z=446(M+1). LC/MS: 1.85 min.

The starting amine, (6,7-cis)-6-amino-4-methyl-7-phenyl-1,4-oxazepan-5-one hydrochloride (30d), was prepared in the following manner:

a. (2,3-trans)-N-(2-Hydroxyethyl)-N-methyl-3-phenyloxirane-2-carboxamide (30a)

To a solution of ethyl (2,3-trans)-3-phenyloxirane-2-carboxylate (10 g, 52.0 mmol) in methanol (20 mL) at −20° C. was added 2-(methylamino)ethanol (4.6 g, 62.0 mmol) followed by catalytic sodium methoxide (25%, 20 drops). The reactionwas then set in a freezer (~20 C) for 10 days, diluted with 10% HCl (10 drops), water (100 mL), extracted with dichloromethane (2×), and the organic layers combined, dried, filtered and evaporated to afford the title compound (30a) (9.7 g, 84%). MS APCI, m/z=222 (M+1). LC/MS: 1.03 min.

b. (6,7-trans)-6-Hydroxy-4-methyl-7-phenyl-1,4-oxazepan-5one (30b)

To a stirred solution of (2,3-trans)-N-(2-hydroxyethyl)-N-methyl-3-phenyloxirane-2-carboxamide (30a) (5.4 g, 24.4 mmol) in anhydrous THF (300 mL) was added 10 mol % of MgI₂ (670 mg, 2.44 mmol, 98% purity) and the mixture heated to reflux overnight, cooled, and evaporated to a crude orange oil. Isocratic flash column chromatography (1% methanol-dichloromethane) returned the title compound (30b)(2.7 g, 50%). MS APCI, m/z=222 (M+1) LC: 1.78 min.(Method A)

c. (6,7-cis)-6-Azido-4-methyl-7-phenyl-1,4oxazepan-5-one (30c)

To an ice cooled solution of (6,7-trans)-6-hydroxy-4-methyl-7-phenyl-1,4-oxazepan-5-one(30b) (900 mg, 4.1 mmol) in dichloromethane (20 mL) was added lutidine ((524 μL, 4.5 mmol), followed by dropwise addition of triflic anhydride (753 μL, 4.4 mmol) in dichloromethane (3 mL) and the mixture stirred at 0° C. for 20 min, concentrated under vacuo to give crude triflate (containing 32% starting (30b)). The crude intermediate dissolved in DMF (5 L), cooled to 0° C., sodium azide (1.33 g, 20.5 mmol) added all at once. The mixture stirred at 0° C. for 1 h., then at RT overnight. The mixture diluted with water (50 mL) and extracted with ethyl acetate (2×). The organic extract was collected, washed consecutively with saturated aqueous sodium bicarbonate (2×), and brine, dried, filtered and evaporated (1.1 g dark oil). The crude product was purified by flash chromatography (3% methanol-dichloromethane) to yield nearly pure title (30c) (385 mg, 38%). MS APCI, m/z=247 (M+1) 218 (M+1−N₂). LC/MS: 1.75 min.

d. (6,7-cis)6-Amino-4-methyl-7-phenyl-1,4-oxazepan-5-one hydrochloride (30d)

A mixture of (6,7-cis)-6-azido-4-methyl-7-phenyl-1,4-oxazepan-5-one(30c) (300 mg, 1.54 mmol) and 10% Pd/C (30 mg, DeGussa type 50% wt water) in absolute ethanol (45 mL) and 1N HCl (3 mL, 3.0 mmol) was hydrogenated at 20 psi for 3 days. The reaction mixture was filtered through diatomaceous earth and concentrated in vacuo to afford the title compound as a white solid (170 mg, 43%). ¹H NMR (300 MHz, d6-DMSO) δ3.02 (s, 3H), 3.43 (m, 2H), 3.91-4.17 (m, 2H), 4.85 (m, 1H), 5.10 (m, 1), 7.27-7.45 (m, 5H), 8.32 (br, 3H). MS APCI, m/z=221 (M+1). LC/MS: 0.68 min.

Example 31

N²-[(3,5-Difluorophenyl)acetyl]-N¹-[(2S,6S,7R)-4-methyl-5-oxo-2,7-diphenyl-1,4-oxazepan-6-yl]-L-alaninamide (31)

Using a procedure similar to that described in example 11, except using (2SR,6SR,7RS)-6-amino-4-methyl-2,7-diphenyl-1,4-oxazepan-5-one hydrochloride (31d) (100 mg, 0.34 mmol) as the amine component, the title compound (31) was obtained in a 1:1 mixture with the 6R,7S diastereomer (160 mg, 90%) as a white solid. ¹H NMR (300 MHz, CDCl₃) δ0.73 (d, 1.5H), 1.13 (d, 1.5H), 2.88 (s, 1.5H), 2.92 (s, 1.5H), 3.45 (s, 2H), 3.53 (m, 1H), 4.1-4.3 (m, 2H), 4.86 (m, 1H), 5.13 (dd, 1H), 5.30 (m, 1H), 5.61 (d, 0.5H), 6.06 (d, 0.5H), 6.68-6.92 (m, 3H), 7.2-7.4 (m, 11H). MS ES+, m/z=522(M+1). HPLC: 2.93 min. (Method A).

The starting amine, (6,7-cis)-6-amino-4-methyl-7-phenyl-1,4-oxazepan-5-one hydrochloride (31d), was prepared in the following manner:

a. (2,3-trans)-N-(2-Hydroxy-2-phenylethyl)-N-methyl-3-phenyloxirane-2-carboxamide (31a)

To a solution of ethyl (2,3-trans)-3-phenyloxirane-2-carboxylate (5.0 g, 23.9 mmol) in methanol (10 mL) at −20° C. was added 2-(methylamino)-1-phenylethanol (4.29 g, 28.4 mmol) followed by catalytic sodium methoxide (25%, 10 drops). The reaction was placed in a freezer (~−20C) for 2 days, filtered and washed with cold methanol to afford the title compound (31a) as a white solid (3.3 g, 460%).

b. (2RS,6SR,7SR-6-Hydroxy-4-methyl-2,7-diphenyl-1,4-oxazepan-5-one (31b)

To a stirred solution of (2,3-trans)-N-(2-hydroxy-2-phenylethyl)-N-methyl-3-phenyloxirane-2-carboxamide (31a) (2.1 g, 7.6 mmol) in anhydrous THF (300 mL) was added 10 mol % of $MgI_2$ (215 mg, 0.76 mmol, 98% purity) and the mixture heated to reflux over a weekend, cooled, and evaporated to an orange oil. Isocratic flash column chromatography (1% methanol-dichloromethane) afforded the title compound (31b) (900 mg, 43%). MS APCI, m/z=298 (M+Na). LC: 2.84 min.(Method A).

c. (2RS,6SR,7RS)-6-Azido-4-methyl-2,7-diphenyl-1,4oxazepan-5-one (31c)

To an ice cooled solution of (2RS,6SR,7SR)-6-hydroxy-4-methyl-2,7-diphenyl-1,4-oxazepan-5-one (31b) (1.9 g, 6.39 mmol) in dichloromethane (45 mL) was added lutidine (1.12 mL, 9.6 mmol), followed by dropwise addition of triflic anhydride (1.6 mL, 9.6 mmol) in dichloromethane (5 mL), and the mixture stirred at 0° C. for 20 min, concentrated under vacuo (cold), then under high vacuum for 20 min to give crude triflate. The crude intermediate in DMF (5 mL) was cooled to 0° C. and sodium azide (2.1 g, 32.0 mmol) added in one portion. The mixture stirred at 0° C. for 1 h., then at RT overnight. The reaction diluted with water (100 mL), extracted with ethyl acetate (3×), the organic extract was collected and washed consecutively with saturated aqueous sodium bicarbonate (2×), and brine, dried, filtered and evaporated to a dark oil. The crude product was purified by flash chromatography (3%methanol-dichloromethane) to yield nearly pure title (31c) (1.0 g, 48%). MS APCl m/z=272(M+1−$N_2$). LC/MS: 2.36min.

d. (2SR,6SR,7RS)-6-Amino-4-methyl-2,7-diphenyl-1,4-oxazepan-5-one hydrochloride (31d)

Using a procedure similar to that described in example 30, part d, except using (2RS,6SR,7RS)-6-azido-4-methyl-2,7-diphenyl-1,4-oxazepan-5-one (31c) (1.0 g, 3.1 mmol) as the azido component, the title compound (31d) was obtained as a white solid (940 mg, 94%).

$^1$H NMR (300 MHz, d6-DMSO) δ2.33 (s, 3H), 3.64 (m, 1H), 4.22 (m, 1H), 4.86 (m, 1H), 5.08 (m, 1H), 5.26 (d, 1H, J=6.6 Hz), 7.27-7.50 (m, 10H), 8.18 (br, 3H). MS APCI, m/z=297(M+1).

Example 32

$N^2$-[(3,5-Difluorophenyl)acetyl]-$N^1$-[(6R,7R)-4-methyl-5-oxo-7-phenyl-1,4-thiazepan-6-yl]-L-alaninamide (32)

Using a procedure similar to that described in example 11, except using (6,7-cis)-6-amino-4-methyl-7-phenyl-1,4-thiazepan-5-one (32c) (50mg,0.211 mmol) as the amine component, the title compound (32) was obtained in a 1:1 mixture with the 6S,7S diastereomer (72 mg, 74%) as a white foam. $^1$H NMR (300 MHz, $CDCl_3$) δ0.87 (d, 1.5H), 1.18 (d, 1.5H), 2.87-3.08 (m, 2H), 3.13 (s, 3H), 3.46 (s, 1H), 3.48 (s, 1H), 3.6-3.7 (m, 1H), 3.9-4.1 (m, 1H), 4.25 (m, 1H), 4.37 (dd, 1H), 5.35 (q, 1H), 5.83 (d, 0.5H), 6.07 (d, 0.5H), 6.68-6.96 (m, 4H), 7.18 (m, 2H), 7.26 (m, 3H). MS APCI, m/z=462(M+1). LC/MS: 1.88 min.

The starting amine, (6,7-cis)-6-amino-4-methyl-7-phenyl-1,4-thiazepan-5-one (32c)), was prepared in the following manner:

a. tert-Butyl [(6,7-cis)-5-oxo-7-phenyl-1,4-thiazepan-6-yl]carbamate (32a)

To an ice cooled solution of (6,7-cis)-6-amino-7-phenyl-1,4-thiazepan-5-one hydrobromide (7d) (165 mg, 0.52 mmol) in dichloromethane (5 mL) under $N_2$ was added TEA (153 μL, 1.09 mmol), followed by di-tert-butyl carbonate (124 mg, 0.565 mmol). The mixture was stirred at 0° C. for 30 min. and at RT for 2 h, the volume reduced, and the residue partitioned between water and ethyl acetate. The organic extract was washed with brine, dried, filtered and evaporated to yield the title compound (32a) as a clear oil.

b. tert-Butyl [(6,7-cis)-4-methyl-5-oxo-7-phenyl-1,4-thiazepan-6-yl]carbamate (32b)

Using a procedure similar to that described in example 2 part, except using tert-butyl [(6,7-cis)-5-oxo-7-phenyl-1,4-thiazepan-6-yl]carbamate (32a) (74 mg, 0.22 mmol) as the amide component, and iodomethane (14 μL, 0.22 mmol) as the electrophile afforded crude title compound as an oil. Isocratic flash column chromatography (25% ethyl acetate-hexanes) afforded pure title compound (32b) (63 mg, 82%) as a clear oil.

c. (6,7-cis)-6-Amino-4-methyl-7-phenyl-1,4-thiazepan-5-one trifluoracetate (32c)

To an ice cooled solution of tert-butyl [(6,7-cis)-4-methyl-5-oxo-7-phenyl-1,4-thiazepan-6-yl]carbamate (32b) (133 mg, 0.396 mmol) was added 20% TFA in dichloromethane (3 mL), the mixture stirred at 0° C. for 1.5 h and at RT for 1 h, evaporated and placed under high vacuum overnight. Trituration with ether returned the title compound (32c) as a white solid (115 mg, 82%). $^1$H NMR (300 MHz, d6-DMSO) δ2.84-2.94 (m, 1H), 3.07 (s, 3H), 3.18 (m, 1H), 3.80-3.91 (m, 1H), 4.21 (m, 2H), 5.17 (d, 1H, J=3.5 Hz), 7.22 (m, 2H), 7.33 (m, 3H), 8.17 (br, 3H). MS APCI, m/z=237(M+1). LC/MS: 0.79 min.

Example 33

N²-[(3,5-Difluorophenyl)acetyl]-N¹-[(3R,6S,7)-4-methyl-5-oxo-3,7-diphenyl-1,4-oxazepan-6-yl]-L-alaninamide (33)

Using a procedure similar to that described in example 11, except using (3R,-6,7-cis)-6-amino-4-methyl-3,7-diphenyl-1,4-oxazepan-5-one hydrochloride (33d) (60 mg,0.180 mmol) as the amine component, afforded crude product (100 mg). After filtering thru a small plug of silica (chloroform) the title compound (30) was obtained in a 1:1 mixture with the 6R,7S diastereomer (55 mg, 59%) as a white foam.
¹H NMR (300 MHz, CDCl₃) δ1.04 (d, 3H), 2.78 (s, 3H), 3.42 (s, 2H), 4.00, (m, 2H), 4.41 (t, 1H), 5.00 (d, 1H), 5.23 (m, 1H), 5.50 (m, 2H), 6.76 (m, 3.5H), 7.25-7.35 (m, 7.5H), 7.44 (m, 3H). MS APCI, m/z=522(M+1). LC/MS: 2.30 min.

The starting amine, (3R-6,7-cis)-6-amino-4-methyl-3,7-diphenyl-1,4-oxazepan-5-one hydrochloride (33d), was prepared in the following manner:

a. (2RS,3RS)—N-[(1R)-2-Hydroxy-1-phenylethyl]-N-methyl-3-phenyloxirane-2-carboxamide (33a)

To a solution of ethyl (2,3-trans)-3-phenyloxirane-2-carboxylate (13.4 g, 70.2 mmol) in methanol (35 mL) at −20° C. was added the (2R)-2-(methylamino)-2-phenylethanol (12.6 g, 83.4 mmol) [Karim, A., et al., J. Organometallic Chem. (1986), 317(1), 93-104.], followed by catalytic sodium methoxide (25%, 30 drops). The reaction mixture was placed in a freezer (~−20° C.) for 3 days, diluted with 10% HCl (10 drops), water (100 mnL), and extracted with dichloromethane (2×). The combined organic layers were dried, filtered and evaporated to afford the title compound (33a) (12.2 g, 63%). MS APCI, m/z=276 (M+1), 298 (M+Na). HPLC: 5.68, 5.74 min (Method E).

b. (3R,6R,7R)-6-Hydroxy-4-methyl-3,7-diphenyl-1,4-oxazepan-5-one (33b)

To a stirred solution of (2RS,3RS)—N-[(1S)-2-hydroxy-1-phenylethyl]-N-methyl-3-phenyloxirane-2-carboxamide (30a) (1.7 g, 5.72 mmol) in anhydrous toluene (120 mL) was added MgI₂ (1.6 g, 5.72 mmol, 98% purity) and the mixture vigorously stirred at RT for 32 h. The mixture was treated with saturated ammonium chloride (50 mL) and water (50 mL) and stirred for 30 min. The separated organic layer was washed consecutively with saturated ammonium chloride and brine, dried, filtered and evaporated to an orange oil (1.6 g). Isocratic flash column chromatography (2:1 hexanes-ethyl acetate) separated the title compound (33b) (400 mg, 24%) as a white solid from the (3S,6S,7R) diastereomer (1.0 g, 59%). There was a significant NOE observed between proton 3 and proton 7. HPLC: 1.78 min (Method A).

c. (3R,6S,7R)-6-Azido-4-methyl-3,7-diphenyl-1,4-oxazepan-5-one (33c)

Using a procedure similar to Example 31 part c, except using (3R,6R,7R)-6-hydroxy-4-methyl-3,7-diphenyl-1,4-oxazepan-5-one (33b) (305 mg, 1.02 mmol) as reactant, the pure title compound (33c) (385 mg, 38%) was obtained as an off white solid d. (3R,6S,7R)-6-amino-3,7-diphenyl-1,4-oxazepan-5-one hydrochloride (33d)

Using a procedure similar to that described in example 30, part d, except using (3R,6S,7R)-6-azido-4-methyl-3,7-diphenyl-1,4-oxazepan-5-one (33c) (1.0 g, 3.1 mmol) as the azido component, gave the title compound (31) (170 mg, 96%) as a white solid. ¹H NMR (300 MHz, d6-DMSO) δ2.61 (s, 3H), 4.03 (m, 1H), 4.29 (m, 1H), 5.10 (d, 1H, J=7.9 Hz), 5.38 (m, 1H), 5.52 (m, 1H), 7.31-7.52 (m, 10H), 7.94 (br, 3H). MS APCI, m/z=297(M+1).

Example 34

(2S)-2-Hydroxy-4-methyl-N-((1S)-2-[(6S,7R)-4-methyl-5-oxo-7-phenyl-1,4-oxazepan-6-yl]amino-2-oxo-1-phenylethyl)pentanamide (34)

Using a procedure similar to that described in example 28, except using (²S)-2-amino-N-[(6,7-cis)-4-methyl -5-oxo-7-phenyl-1,4-oxazepan-6-yl]-2-phenylacetamide (34b) (73 mg,0.207 mmol) as the amine component, afforded crude product as an oil. After filtering thru a small plug of silica (chloroform), the title compound (34) was obtained in a 1:1 mixture with the 6R,7S diastereomer (80 mg, 83%) as an off white solid. ¹H NMR (300 MHz, CDCl₃) δ 0.92 (dd, 6H), 1.52 (m, 3H), 1.82 (m, 1H), 2.58 (d, 1H), 3.03 (s, 1.5H), 3.09 (s, 1.5H), 3.17 (m, 0.5H), 3.41 (m, 0.5H), 3.70 (m, 1.5H), 3.90 (m, 1.5H), 4.92 (d, 0.5H), 5.03 (d, 0.5H), 5.11 (t, 0.5H), 5.17 (d, 0.5H), 5.23 (t, 0.5H), 5.33 (d, 0.5H), 6.63 (d, 0.5H), 6.79 (d, 0.5H), 6.99 (m, 2H), 7.09 (t, 1H), 7.1-7.4 (m, 7H). MS APCI, m/z=468(M+1). LC/MS: 2.06 min.

The starting amine, (2S)-2-amino-N-[(6,7-cis)-4-methyl-5-oxo-7-phenyl-1,4-oxazepan-6-yl]-2-phenylacetamide (b), was prepared in the following manner:

a. tert-Butyl ((1S)-2-{[(6,7-cis)-4-methyl-5-oxo-7-phenyl-1,4-oxazepan-6-yl]amino}-2-oxo-1-phenylethyl)carbamate (34a)

To a suspension of (6,7-cis)-6-amino-4-methyl-7-phenyl-1,4-oxazepan-5-one hydrochloride (30d) (300 mg, 1.17 mmol) in dichloromethane (30 ml) at 0° C. under N₂ was added (2S)-[(tert-butoxycarbonyl)amino](phenyl)acetic acid (293 mg, 1.17 mmol) followed by NMM (128 μL, 1.17 mmol) and the mixture stirred 5 min. until solution cleared. To the reaction was added HOBt-hydrate (389 mg, 2.60 mmol), EDAC.HCl (336 mg, 1.76 mmol) and NMM (193 μL, 1.76 mmol). The reaction mixture was stirred 2 h at 0° C., concentrated in vacuo and partitioned between water and ethyl acetate. The organic phase was collected and consecutively washed with 0.25 N HCl (2×), water, brine, dried and the solvent removed in vacuo to give the title compound (34a) (380 mg, 72%) as a off white solid. MS APCI, m/z=454 (M+1) 476 (M+Na), LC/MS: 2.15 min.

b. (2S)-2-Amino-N-[(6,7-cis)-4-methyl-5oxo-7-phenyl-1,4-oxazepan-6-yl]-2-phenylacetamide trifluoroacetate (34b)

Using a procedure similar to that described in example 29, part b, except using tert-butyl ((1S)-2-{[(6,7-cis)-4-methyl-5-oxo-7-phenyl-1,4-oxazepan-6-yl]amino}-2-oxo-1-phenylethyl)carbamate (26a) (320 mg, 0.706 mmol), as the protected amine component, the title compound (26b) (220 mg, 67%) was obtained as a white solid ¹H NMR (300 MHz, d6-DMSO) δ2.77 (s, 1.5H), 2.95 (s, 1.5H), 3.22 (m, 1H), 3.72 (m, 2H), 3.98 (m, 1H), 4.75 (m, 0.5H), 4.90 (m, 1H), 4.96 (m, 0.5H), 5.17 (m, 1H), 6.89-7.05 (m, 2H), 7.12 (m, 0.5H), 7.21-7.52 (m, 8.5H), 8.55 (br, 3H). MS APCI, m/z=354(M+1).

Example 35

(2S)-2-[(3,5-Difluorophenyl)acetyl]amino-N-[(6S, 7R)-4-methyl-5-oxo-7-phenyl-1,4-oxazepan-6-yl]-2-phenylacetamide (35)

Using a procedure similar to that described in example 28, except using (2S)-2-amino-N-[(6,7-cis)-4-methyl-5-oxo-7-phenyl-1,4-oxazepan-6-yl]-2-phenylacetamide (26b) (73.0 mg, 0.207 mmol) as the amine component and (3,5-difluorophenyl)acetic acid (36.0 mg, 0.207 mmol) as the acid component, afforded crude product as an oil. After filtering thru a small plug of silica (chloroform), the title compound (35) was obtained in a 1:1 mixture with the 6R,7S diastereomer (75 mg, 71%) as a white foam. $^1$H NMR (300 MHz, CDCl$_3$) 3.00 (s, 1.5H), 3.08 (s, 1.5H), 3.13 (m, 1H), 3.39 (m, 1H;), 3.49 (s, 1H), 3.50 (s, 1H), 3.69 (m, 1.5H), 3.88 (m, 1.5H), 4.89 (d, 0.5H), 5.0-5.1 (m, 1.5H), 5.18 (t, 0.5H), 5.28 (d, 0.5H), 6.56 (d, 0.5H), 6.6-6.8 (m, 4H), 6.94 (t, 2H), 7.05 (t, 1H), 7.1-7.3 (m, 6.5H). MS APCI, m/z=508(M+1). LC/MS: 2.15 min.

Example 36

(2S)-2-Cyclohexyl-2-[(3,5-difluorophenyl)acetyl]amino-N-[(3R,6S,7R)-4-methyl-5-oxo-3,7-diphenyl-1,4-oxazepan-6-yl]acetamide (36)

Using a procedure similar to that described in example 11, except using (2S)-2-amino-2-cyclohexyl-N-[(3R,6S,7R)-4-methyl-5-oxo-3,7-diphenyl-1,4-oxazepan-6-yl]acetamide (36b) (42 mg, 0.097 mmol) as the amine component and (3,5-difluorophenyl)acetic acid (17 mg, 0.10 mmol) as the acid component, afforded crude product. Recrystallized from ether returned the title compound (36) (33 mg, 58%) as a white solid. $^1$H NMR (300 MHz, CDCl$_3$) δ0.66 (m, 1H), 0.82 (m, 1H), 1.11 (m, 4H), 1.59, (m, 4H), 2.77 (s, 3H), 3.45 (s, 2H), 3.87 (dd, 1H), 3.99 (dd, 1H), 4.37 (t, 1H), 4.98 (d, 1H), 5.23 (m, 1H), 5.51 (t, 1H), 5.64 (d, 1H), 6.7-6.85 (m, 3H), 7.26 (m, 7H), 7.36 (d, 2H), 7.44 (m, 13H). MS APCI, m/z=590(M+1). LC/MS: 2.59 min.

The starting amine, (2S)-2-amino-2-cyclohexyl-N-[(3R, 6S,7R)-4-methyl-5-oxo-3,7-diphenyl-1,4-oxazepan-6-yl]acetamide (36b), was prepared in the following manner:

a. tert-Butyl ((1S)-1-cyclohexyl-2-{[(6S,7R)-4-methyl-5-oxo-7-phenyl-1,4oxazepan-6-yl]amino}-2-oxoethyl)carbamate (36a)

Using a procedure similar to that described in example 11, except using (3R,6S,7R)-6-amino-4-methyl-3,7-diphenyl-1,4-oxazepan-5-one hydrochloride (33d) (53.0 mg, 0.159 mmol) as the amine component and (2S)-[(tert-butoxycarbonyl)amino](cyclohexyl)acetic acid (41.0 mg, 0.159 mmol) as the acid component, yielded the title compound (36a) (55 mg, 64%) as a white solid.

b. (2S)-2-Amino-2-cyclohexyl-N-[(3R,6S,7R)-4-methyl-5-oxo3,7-diphenyl-1,4-oxazepan-6-yl]acetamide (36b)

Using a procedure similar to that described in example 29, part b, except using tert-butyl ((1S)-1-cyclohexyl-2-{[(6S, 7R)-4-methyl-5-oxo-7-phenyl-1,4-oxazepan-6-yl]amino}-2-oxoethyl)carbamate (36a) (52 mg, 0.10 mmol), as the protected amine component, the title compound was obtained as the TFA salt. The salt was partitioned between saturated NaHCO$_3$-ethyl acetate, the organic extract washed with brine, dried, filtered and evaporated to afford pure title compound (36b) (42 mg, 99%) as a white solid. $^1$H NMR (300 MHz, CDCl$_3$) δ0.77-1.75(m, 13H), 2.80 (s, 3H), 2.84 (ma 1H), 4.01 (m, 1H), 4.43 (m, 1H), 4.99 (d, 1H, J=7.4 Hz), 5.23 (m, 1H), 5.56 (m, 1H), 7.26-7.49 (m, 10H), 7.78 (br, 1H). MS APCI, m/z=436(M+1), LC/MS: 1.73

Example 37

(2S)-2-[(3,5-Difluorophenyl)acetyl]amino-N-[(3R, 6S,7R)-4-methyl-5-oxo-3,7-diphenyl-1,4oxazepan-6-yl]-2-phenylacetamide (37)

To a solution of (2S)-2-amino-N-[(3R,6S,7R)-4methyl-5-oxo-3,7-diphenyl-1,4-oxazepan-6-yl]-2-phenylacetamide (37b) (42 mg, 0.098 mmol) in dichloromethane (5 ml) at 0° C. under N$_2$ was added the (3,5-difluorophenyl)acetic acid (17 mg, 0.098 mmol), HOBt-hydrate (33 mg, 0.215 mmol), EDAC.HCl (28 mg, 0.147 mmol) and NMM (18 μL, 0.147 mmol). The reaction mixture was stirred 1 h at 0° C., concentrated in vacuo and partitioned between 0.25N HCl (10 ml) and ethyl acetate (10 ml). The organic phase was collected and consecutively washed with 0.25N HCl (2×), water, saturated NaHCO$_3$, and brine, dried and the solvent removed in vacuo to yield an oil. After filtering thru a small plug of silica (chloroform) the title compound (37) was obtained (35 mg, 61%) as a white solid. $^1$H NMR (300 MHz, CDCl$_3$) δ2.67 (s, 3H), 3.49 (s, 2H), 3.97 (dd, 1H), 4.34 (t, 1H), 4.80 (d, 1H), 5.01 (d, 1H), 5.21 (dd, 1H), 5.46 (t, 1H), 6.48 (d, 1H), 6.7-6.8 (m, 3H), 7.02 (m, 2H), 7.2-7.3 (m, 10.5H), 7.40 (m, 3.5I). MS APCI, m/z=584(M+1). LC/MS: 2.51 min.

The starting amine, racemic (2S)-2-amino-N-[(3R,6S, 7R)-4-methyl-5-oxo-3,7-diphenyl-1,4-oxazepan-6-yl]-2-phenylacetamide (37b), was prepared in the following manner:

a. tert-Butyl (2-{[(3S,6R,7S)-4-methyl-5-oxo-3,7-diphenyl-1,4-oxazepan-6-yl]amino}-2-oxo-1-phenylethyl)carbamate (37a)

Using a procedure similar to that described in example 11, except using (3R,6S,7R)-6-amino-4-methyl-3,7-diphenyl-1, 4-oxazepan-5-one hydrochloride (33d) (53 mg, 0.159 mmol) as the amine component and (2S)-[(tert-butoxycarbonyl)amino]phenylacetic acid (40 mg, 0.159 mmol) as the acid component, the title compound (37a) (55 mg, 64%) was obtained as a white solid. MS APCI, m/z=552(M+Na). LC/MS:2.61 min.

b. (2S)-2-Amino-N-[(3R,6R,7S)-4-methyl-5-oxo-3, 7-diphenyl-1,4-oxazepan-6-yl]-2-phenylacetamide (37b)

Using a procedure similar to that described in example 25, part c, except using tert-butyl (2-{[(3S,6R,7S)-4-methyl-5- oxo-3,7-diphenyl-1,4-oxazepan-6-yl]amino}-2-oxo-1-phenylethyl)carbamate (37a) (52 mg, 0.10 mmol), the title compound (27b) (42 mg, 99%) was obtained as a white solid. $^1$H NMR (300 MHz, CDCl$_3$) δ2.77 (s, 3H), 3.99 (m, 1H), 4.16 (m, 1H), 4.40 (m, 1H), 4.97 (d, 1H, J=7.4 Hz), 5.25 (m, 1H), 5.57 (m, 1H), 6.84 (m, 2H), 7.13-7.52 (m, 15H), 7.88 (m, 1H). MS APCI, m/z=430 (M+1). LC/MS: 1.66 min.

Example 38

N$^2$-[(3,5-Difluorophenyl)acetyl]-N$^1$-[(6S,7R)-4-(4-methoxybenzyl)-5-oxo-7-phenyl-1,4-oxazepan-6-yl]-L-alaninamide (38)

Using a procedure similar to that described in example 11, except using (6,7-cis)-6-amino-4-(4-methoxybenzyl)-7-phenyl-1,4-oxazepan-5-one hydrochloride (38d) (100 mg, 0.275 mmol) as the amine component, the title compound (38) was obtained in a 1:1 mixture with the 6R,7S diastereomer (139 mg, 91%) as a white foam. $^1$H NMR (300 MHz, CDCl$_3$) δ0.87 (d, 1.5H), 1.21 (d, 1.5H), 3.34 (m, 1H), 3.45 (s, 1H), 3.46 (s, 1H), 3.59 (m, 2H), 3.72 (m, 1H), 3.39 (s, 3H), 4.30 (m, 1H), 4.49 (dd, 1H), 4.79 (dd, 1H), 5.00 (dd, 1H), 5.22 (1, 1H), 5.79 (d, 0.5H), 6.08 (d, 0.5H), 6.7-6.9 (m, 5.5H), 6.97 (d, 0.5H), 7.16 (t, 2H), 7.29 (m, 5H), MS APCI m/z=552 (M+1). LC/MS: 2.29 min.

The starting amine, (6,7-cis)-6-amino-4-methyl-7-phenyl-1,4-oxazepan-5-one hydrochloride (38d), was prepared in the following manner:

a. (2,3-trans)-N-(2-Hydroxyethyl)-N-(4-methoxybenzyl)-3-phenyloxirane-2-carboxamide (38a)

Using a procedure similar to that described in example 31 part a, except using 2-[(4-methoxybenzyl)amino]ethanol (5.85 g, 32.3 mmol) as the amine component, the title compound (38a) (8.3 g, 93%) was obtained as a white solid.

b. (6,7-trans)-6-Hydroxy-4-(4methoxybenzyl-7-phenyl-1,4-oxazepan-5one (38b)

To a stirred solution of (2,3-trans)-N-(2-hydroxyethyl)-N-(4-methoxybenzyl)-3-phenyloxirane-2-carboxamide (38a) (3.9 g, 11.9 mmol) in anhydrous THF (350 mL) was added 20 mol % of MgI$_2$ (667 mg, 2.4 mmol, 98% purity) and the mixture heated to reflux for 1 h, cooled, evaporated, and partitioned between ethyl acetate and saturated ammonium chloride. The organic layer was washed with saturated ammonium chloride, dried, filtered, and evaporated to an orange oil. Isocratic flash column chromatography (40% ethyl acetate-hexanes) returned the title compound (38b) (3.4 g, 89%) as a white solid.

c. (6,7-cis)-6-Azido-4-(4-methoxybenzyl)-7-phenyl-1,4oxazepan-5one (38c)

Using a procedure similar to that described in example 31 part c, except using (6,7-trans)-6-hydroxy-4-(4-methoxybenzyl)-7-phenyl-1,4-oxazepan-5-one (38b) (2.3 g, 7.03 mmol) as the alcohol component, the title compound (38c) (1.4 g, 58%) was obtained as a light yellow oil. MS APCI, m/z=353(M+1). LC/MS: 2.63 min (Method D).

d. (6,7-cis)-6-Amino-4-(4methoxybenzyl)-7-phenyl-1,4-oxazepan-5-one hydrochloride (38d)

Using a procedure similar to that described in example 30, part d, except using (6,7-cis)-6-azido-4-(4-methoxybenzyl)-7-phenyl-1,4-oxazepan-5-one (38c) (1.35 g, 3.84 mmol) as the azido component, the title compound (38d) (1.3 g, 93%) was obtained as a white solid. $^1$H NMR (300 MHz, CDCl$_3$) δ1.62 (bs, 2H), 3.28 (dd, 1H J=6.6, 10.0 Hz), 3.50 (m, 1H), 3.79 (s, 3H), 3.82-3.92 (m, 2H), 4.08 (s, 1H), 4.59 (dd, 2H, J=14, 19 Hz), 4.83 (s, 1H), 6.83 (d, 2H), J=8.8 Hz), 7.17 (d, 2H, J=8.8 Hz), 7.27-7.44 (m, 5H). MS APCI, m/z=327 (M+1). LC/MS: 1.46 min.

Example 39

N$^2$-[(3,5-Difluorophenyl)acetyl]-N$^1$-[(2R,3S,5a,S9aS)-5-methyl-4-oxo-2-phenyldecahydro-1,5-benzoxazepin-3-yl]-L-alaninamide (39)

Using a procedure similar to that described in example 11, except using (2R,3S,5aS,9aS)-3-amino-5-methyl-2-phenyloctahydro-1,5-benzoxazepin-4(5H)-one (39d) (110 mg, 0.401 mmol) as the amine component, afforded a crude oil (200 mg). Flash column chromatography (60-100% ethyl acetate-hexanes) returned the title compound (39) (95 mg, 48%) as a white solid. $^1$H NMR (300 MHz, CDCl$_3$) δ1.28 (d, 3H), 1.45 (m, 4H), 1.87 (m, 2H), 2.17 (m, 2H), 3.05 (s, 3H), 3.15 (dt, 1H), 3.52 (s, 2H), 4.23 (m, 1H), 4.29 (t, 1H), 5.25 (d, 1H), 5.43 (t, 1H), 6.02 (d, 1H, 6.46 (d, 1H), 6.73 (dt, 1H), 6.82 (m, 1.5H), 7.10 (m, 2H), 7.35 (m, 3.5H). MS APCI, m/z=500(M+1). LC/MS: 2.42 min.

The starting amine, (2R,35,5aS,9aS)-3-amino-5-methyl-2-phenyloctahydro-1,5-benzoxazepin-4(5H)-one (39d), was prepared in the following manner:

a. (2,3-trans)-N-[(1S,2S)-2-Hydroxycyclohexyl]-N-methyl-3-phenyloxirane-2-carboxamide (39a)

To a solution of ethyl (2,3-trans)-3-phenyloxirane-2-carboxylate (4.45 g, 23.3 mmol) in methanol (12 mL) at −20° C. was added (1S,2S)-2-(methylamino)cyclohexanol (3.0 g, 23.3 mmol) [Lu, X. et al, Org. Proc. R&D, 2001, 5,184-185.] followed addition of catalytic sodium methoxide (25%, 12 drops). The reaction was placed in a freezer (~−20 C) for 6 days, the solvent evaporated and the residue purified by flash column chromatography eluting (2% methanol-chloroform) to afford the title compound (39a) (3.5 g, 55%). MS APCl m/z=276(M+1). LC/MS: 1.77 min.

b. (2R,3S,5aR,9aS)-3Hydroxy-5-methyl-2-phenyloctahydro-1,5-benzoxazepin-4(5H)-one (39b)

To a stirred solution of (2,3-trans)-N-[(1S,2S)-2-hydroxycyclohexyl]-N-methyl-3-phenyloxirane-2-carboxamide (39a) (3.6 g, 13.1 mmol) in anhydrous THF (500 mL) was added MgI$_2$ (730 mg, 2.62 mmol, 98% purity) and the mixture stirred at refiux 16 h, cooled, the volume reduced to ~150 mL under vacuo. The residue was partitioned between ethyl acetate (300 mL) and saturated ammonium chloride (200 mL), stirred 15 min and the organic layer washed with saturated ammonium chloride, brine, dried, filtered, and evaporated to a crude orange oil (3.8 g). After recrystallization from ethyl acetate-hexanes, the title compound (39b) (1.35 g, 75%, 37.5% based on total 39a) was obtained as a white solid. MS APCI, m/z=276(M+1). LC/MS: 2.13 min.

c. (2R,3R,5aR,9aS)-3-Azido-5-methyl-2-phenyloctahydro-1,5-benzoxazepin-4(5H)-one (30c)

Using a procedure similar to that described in example 31 part c, except using (2R,3S,5aR,9aS)-3-hydroxy-5-methyl-2-phenyloctahydro-1,5-benzoxazepin-4(5H)-one (39b) (1.3 g, 4.72 mmol) as the alcohol component, pure title compound (30) (500 mg, 35%) was obtained. MS APCI, m/z=301 (M+1) 272(M+1–$N_2$). LC/MS: 6.84 min (Method E).

d. (2S,3R,5aR,9aS)-3-Amino-5-methyl-2-phenyloctahydro-1,5-benzoxazepin-4(5H)-one hydrochloride (39d)

Using a procedure similar to that described in example 31 part c, except using (2R,3R,5aR,9aS)-3-azido-5-methyl-2-phenyloctahydro-1,5-benzoxazepin-4(5H)-one (39b), (350 mg, 1.17 mmol) as the azido reactant, afforded a crude semi-solid. Free based was obtained (ethyl acetate-saturated NaHCO3) and the material purified by flash column chromatography (5% methanol-dichloromethane) to afford the title compound (39d) (110 mg, 34%) as an off white solid. $^1$H NMR (300 MHz, CDCl$_3$) δ1.24-1.41 (m, 4H), 1.48 (br 2H), 1.85 (m, 2H), 2.16 (m, 2H), 3.04 (s, 3H), 3.14 (m, 1H), 4.05 (m, 1H), 4.36 (d, 1H, J=6.0 Hz), 5.02 (d, 1H, J=6.0 Hz), 7.21-7.34 (m, 5H). MS APCI, m/z=275 (M+1). LC/MS:1.40 min.

Example 40

(2S)-2-[(3,5Difluorophenyl)acetyl]amino-N-[(6S, 7R)-4-(4-methoxybenzyl)-5-oxo-7-phenyl-1,4-oxazepan-6-yl]-2-phenylacetamide (40)

Using a procedure similar to that described in example 28, except using (2S)-2-amino-N-[(6,7-cis)-4-(4-methoxybenzyl)-5-oxo-7-phenyl-1,4-oxazepan-6-yl]-2-phenylacetamide hydrochloride (40b) (120 mg,0.242 mmol) as the amine component and (3,5-difluorophenyl)acetic acid (42 mg, 0.242 mmol) as the acid component, afforded crude product as an oil. Flash column chromatography (20% ethyl acetate-dichloromethane) returned the title compound (40) (pure diastereomer) (42 mg, 57%) as a white solid. $^1$H NMR (300 MHz, CDCl$_3$) δ3.33 (m, 1H), 3.51 (s, 2H), 3.52-3.75 (m, 4H), 3.77 (t, 3H), 4.45 (d, 1H), 4.72 (d, 1H), 4.93 (d, 1H), 5.22 (t, 1H), 5.31 (t, 1H), 6.64-6.82 (m, 6H), 6.93-7.31 (m, 12H). MS APCI m/z=614(M+1). HPLC: 4.48 min (Method B).

The starting amine, (2S)-2-amino-N-[(6,7-cis)-4-(4-methoxybenzyl)-5-oxo-7-phenyl-1,4-oxazepan-6-yl]-2-phenylacetamide hydrochloride (40b), was prepared in the following manner:

a. tert-Butyl ((1S)-2-{[(6,7-cis)-4-(4-methoxybenzyl)-5-oxo-7-phenyl-1,4-oxazepan-6-yl]amino}-2-oxo-1-phenylethyl)carbamate (40a)

Using a procedure similar to that described in example 26 part a, except using (2S-6,7-cis)-6-amino-4-methyl-2,7-diphenyl-1,4-oxazepan-5-one (38d) (150 mg, 0.46 mmol) as the amine component, the title compound (40a) (220 mg, 86%) was obtained as a white solid. MS APCI, m/z=560 (M+1). LC/MS: 2.78 min.

b. (2S)-2-Amino-N-[(6,7-cis)-4-(4-methoxybenzyl)-5-oxo-7-phenyl-1,4oxazepan-6yl]-2-phenylacetamide hydrochloride (40b)

Using a procedure similar to that described in example 29 part b, except using tert-butyl ((1S)-2-{[(6,7-cis)-4-(4-methoxybenzyl)-5-oxo-7-phenyl-1,4-oxazepan-6-yl]amino}-2-oxo-1-phenylethyl)carbamate (40a) (195 mg, 0.35 mmol) as the protected amine component, the title compound was obtained as the TFA salt The salt was freed (ethyl acetate-saturated sodium bicarbonate) and an ethyl acetate solution of the free base treated with HCl-ether until pH 1, evaporated and treated with ether to afford the title compound (40b) (147 mg, 85%) as a white solid. $^1$H NMR (300 MHz, D6 DMSO) δ3.56 (m, 2H), 3.72 (s, 1.5 H), 3.74 (s, 1.5 H), 3.83 (m, 1H), 4.11 (d, 0.5H), 4.42 (d, 0.5H), 4.56 (s, 0.5 H), 4.61, (s, 0.5 H), 4.77 (s, 0.5 H), 5.02, (m, 1.5 H), 5.22 (m, 1H), 6.74 (d, 1H), 6.87-6.97 (m, 4H), 7.01 (t, 1H), 7.12-7.23 (m, 2H), 7.24-7.50 (m, 7 H), 8.52 (d, 0.5 H), 8.62 (m, 3H), 8.84 (d, 0.5 H). MS APCI, m/z=460(M+1). LC/MS 1.88/ 1.96 min.

Example 41

$N^2$-[(3,5-Difluorophenyl)acetyl]-$N^1$-[(2R,3R)-2-(4-methoxyphenyl)-4-oxo-2,3,4,5-tetrahydro-1,5-benzothiazepin-3-yl]-L-alaninamide (41)

To a stirred solution of (2,3-cis)-3-amino-2-(4-methoxyphenyl)-2,3-dihydro-1,5-benzothiazepin-4(5H)-one hydrobromide (41d) (70 mg, 0.184 mmol) in dichloromethane (1 mL) under nitrogen was added N-[(3,5-difluorophenyl) acetyl]-L-alanine (1e) (45 mg, 0.185 mmol), HOBt (31 mg, 0.229 mmol), NMM (46 mg, 0.459 mmol) and EDAC-HCl (43 mg, 0.224 mmol). The mixture was stirred overnight at ambient temperature then evaporated. The residue was dissolved in ethyl acetate and extracted in succession with saturated sodium bicarbonate, 1N aqueous HCl, and brine. The organic solution was dried, filtered and evaporated. The residue was purified by flash chromatography on silica gel eluting with 1:1 (v/v) dichloromethane:ethyl acetate to afford the title compound in a 1:1 mixture with the 2S,3S diastereomer (88 mg, 90%) as a white solid. $^1$H NMR (300 MHz, CDCl$_3$) δ0.99 (d, 1.5H, J=7.0 Hz), 1.18 (d, 1.5H, J=7.0 Hz), 3.42 (s, 1H), 3.44 (s, 1H), 3.78 (s, 1.5H), 3.81 (s, 1.5H), 4.24 (m, 0.5H), 4.43 (m, 0.5H), 4.84 (q, 1H, J=7.0 Hz), 5.22 (m, 1H), 5.90 (d, 0.5H), 6.10 (d, 0.5H), 6.38 (d, 0.5H), 6.55 (d, 0.5H), 6.64-6.92 (m, 4H), 7.11 (m, 1H), 7.19-7.46 (m, 5H), 7.71 (m, 1.5H), 8.09 (s, 0.5H). MS APCI, m/z=548 (M+Na). LC/MS: 4.43 min.

The precursor (2,3-cis)-3-amino-2-(4-methoxyphenyl)-2,3-dihydro-1,5-benzothiazepin-4(5H)-one hydrobromide (41d) was prepared as follows:

a. Methyl (2Z)-2-{[(benzyloxy)carbonyl]amino}-3-(4-methoxyphenyl)acrylate (41a)

Using a procedure similar to that described in example 1 part a, except using 4-methoxybenzaldehyde (730 μl, 6.0 mmol) as the aldehyde component, the title compound was obtained as an oil (1.6 g, 78%). $^1$H NMR (300 MHz, CDCl$_3$) δ3.79 (s, 3H), 3.82 (s, 3H), 5.15 (s, 2H),6.20 (bs, 1H), 6.85 (d, 2H), 7.34 (m, 5H), 7.49 (d, 2H). MS APCI, m/z=342 (M+1).

b. Methyl β[(2-aminophenyl)thio]-N-[(benzyloxy)carbonyl]-4-methoxyphenylalaninate (41b)

Using a procedure similar to that described in example 10 (stirred 12 days), part b, except using methyl (2Z)-2-{[(benzyloxy)carbonyl]amino}-3-(4-methoxyphenyl)acrylate (41a) (1.5 g, 4.4 mmol), the product was obtained as a crude solid (2.0 g). Recrystallized from ethyl acetate—hexanes to afford the title compound (1.1 g, 54%) as white solid (91:9 mixture (erythro:threo)). $^1$H NMR (300 MHz, CDCl$_3$) δ3.43(s, 3H), 3.78 (s, 3H) 4.25(s, 2H), 4.56 (d, 2H, J=4.8 Hz), 4.77 (m, 1H), 5.10, (dd, 2H,), 5.83 (d, 1H), 6.58 (t, 1H, J=6.0 Hz), 6.67 (d, 1H, J=8.3 Hz), 6.77 (d, 2H, J=8.7 Hz), 7.09 (t, 1H, J=7.9 Hz), 7.20 (m, 3H), 7.36 (m, 4H). MS APCI, m/z=467 (M+1). LC/MS: 2.65 min.

c. Benzyl [(2,3-cis)-2-(4-methoxyphenyl)-4-oxo-2,3,4,5-tetrahydro-1,5-benzothiazepin-3-yl]carbamate (41c)

A suspension of methyl β-[(2-aminophenyl)thio]-N-[(benzyloxy)carbonyl]-4-methoxyphenylalaninate (41b) (9:1, 1.1 g, 2.36 mmol) and pTSA (catalytic) in xylenes (20 mL) was heated to reflux for 2 h, using a Dean-Stark apparatus. The mixture was then cooled, resulting in precipitation of the trans product as a white solid (80 mg, 95:5 trans). The filtrate (950 mg) was evaporated and crystallized from ether to afford a still impure product (740 mg). This solid was heated in ethyl acetate and filtered to give pure title compound (600 mg, 64%) as a white solid. $^1$H NMR (300 MHz, DMSO-d6) δ 3.76 (s, 3H), 4.49 (t, 1H, J=7.4 Hz)), 4.95 (s, 3H), 5.13 (d, 1H, J=7.0 Hz), 5.96 (d,1H), 6.90 (d, 2H, J=8.3 Hz), 7.31 (m, 9H), 7.49 (t, 1 H), 7.66 (t, 1H, 7.5 Hz), 10.48 (s, 1H). MS APCI, m/z=457(M+Na). LC/MS: 2.66 min.

d. (2,3-cis)-3-Amino-2-(4-methoxyphenyl)-2,3-dihydro-1,5-benzothiazepin-4(5H)-one hydrobromide (41d)

To benzyl [(2,3-cis)-2-(4-methoxyphenyl)-4-oxo-2,3,4,5-tetrahydro-1,5-benzothiazepin-3-yl]carbamate (41c) (380 mg, 0.87 mmol) in 6 ml HOAc was added 30% HBr/HOAc (2mL). The stirred suspension became a homogeneous solution over 20 min. The reaction stirred at room temperature for 2 hours. The volume was reduced to ~2-3 ml, diluted with ether to afford the hydrobromide salt of the title compound (0.75 g, 95%) as a white solid.

$^1$H NMR (300 MHz, DMSO-d6) δ 3.79 (s,3H), 4.23 (d, 1H, J=7.4 Hz), 5.19 (d, 1H, J=7.4 Hz),6.99 (d, 2H,), 7.25 (d,1H), 7.30 (t, 1H), 7.45 (d, 2H), 7.51 (t, 1 H), 7.68 (d, 1H, 7.5 Hz), 7.98 (bs, 3H), 10.83 (s, 1H). MS APCI, m/z=323 (M+Na). LC/MS: 1.63 min.

Example 42

N$^1$-[(2R,3R)-7-chloro-2-(2,5-difluorophenyl)-4-oxo-2,3,4,5-tetrahydro-1,5-benzothiazepin-3-yl]-N$^2$-[(2S)-2-(3,5-difluorophenyl)-2-hydroxyacetyl]-L-alaninamide (42)

To a stirred solution of (2,3-cis)-3-amino-7-chloro-2-(2,5-difluorophenyl)-2,3-dihydro-1,5-benzothiazepin-4(5H)-one (92d) (131 mg, 0.384 mmol) in dichloromethane (3 mL) and DMF (0.5 mL) under nitrogen was added N-[(2S)-2-(3,5-difluorophenyl)-2-hydroxyacetyl]-L-alanine (78b) (100 mg, 0.386 mmol), HOBt (66 mg, 0.488 mmol), NMM (49 mg, 0.484 mmol) and EDAC-HCl (100 mg, 0.521 mmol). The mixture was stirred overnight at ambient temperature. The reaction was diluted with water and extracted with ethyl acetate. The organic solution was dried, filtered and evaporated. The residue was purified by flash chromatography on silica gel eluting with 2:1 (v/v) hexanes:ethyl acetate to afford the title compound in a 1:1 mixture with the 2S,3S diastereomer (119 mg, 90%) as a white solid. $^1$H NMR (300 MHz, CDCl$_3$) δ1.14 (d, 1.5H, J=7.0 Hz), 1.26 (d, 1.5H, J=7.0 Hz), 3.92 (d, 0.5H, J=4.4 Hz), 4.08 (d, 0.5H, J=4.4 Hz), 4.41 (m, 0.5H), 4.56 (m, 0.5H), 4.82-5.03 (m, 2H), 5.64 (d, 0.5H, J=5.6 Hz), 5.68(d, 0.5H, J=5.6 Hz), 6.72 (m, 1H), 6.85-7.32 (m, 8H), 7.50 (m, 1H), 7.63 (m, 1H), 8.26 (s, 0.5H), 8.73 (s, 0.5H). MS APCI, m/z=582 (M+1). LC/MS: 2.61 min.

Example 43

N$^2$-[(2S)-2-hydroxy-4-methyl-1-oxopentyl]-N$^1$-[(2R,3s)-4-oxo-2-phenyl-2,3,4,5-tetrahydro-1,5-benzoxazepin-3-yl]-L-alaninamide (43)

To a stirred solution of N$^1$-[(2,3-cis)-4-oxo-2-phenyl-2,3,4,5-tetrahydro-1,5-benzoxazepin-3-yl]-L-alaninamide (43a) (160 mg, 0.492 mmol) in 1:1 (v/v) dichloromethane:DMF (4 mL) under nitrogen was added (S)-2-hydroxyisocaproic acid (71 mg, 0.537 mmol), HOBt (81 mg, 0.600 mmol), NMM (61 mg, 0.603 mmol) and EDAC-HCl (115 mg, 0.599 mmol). The mixture was stirred overnight at ambient temperature then diluted with aqueous sodium bicarbonate and extracted with ethyl acetate. The organic extract was washed with 15% aqueous citric acid and brine then dried and evaporated. The residue was purified by flash chromatography on silica gel eluting first with 1:1 (v/v) hexanes:ethyl acetate then with ethyl acetate to afford the title compound in a 1:1 mixture with the 2S,3R diastereomer (125 mg, 58%) as a yellow solid. $^1$H NMR (300 MHz, Acetone-d6) δ0.91 (m, 7H), 1.21 (m, 3H), 1.49 (m, 1H), 1.86 (m, 1H), 2.80 (br, 1H), 4.01 (m, 1H), 4.46 (m, 1H), 5.14 (m, 1H), 5.76 (m, 1H), 6.92 (m, 1H), 7.19-7.54 (m, 10H), 9.33 (br, 1H). MS APCI, m/z=462 (M+Na). LC/MS: 2.06 min.

The precursor N$^1$-[(2,3-cis)-4-oxo-2-phenyl-2,3,4,5-tetrahydro-1,5-benzoxazepin-3-yl]-L-alaninamide (43a) was prepared as follows:

a. N$^1$-[(2,3-cis)-4-Oxo-2-phenyl-2,3,4,5-tetrahydro-1,5benzoxazepin-3-yl]-L-alaninamide (43a)

Trifluoroacetic acid (5 mL) was added to a solution of N$^2$-[tert-butoxycarbonyl]-N$^1$-[(2,3-cis)-4-oxo-2-phenyl-2,3,4,5-tetrahydro-1,5-benzoxazepin-3-yl]-L-alaninamide (6f) (250 mg, 0.587 mmol) in dichloromethane (10 mL) at 0° C. under nitrogen. The mixture was stirred for 2 h then evaporated. The residue was dissolved in ethyl acetate and extracted with saturated aqueous sodium bicarbonate. The organic solution was dried, filtered and evaporated to afford the title compound as a yellow oil (165 mg, 86%). MS APCI, m/z=326 (M+1). LC/MS: 1.41 and 1.49 min. (diastereomers evident).

Example 44

N$^2$-[(3,5-Difluorophenyl)acetyl]-N$^1$-[(2R,3S)-5-methyl-4-oxo-2-phenyl-2,3,4,5-tetrahydro-1,5-benzoxazepin-3-yl]-L-alaninamide (44)

Sodium hydride (7 mg, 0.183 mmol) was added to a solution of N$^2$-[(3,5-difluorophenyl)acetyl]-N$^1$-[(2,3-cis)-4- oxo-2-phenyl-2,3,4,5-tetrahydro-1,5-benzoxazepin-3-yl]-L-alaninamide (44a) (77 mg, 0.161 mmol) in DMF (1 mL) under nitrogen. After stirring for 5 min. at ambient temperature iodomethane (25 mg, 0.176 mmol) was added. After 4 h the reaction was quenched with 1N aqueous HCl, diluted with water and extracted with ethyl acetate. The residue obtained after evaporation of the organic extract was purified by flash chromatography on silica gel eluting with 1:1 (v/v) hexanes:ethyl acetate then with ethyl acetate to afford the title compound in a 1:1 mixture with the 2S,3R diastereomer (70 mg, 78%) as a white powder. $^1$H NMR (300 Hz, CDCl$_3$) δ1.08 (d, 1.5H, J=7.0 Hz), 1.21 (d, 1.5H, J=7.0 Hz), 3.42-3.52 (m, 5H), 4.17-4.34 (m, 1H), 5.08 (m, 1H), 5.69 (m, 1H), 5.88-6.03 (m, 1H), 6.25 (m, 1H), 6.65-6.83 (m, 3H), 7.25-7.40 (m, 9H). MS APCI, m/z=516 (M+Na). LC/MS: 2.29 min.

The required N$^2$-[(3,5-difluorophenyl)acetyl]-N$^1$-[(2,3-cis)-4-oxo-2-phenyl-2,3,4,5-tetrahydro-1,5-benzoxazepin-3-yl]-L-alaninamide (a) was prepared as follows:

a. N$^2$-[(3,5-Difluorophenyl)acetyl]-N$^1$-[(2,3-cis)-4-oxo-2-phenyl-2,3,4,5-tetrahydro-1,5-benzoxazepin-3-yl]-L-alaninamide (44a)

To a stirred solution of (2,3-cis)-3-amino-2-phenyl-2,3-dihydro-1,5-benzoxazepin-4(5H)-one hydrochloride (6e) (103 mg, 0.356 mmol) in DMF (4 mL) under nitrogen at ambient temperature was added N-[(3,5-difluorophenyl)acetyl]-L-alanine (1e) (95 mg, 0.391 mmol), HOBt (58 mg, 0.427 mmol), NMM (71 mg, 0.700 mmol) and EDAC-HCl (82 mg, 0.427 mmol). After 6 h the reaction was diluted with water and extracted three times with ethyl acetate. The combined organic extracts were dried, filtered and evaporated. The residue was purified by flash chromatography on silica gel eluting first with 1:1 (v/v) hexanes:ethyl acetate and then with ethyl acetate to afford the title compound (75 mg, 43%) as a white solid. MS APCI, m/z=480 (M+1). LC/MS: 2.31 min. $^1$H NMR (300 MHz, DMSO-d6) δ1.05 (d, 1.5H, J=7 Hz), 1.11 (d, 1.5H, J=7 Hz), 3.44 (m, 2H), 4.27 (m, 1H), 4.97 (m, 1H), 5.60 (t, 1H, J=6 Hz), 6.86-7.50 (m, 13H), 8.24 (d, 0.5H, J=7 Hz), 8.33 (d, 0.5H, J=7 Hz), 10.30 (d, 1H, J=7 Hz).

Example 45

N$^1$-[(2R,3R)-7-Chloro-2-(2,5-difluorophenyl)-5-methyl-4 oxo-2,3,4,5-tetrahydro-1,5-benzothiazepin-3-yl]-N$^2$-[(3,5-difuorophenyl)acetyl]-L-alaninamide (45)

To a stirred solution of N$^1$-[(2R,3R)-7-chloro-2-(2,5-difluorophenyl)-4-oxo-2,3,4,5-tetrahydro-1,5-benzothiazepin-3-yl]-N$^2$-[(3,5-difluorophenyl)acetyl]-L-alaninamide (92) (100 mg, 0.177 mmol) in DMF (800 uL) under nitrogen at ambient temperature was added sodium hydride powder (60% in mineral oil) (7 mg, 0.182 mmol). After 5 minutes, iodomethane (25 mg, 0.176 mmol) was added via microsyringe. After stirring for 3½ hours, the reaction was carefully quenched with 1N aqueous HCl then diluted with water and extracted with ethyl acetate. The organic extracts were combined and evaporated. The residue was purified by flash chromatography on silica gel eluting first with 1:1 (v/v) hexanes:ethyl acetate and finally with ethyl acetate to afford the title compound (85 mg, 82%) as a white solid. $^1$H NMR (300 MHz, Acetone-d6) δ1.07 (d, 1.5H, J=7.0 Hz), 1.13 (d, 1.5H, J=7.0 Hz), 3.46-3.58 (m, 5H), 4.28 (m, 0.5H), 4.40 (m, 0.5H), 4.87 (m, 1H), 5.52 (m, 1H), 6.80-6.98 (m, 3H), 7.11-7.26 (m,3H), 7.33 (m, 0.5H), 7.40-7.51 (m, 2.5H), 7.70 (d, 1H, J=2.2 Hz), 7.81 (d, 1H, J=8.3 Hz). MS APCI, m/z=580 (M+1). LC/MS: 2.89 min.

Example 46

N$^2$-[(3,5-Difluorophenyl)acetyl]-N$^1$-(2R,3S)-5-[2-(dimethylamino)ethyl]-4-oxo-2-phenyl-2,3,4,5-tetrahydro-1,5-benzoxazepin-3-yl-L-alaninamide hydrochloride(46)

A gentle stream of hydrogen chloride gas was bubbled through a solution of tert-butyl {(2,3-cis)-5-[2-(dimethylamino)ethyl]-4oxo-2-phenyl-2,3,4,5-tetrahydro-1,5-benzoxazepin-3-yl}carbamate (46b) (72 mg, 0.169 mmol) in ethyl acetate (10 mL) at 0° C. for 5 min. The solvent was evaporated and the residue dissolved in DMF (3 mL). N-[(3,5-difluorophenyl)acetyl]-L-alanine (1e) (73 mg, 0.300 mmol), HOBt (54 mg, 0.400 mmol), NMM (61 mg, 0.600 mmol) and EDAC-HCl were added in succession to the stirred solution and the mixture kept at ambient temperature overnight. The reaction was diluted with aqueous sodium carbonate and extracted with ethyl acetate. The residue obtained after evaporation of the organic phase was purified by flash chromatography on silica gel eluting first with 40:1 (v/v) then with 20:1 (v/v) chloroform:methanol. Evaporation of the product containing fractions afforded an oil which was dissolved in dichloromethane and treated with a slight excess of ethereal hydrogen chloride. Evaporation of the solution afforded the title compound in a 1:1 mixture with the 2S,3R diastereomer (30 mg, 30%/o) as a white solid. $^1$H NMR (300 MHz, DMSO-d6) δ1.03 (d, 1.5H, J=7.0 Hz), 1.08 (d, 1.5H, J=7.0 Hz), 2.85 (m, 6H), 3.40 (m, 4H), 4.25 (m, 3H), 5.00 (m, 1H), 5.54 (m, 1H), 6.85-7.48 (m, 12H), 7.61 (m, 1H), 8.23 (d, 0.5H, J=7.0), 8.34 (d, 0.5H, J=7.0). MS APCI, m/z=551 (M+1). LC/MS: 2.16 min.

The precursor tert-butyl {(2,3-cis)-5-[2-(dimethylamino) ethyl]-4-oxo-2-phenyl-2,3,4,5-tetrahydro-1,5-benzoxazepin-3-yl}carbamate (46b) was prepared as follows:

a. tert-Butyl [(2,3-cis)-4-oxo-2-phenyl-2,3,4,5-tetrahydro-1,5-benzoxazepin-3-yl]carbamate (46a)

To a stirred solution of (2,3-cis)-3-amino-2-phenyl-2,3-dihydro-1,5-benzoxazepin-4(5H)-one (6e) (700 mg, 3.207 mmol) in dichloromethane (30 mL) under nitrogen at 0° C. was added triethylamine (324 mg, 3.21 mmol) and di-tert-butyl dicarbonate (700 mg, 3.208 mmol). The mixture was allowed to warm to ambient temperature and stirred for 24 h. The solvent was evaporated and the residue purified by flash chromatography on silica gel eluting first with dichloromethane and finally with 20:1 (v/v) dichloromethane:ethyl acetate to afford the title compound (943 mg, 83%) as a white solid. TLC 2:1 (v/v) hexane:ethyl acetate R$_f$=0.50. $^1$H NMR (300 MHz, CDCl$_3$) δ1.39 (s, 9H), 4.90-5.05 (m, 2H), 5.76 (d, 1H, J=6.8 Hz), 7.05 (m, 1H), 7.14-7.29 (m, 3H), 7.36-7.53 (m, 6H). MS ES+, m/z=377 (M+Na). LC/MS: 1.93 min.

b. tert-Butyl {(2,3-cis)-5-[2-(dimethylamino)ethyl]-4-oxo-2-phenyl-2,3,4,5-tetrahydro-1,5-benzoxazepin-3-yl}carbamate (46b)

To a stirred solution of tert-butyl [(2,3-cis)-4-oxo-2-phenyl-2,3,4,5-tetrahydro-1,5-benzoxazepin-3-yl]carbamate (46a) (70 mg, 0.197 mmol) and 2-(dimethylamino)ethyl-chloride hydrochloride (43 mg, 0.296 mmol) in methyl isobutyl ketone (5 mL) was added 1M aqueous sodium hydroxide (985 μL) and a catalytic amount of tetrabutylammonium iodide. The biphasic mixture was stirred and heated at reflux for 8 h. The reaction was diluted with aqueous sodium carbonate and extracted with ethyl acetate. The residue from the organic extract was purified by flash chromatography on silca gel eluting with 20:1 (v/v) chloroform:methanol to afford the title compound (72 mg, 86%) white solid. MS ES+, m/z=448 (M+Na). HPLC (Method A): 2.52 min.

Example 47

$N^1$-[(2R,3R)-7-Chloro-2-(2,5-difluorophenyl)-4-oxo-5-phenyl-2,3,4,5-tetrahydro-1,5-benzothiazepin-3-yl]-$N^2$-[(3,5-difluorophenyl)acetyl]-L-alaninamide (47)

To a stirred solution of (2,3-cis)-3-amino-7-chloro-2-(2,5-difluorophenyl)-5-phenyl-2,3-dihydro-1,5-benzothiazepin-4(5H)-one (47b) (157 mg, 0.376 mmol) in DMF (1 mL) was added N-[(3,5-difluorophenyl)acetyl]-L-alanine (1e) (131 mg, 0.539 mmol), HOBt (92 mg, 0.681 mmol), NMM (55 mg, 0.544 mmol) and EDAC-HCl (130 mg, 0.678 mmol). The mixture was stirred at ambient temperature under nitrogen overnight. The reaction mixture was diluted with water and extracted with ethyl acetate three times. The combined organic extracts were washed in succession with saturated aqueous sodium bicarbonate and 1N aqueous HCl. The organic solution was dried, filtered and evaporated. The residue was purified by flash chromatography on silica gel eluting first with 5:1 (v/v) hexanes:ethyl acetate, then with 3:1 (v/v) hexanes:ethyl acetate and finally with 1:1 (v/v) hexanes:ethyl acetate to afford the title compound (45 mg, 19%) as a white solid. The (2S,3S) diastereomer eluted first followed by the title (2R,3R) compound. $^1$H NMR (300 MHz, CDCl$_3$) δ1.23 (d, 3H, J=6.6 Hz), 3.47 (s, 2H), 4.25 (m, 1H), 5.00 (t, 1H, J=7.4 Hz), 5.60 (d, 1H), 5.92 (d, 1H) 6.38 (d, 1H), 6.69-6.84 (m, 3H), 6.88-7.03 (m, 2H), 7.07 (d, 1H), 7.27 (m, 3H), 7.42 (m, 4H), 7.74 (d, 8.3 Hz). ES+, m/z=664 (M+Na).

The required (2,3-cis)-3-amino-7-chloro-2-(2,5-difluorophenyl)-5-phenyl-2,3-dihydro-1,5-benzothiazepin-4(5H)-one (47b) was prepared as follows:

a. Benzyl [(2,3-cis)-7-chloro-2-(2,5-difluorophenyl)-4-oxo-5-phenyl-2,3,4,5-tetrahydro-1,5-benzothiazepin-3-yl]carbamate (47a)

A stirred mixture of benzyl [(2R,3R)-7-chloro-2-(2,5-difluorophenyl)-4-oxo-2,3,4,5-tetrahydro-1,5-benzothiazepin-3-yl]carbamate (92b) (237 mg, 0.500 mmol), bromobenzene (2 mL), potassium acetate (75 mg, 0.760 mmol) and copper powder (125 mg, 1.960 mmol) was heated at 150° C. for 24 hours. The reaction mixture was cooled to ambient temperature and applied to a silica gel column (10 g) pre-equilibrated with 2:1 (v/v) hexanes:dichloromethane. The column was eluted with dichloromethane and the product containing fractions were pooled and evaporated. The residue was triturated with a small volume of diethyl ether to afford the title compound (215 mg, 78%) as a white solid. TLC $R_f$=0.40 (dichloromethane).

$^1$H NMR (300 MHz, DMSO-d6) δ4.80 (m, 1H), 4.99 (s, 2H), 5.45 (d, 1H, J=7.4 Hz), 7.09-7.64 (m, 16H), 7.88 (d, 1H, J=8.3 Hz). MS APCI, m/z=551 (M+1). HPLC (Method A): 4.09 min.

b. (2,3-cis)-3-Amino-7-chloro-2-(2,5-difluorophenyl)-5-phenyl-2,3-dihydro-1,5-benzothiazepin-4(5H)-one (47b)

Benzyl [(2,3-cis)-7-chloro-2-(2,5-difluorophenyl)-4-oxo-5-phenyl-2,3,4,5-tetrahydro-1,5-benzothiazepin-3-yl]carbamate (a) (208 mg, 0.377 mmol) was suspended in 30% HBr/acetic acid (2 mL) and stirred for 90 min. at ambient temperature as the solid gradually dissolved forming a yellow solution. Diethyl ether (15 mL) was added to the reaction and the mixture carefully poured into saturated aqueous sodium carbonate. The organic phase was separated. The aqueous phase was extracted twice with ethyl acetate. The combined organic extracts were evaporated to afford the title compound (157 mg, 99%). MS APCl m/z=417 (M+1). LC/MS: 2.35 min.

Example 48

N-[(3,5-Difluorophenyl)acetyl]-N-[(6R,7R)-5-oxo-7-phenyl-1,4-thiazepan-6-yl]-L-phenylalaninamide (48)

To a stirred solution of N-[(6,7-cis)-5-oxo-7-phenyl-1,4-thiazepan-6-yl]-L-phenylalaninamide (48c) (88 mg, 0.239 mmol) in dichloromethane (4 mL) was added 3,5-difluorophenylacetic acid (52 mg, 0.302 mmol), HOBt (41 mg, 0.304 mmol), NMM (40 mg, 0.396 mmol) and EDAC-HCl (58 mg, 0.303 mmol). The mixture was stirred at ambient temperature under nitrogen overnight The solvent was evaporated and the residue was purified by flash chromatography on silica gel eluting with a gradient from 50% ethyl acetate: 50% hexanes to 100% ethyl acetate to afford the title compound in a 1:1 mixture with the 6S,7S diastereomer (99 mg, 79%) as a white solid. $^1$H NMR (300 MHz, CDCl$_3$) δ2.70-3.09 (m, 4H), 3.35-3.44 (m, 2M), 3.62-3.88 (m, 2H), 4.27 (t, 1H, J=4.4 Hz), 4.73 (m, 0.5H), 4.83 (m, 0.5H), 5.26 (m, 1H), 5.85 (br d, 0.5H), 6.05 (br d, 0.5H), 6.29 (br t, 0.5H), 6.56 (br, t, 0.5H), 6.58-6.80 (m, 3H), 6.98 (m, 2H), 7.11-7.28 (m, 9H). MS APCI, m/z=524 (M+1).

LC/MS: 2.63 min.

The required N-[(6,7-cis)-5-oxo-7-phenyl-1,4-thiazepan-6-yl]-L-phenylalaninamide (48c) was prepared as follows:

a. (6,7-cis)-6-Amino-7-phenyl-1,4-thiazepan-5-one hydrobromide (48a)

Benzyl (6,7 cis)-5-oxo-7-phenyl-1,4-thiazepan-6-ylcarbamate (7c) (890 mg, 2.497 mmol) was suspended in 30% HBr/HOAc (3 mL). After stirring for 1 h at ambient temperature the suspension became a yellow solution. The reaction was poured into diethyl ether (60 mL) and the resulting precipitate was collected and dried in-vacuo to afford the title compound (680 mg, 90%) as a white solid. $^1$H NMR (300 MHz, DMSO-d6) δ2.78-3.06 (m, 2H), 3.61-3.87 (m, 2H), 4.14 (d, 1H, J=3.0 Hz), 5.00 (d, 1H, 3.0 Hz), 7.35 (s, 5H), 8.19 (br s, 3H), 8.61 (br t, 1H, J=6.0 Hz). MS APCI, m/z=223 (M+1).

b. N-(tert-Butoxycarbonyl)-N-[(6,7-cis)-5oxo-7-phenyl-1,4thiazepan-6-yl]-L-phenylalaninamide (48b)

To a stirred solution of (6,7-cis)-6-amino-7-phenyl-1,4-thiazepan-5-one hydrobromide (48a) (150 mg, 0.497 mmol) in DMF (2 mL) under nitrogen was added, N-(tert-butoxycarbonyl)-L-phenylalanine (144 mg, 0.544 mmol), HOBt (100 mg, 0.742 mmol), NMM (75 mg, 0.742 mmol) and EDAC-HCl (142 mg, 0.742 mmol). The mixture was stirred at ambient temperature overnight. The reaction mixture was diluted with saturated aqueous sodium bicarbonate and extracted with ethyl acetate. The organic solution was separated, extracted in succession with 1N aqueous HCl and brine then dried, filtered and evaporated to afford the title compound (227 mg, 97%) as a white solid. $^1$H NMR (300 MHz, CDCl$_3$) δ1.33 (s, 4.5H), 1.37 (s, 4.5H), 2.70-3.10 (m, 5H), 3.60-3.90 (m, 2H), 4.26 (d, 0.5H, J=3.9 Hz), 4.34 (d, 0.5H, J=3.9 Hz), 4.41 (br, 1H), 4.78 (br, 0.5H1), 4.92 (br, 0.5H), 5.30 (m, 1H), 6.16 (m, 0.5H), 6.32 (br, 0.5H), 7.08-7.32 (m, 10H). MS APCI m/z=470 (M+1). LC/MS: 2.68 min.

c. N-[(6,7-cis)-5-Oxo-7-phenyl-1,4-thiazepan-6-yl]-L-phenylalaninamide (48c)

N-(tert-butoxycarbonyl)-N-[(6,7-cis)-5-oxo-7-phenyl-1,4-thiazepan-6-yl]-L-phenylalaninamide (48b) (227 mg, 0.483 mmol) was dissolved in 3:1 (v/v) dichloromethane:trifluoroacetic acid (10 mL) and kept at ambient temperature for 1 h. The solution was evaporated and the residue partitioned between ethyl acetate and saturated aqueous sodium bicarbonate. The organic solution was separated, dried, filtered and evaporated to afford the title compound (177 mg, 99%) as a yellow oil. MS APCI, m/z=370 (M+1). LC/MS: 1.22 min. MS APCI, m/z=370 (M+1). LC/MS: 1.49 min. (diastereomers evident)

Example 49

N$^2$-[(2S)-2-Hydroxy-4-methylpentanoyl]-N$^1$-[(6R,7R)-5-oxo-7-phenyl-1,4-thiazepan-6-yl]-L-phenylalaninamide (49)

To a stirred solution of N-[(6,7-cis)-5-oxo-7-phenyl-1,4-thiazepan-6-yl]-L-phenylalaninamide (48c) (88 mg, 0.239 mmol) in dichloromethane (4 mL) was added (S)-2-hydroxyisocaproic acid (40 mg, 0.294 mmol), HOBt (41 mg, 0.304 mmol), NMM (40 mg, 0.396 mmol) and EDAC-HCl (58 mg, 0.303 mmol). The mixture was stirred at ambient temperature under nitrogen overnight. The solvent was evaporated and the residue was purified by flash chromatography on silica gel eluting with a gradient from 50% ethyl acetate: 50% hexanes to 100% ethyl acetate to afford the title compound in a 1:1 mixture with the 6S,7S diastereomer (101 mg, 87%) as a white solid. $^1$H NMR (300 MHz, CDCl$_3$) δ0.88 (m, 6H), 0.95 (m, 1H), 1.22-1.50 (m, 2H), 1.72 (m, 1H), 2.69-3.15 (m, 5H), 3.64-3.87 (m, 2H), 4.02 (m, 1H), 4.22 (d, 0.5H, J=3.9 Hz), 4.28 (d, 0.5H, J=3.9 Hz), 4.70-4.89 (m, 1H), 5.30 (m, 1H) 6.32 (br t, 0.5H), 6.55 (br t, 0.5H), 6.86 (d, 0.5H, J=8.5 Hz), 7.00 (d, 0.5H, J=8.5 Hz), 7.07-7.30 (m, 10H). MS APCI, m/z=484 (M+1). LC/MS: 2.47 min.

Example 50

(2S)-2-[(3,5-Difluorophenyl)acetyl]amino-N-[(6R,7R)-5-oxo-7-phenyl-1,4-thiazepan-6-yl]-2-phenylacetamide (50)

To a stirred solution of (2S)-2-amino-N-[(6,7-cis)-5-oxo-7-phenyl-1,4-thiazepan-6-yl]-2-phenylacetamide (50b) (82 mg, 0.230 mmol) in dichloromethane (4 mL) was added 3,5-difluorophenylacetic acid (52 mg, 0.302 mmol), HOBt (41 mg, 0.304 mmol), NMM (40 mg, 0.396 mmol) and EDAC-HCl (58 mg, 0.303 mmol). The mixture was stirred at ambient temperature under nitrogen overnight. The solvent was evaporated and the residue was purified by flash chromatography on silica gel eluting with a gradient from 50% ethyl acetate: 50% hexanes to 100% ethyl acetate to afford the title compound in a 1:1 mixture with the 6S,7S diastereomer (86 mg, 73%) as a white solid. $^1$H NMR (300 MHz, CDCl$_3$) δ2.72 (m, 1H), 2.98 (m, 0.5H), 3.14 (m, 0.5H), 3.53 (s, 1H), 3.54 (s, 1H), 3.55-3.90 (m, 2H), 3.97 (d, 0.5H, J=3.5 Hz), 4.33 (d, 0.5H, J=3.5 Hz), 2.26 (m, 1H), 5.48 (d, 0.5H, J=7.0 Hz), 5.70 (d, 0.5H, J=7.0 Hz), 6.28 (br t, 0.5H), 6.64-6.87 (m, 4.5H), 6.90-7.05 (m, 1.5H), 7.11 (m, 1H), 7.18-7.36 (m, 8.5H). MS APCI, m/z 510 (M+1). LC/MS: 2.57 min.

The precursor (2S)-2-amino-N-[(6,7-cis)-5-oxo-7-phenyl-1,4-thiazepan-6-yl]-2-phenylacetamide (50b) was prepared as follows:

a. tert-Butyl ((1S)-2-oxo-2-{[(6,7-cis)-5-oxo-7-phenyl-1,4-thiazepan-6-yl]amino}-1-phenylethyl)carbamate (50a)

To a stirred solution of (6,7-cis)-6-amino-7-phenyl-1,4-thiazepan-5-one hydrobromide (48a) (150 mg, 0.497 mmol) in DMF (2 mL) under nitrogen was added, (2S)-[(tert-butoxycarbonyl)amino](phenyl)acetic acid (137 mg, 0.544 mmol), HOBt (100 mg, 0.742 mmol), NMM (75 mg, 0.742 mmol) and EDAC-HCl (142 mg, 0.742 mmol). The mixture was stirred at ambient temperature overnight. The reaction mixture was diluted with saturated aqueous sodium bicarbonate and extracted with ethyl acetate. The organic solution was separated, extracted in succession with 1N aqueous HCl and brine then dried, filtered and evaporated to afford the title compound (221 mg, 97%) as a white solid. $^1$H NMR (300 MHz, CDCl$_3$) δ1.40 (br s, 9H), 2.74 (m, 1H), 2.98-3.20 (m, 1H), 3.56-3.95 (m, 2H), 4.03 (br d, 0.5H), 4.37 (d, 0.5H, J=3.9 Hz), 5.12-5.44 (m, 2H), 5.61 (br d, 0.5H), 5.84 (br d, 0.5H), 6.21 (br 0.5H), 6.58 (br, 0.5H), 6.79 (br d, 1H), 6.96-7.19 (m, 2H), 7.22-7.38 (m, 8H). MS APCI, m/z=456 (M+1). LC/MS: 2.63 min.

b. (2S)-2-Amino-N-[(6,7-cis)-5-oxo-7-phenyl-1,4-thiazepan-6-yl]-2-phenylacetamide (50b)

tert-Butyl ((1S)-2-oxo-2-{[(6,7-cis)-5-oxo-7-phenyl-1,4-thiazepan-6-yl]-amino}-1-phenylethyl)carbamate (50a) (221 mg, 0.485 mmol) was dissolved in 3:1 (v/v) dichloromethane:trifluoroacetic acid (10 mL) and kept at ambient temperature for 1 h. The solution was evaporated and the residue partitioned between ethyl acetate and saturated aqueous sodium bicarbonate. The organic solution was separated, dried, filtered and evaporated to afford the title compound (165 mg, 95%) as a yellow oil. MS APCI, m/z=356 (M+1). LC/MS: 1.10 min. MS APCI, m/z=356 (M+1). LC/MS: 1.33 min. (diastereomers evident).

Example 51

(2S)-2-Hydroxy-4-methyl-N-((1S)-2-oxo-2-[(6R,7R)-5-oxo-7-phenyl-1,4-thiazepan-6-yl]amino-1-phenylethyl)pentanamide (51)

To a stirred solution of (2S)-2-amino-N-[(6,7-cis)-5-oxo-7-phenyl-1,4-thiazepan-6-yl]-2-phenylacetamide (50b) (82 mg, 0.230 mmol) in dichloromethane (4 mL) was added (S)-2-hydroxyisocaproic acid (40 mg, 0.294 mmol), HOBt (41 mg, 0.304 mmol), NMM (40 mg, 0.396 mmol) and EDAC-HCl (58 mg, 0.303 mmol). The mixture was stirred at ambient temperature under nitrogen overnight The solvent was evaporated and the residue was purified by flash chromatography on silica gel eluting with a gradient from 50% ethyl acetate: 50% hexanes to 100% ethyl acetate to afford the title compound in a 1:1 mixture with the 6S,7S diastereomer (81 mg, 75%) as a white solid. $^1$H NMR (300 MHz, CDCl$_3$) δ0.93 (m, 7H), 1.82 (m, 2H), 2.74 (m, m, 1H), 2.97-3.22 (m, 1H), 3.56-3.90 (m, 2H), 4.03 (d, 0.5H, J=3.5 Hz), 4.17 (m, 1H), 4.36 (d, 0.5H, J=3.5 Hz), 5.25-5.38 (m, 1H), 5.48 (d, 0.5H, J=7.4 Hz), 5.71 (d, 0.5H, J=7.4 Hz), 6.30 (m, 0.5H), 6.72 (m, 0.5H), 6.80 (d, 1H, J=7.4 Hz), 7.01 (t, 1H, J=7.4 Hz), 7.11-7.36 (m, 10H), 7.50 (br d, 0.5H), 7.69 (br d, 0.5H). MS APCI, m/z=470 (M+1). LC/MS: 2.39 min.

Example 52

N$^2$-[(3,5-Difluorophenyl)acetyl]-N$^1$-[(6R,7R)-5-oxo-7-phenyl-1,4-thiazepan-6-yl]-L-leucinamide (52)

To a stirred solution of N$^1$-[(6,7-cis)-5-oxo-7-phenyl-1,4-thiazepan-6-yl]-L-leucinamide (52b) (67 mg, 0.200 mmol) in dichloromethane (4 mL) was added 3,5-difluorophenylacetic acid (52 mg, 0.302 mmol), HOBt (41 mg, 0.304 mmol), NMM (40 mg, 0.396 mmol) and EDAC-HCl (58 mg, 0.303 mmol). The mixture was stirred at ambient temperature under nitrogen overnight. The solvent was evaporated and the residue was purified by flash chromatography on silica gel eluting with a gradient from 50% ethyl acetate: 50% hexanes to 100% ethyl acetate to afford the title compound in a 1:1 mixture with the 6S,7S diastereomer (76 mg, 0.155 mmol, 77%) as a white solid. $^1$H NMR (300 MHz, CDCl$_3$) δ0.74-0.89 (m, 6H), 1.32 (m, 3H), 2.75 (m, 1H), 3.00 (m, 1H), 3.49 (s, 1H), 3.51 (s, 1H), 3,63-3.89 (m, 2H), 4.24 (d, 0.5H, 4.1 Hz), 4.31 (d, 0.5H, J=4.1 Hz), 4.59 (m, 0.5H), 4.70 (m, 0.5H), 5.13 (m, 0.5H), 5.32 (m, 0.5H), 6.05 (br d, 0.5H), 6.17 (br d, 0.5H), 6.54 (m, 0.5H), 6.66-6.88 (m, 3H), 6.95 (m, 0.5H), 7.12-7.30 (m, 5.5H), 7.36 (br d, 0.5H). MS APCI, m/z=490 (M+1). LC/MS: 2.56 min.

The precursor N$^1$-[(6,7-cis)-5-oxo-7-phenyl-1,4-thiazepan-6-yl]-L-leucinamide (52b) was prepared as follows:

a. N$^2$-(tert-Butoxycarbonyl)-N$^1$-[(6,7-cis)-5-oxo-7-phenyl-1,4-thiazepan-6-yl]-L-leucinamide (52a)

To a stirred solution of (6,7-cis)-6-amino-7-phenyl-1,4-thiazepan-5-one hydrobromide (48a) (150 mg, 0.497 mmol) in DMF (2 mL) under nitrogen was added, N-(tert-butoxycarbonyl)-L-leucine (126 mg, 0.544 mmol), HOBt (1.00 mg, 0.742 mmol), NMM (75 mg, 0.742 mmol) and EDAC-HCl (142 mg, 0.742 mmol). The mixture was stirred at ambient temperature overnight. The reaction mixture was diluted with saturated aqueous sodium bicarbonate and extracted with ethyl acetate. The organic solution was separated, extracted in succession with 1N aqueous HCl and brine then dried, filtered and evaporated to afford the title compound (211 mg, 97%) as a white solid. $^1$H NMR (300 MHz, CDCl$_3$) δ0.80-0.95 (m, 6H), 1.41 (m, 9H), 1.56 (m, 3H), 2.79 (m, 1H), 3.04 (m, 1H), 3.63-3.93 (m, 2H), 4.19 (m, 1H), 4.36 (t, 1H, 4.0 Hz), 4.75 (br, 0.5H), 4.87 (br, 0.5H), 5.27 (br, 0.5H), 6.49 (br, 0.5H), 7.27 (m, 6H). MS APCI, m/z=436 (M+1). LC/MS: 2.64 min.

b. N$^1$-[(6,7-cis)-5-Oxo-7-phenyl-1,4-thiazepan-6-yl]-L-leucinamide (52b)

N$^2$-(tert-Butoxycarbonyl)-N$^1$-[(6,7-cis)-5-oxo-7-phenyl-1,4-thiazepan-6-yl]-L-leucinamide (52a) (210 mg, 0.482 mmol) was dissolved in 3:1 (v/v) dichloromethane:trifluoroacetic acid (10 mL) and kept at ambient temperature for 1 h. The solution was evaporated and the residue partitioned between ethyl acetate and saturated aqueous sodium bicarbonate. The organic solution was separated, dried, filtered and evaporated to afford the title compound (135 mg, 83%) as a yellow oil. MS APCI, m/z=336 (M+1). LC/MS: 1.06 min. MS APCI m/z=336 (M+1). LC/MS: 1.36 min. (diastereomers evident).

Example 53

N$^2$-[(2S)-2-Hydroxy-4-methylpentanoyl]-N$^1$-[(6R,7R)-5-oxo-7-phenyl-1,4-thiazepan-6-yl]-L-leucinamide (53)

To a stirred solution of N$^1$-[(6,7-cis)-5-oxo-7-phenyl-1,4-thiazepan-6-yl]-L-leucinamide (52b) (67 mg, 0.200 mmol) in dichloromethane (4 mL) was added (S)-2-hydroxyisocaproic acid (40 mg, 0.294 mmol), HOBt (41 mg, 0.304 mmol), NMM (40 mg, 0.396 mmol) and EDAC-HCl (58 mg, 0.303 mmol). The mixture was stirred at ambient temperature under nitrogen overnight. The solvent was evaporated and the residue was purified by flash chromatography on silica gel eluting with a gradient from 50% ethyl acetate: 50% hexanes to 100% ethyl acetate to afford the title compound in a 1:1 mixture with the 6S,7S diastereomer (73 mg, 81%) as a white solid. $^1$H NMR (300 MHz, CDCl$_3$) δ0.80-1.00 (m, 14H), 1.33-1.93 (m, 5H), 2.74-2.86 (m, 1H), 2.97-3.14 (m, 1H), 3.68-3.90 (m, 2H), 4.10 (m, 1H), 4.32 (d, 1H, 4 Hz), 4.51 (m, 0.5H), 4.61 (m, 0.5H), 5.23 (m, 0.5H), 5.32 (m, 0.5H), 6.48 (br, 0.5H), 6.78 (m, 1H), 6.93 (br d, 0.5H), 7.27 (m, 6H). MS APCI, m/z=450 (M+1).
LC/MS: 2.40 min.

Example 54

N$^2$-[(3,5-Difluorophenyl)acetyl]-N$^1$-[(6R,7R)-5-oxo-7-phenyl-14-thiazepan-6-yl]-L-valinamide (54)

To a stirred solution of N$^1$-[(6,7-cis)-5-oxo-7-phenyl-1,4-thiazepan-6-yl]-L-valinamide (54b) (65 mg, 0.202 mmol) in dichloromethane (4 mL) was added 3,5-difluorophenylacetic acid (52 mg, 0.302 mmol), HOBt (41 mg, 0.304 mmol), NMM (40 mg, 0.396 mmol) and EDAC-HCl (58 mg, 0.303 mmol). The mixture was stirred at ambient temperature under nitrogen overnight. The solvent was evaporated and the residue was purified by flash chromatography on silica gel eluting with a gradient from 50% ethyl acetate: 50% hexanes to 100% ethyl acetate to afford the title compound in a 1:1 mixture with the 6S,7S diasereomer (62 mg, 64%) as a white solid. $^1$H NMR (300 Mz, CDCl$_3$) δ0.68-0.89 (m, 6H), 1.78-2.05 (m, 1H), 2.69-2.80 (m, 1H), 3.02 (m, 1H), 3.51 (s, 1H), 3.54 (s, 1H), 3.67-3.91 (m, 2H), 4.24 (d, 0.5H, J=4.0 Hz), 4.29 (d, 0.5H, J=4.0 Hz), 4.38 (m, 0.5H), 4.53 (m, 0.5H), 5.22 (m, 0.5H), 5.35 (m, 0.5H), 6.32 (m, 1H), 6.63-6.94 (m, 5H), 7.13-7.31 (m, 5H). MS APCI, m/z=476 (M+1). LC/MS: 2.46 min.

The precursor N$^1$-[(6,7-cis)-5-oxo-7-phenyl-1,4-thiazepan-6-yl]-L-valinamide (54b) was prepared as follows:

a. N$^2$-(tert-Butoxycarbonyl)-N$^1$-[(6,7-cis)-5-oxo-7-phenyl-1,4-thiazepan-6-yl]-L-valinamide (54a)

To a stirred solution of (6,7-cis)-6-amino-7-phenyl-1, 4thiazepan-5-one hydrobromide (48a) (150 mg, 0.497 mmol) in DMF (2 mL) under nitrogen was added, N-(tert-butoxycarbonyl)-L-valine (118 mg, 0.544 mmol), HOBt (100 mg, 0.742 mmol), NMM (75 mg, 0.742 mmol) and EDAC-HCl (142 mg, 0.742 mmol). The mixture was stirred at ambient temperature overnight. The reaction mixture was diluted with saturated aqueous sodium bicarbonate and extracted with ethyl acetate. The organic solution was separated, extracted in succession with 1N aqueous HCl and brine then dried, filtered and evaporated to afford the title compound (189 mg, 90%/o) as a white solid. $^1$H NMR (300 MHz, CDCl$_3$) δ0.84 (m, 6H), 1.42 (m, 9H), 1.89-2.14 (m, 1H), 2.73-2.84 (m, 1H), 2.98-3.14 (m, 1H), 3.80 (m, 2H), 4.32 (d, 1H, J=4.0 Hz), 5.03 (m, 1H), 5.36 (m, 1H), 6.37-6.60 (br m, 1H), 7.09-7.31 (m, 3H), 7.44 (m, 2H), 7.80 (m, 2H). MS APCI, m/z=422 (M+1). LC/MS: 2.50 min.

b. N$^1$-[(6,7-cis)-5-oxo-7-phenyl-1,4-thiazepan-6-yl]-L-valinamide (54b)

N$^2$-(tert-Butoxycarbonyl)-N$^1$-[(6,7-cis)-5-oxo-7-phenyl-1,4-thiazepan-6-yl]-L-valinamide (54a) (189 mg, 0.449 mmol) was dissolved in 3:1 (v/v) dichloromethane:trifluoroacetic acid (10 mL) and kept at ambient temperature for 1 h. The solution was evaporated and the residue partitioned between ethyl acetate and saturated aqueous sodium bicarbonate. The organic solution was separated, dried, filtered and evaporated to afford the title compound (130 mg, 90%) as a yellow oil. MS APCI, m/z=322 (M+1). LC/MS: 0.70 min. MS APCI, m/z=322 (M+1). LC/MS: 1.20 min. (diastereomers evident).

Example 55

N$^2$-[(2S )-2-Hydroxy-4-methylpentanoyl]-N$^1$-[(6R, 7R)-5-oxo-7-phenyl-1,4-thiazepan-6-yl]-L-valinamide (55)

To a stirred solution of N$^1$-[(6,7-cis)-5-oxo-7-phenyl-1,4-thiazepan-6-yl]-L-valinamide (54b) (65 mg, 0.202 mmol) in dichloromethane (4 mL) was added (S)-2-hydroxyisocaproic acid (40 mg, 0.294 mmol), HOBt (41 mg, 0.304 mmol), NMM (40 mg, 0.396 mmol) and EDAC-HCl (58 mg, 0.303 mmol). The mixture was stirred at ambient temperature under nitrogen overnight. The solvent was evaporated and the residue was purified by flash chromatography on silica gel eluting with a gradient from 50% ethyl acetate: 50% hexanes to 100% ethyl acetate to afford the title compound in a 1:1 mixture with the 6S,7S diastereomer (63 mg, 72%) as a white solid. $^1$H NMR (300 MHz, CDCl$_3$) δ0.70-1.04 (m, 13H), 1.60 (m, 2H), 1.80 (br 1H), 1.90-2.19 (m, 1H), 2.78 (m, 1H), 3.06 (m, 1H), 3.68-3.94 (m, 2H), 4.13 (m, 1H), 4.24-4.48 (m, 21H), 5.13 (m, 0.5H), 5.31 (m, 0.5H), 5.38 (m, 0.5H), 6.53 (m, 0.5H), 6.63 (m, 0.5H), 7.01 (m, 1H), 7.16 (m, 0.5H), 7.23-7.32 (m, 5H). MS APCI m/z=436 (M+1). LC/MS: 2.31 mm Example 56

N$^1$-[(2R,3S)-7-Chloro-4-oxo-2-phenyl-2,3,4,5-tetrahydro-1,5-benzoxazepin-3-yl]-N$^2$-[(3,5-difluorophenyl)acetyl]-L-alaninamide (56)

To a stirred solution of (2,3-cis)-3-amino-7-chloro-2-phenyl-2,3-dihydro-1,5-benzoxazepin-4(5H)-one (56e) (100 mg, 0.346 mmol) in dichloromethane (3 mL) was added N-[(3,5-difluorophenyl)acetyl]-L-alanine (1e) (93 mg, 0.382 mmol), HOBt (57 mg, 0.422 mmol), NMM (43 mg, 0.425 mmol) and EDAC-HCl (80 mg, 0.417 mmol). The mixture was stirred at ambient temperature under nitrogen overnight. The reaction mixture was diluted with water and extracted with ethyl acetate three times. The combined organic extracts were washed in succession with saturated aqueous sodium bicarbonate and 1N aqueous HCl. The organic solution was dried, filtered and evaporated. The residue was purified by flash chromatography on silica gel eluting with 1:1 (v/v) hexane:ethyl acetate to afford the title compound in a 1:1 mixture with the 2S,3R diastereomer (120 mg, 67%) as a white solid. $^1$H NMR (300 MHz, CDCl$_3$) δ1.08 (d, 1.5H, J=7.0 Hz), 1.24 (d, 1.5H, J=7.0 Hz), 3.44 (s, 1H), 3.50 (s, 1H), 4.48 (m, 0.5H), 4.62 (m, 0.5H), 4.98 (t, 0.5H), 5.11 (t, 0.5H), 5.76 (m, 1H), 6.11 (d, 0.5H), 6.24 (d, 0.5H), 6.53-6.87 (m, 3H), 7.04 (m, 1H), 7.18-7.42 (m, 8H), 7.84 (s, 0.5H),8.41 (s, 0.5H). MS APCI, m/z=514 (M+1). LC/MS: 2.47 min.

The precursor (2,3-cis)-3-amino-7-chloro-2-phenyl-2,3-dihydro-1,5-benzoxazepin-4(5H)-one (56e) was prepared as follows:

a. erythro Ethyl 2-hydroxy-3-(4-chloro-2-nitrophenoxy)-3-phenylpropanoate (56a)

To a stirred mixture of 4-chloro-2-nitrophenol (11.68 g, 67.32 mmol), ethyl 3-phenyloxirane-2-carboxylate (9.61 g, 50.00 mmol) in ethanol (200 mL) was added portionwise 60% sodium hydride (738 mg, 20.00 mmol) and the red mixture stirred at reflux for 3 days. The solvent was removed in vacuo. The residue was dissolved in chloroform and extracted three times with 10% aqueous potassium carbonate. The organic layer was washed with water and brine, dried, filtered and evaporated to afford a brown residue. The residue was dissolved in a minimal volume of chloroform and precipitated by adding diethyl ether to afford the title compound (5.970 g,33%) as an off-white solid. $^1$H NMR (300 MHz, DMSO-d6) δ1.16 (t, 3H, J=7.0 Hz), 4.09 (q, 2H, J=7.0 Hz), 4.29 (t, 1H, J=7.0 Hz), 5.63 (d, 1H, J=7.0 Hz), 6.09 (d, 1H, J=7.0 Hz), 7.19-7.60 (m, 7H), 7.97 (d, 1H, J=2.6 Hz). MS APCI, m/z=388 (M+Na).
LC/MS: 2.78 min.

b. erythro Ethyl 2-hydroxy-3-(4-chloro-2-nitrophenoxy)-3-phenylpropanoate (56b)

To a solution of erythro ethyl 2-hydroxy-3-(4-chloro-2-nitrophenoxy)-3-phenylpropanoate (56a) (5.870 g, 16.048 mmol) in ethanol (200 mL) was added 5% palladium on carbon (200 mg) and the mixture was hydrogenated at 35 psi on a Parr shaker for 45 min. The reaction mixture was filtered through diatomaceous earth and the resulting solution concentrated in-vacuo. The residue was purified by flash chromatography on silica gel eluting first with chloroform and then 60:1 (v/v) chloroform:ethanol to afford the title compound (3.150 g, 58%) as a red oil. TLC R$_f$=0.21 (60:1 chloroform:ethanol). MS APCI, m/z=336 (M+1). LC/MS: 2.00 min.

c. (2,3-trans)-7-Chloro-3-hydroxy-2-phenyl-2,3-dihydro-1,5-benzoxazepin-4(5H)-one (56c)

To a stirred solution of erythro ethyl 2-hydroxy-3-(4-chloro-2-nitrophenoxy)-3-phenylpropanoate (56b) (3.070 g, 9.143 mmol) in THF (40 mL) cooled to 0° C. was added a solution of lithium hydroxide monohydrate (422 mg, 10.057 mmol) in water (20 mL) and methanol (2 mL). After 1 h the cooling bath was removed and the mixture stirred an additional 2 h at ambient temperature. The reaction was re-cooled to 0° C. and 1N aqueous hydrochloric acid (14.3 mL) was added. Solvent was then removed in-vacuo. The residue was dissolved in DMF (50 mL), HOBt (2.00 g, 14.804 mmol), NMM (1.510 g, 14.950 mmol), and EDAC (2.880 g, 15.023 mmol) were added and the mixture stirred overnight under nitrogen at ambient temperature. Solvent was removed in-vacuo at 40° C. and the residue partitioned between water and ethyl acetate. The organic solution was separated, washed in succession with saturated aqueous sodium bicarbonate, 1N aqueous HCl and brine, then dried, filtered and evaporated. The residue was purified by flash chromatography (3:1 hexane:ethyl acetate) to afford the title compound (1.120 g, 42%) as a white solid. TLC $R_f$=0.19 (3:1 hexane:ethyl acetate). $^1$H NMR (300 MHz, CDCl$_3$) δ3.65 (d, 1H, J=4.8 Hz), 4.62 and 4.65 (dd, 1H, J=4.8 Hz), 5.29 (d, 1H, J=9.6 Hz), 6.80 (m, 1H), 7.02-7.09 (m, 2H), 7.41 (s, 5H), 7.89 (s, 1H). MS APCI, m/z=290 (M+1). LC/MS: 2.35 min.

d. (2,3-cis)-3-Azido-7-chloro-2-phenyl-2,3-dihydro-1,5-benzoxazepin-4(5H)-one (56d)

Trifluoromethanesulfonyl chloride (926 mg, 5.495 mmol) was added via syringe to a solution of (2,3-trans)-7-chloro-3-hydroxy-2-phenyl-2,3-dihydro-1,5-benzoxazepin-4(5H)-one (56c) (1.064 g, 3.672 mmol) and triethylamine (634 mg, 6.277 mmol) in dichloromethane (25 mL) under nitrogen at −20° C. The mixture was kept at -20° C. for 18 h. Additional triethylamine (1.268 g, 12.554 mmol) and trifluoromethanesulfonyl chloride (1.852 g, 10.990 mmol) were added and the mixture kept at −20° C. for an additional 24h. Again, additional trifluoromethanesulfonyl chloride (926 mg, 5.495 mmol) and triethylamine (634 mg, 6.277 mmol) were added and the mixture kept at −20° C. for an additional 5 h. The reaction was concentrated in-vacuo without heating, and the resulting residue immediately dissolved in DMF (10 mL) at 0° C. under nitrogen. Sodium azide (1.190 g, 18.305 mmol) was added to the solution and the mixture allowed to warm to ambient temperature over 30 min. After an additional 2 h the reaction was diluted with water and extracted with ethyl acetate three times. The combined organic extracts were washed in succession with saturated aqueous sodium bicarbonate, 1N aqueous HCl and brine. The organic solution was dried, filtered and evaporated and the residue purified by flash chromatography on silica gel eluting with dichloromethane and then with 100:2 (v/v) dichloromethane:methanol to afford the title compound (410 mg, 35%) as a foamy white solid. TLC $R_f$=0.20 (dichloromethane) $^1$H NMR (300 MHz, CDCl$_3$) δ4.46 (d, 1H, J=5.7 Hz), 5.54 (d, 1H, J=5.7 Hz), 7.05 (s, 1H), 7.16 (s, 2H), 7.39-7.47 (m, 3H), 7.49-7.57 (m, 2H), 7.86 (s, 1H). MS APCI, m/z=287 (M+1−N$_2$).
LC/MS: 2.54 min.

e. (2,3-cis)-3-Amino-7-chloro-2-phenyl-2,3-dihydro-1,5-benzoxazepin-4(5H)-one (56e)

To a stirred solution of (2,3cis)-3-azido-7-chloro-2-phenyl-2,3-dihydro-1,5-benzoxazepin-4(5H)-one (56d (385 mg, 1.223 mmol) in tetrahydrofuran (10 mL) was added water (33 μL) and triphenylphosphine (337 mg, 1.285 mmol). After 18 h at ambient temperature water (1 mL) was added. After an additional 1 h the solvent was evaporated and the residue was purified by flash chromatography on silica gel eluting with 100:3 (v/v) dichloromethane:methanol to afford the title compound (216 mg, 61%) as a white solid. TLC $R_f$=0.25 (100:3 (v/v) dichloromethane: methanol). $^1$H NMR (300 MHz, CDCl$_3$) 1.46 (br, 2H), .4.12 (d, 1H, J=6.6 Hz), 5.55 (d, 1H, J=6.6 Hz), 7.05 (s, 1H), 7.18 (m, 2H), 7.36-7.73 (m, 6H). MS APCI, m/z=289 (M+1). LC/MS: 1.54 min.

Example 57

(2S)—N-((1S)-2-[(2R,3S)-7-Chloro-4-oxo-2-phenyl-2,3,4,5-tetrahydro-1,5-benzoxazepin-3-yl]amino-2-oxo-1-phenylethyl)-2-hydroxy4-methylpentanamide (57)

To a stirred solution of (2S)-2-amino-N-[(2,3-cis)-7-chloro 4-oxo-2-phenyl-2,3,4,5-tetrahydro-1,5-benzoxazepin-3-yl]-2-phenylacetamide (57b) (80 mg, 0.199 mmol) in dichloromethane (4 mL) were added (S)-2-hydroxyisocaproic acid (30 mg, 0.192 mmol), HOBt (34 mg, 0.251 mmol), NMM (26 mg, 0.257 mmol) and EDAC-HCl (48 mg, 0.250 mol) in succession and the mixture stirred overnight under nitrogen at ambient temperature. The reaction mixture was diluted with water and extracted with ethyl acetate three times. The combined organic extracts were washed in succession with saturated aqueous sodium bicarbonate and 1N aqueous HCl. The organic solution was dried, filtered and evaporated. The residue was purified by flash chromatography on silica gel eluting with 50:1 (v/v) chloroform:methanol to afford the title compound as a 1:1 mixture with the 2S,3R diastereomer (96 mg, 93%) as a white solid. $^1$H NMR (300 MHz, CDCl$_3$) δ0.93 (m, 7H), 1.81 (m, 2H), 2.60 (br, 1H), 4.09 (m, 0.5H), 4.21 (m, 0.5H), 5.14 (m, 1H), 5.45 (m, 0.5H), 5.53-5.68 (m, 1H), 5.82 (m, 0.5H), 6.57 (m, 1H), 6.90-7.11 (m, 4H), 7.15-7.60 (m, 10H), 7.78 (s, 0.5H), 8.34 (s, 0.5H). MS APCI, m/z=536 (M+1). LC/MS: 2.43 min.

The precursor (2S)-2-amino-N-[(2,3-cis)-7-chloro-4-oxo-2-phenyl-2,3,4,5-tetrahydro-1,5-benzoxazepin-3-yl]-2-phenylacetamide (57b) was prepared as follows:

a. tert-Butyl ((1S)-2{[(2,3-cis)-7-chloro-4-oxo-2-phenyl-2,3,4,5-tetrahydro-1,5-benzoxazepin-3-yl]amino}-2oxo-1-phenylethyl)carbamate (57a)

To a stirred solution of (2,3cis)-3-amino-7-chloro-2-phenyl-2,3-dihydro-1,5-benzoxazepin-4(5H)-one (56e) (90 mg, 0.312 mmol) in dichloromethane (3 mL) was added (2S)-[(tert-butoxycarbonyl)amino](phenyl)acetic acid (86 mg, 0.342 mmol), HOBt (47 mg, 0.347 mmol), NMM (50 mg, 0.495 mmol) and EDAC-HCl (66 mg, 0.344 mmol). The mixture was stirred at ambient temperature under nitrogen overnight. The reaction mixture was diluted with water and extracted with ethyl acetate three times. The combined organic extracts were washed in succession with saturated aqueous sodium bicarbonate and 1N aqueous HCl. The organic solution was dried, filtered and evaporated. The residue was purified by flash chromatography on silica gel eluting with 3:1 (v/v) hexane: ethyl acetate to afford the title compound (111 mg, 68%) as a white solid. $^1$H NMR (300 MHz, CDCl$_3$) δ1.35 (s, 4.5H), 1.45 (s, 4.5H), 5.03-5.29 (m, 1.5H), 5.41-5.63 (m, 1.5H), 5.74-5.86 (m, 1H) 6.54-6.80 (br, 1H), 6.92 (m, 1.5 H), 6.99-7.13 (m, 2.5H), 7.15-7.41 (m, 9H), 7.75 (br, 0.5H), 8.44 (br, 0.5H). MS APCI, m/z=544 (M+Na). LC/MS: 2.75 min.

b. (2S)-2-Amino-N-[(2,3-cis)-7-chloro-4-oxo-2-phenyl-2,3,4,5-tetrahydro-1,5-benzoxazepin-3-yl]-2-phenylacetamide (57b)

Trifluoroacetic acid (1 mL) was added to a solution of tert-butyl ((1S)-2-{[(2,3-cis)-7-chloro-4-oxo-2-phenyl-2,3,4,5-tetrahydro-1,5-benzoxazepin-3-yl]amino}-2-oxo-1-phenylethyl)carbamate (57a) (100 mg, 0.192 mmol) in dicloromethane (3 mL) at 0° C. The solution was allowed to warm to ambient temperature and stirred 1 h and then the solvent was evaporated. The residue was dissolved in ethyl acetate and extracted with aqueous sodium bicarbonate. The organic solution was dried and evaporated to afford the title compound (80 mg, 99%) which was used in the next step without additional purification. $^1$H NMR (300 MHz, CDCl$_3$) δ1.72 (br s, 2H), 4.55 (m, 1H), 5.22 (m, 1H), 5.67 (m, 1H), 7.04 (m, 2H), 71.3-7.44 (m, 11H), 7.55 (m, 2H). MS APCI, m/z=422 (M+1). LC/MS: 2.00 min.

Example 58

(2S)-2-[(3,5-Difluorophenyl)acetyl]amino-N-[(2R,3S)-4-oxo-2-phenyl-2,3,4,5-tetrahydro-1,5-benzoxazepin-3-yl]-2-phenylacetamide (58)

To a stirred solution of (2S)-2-amino-N-[(2,3-cis)-4-oxo-2-phenyl-2,3,4,5-tetrahydro-1,5-benzoxazepin-3-yl]-2-phenylacetamide (58b) (108 mg, 0.279 mmol) in dichloromethane (3 mL) under nitrogen was added 3,5-difluorophenylacetic acid (58 mg, 0.336 mmol), HOBt (50 mg, 0.370 mmol), NMM (42 mg, 0.416 mmol) and EDAC-HCl (71 mg, 0.370 mmol). The mixture was stirred overnight at ambient temperature then evaporated. The residue was dissolved in ethyl acetate and extracted in succession with saturated sodium bicarbonate, 1N aqueous HCl, and brine. The organic solution was dried, filtered and evaporated. The residue was purified by flash chromatography on silica gel eluting with 100:1 (v/v) chloroform:methanol to afford the title compound as a 1:1 mixture with (2S)-2-[(3,5-difluorophenyl)acetyl]amino-N-[(2S,3R)-4-oxo-2-phenyl-2,3,4,5-tetrahydro-1,5-benzoxazepin-3-yl]-2-phenylacetamide (110 mg, 73%) as a white solid. $^1$H NMR (300 MHz, CDCl$_3$) δ3.47 (s, 1H), 3.56 (s, 1H), 5.07 (m, 1H), 5.45 (d, 0.5H, 7.0 Hz), 5.56 (d, 0.5H, 7.0 Hz), 5.71 (d, 0.5H, 7.0 Hz), 5.82 (d, 0.5H, 7.0 Hz), 6.52 (m, 1H), 6.72 (m, 2H), 6.80-7.09 (m, 4H), 7.11-7.40 (m, 12H), 7.65 (s, 0.5H), 8.29 (s, 0.5H). MS APCI, m/z=542 (M+1). LC/MS: 2.58 min.

The precursor (2S)-2-amino-N-[(2,3-cis)-4oxo-2-phenyl-2,3,4,5-tetrahydro-1,5-benzoxazepin-3-yl]-2-phenylacetamide (58b) was prepared as follows:

a. tert-Butyl ((1S)-2-oxo-2-{[(2,3-cis)-4-oxo-2-phenyl-2,3,4,5-tetrahydro-1,5-benzoxazepin-3-yl]amino}-1-phenylethyl)carbamate (58a)

To a stirred solution of (2,3-cis)-3-amino-2-phenyl-2,3-dihydro-1,5-benzoxazepin-4(5H)-one (6e) (98 mg, 0.337 mmol) in dichloromethane (3 mL) was added (2S)-[(tert-butoxycarbonyl)amino](phenyl)acetic acid (93 mg, 0.370 mmol), HOBt (55 mg, 0.407 mmol), NMM (68 mg, 0.673 mmol) and EDAC-HCl (78 mg, 0.407 mmol). The mixture was stirred at ambient temperature under nitrogen overnight. The reaction mixture was diluted with water and extracted with ethyl acetate three times. The combined organic extracts were washed in succession with saturated aqueous sodium bicarbonate and 1N aqueous HCl. The organic solution was dried, filtered and evaporated. The residue was purified by flash chromatography on silica gel eluting with 2:1 (v/v) hexane:ethyl acetate to afford the title compound (146 mg, 89%) as a yellow solid. $^1$H NMR (300 MHz, CDCl$_3$) δ1.34 (s, 4.5H), 1.44 (s, 4.5H), 5.17 (m, 1H), 5.55 (m, 1H), 5.73 (d, 0.5H, J=7.5 Hz), 5.85 (d, 0.5H, J=7.0 Hz), 6.44-6.73 (br, 1H), 6.91-7.12 (m, 3H), 7.14-7.41 (m, 12H), 7.63 (br s, 0.5H), 8.15 (br, 0.5H). MS APCI, m/z=510 (M+Na). LC/MS: 2.60 min.

b. (2S)-2-Amino-N-[(2,3-cis)-4oxo-2-phenyl-2,3,4,5-tetrahydro-1,5-benzoxazepin-3-yl]-2-phenylacetamide (58b)

Trifluoroacetic acid (1 mL) was added to a solution of tert-butyl ((1S)-2-oxo-2-{[(2,3-cis)-4oxo-2-phenyl-2,3,4,5-tetrahydro-1,5-benzoxazepin-3-yl]amino}-1-phenylethyl)carbamate (58a) (136 mg, 0.279 mmol) in dichloromethane (3 mL) at 0° C. The solution was allowed to warm to ambient temperature and stirred 1 h. The solvent was evaporated and the residue was dissolved in ethyl acetate and extracted with aqueous sodium bicarbonate. The organic solution was dried and evaporated to afford the title compound (108 mg, 99%) which was used in the next step without additional purification. $^1$H NMR (300 MHz, CDCl$_3$) δ1.71 (br s, 2H), 4.44 (m, 1H), 5.23 (m, 1H), 5.70 (m, 1H), 6.98-7.60 (m, 16H). MS APCI, m/z=388 (M+1). LC/MS: 1.72 min. MS APCI, m/z=388 (M+1). LC/MS: 1.82 min. (diastereomers evident).

Example 59

N$^2$-[(3,5-Difluorophenyl)acetyl]-N$^2$-[(2R,3S)-4-oxo-2-phenyl-2,3,4,5-tetrahydro-1,5-benzoxazepin-3-yl]-L-serinamide (59)

Using a procedure similar to that described in Example 1, except using (2,3-cis)-3-amino-2-phenyl-2,3-dihydro-1,5-benzoxazepin-4(5H)-one hydrochloride (6e) (61.1 mg) as the amine component, and N-[(3,5-difluorophenyl)acetyl]-L-serine (4b) (66.5 mg) as the acid component, the title compound (59) was obtained as a white solid. Purification by flash chromatography (2-10% methanol gradient in dichloromethane) provided the white solid title compound (97.5 mg) as a 1:1 mixture with the 2S,3R diastereomer. $^1$H NMR (300 MHz, CDCl$_3$) δ3.00-3.179 (m, 1H), 3.37-3.54 (m, 4H), 3.70-3.83 (m, 1H), 4.37-4.50 (m, 1H), 5.09-5.18 (m, 1H), 5.74 (d, 1H, J=7 Hz), 6.55-7.51 (m, 13H), 8.24-8.39 (m, 1H). MS APCI, m/z=496 (M+1). LC/MS: 2.14 min.

Example 60

(2S)-2-Cyclohexyl-2-[(3,5-difluorophenyl)acetyl] amino-N-[(2R,3S)4-oxo-2-phenyl-2,34,5tetrahydro-1,5-benzoxazepin-3-yl]acetamide (60)

To a stirred solution of (2S)-2-amino-N-[(2,3-cis)-4oxo-2-phenyl-2,3,4,5-tetrahydro-1,5-benzoxazepin-3-yl]-2-cyclohexylacetamide (60b) (137 mg, 0.350 mmol), 3,5-difluorophenylacetic acid (67 mg, 0.389 mmol), HOBt (59 mg, 0.437 mmol) and NMM (45 mg, 0.455 mmol) in dichloromethane (5mL) under nitrogen at 0° C. was added EDAC-HCl (83 mg, 0.432 mmol). The mixture was kept at 0° C. for 30 min. then stirred overnight at ambient temperature. The reaction was diluted with ethyl acetate and extracted in succession with saturated sodium bicarbonate, 1N aqueous HCl, and brine. The organic solution was dried, filtered and evaporated. The residue was purified by flash chromatography on silica gel eluting with 1:1 (v/v) hexane:ethyl acetate to afford the title compound as a 1:1 mixture with the 2S,3R diastereomer (110 mg, 57%) as a white solid. $^1$H NMR (300 MHz, DMSO-d6) δ0.72-1.22 (m, 5H), 1.29-1.70 (m, 5H), 3.27 (s, 2H), 3.52 (m, 1H), 4.13 (m, 0.5H), 4.28 (m, 0.5H), 4.98 (m, 0.5H), 5.08 (m, 0.5H), 5.58 (m, 1H), 6.87-7.56 (m, 13H), 8.03 (br d, 0.5H), 8.17 (br d, 0.5H), 10.26 (s, 0.5H), 10.30 (s, 0.5H). MS APCI, m/z=548 (M+1). LC/MS: 2.49 min.

The precursor (2S)-2-amino-N-[(2,3-cis)-4-oxo-2-phenyl-2,3,4,5-tetrahydro-1,5-benzoxazepin-3-yl]-2-cyclohexylacetamide (60b) was prepared as follows:

a. tert-Butyl ((1S)-1-cyclohexyl-2-oxo-2-{[(2,3-cis)-4-oxo-2-phenyl-2,3,4,5-tetrahydro-1,5-benzoxazepin-3-yl]amino}ethyl)carbamate (60a)

To a stirred solution of (2,3-cis)-3-amino-2-phenyl-2,3-dihydro-1,5-benzoxazepin-4(5H)-one (6e) (254 mg, 1.000 mmol) in dichloromethane (10 mL) under argon was added BOC-L-cyclohexylglycine (257 mg, 1.000 mmol) and HOBt (176 mg, 1.300 mmol). The solution was cooled to 0° C., N (135 mg, 1.366 mmol) and EDAC-HCl (249 mg, 1.299 mmol) were added. The reaction was allowed to warm to ambient temperature and stirred under argon overnight. The reaction mixture was diluted with ethyl acetate and extracted in succession with saturated aqueous sodium bicarbonate, 1N aqueous HCl, and brine. The organic solution was dried, filtered and evaporated. The residue was purified by flash chromatography on silica gel eluting with 3:1 (v/v) hexane:ethyl acetate to afford the title compound (408 mg, 83%) as a yellow solid. TLC R$_f$=0.23 (3:1 (v/v) hexane:ethyl acetate). $^1$H NMR (300 MHz, CDCl$_3$) δ0.77-1.78 (m, 20H), 3.90 (m, 0.5H), 4.17 (m, 0.5H), 4.97 (m, 1H), 5.17 (m, 1H), 5.80 (m, 1H), 6.42-6.62 (m, 1H), 7.08 (m, 1H), 7.14-7.47 (m, 8H), 7.59 (br s, 0.5H), 8.05 (br s, 0.5H). MS APCI, m/z=494 (M+1). LC/MS: 2.61 min.

b. (2S)-2-Amino-N-[(2,3-cis)-4-oxo-2-phenyl-2,3,4,5-tetrahydro-1,5-benzoxazepin-3-yl]-2-cyclohexylacetamide (60b)

Trifluoroacetic acid (2 mL) was added to a stirred solution of tert-butyl ((1S)-1-cyclohexyl-2-oxo-2-{[(2,3-cis)-4-oxo-2-phenyl-2,3,4,5-tetrahydro-1,5-benzoxazepin-3-yl] amino}ethyl)carbamate (60a) (345 mg, 0.699 mmol) at ambient temperature. The solution was stirred for 90 min. then evaporated. The residue was dissolved in ethyl acetate and extracted in succession with aqueous sodium bicarbonate and brine. The organic solution was dried and evaporated to afford the title compound (275 mg, 99%) as a yellow solid which was used in the next step without additional purification. MS APCI, m/z=394 (M+1). LC/MS: 1.54 min. MS APCI, m/z=394 (M+1). LC/MS: 1.71 min. (diastereomers evident).

Example 61

(2S)—N-((1S)-1-Cyclohexyl-2oxo-2-[(2R,3S)-4-oxo-2-phenyl-2,3,4,5-tetrahydro-1,5-benzoxazepin-3-yl]aminoethyl)-2-hydroxy-4-methylpentanamide (61)

To a stirred solution of (2S)-2-amino-N-[(2,3-cis)-4-oxo-2-phenyl-2,3,4,5-tetrahydro-1,5-benzoxazepin-3-yl]-2-cyclohexylacetamide (60b) (137 mg, 0.350 mmol), (S)-2-hydroxyisocaproic acid (52 mg, 0.394 mmol), HOBt (59 mg, 0.437 mmol) and NMM (45 mg, 0.455 mmol) in dichloromethane (5mL) under nitrogen at 0° C. was added EDAC-HCl (83 mg, 0.432 mmol). The mixture was kept at 0° C. for 30 min. then stirred overnight at ambient temperature. The reaction was diluted with ethyl acetate and extracted in succession with saturated sodium bicarbonate, 1N aqueous HCl, and brine. The organic solution was dried, filtered and evaporated. The residue was purified by flash chromatography on silica gel eluting with 1:1 (v/v) hexane:ethyl acetate to afford the title compound in a 1:1 mixture with the 2S,3R diastereomer (144 mg, 81%) as a white solid. $^1$H NMR (300 MHz, DMSO-d6) δ0.75-1.86 (m, 20H), 3.83 (m, 1H), 4.22 (m, 0.5H), 4.37 (m, 0.5H), 5.06 (m, 1H), 5.46 (m, 1H), 5.58 (m, 1H), 7.10-7.27 (m, 4H), 7.31-7.44 (m, 5.5H), 7.55 (br d, 0.5H), 7.71 (m, 0.5H), 7.88 (m, 0.5H), 10.25 (s, 0.5H), 10.28 (s, 0.5H). MS APCI, m/z=508 (M+1). LC/MS: 2.41 min.

Example 62

3-Cyclohexyl-N$^2$-[(3,5-difluorophenyl)acetyl]-N$^1$-[(6R,7R)-5oxo-7-phenyl-1,4thiazepan-6-yl]-L-alaninamide (62)

To a stirred solution of 3-cyclohexyl-N$^1$-[(6,7-cis)-5-oxo-7-phenyl-1,4-thiazepan-6-yl]-L-alaninamide (62b) (115 mg, 0.306 mmol) in dichloromethane (6 mL) was added 3,5-difluorophenylacetic acid (56 mg, 0.325 mmol), HOBt (50 mg, 0.370 mmol), NMM (37 mg, 0.366 mmol) and EDAC-HCl (70 mg, 0.365 mmol). The mixture was stirred at ambient temperature under nitrogen overnight. The solvent was evaporated, the residue dissolved in ethyl acetate and extracted in succession with saturated sodium bicarbonate, 1N aqueous HCl, and brine. The organic solution was dried, filtered and evaporated. The residue was purified by flash chromatography on silica gel eluting with 1:1 (v/v) dichloromethane:ethyl acetate to afford the title compound in a 1:1 mixture with the 6S,7S diastereomer (45 mg, 28%) as a white solid. TLC R$_f$=0.27 (1:1 dichloromethane:ethyl acetate). $^1$H NMR (300 MHz, CDCl$_3$) δ0.84 (m, 3H), 1.00-1.44 (m, 6H), 1.48-1.70 (m, 4H), 2.80 (m, 1H), 3.07 (m, 1H), 3.50 (m, 2H), 3.80 (m, 2H), 4.33 (d, 1H, J=4.4 Hz), 4.41 (m, 1H), 5.32 (m, 1H), 5.81 (d, 1H, J=7.9 Hz), 6.23 (br t, 1H), 6.68-6.87 (m, 3H), 7.04, d, J=6.1 Hz), 7.27 (s, 5H). MS APCI, m/z=530 (M+1). LC/MS: 2.55 min.

The precursor 3-cyclohexyl-N$^1$-[(6,7-cis)-5-oxo-7-phenyl-1,4-thiazepan-6-yl]-L-alaninamide (62b) was prepared as follows:

a. N-(tert-butoxycarbonyl)-3-cyclohexyl-N$^1$-[(6,7-cis)-5-oxo-7-phenyl-1,4-thiazepan-6-yl]-L-alaninamide (62a)

To a stirred solution of (6,7-cis)-6-amino-7-phenyl-1,4thiazepan-5-one hydrobromide (48e) (208 mg, 0.686 mmol) in dichloromethane (10 mL) under nitrogen was added, N-(tert-butoxycarbonyl)-3-cyclohexyl-L-alanine (205 mg, 0.755 mmol), HOBt (112 mg, 0.829 mmol), NMM (166 mg, 1.643 mmol) and EDAC-HCl (158 mg, 0.824 mmol). The mixture was stirred at ambient temperature overnight. The reaction mixture was diluted with saturated aqueous sodium bicarbonate and extracted with ethyl acetate. The organic solution was separated, extracted in succession with 1N aqueous HCl and brine then dried, filtered and evaporated to afford the title compound (326 mg, 99%) as a white solid. $^1$H NMR (300 MHz, CDCl$_3$) δ0.87 (m, 2H), 1.03-1.86 (m, 20H), 2.79 (m, 1H), 3.03 (m, 1H), 3.78 (m, 2H), 4.19 (m, 1H), 4.36 (t, 1H, J=4.0 Hz), 4.65-4.90

(br m, 1H), 5.31 (m, 1H), 6.18-6.47 (br m, 1H), 7.15 (br, 1H), 7.29 (s, 5H). MS APCI, m/z=498 (M+Na). LC/MS: 2.50 min.

b. 3-Cyclohexyl-N¹-[(6,7-cis)-5-oxo-7-phenyl-1,4-thiazepan-6-yl]-L-alaninamide (62b)

N²-(tert-Butoxycarbonyl)-3-cyclohexyl-N¹-[(6,7-cis)-5-oxo-7-phenyl-1,4-thiazepan-6-yl]-L-alaninamide (62a) (325 mg, 0.683 mmol) was dissolved in 3:1 (v/v) dichloromethane:trifluoroacetic acid (8 mL) and kept at ambient temperature for 2 h. The solution was evaporated and the residue partitioned between ethyl acetate and saturated aqueous sodium bicarbonate. The organic solution was separated, dried, filtered and evaporated to afford the title compound (252 mg, 98%) as a yellow oil. $^1$H NMR (300 MHz, CDCl$_3$) δ0.91 (m, 2H), 1.02-1.79 (m, 13H), 2.85 (m, 1H), 3.03 (m, 1H), 3.32 (m, 1H), 3.66-3.94 (m, 2H), 4.40 (m, 1H), 5.35 (m, 1H), 6.16 (m, 1H), 7.29 (m, 5H), 7.86 (br d, 0.5H), 8.06 (br d, 0.5H). MS APCI, m/z=376 (M+1). LC/MS: 1.48 min. MS APCI, m/z=376 (M+1). LC/MS: 1.68 min. (diastereomers evident).

Example 63

N²-[(3,5-Difluorophenyl)acetyl]-N¹-[(2S,3R)-5-(2-morpholin-4-ylethyl)-4-oxo-2-phenyl-2,3,4,5-tetrahydro-1,5-benzoxazepin-3-yl]-L-alaninamide hydrochloride (63)

A solution of 63d (260 mg) in methanol (10 mL) was treated with morpholine (87 µL) and acetic acid (172 µL) followed by sodium cyanoborohydride (80 mg). The reaction mixture was stirred for 16 h, acidified with hydrochloric acid (5 drops) and stirred for additional 1 h. At the end of this period upon concentration under reduced pressure the reaction mixture was diluted with dichloromethane (100 mL) and washed with aqueous sodium carbonate solution. The organic layer was dried over potassium carbonate and concentrated under reduced pressure and the crude product was purified by column chromatography over silica gel. Product obtained after elution with dichloromethane:methanol (20:1) was dissolved in methanol (1 mL) and treated with HCl (1 mL of 2M solution in ether) and diluted with ether (70 mL). The solid thus obtained was filtered to afford the title compound in 1:1 mixture with the (2R,3R) diastereomer (150 mg) as a white solid: $^1$H NMR (300 MHz, d6-DMSO) δ 1.07 (m, 3H), 3.79 (m, 2H), 3.95 (m, 2H), 4.22 (m, 2H), 4.40 (m, 1H), 4.938 (m, 1H), 5.54 (t, 1H, J=6 Hz), 7.899-7.39 (m, 13H), 7.63 (m, 1H), 8.27 (d, 0.5H, J=7 Hz), 8.355 (d, 0.5H, J=7 Hz). MS APCI, m/z=593 (M+1). LC/MS: 2.02 min.

The starting aldehyde N²-[(3,5-difluorophenyl)acetyl]-N¹-[(2S,3R)4-oxo-5-(2-oxoethyl)-2-phenyl-2,3,4,5-tetrahydro-1,5-benzoxazepin-3-yl]-L-alaninamide (63d) was prepared in the following manner:

a. tert-Butyl [(2,3-cis)-5-allyl-4-oxo-2-phenyl-2,3,4,5-tetrahydro-1,5-benzoxazepin-3-yl]carbamate (63a)

A solution of tert-butyl [(2,3-cis)-4-oxo-2-phenyl-2,3,4,5-tetrahydro-1,5-benzoxazepin-3-yl]carbamate (46a) (750 mg) in THF(10 mL) was treated with powdered KOH (123 mg), tetrabutylammonium bromide(64 mg) and allylbromide (484 mg). Upon stirring for 16 h the reaction mixture was filtered, the precipitate washed with ethyl acetate (2×20 mL) and the filtrate was concentrated under reduced pressure. The product was purified by column chromatography over silica gel. Elution with 9:1 dichloromethane:ethyl acetate afforded the title product (792 mg). $^1$H NMR (300 MHz, CDCl$_3$) δ 1.37 (s, 9H), 4.46 (dd, 1H, J=5 Hz, J=16 Hz), 4.97 (d, 1H, J=4 Hz), 5.23(m, 2H), 5.66(t, 1H, J=3 Hz), 5.93 (m, 1H), 7.30(m, 9H). MS APCI, m/z=295 (M+1). LC/MS: 2.72 min.

b. (2,3-cis)-5-Allyl-3-amino-2-phenyl-2,3-dihydro-1,5-benzoxazepin-4(5H)-one (63b)

A solution of tert-butyl [(2S,3R)-5-allyl-4-oxo-2-phenyl-2,3,4,5-tetrahydro-1,5-benzoxazepin-3-yl]carbamate (63a) (792 mg) in dichloromethane (10 mL) was treated with phenol(470 mg) and trifluoroacetic acid (10 mL). Upon stirring for 30 min the reaction mixture was concentrated under reduced pressure, treated with 5% HCl and extracted with ether (100 mL). The aqueous layer was basified with potassium carbonate and extracted with dichloromethane (2×10 mL). The organic layer was dried over anhydrous potassium carbonate and concentrated under reduced pressure to afford the title product (430 mg). $^1$H NMR (300 MHz, CDCl$_3$) δ 4.12 (d, 1H, J=6 Hz), 4.50 (d, d, 1H, J=6 Hz, J=15 Hz), 4.62 (d, d, 1H, J=6 Hz, J=15 Hz), 5.25(m, 2H), 5.46(d, 1H, J=7 Hz), 5.98(m, 1H), 7.30 (m, 9H).

c. N¹-[(2R,3S)-5-Allyl-4-oxo-2-phenyl-2,3,4,5-tetrahydro-1,5-benzoxazepin-3-yl]-N²-[3,5-difluorophenyl)acetyl]-L-alaninamide (63c)

A method similar to that described for 97e was used except that (2,3-cis)-5-allyl-3-amino-2-phenyl-2,3-dihydro-1,5-benzoxazepin-4(5H)-one (63b) (430 mg) was the amine component and N-[(3,5-difluorophenyl)acetyl]-L-alanine (1e) was the acid component to afford the title compound as a 1:1 mixture with the (2S,3R) diastereomer (582 mg). $^1$H NMR (300 MHz, C$_6$D$_6$) δ 0.93 (d, 1.5H, J=7 Hz), 1.05(d, 1.5H, J=7 Hz), 3.47 (two peaks, 2H), 4.22-4.67 (m, 3H), 5.06(m, 1H), 5.26(m, 2H), 5.68(m, 1H), 5.90(m,1H), 6.25(d, 1H, J=7 Hz), 6.72(m, 2H), 6.25-7.38 (m, 10H). MS APCI, m/z=520 (M+1). LC/MS: 2.46 min.

d. N²-[(3,5-Difluorophenyl)acetyl]-N¹-[(2R,3S)-4-oxo-5-(2-oxoethyl)-2-phenyl-2,3,4,5-tetrahydro-1,5-benzoxazepin-3-yl]-L-alaninamide(63d)

A solution of 63c (582 mg) in THF(10 mL) was treated with a solution sodium periodate (530 mg) in water (10 mL) followed by a 4% solution of OsO$_4$(1 mL). The reaction mixture was stirred for 16 h, diluted with sodium bisulfite solution (20 mL) and extracted with ethyl acetate (2×100 mL). The organic layers were washed with NaCl solution, dried over magnesium sulfate and concentrated under reduced pressure. The product thus obtained was dissolved in THF (50 mL) and treated with a solution sodium periodate (530 mg) in water (50 mL). After stirring for 16 h the reaction mixture was concentrated under reduced pressure and extracted with dichloromethane (2×100 mL). The organic layers were concentrated under reduced pressure and the product was purified by chromatography to obtain the title compound in 1:1 mixture with the (2S,3R) diastereomer (417 mg). $^1$H NMR (300 MHz, CDCl$_3$) δ 1.05 (m, 3H), 3.47 (two peaks, 2H), 6.74(m, 2H), 7.25-7.60 (m, 12H).

Example 64

$N^2$-[(3,5-Difluorophenyl)acetyl]-$N^1$-[(2R,3S)-4-oxo-2-phenyl-2,3,4,5-tetrahydro-1,5-benzoxazepin-3-yl]-L-leucinamide (64)

To a stirred solution of $N^1$-[(2R,3S)-4-oxo-2-phenyl-2,3,4,5-tetrahydro-1,5-benzoxazepin-3-yl]-L-leucinamide (64 g) (65 mg, 0.177 mmol) in dichloromethane (2 mL) was added 3,5-difluorophenylacetic acid (35 mg, 0.230 mmol), HOBt (31 mg, 0.230 mmol), NMM (25 mg, 0.248 mmol) and EDAC-HCl (44 mg, 0.230 mmol). The mixture was stirred at ambient temperature under nitrogen overnight. The reaction mixture was diluted with water and extracted with ethyl acetate three times. The combined organic extracts were washed in succession with saturated aqueous sodium bicarbonate and 1N aqueous HCl. The organic solution was dried, filtered and evaporated. The residue was purified by flash chromatography on silica gel eluting with 6:1 (v/v) dichloromethane:ethyl acetate to afford the title compound in a 1:1 mixture with the 2S,3R diastereomer (65 mg, 70%) as a white solid. TLC $R_f$=0.31 (6:1 dichloromethane:ethyl acetate). $^1$H NMR (300 MHz, CDCl$_3$) δ0.82 (m, 6H), 1.21-1.55 (m, 3H), 3.48 (s, 2H), 4.28 (m, 1H), 5.15 (t, 1H, J=7.2 Hz), 5.76 (m, 2H), 6.27 (d, 1H, J=7.0 Hz), 6.78 (m, 3H), 7.06 (m, 1H), 7.15-7.42 (m, 8H), 7.55 (br s, 1H). MS APCI, m/z=510 (M+1). LC/MS: 2.40 min.

The precursor $N^1$-[(2R,3S)-4-oxo-2-phenyl-2,3,4,5-tetrahydro-1,5-benzoxazepin-3-yl]-L-leucinamide (64 g) was prepared as follows:

a. Potassium (2R,3S)-3-phenyloxirane-2-carboxylate (64a)

A stirred suspension of (1R)-1-phenylethanaminium (2R,3S)-3-phenyloxirane-2-carboxylate [K. Horada, J. Org. Chem., 31, 1407, 1966] (28.54 g, 0.10 mole) in ethanol (60 mL) and water (15 mL) was treated rapidly with a solution of KOH (9.5 g, 0.17 mole) in ethanol (60 mL). The mixture was stirred at ambient temperature for 20 min, ethyl ether (150 mL) added, the mixture stirred an additional 10 min and the white solid filtered off and washed with ethyl ether. A second crop was obtained by dilution of the filtrate with ethyl ether to 500 mL. Both samples were dried in vacuo. The pH of a small sample of crop 1 in water was 8 to 9 while a sample of crop 2 had pH=14. Crop 2 was thus stirred with 15 mL of absolute ethanol for 15 min, filtered, washed with acetone and dried in vacuo. Crop 1 (16.23 g, 80%) [α]D 25=−146° (c=1.0, H$_2$O) and crop 2 (3.03 g 15%) [α]D 25=−143° (c=1.2, H$_2$O). $^1$H NMR (300 MHz, DMSO-d6) δ2.97 (d, 1H, J=1.8 Hz), 3.66 (d, 1H, J=1.8 Hz), 7.22-7.35 (m, 5 H). HPLC (Method B): 2.74 min.

b. (2R,3S)—N-(2-Hydroxyphenyl)-3-phenyloxirane-2-carboxamide (64b)

To a stirred suspension of potassium (2R,3S)-3-phenyloxirane-2-carboxylate (64a) (4.040 g, 20.00 mmol) in dry THF (100 mL) under nitrogen cooled in an ice-water bath was added isobutyl chloroformate (2.730 g, 20.00 mmol) slowly via syringe. NMM (0.460 mg, 4.55 mmol) was added and the mixture stirred while gradually warming to 10° C. over 75 min. The mixture was cooled to 0° C. and 2-aminophenol was added, then the cooling bath was removed and the reaction stirred at ambient temperature for 24 h. The reaction was diluted with diethyl ether (100 mL) then filtered through diatomaceous earth to remove suspended solids. Rotary evaporation of the solution afforded a yellow solid that was triturated with diethyl ether and collected by filtration. The solid was rinsed on the filter with additional diethyl ether to afford pure title compound (3.920 g, 77%) as an off-white solid. $^1$H NMR (300 MHz, DMSO-d6) δ4.00 (d, 1H, J=1.8 Hz), 4.22 (d, 1H, J=1.8 Hz), 6.80 (m, 1H), 6.87-7.00 (m, 2H), 7.40 (s, 5H), 7.95 (d, 1H, J=7.9 Hz), 9.27 (s, 1H), 9.97 (s, 1H). $^{13}$C-DEPT NMR (75 MHz, DMSO-d6) δ57.7 (CH), 58.4 (CH), 115.5 (CH), 119.4 (CH), 121.6 (CH), 125.1 (CH), 125.8 (C), 126.5 (CH), 128.9 (CH), 129.1 (CH), 135.9 (C), 147.7 (C), 165.4 (C). MS APCI, m/z=256 (M+l). LC/MS: 2.12 min.

c. (2R,3R)-3-Hydroxy-2-phenyl-2,3-dihydro-1,5-benzoxazepin-4(5H)-one (64c)

Scandium triflate (730 mg, 1.48 mmol) was added to a stirred suspension of (2R,3S)-N-(2-hydroxyphenyl)-3-phenyloxirane-2-carboxamide (64b) in dry acetonitrile (150 mL) under nitrogen. The mixture was stirred at ambient temperature for 24 hours then heated at reflux for an additional 1 hour. The solvent was evaporated, the residue dissolved in ethyl acetate, and filtered through diatomaceous earth. Evaporation afforded an off-white solid which was purified by flash chromatography on silica gel eluting with 10:1 (v/v) dichloromethane:ethyl acetate to afford the title compound (2.290 g, 60%) as a white solid. TLC $R_f$=0.20 (10:1 dichloromethane:ethyl acetate). $^1$H NMR (300 MHz, CDCl$_3$) δ3.70 (d, 1H, J=5 Hz), 4.63 (m, 1H), 5.28 (d, 1H, J=10 Hz), 6.89 (m, 1H), 7.02-7.16 (m, 3H), 7.35-7.47 (m, 5H), 7.78 (br, 1H). MS APCI, m/z=256 (M+1). LC/MS: 1.84 min. [α]D 25=+288° (c=5.0, CHCl$_3$).

d. (2R,3S)-3-Azido-2-phenyl-2,3-dihydro-1,5-benzoxazepin-4(5H)-one (64d)

Triethylamine (1.667 g, 16.472 mmol) was added via syringe to a stirred solution of (2R,3R)-3-hydroxy-2-phenyl-2,3-dihydro-1,5-benzoxazepin-4(5H)-one (6 c (2.532 g, 9.922 mmol) in dichloromethane (90 mL) under nitrogen at −40° C. Next trifluoromethanesulfonyl chloride (2.541 g, 15.080 mmol) was added slowly via syringe and the mixture kept at −25° C. for 2 h. Additional triethylamine (1.667 g, 16.472 mmol) was added followed by trifluoromethanesulfonyl chloride (2.541 g, 15.080 mmol) and the reaction was kept for 8 h at −25° C. Again, additional triethylamine (1.667 g, 16.472 mmol) was added via syringe followed by trifluoromethanesulfonyl chloride (2.541 g, 15.080 mmol) and the reaction was kept for 24 h at −25° C. The solvent was evaporated without heating under reduced pressure and the residue dissolved in DMF (25 mL). Sodium azide (3.000 g, 46.15 mmol) was added to the stirred DMF solution at −10° C. and the reaction was allowed to warm to ambient temperature. After 2 h the reaction was diluted with water (300 mL) and extracted three times with ethyl acetate. The combined organic extracts were washed with saturated aqueous sodium bicarbonate and then with brine. The organic solution was dried, filtered and evaporated. The residue was purified by flash chromatography an silica gel eluting with 30:1 (v/v) dichloromethane:ethyl acetate to afford the title compound as an off-white solid. TLC $R_f$=0.35 (20:1 (v/v) dichloromethane:ethyl acetate). $^1$H NMR (300 MHz, CDCl$_3$) δ4.45 (d, 1H, J=6 Hz), 5.56 (d, 1H, J=6 Hz), 7.00-7.07 (m, 1H), 7.10-7.26 (m, 3H), 7.40-7.46 (m, 3H), 7.51-7.61 (m, 3H). MS APCI, m/z=253 (M+1−N$_2$). LC/MS: 2.25 min. [α]$^D$$_{25}$=−179° (c=5.0, CHCl$_3$)

e. (2R,3S)-3-Amino-2-phenyl-2,3-dihydro-1,5-benzoxazepin-4(5H)-one (64e)

To a solution of (2R,3S)-3-azido-2-phenyl-2,3-dihydro-1,5-benzoxazepin-4(5H)-one (64d) (1.128 g, 4.024 mmol)) in ethanol (80 mL) was added 1N hydrochloric acid (4.43 mL) and 5% palladium on carbon (60 mg). The reaction was purged with hydrogen and stirred for 2 h under a balloon of hydrogen. The reaction was purged with nitrogen then filtered through diatomaceous earth. The solvent was evaporated to afford a white solid that was then partitioned between ethyl acetate and saturated aqueous sodium bicarbonate while stirring. The organic phase was separated and the aqueous phase extracted an additional two times with ethyl acetate. The combined organic extracts were dried, filtered and evaporated to afford the title compound (973 mg, 95%) as an off-white solid. $^1$H NMR (300 MHz, DMSO-d6) δ1.36 (br, 2H), 3.93 (d, 1H, J=6.2 Hz), 5.45 (d, 1H, J=6.2 Hz), 7.06-7.22 (m, 4H), 7.32-7.46 (m, 5H), 9.96 (br, 1H). MS APCI, m/z=255 (M+1). LC/MS: 1.29 min.

f. $N^2$-[tert-Butoxycarbonyl]-$N^1$-[(2R,3S)-4-oxo-2-phenyl-2,3,4,5-tetrahydro-1,5-benzoxazepin-3-yl]-L-leucinamide (64f)

To a stirred solution of (2R,3S)-3-amino-2-phenyl-2,3-dihydro-1,5-benzoxazepin-4(5H)-one (64e) (50 mg, 0.197 mmol), and HOBt (33 mg, 0.2144 mmol), in dichloromethane (2 mL) was added NMM (50 mg, 0.495 mmol), and EDAC-HCl (46 mg, 0.240 mmol). The mixture was stirred at ambient temperature overnight under nitrogen. The reaction was diluted with ethyl acetate and extracted with 10% aqueous citric acid. The organic solution was dried and evaporated. The residue was purified by flash chromatography on silica gel eluting with 10:1 (v/v) dichloromethane:ethyl acetate to afford the title compound (85 mg, 92%) as a white solid. $^1$H NMR (300 MHz, CDCl$_3$) δ0.88 (t, 6H, J=5.9 Hz), 1.19-1.65 (m, 12H), 3.96 (m, 1H), 4.65 (m, 1H), 5.17 (t, 1H, J=7.0 Hz), 5.84 (d, 1H), J=7.0 Hz), 6.45 (br d, 1H, J=7.0 Hz), 7.06 (m, 1H), 7.23 (m, 3H), 7.38 (m, 5H), 7.60 (br s, 1H). MS APCI, m/z=490 (M+Na). LC/MS: 2.42 min.

g. $N^1$-[(2R,3S)-4-Oxo-2-phenyl-2,3,4,5-tetrahydro-1,5-benzoxazepin-3-yl]-L-leucinamide (64 g)

$N^2$-[tert-Butoxycarbonyl]-$N^1$-[(2R,3S)-4-oxo-2-phenyl-2,3,4,5-tetrahydro-1,5-benzoxazepin-3-yl]-L-leucinamide (64f) (83 mg, 0.177 mmol) was dissolved in 5:1 (v/v) dichloromethane:trifluoroacetic acid and kept at ambient temperature for 1 h. The solution was evaporated and the residue dissolved in ethyl acetate. The solution was extracted in succession with saturated aqueous sodium bicarbonate and brine then the organic solution was dried, filtered and evaporated to afford the title compound (65 mg, 99%) as a yellow oil. MS APCI, m/z=368 (M+1). LC/MS: 1.63 min.

Example 65

(2S)-2-[(3,5-Difluorophenyl)acetyl]amino-2-(4-fluorophenyl)-N-[(2R,3S)-4-oxo-2-phenyl-2,3,4,5-tetrahydro-1,5-benzoxazepin-3-yl]acetamide (65)

To a stirred solution of (2S)-2-amino-2-(4-fluorophenyl)-N-[(2R,3S)-4-oxo-2-phenyl-2,3,4,5-tetrahydro-1,5-benzoxazepin-3-yl]acetamide (65b) (81 mg, 0.199 mmol) in dichloromethane (2mL) under nitrogen was added 3,5-difluorophenylacetic acid (40 mg, 0.232 mmol), HOBt (35 mg, 0.259 mmol), NMM (30 mg, 0.297 mmol) and EDAC-HCl (50 mg, 0.261 mmol). The mixture was stirred 5 h at ambient temperature then evaporated. The residue was dissolved in ethyl acetate and extracted in succession with saturated sodium bicarbonate, 1N aqueous HCl, and brine. The organic solution was dried, filtered and evaporated. The residue was purified by flash chromatography on silica gel eluting with 6:1 (v/v) dichloromethane:ethyl acetate (TLC R$_f$=0.42) to afford the title compound (85 mg, 76%) as a white solid. $^1$H NMR (300 MHz, CDCl$_3$) δ3.54 (s, 2H), 5.08 (t, 1H, J=7.0 Hz), 5.19 (d, 1H, J=6.5 Hz), 5.79 (d, 1H, J=7.0 Hz), 6.16 (br d, 1H, J=6.5 Hz), 6.62 (br d, 1H, J=7.0 Hz), 6.66-6.86 (m, 3H), 6.87-7.04 (m, 3H), 7.08-7.39 (m, 10H), 7.50 (br s, 1H). MS APCI, m/z=560 (M+1). LC/MS: 2.61 min.

The precursor (2S)-2-amino-2-(4-fluorophenyl)-N-[(2R,3S)-4-oxo-2-phenyl-2,3,4,5-tetrahydro-1,5-benzoxazepin-3-yl]acetamide (b) was prepared as follows:

a. tert-Butyl ((1S)-1-(4-fluorophenyl)-2-oxo-2-{[(2R,3S)-4-oxo-2-phenyl-2,3,4,5-tetrahydro-1,5-benzoxazepin-3-yl]aminol}ethyl)carbamate (65a)

To a stirred solution of (2S)-[(tert-butoxycarbonyl)amino](4-fluorophenyl)acetic acid (269 mg, 1.00 mmol) and (2,3-cis)-3-amino-2-phenyl-2,3-dihydro-1,5-benzoxazepin-4(5H)-one (6e) (254 mg, 1.00 mmol) in dichloromethane (10 ml) under nitrogen was added NMM (111 mg, 1.100 mmol), HOBt (162 mg, 1.20 mmol) and EDAC-HCl (211 mg, 1.10 mmol). The mixture was stirred overnight at ambient temperature then the solvent was evaporated and the residue partitioned between ethyl acetate and 1N aqueous HCl. The organic phase was separated then washed with saturated aqueous sodium bicarbonate, dried and evaporated. The residue was purified by flash chromatography on silica gel eluting with 10:1 (v/v) dichloromethane:ethyl acetate. The desired 2R,3S diastereomer eluted first R$_f$=0.27) and the 2S,3R diastereomer eluted later (R$_f$=0.20). The fractions containing the early eluting diastereomer were combined and evaporated to afford the title compound (202 mg, 40%) as a white solid. $^1$H NMR (300 MHz, CDCl$_3$) δ1.41 (s, 9H), 4.94 (br, 1H), 5.09 (m, 1H), 5.48 (d, 1H, J=6.6 Hz), 5.83 (d, 1H J=7.0 Hz), 6.33 (br, 1H), 6.91-7.04 (m, 3H), 7.12-7.28 (m, 5H), 7.38 (s, 5H), 7.48 (br, 1H). MS APCI, m/z=528 (M+Na). LC/MS: 2.06 min.

b. (2S)-2-Amino-2-(4-fluorophenyl)-N-[(2R,3S)-4-oxo-2-phenyl-2,3,4,5-tetrahydro-1,5-benzoxazepin-3-yl]acetamide (65b)

tert-Butyl ((1S)-1-(4-fluorophenyl)-2-oxo-2-{[(2R,3S)-4-oxo-2-phenyl-2,3,4,5-tetrahydro-1,5-benzoxazepin-3-yl]amino}ethyl)carbamate (65a) (202 mg, 0.400 mmol) was dissolved in 5:1 (v/v) dichloromethane:trifluoroacetic acid (4 mL) and kept at ambient temperature for 1 h. The solution was evaporated and the residue was dissolved in ethyl acetate and extracted with saturated aqueous sodium bicarbonate. The organic solution was dried and evaporated to afford the title compound (160 mg, 99%) as a yellow oil. MS APCI, m/z=406 (M+1). LC/MS: 1.60 min.

Example 66

(2S)-2-[(Cyclohexylacetyl)amino]-2-(4-fluorophenyl)-N-[(2R,3S)-4oxo-2-phenyl-2,3,4,5-tetrahydro-1, 5-benzoxazepin-3-yl]acetamide (66)

To a stirred solution of (2S)-2-amino-2-(4fluorophenyl)-N-[(2R,3S )-4-oxo-2-phenyl-2,3,4,5-tetrahydro-1,5-benzoxazepin-3-yl]acetamide(65b) (81 mg, 0.199 mmol) in dichloromethane (2 mL) under nitrogen was added cyclohexylacetic acid (35 mg, 0.246 mmol), HOBt (35 mg, 0.259 mmol), NMM (30 mg, 0.297 mmol) and EDAC-HCl (50 mg, 0.261 mmol). The mixture was stirred 5 h at ambient temperature then evaporated. The residue was dissolved in ethyl acetate and extracted in succession with saturated sodium bicarbonate, 1N aqueous HCl, and brine. The organic solution was dried, filtered and evaporated. The residue was purified by flash chromatography on silica gel eluting with 6:1 (v/v) dichloromethane:ethyl acetate to afford the title compound (89 mg, 84%) as a white solid. TLC $R_f$=0.42 (6:1 dichloromethane:ethyl acetate). $^1$H NMR (300 MHz, CDCl$_3$) δ0.81-1.37 (m, 5H), 1.59-1.87 (m, 6H), 2.09 (d, 2H, J=6.5 Hz), 5.09 (t, 1H, J=7.0 Hz), 5.26 (d, 1H, J=7.0 Hz), 5.83 (d, 1H, J=7.0 Hz), 6.24 (br d, 1H, J=6.5 Hz), 6.48 (br d, 1H, J=6.5 Hz), 6.88-7.05 (m, 3H), 7.12-7.30 (m, 5H), 7.36 (s, 5H), 7.56 (br s, 1H). MS APCI, m/z=530 (M+1).
LC/MS: 2.69 min.

Example 67

N$^2$-[(3,5-Difluorophenyl)acetyl]-N$^1$-[(2R,3S)-4-oxo-2-phenyl-5-prop-2-yn-1-yl-2,3,4,5-tetrahydro-1,5-benzoxazepin-3-yl]-L-alaninamide (67)

To a stirred solution of (2R,3S)-3-amino-2-phenyl-5-prop-2-yn-1-yl-2,3-dihydro-1,5-benzoxazepin-4(5H)-one (67c) (65 mg, 0.222 mmol) in dichloromethane (3 mL) was added N-[(3,5-difluorophenyl)acetyl]-L-alanine (1e) (65 mg, 0.267 mmol), HOBt (40 mg, 0.296 mmol), NMM (31 mg, 0.306 mmol) and EDAC-HCl (55 mg, 0.286 mmol). After stirring at ambient temperature under nitrogen overnight the solvent was evaporated and the residue partitioned between ethyl acetate and saturated aqueous sodium bicarbonate. The organic solution was separated, washed with 1N aqueous HCl then dried, filtered and evaporated. The residue was purified by recrystallization from 1:1 (v/v) ethyl acetate: hexanes to afford the title compound (86 mg, 74%) as a white solid. TLC $R_f$=0.25 (diethyl ether). $^1$H NMR (300 MHz, CDCl$_3$) δ1.22 (d, 3H, J=7.0 Hz), 2.31 (m, 1H), 3.48 (s, 2H), 4.23 (m, 1H), 4.69 (d, 2H, J=2.2 Hz), 5.11 (t, 1H, J=7.0 Hz), 5.69 (d, 1H, J=7.4 Hz), 5.87 (d, 1H), 6.18 (d, 1H), 6.69-6.86 (m, 3H), 7.26-7.53 (m, 9H). MS APCI, m/z=518 (M+1). LC/MS: 2.63 min.

The precursor (2R,3S)-3-amino-2-phenyl-5-prop-2-yn-1-yl-2,3-dihydro-1,5-benzoxazepin-4(5H)one (67c) was prepared as follows:

a. tert-Butyl [(2R,3S)-4-oxo-2-phenyl-2,3,4,5-tetrahydro-1,5-benzoxazepin-3-yl]carbamate (67a)

To a stirred solution of (2R,3S)-3-amino-2-phenyl-2,3-dihydro-1,5-benzoxazepin-4(5H)-one (64e) (700 mg, 3.207 mmol) in dichloromethane (30 mL) under nitrogen at 0° C. was added triethylamine (324 mg, 3.21 mmol) and di-tert-butyl dicarbonate (700 mg, 3.208 mmol). The mixture was allowed to warm to ambient temperature and stirred for 24 h. The solvent was evaporated and the residue purified by flash chromatography on silica gel eluting first with dichloromethane and finally with 20:1 (v/v) dichloromethane:ethyl acetate to afford the title compound (943 mg, 83%) as a white solid. TLC $R_f$=0.50 (2:1 hexane:ethyl acetate). $^1$H NMR (300 MHz, CDCl$_3$) δ1.39 (s, 9H), 4.90-5.05 (m, 2H), 5.76 (d, 1H, J=6.8 Hz), 7.05 (m, 1H), 7.14-7.29 (m, 3H), 7.36-7.53 (m, 6H). MS ES+, m/z=377 (M+Na).
LC/MS: 1.93 min.

b. tert-Butyl [(2R,3S)-4-oxo-2-phenyl-5-prop-2-yn-1-yl-2,3,4,5-tetrahydro-1,5-benzoxazepin-3-yl]carbamate (67b)

To a stirred solution of tert-butyl [(2R,3S)-4-oxo-2-phenyl-2,3,4,5-tetrahydro-1,5-benzoxazepin-3-yl]carbamate (67a) (160 mg, 0.451 mmol) in DMF (2 mL) was added propargyl bromide (80 mg, 0.672 mmol) and powdered cesium carbonate (219 mg, 0.672 mmol). The mixture was stirred under nitrogen at ambient temperature for 18 h. The reaction was diluted with water and extracted twice with ethyl acetate. The residue obtained from the combined organic extracts was purified by flash chromatography on silica gel eluting with 5:1 (v/v) hexane:ethyl acetate to afford the title compound (143 mg, 80%) as a white solid. TLC $R_f$=0.19 (6:1 hexane:ethyl acetate). $^1$H NMR (300 MHz, CDCl$_3$) δ1.38 (s, 9H), 2.30 (m, 1H), 4.69 (m, 2H), 4.96 (m, 2H), 5.66 (m, 1H), 7.28 (m, 3H), 7.39 (s, 5H), 7.48 (m, 1H). MS APCI, m/z=293 (M+1). LC/MS: 2.86 min.

c. (2R,3S)-3-Amino-2-phenyl-5-prop-2-yn-1-yl-2,3-dihydro-1,5-benzoxazepin-4(5H)-one (67c)

tert-Butyl [(2R,3S)-4-oxo-2-phenyl-5-prop-2-yn-1-yl-2,3,4,5-tetrahydro-1,5-benzoxazepin-3-yl]carbamate (67b) (125 mg, 0.318 mmol) was dissolved in 5:1 (v/v) dichloromethane:trifluoroacetic acid (4 mL) and kept at ambient temperature for 90 min. The solution was evaporated and the residue was dissolved in ethyl acetate and extracted with saturated aqueous sodium bicarbonate. The organic solution was dried and evaporated to afford the title compound (92 mg, 99%) as a white solid. $^1$H NMR (300 MHz, CDCl$_3$) δ1.36 (br s, 2H), 2.29 (t, 1H, J=2.3 Hz), 4.10 (m, 1H), 4.56 and 4.61 (dd, 1H, J=2.4 Hz), 4.76 and 4.81 (dd, 1H, J=2.4 Hz), 5.46 (d, 1H, J=7.4 Hz), 7.27 (m, 3H), 7.38 (m, 3H), 7.47 (m, 3H). MS APCI, m/z=293 (M+1). LC/MS: 1.63 min.

Example 68

N$^2$-[(3,5-Difluorophenyl)acetyl]-N$^1$-[(2R,3S)-7-methoxy-4oxo-2-phenyl-2,3,4,5-tetrahydro-1,5-benzoxazepin-3-yl]-L-alaninamide (68)

To a stirred solution of (2,3-cis)-3-amino-7-methoxy-2-phenyl-2,3-dihydro-1,5-benzoxazepin-4(5H)-one (68e) (230 mg, 0.810 mmol) in dichloromethane (8 mL) was added N-[(3,5-difluorophenyl)acetyl]-L-alanine (1e) (243 mg, 1.003 mmol), HOBt (135 mg, 1.000 mmol), NMM (101 mg, 1.000 mmol) and EDAC-HCl (192 mg, 1.001 mmol). The mixture was stirred at ambient temperature under nitrogen overnight. The reaction mixture was diluted with water and extracted with ethyl acetate three times. The combined organic extracts were washed in succession with saturated aqueous sodium bicarbonate and 1N aqueous HCl. The organic solution was dried, filtered and evaporated. The residue was purified by flash chromatography on silica gel eluting with 3:1 (v/v) dichloromethane:ethyl acetate to afford the title compound in a 1:1 mixture with the 2S,3R diastereomer (310 mg 75%) as a white solid. TLC R$_f$=0.57 (ethyl acetate). $^1$H NMR (300 MHz, CDCl$_3$) δ1.07 (d, 1.5H, J=7.0 Hz), 1.22 (d, 1.5H, J=7.0 Hz), 3.43 (s, 1H), 3.48 (s, 1H), 3.81 (s, 3H), 4.43 (m, 1H), 5.09 (m, 1H), 5.71 (m, 1H), 6.05 (d, 0.5H, J=7.4 Hz), 6.19 (d, 0.5H, J=7.4 Hz), 6.41 (d, 1H, J=6.6 Hz), 6.58 (m, 1H), 6.63-6.87 (m, 4H), 7.18 (d, 1H, J=8.8 Hz), 7.30, (s, 2.5H), 7.36 (s, 2.5H), 7.63 (br, 0.5H), 8.00 (br, 0.5H). MS APCI, m/z=510 (M+1). LC/MS: 2.40 min.

The precursor (2,3-cis)-3-amino-7-methoxy-2-phenyl-2,3-dihydro-1,5-benzoxazepin-4(5H)-one (68e) was prepared as follows:

a. erythro Ethyl 2-hydroxy-3-(4-methoxy-2-nitro-phenoxy)-3-phenylpropanoate (68a)

To a stirred mixture of 4-methoxy-2-nitrophenol (11.87 g, 70 mmol), ethyl 3-phenyloxirane-2-carboxylate (10.39 g, 54 mmol) and ethanol (175 mL) was added portionwise 60% sodium hydride (0.65 g, 16 mmol) and the red mixture stirred at reflux for 9 days. The solvent was removed in vacuo, the residue dissolved in ethyl acetate and extracted three times with 10% aqueous potassium carbonate. The organic layer was washed with water and brine, dried (MgSO$_4$), filtered and the solvent stripped in-vacuo to yield an oil. Column chromatography (dichloromethane then 5% methanol/dichloromethane) afforded (9.5 g, 49%) of slightly impure title compound that was used in the next step without further purification. $^1$H NMR (300 MHz, CDCl$_3$) δ1.21 (t, 3H) 3.25 (d, 1H, J=7.5 Hz) 3.77 (s, 3H), 4.20 (q, 2H) 4.67 (q, 1H, J=3.5, 7.5 Hz), 5.51 (d, 1H, J=3.5 Hz), 6.82 (d, 1H, J=9.2 Hz), 6.92 (dd, 1H, J=9.2, 3.0 Hz), 7.3-7.4 (m, 6H). HPLC (Method A): 3.24 min b. erythro Ethyl 2-hydroxy-3-(4-methoxy-2-nitro-phenoxy)-3-phenylpropanoate (68b)

A mixture of erythro ethyl 2-hydroxy-3-(4-methoxy-2-nitrophenoxy)-3-phenylpropanoate (68a), 5% Pd/C, (50% H$_2$O Degaussa catalyst, 0.5 g) and ethanol (225 mL) was hydrogenated in a Parr apparatus at 42 psi hydrogen for 2.5 h. The catalyst was filtered off through a pad of diatomaceous earth and washed with ethanol. Removal of the solvent returned an orange oil that was purified by column chromatography (dichloromethane, then 10% ethanol/dichloromethane) to yield impure title compound as an viscous orange oil (6.5 g, 74%) which was used in the next step without further purification. $^1$H NMR (300 MHz, CDCl$_3$) δ1.17 (t, 3H), 3.69 (s, 3H), 4.1-4.2 (m, 4H), 4.58 (d, 1H, J=3.5 Hz), 5.31 (d, 1H, J=3.1 Hz), 6.10 (dd, 1H, J=3, 8.8 Hz), 6.32 (d, 1H, J=3 Hz), 6.58 (dd, 1H, J=8.8 Hz), 7.3-7.4 (m, 7H). MS APCI, m/z=332 (M+1). LC/MS: 1.61 min.

c. (2,3-trans)-3-Hydroxy-7-methoxy-2-phenyl-2,3-dihydro-1,5-benzoxazepin-4(5H)-one (68c)

A stirred warmed solution of the above impure erythro ethyl 2-hydroxy-3-(4-methoxy-2-nitrophenoxy)-3-phenyl-propanoate (63b) (6.48 g, 19.6 mmol) in xylene (200 mL) was treated with a catalytic amount of pTSA (0.4 g) and the dark solution was refluxed under Dean-Stark conditions for 18 h. The xylene was stripped in-vacuo and the residue in acetone was preabsorbed on silica gel. Column chromatography (dichloromethane then 4:1 dichloromethane/ethyl acetate) gave a pale yellow solid that was dissolved in a small volume of dichloromethane and treated with hexane. The title compound was obtained by filtration as a pale yellow solid (2.59 g, 46%). $^1$H NMR (300 MHz, CDCl$_3$) δ3.66 (d, 1H, J=5.3Hz), 3.78 (s, 3H), 4.64 (q, J=5.3 Hz, J=9.7 Hz), 5.25 (d, 1H, J=9.7 Hz), 6.58 (d, 1H, J=3.1 Hz), 6.62 (dd, 1H, J=2.6 Hz, J=8.8 Hz), 6.76 (d, 1H, J=8.8 Hz), 7.4-7.5 (m, 5H), 7.65 (bs, 1H, NH). MS APCI, m/z=286 (M+1). LC/MS: 1.73 min.

d. (2,3-cis)-3-Azido-7-methoxy-2-phenyl-2,3-dihydro-1,5-benzoxazepin-4(5H)-one (68d)

Triethylamine (1.353 g, 13.370 mmol) was added via syringe to a stirred solution of (2,3-trans)-3-hydroxy-7-methoxy-2-phenyl-2,3-dihydro-1,5-benzoxazepin-4(5H)-one (68c) (2.542 g, 8.916 mmol) in dichloromethane (100 mL) under nitrogen at −10° C. Next trifluoromethanesulfonyl chloride (2.253 g, 13.369 mmol) was added slowly via syringe and the mixture kept at −10° C. overnight. Additional triethylamine (1.353 g, 13.370 mmol) was added via syringe followed by trifluoromethanesulfonyl chloride (2.253 g, 13.369 mmol) and the reaction was kept for 6 h at −25° C. The reaction was warmed to 0° C. and quenched by addition of 1 N aqueous hydrochloric acid (50 mL). The organic phase was separated, dried, filtered and evaporated. Ethyl acetate was added to the residue and the resulting precipitate collected (recovered alcohol starting material, 1.712 g, 67%). The liquor was evaporated and the residue dissolved in DMF (5 mL). Sodium azide (2.000 g, 30.769 mmol) was added and the mixture stirred for 2 h at ambient temperature. The reaction was diluted with water and extracted with ethyl acetate. The residue from the organic phase was purified by flash chromatography on silica gel eluting with ethyl acetate to afford the title compound (260 mg, 29% accounting for recovered starting material) as a white solid. $^1$H NMR (300 MHz, CDCl$_3$) δ3.79.(s, 3H), 4.43 (d, 1H, J=6.3 Hz), 5.52 (d, 1H, J=6.3 Hz), 6.57 (d, 1H, J=3.1 Hz), 6.73 (dd, 1H, J=8.8, 3.0), 7.15 (d, 1H, J=9.2 Hz), 7.43 (m, 3H), 7.56 (m, 2H), 7.77 (br, 1H). MS APCI, m/z=283 (M+1−N$_2$). LC/MS: 2.35 min e. (2,3-cis)-3-Amino-7-methoxy-2-phenyl-2,3-dihydro-1,5-benzoxazepin)-4(5H-one (68e)

To a solution of (2,3-cis)-3-azido-7-methoxy-2-phenyl-2,3-dihydro-1,5-benzoxazepin-4(5H)-one (68d) (254 mg, 0.818 mmol) in ethanol (10 mL) was added 5% palladium on carbon (30 mg) and 1N hydrochloric acid (1.0 mL). The mixture was stirred for 2 h under a balloon of hydrogen. The mixture was filtered through diatomaceous earth and the solution was evaporated. The solid residue was suspended between ethyl acetate and saturated aqueous sodium bicarbonate and stirred until dissolved. The organic phase was separated, dried, filtered and evaporated. The residue was purified by passing through a plug of silica gel (5 g) eluting with ethyl acetate to afford the title compound (230 mg, 99%) as an off-white solid. TLC R$_f$=0.27 (ethyl acetate). $^1$H NMR (300 MHz, CDCl$_3$) δ1.43 (br, 2H), 3.80 (s, 3H), 4.12 (d, 1H, J=7.0 Hz), 5.50 (d, 1H, J=7.0 Hz), 6.56 (d, 1H, J=3.1 Hz), 6.73 (dd, 1H, J=8.7, 3.1), 7.17 (d, 1H, 8.8 Hz), 7.38 (m, 4H), 7.50 (m, 2H). MS APCI, m/z=285 (M+1). LC/MS: 1.47 min.

Example 69

N²-[(3,5-Difluorophenyl)acetyl]-N¹-[(2R,3S)-5-isopropyl-4-oxo-2-phenyl-2,3 4,5-tetrahydro-1,5-benzoxazepin-3-yl]-L-alaninamide (69)

To a stirred solution of (2R,3S)-3-amino-5-isopropyl-2-phenyl-2,3-dihydro-1,5-benzoxazepin-4(5H)-one (69b) (59 mg, 0.199 mmol) in dichloromethane (2 mL) was added N-[(3,5-difluorophenyl)acetyl]-L-alanine (1e) (59 mg, 0.242 mmol), HOBt (33 mg, 0.245 mmol), NMM (30 mg, 0.297 mmol) and EDAC-HCl (47 mg, 0.245 mmol). After stirring at ambient temperature under nitrogen for 90 min. the solvent was evaporated and the residue partitioned between ethyl acetate and saturated aqueous sodium bicarbonate. The organic solution was separated, washed with 1N aqueous HCl then dried, filtered and evaporated. The residue was purified by flash chromatography on silica gel eluting with 1:1 (v/v) hexane:ethyl acetate to afford the title compound (64 mg, 62%) as a white solid. TLC $R_f$=0.17 (1:1 hexane:ethyl acetate). $^1$H NMR (300 MHz, CDCl$_3$) δ1.21 (d, 3H, J=7.0 Hz), 1.29 (d, 3H, J=7.0 Hz), 1.54 (d, 3H, J=7.0 Hz), 3.47 (s, 2H), 4.22 (m, 1H), 4.77 (m, 1H), 4.93 (t, 1H, J=7.2 Hz), 5.60 (d, 1H, J=7.4 Hz), 5.87 (br d, 1H, J=7.4 Hz), 6.25 (br d, 1H, J=7.0 Hz), 6.67-6.86 (m, 3H), 7.21-7.43 (m, 9H). MS APCI, m/z=522 (M+1). LC/MS: 2.75 min.

The precursor (2R,3S)-3-amino-5-isopropyl-2-phenyl-2,3-dihydro-1,5-benzoxazepin-4(5H)-one (69b) was prepared as follows:

a. tert-Butyl [(2R,3S)-5-isopropyl-4-oxo-2-phenyl-2,3,4,5-tetrahydro-1,5-benzoxazepin-3-yl]carbamate (69a)

To a stirred solution of tert-butyl [(2R,3S)-4-oxo-2-phenyl-2,3,4,5-tetrahydro-1,5-benzoxazepin-3-yl]carbamate(a) (125 mg, 0.352 mmol) in dry DMF (3 mL) under nitrogen was added 2-iodopropane (90 mg, 0.529 mmol) and powdered cesium carbonate (172 mg, 0.529 mmol). The mixture was stirred overnight at ambient temperature then diluted with water and extracted with ethyl acetate three times. The residue from the organic extract was purified by flash chromatography on silica gel eluting with 5:1 (v/v) hexane:ethyl acetate to afford the title compound (82 mg, 58%) as a white solid. TLC $R_f$=0.35 (5:1 hexane:ethyl acetate). $^1$H NMR (300 MHz, CDCl$_3$) δ1.28 (d, 6H, J=7.0 Hz), 1.37 (s, 9H), 4.81 (m, 2H), 4.99 (m, 1H), 5.58 (d, 1H, J=7.0 Hz), 7.19-7.48 (m, 9H). MS APCI, m/z=397 (M+1). LC/MS: 2.75 min.

b. (2R,3S)-3-Amino-5-isopropyl-2-phenyl-2,3-dihydro-1,5-benzoxazepin-4(5H)-one (69b)

tert-Butyl [(2R,3S)-5-isopropyl-4-oxo-2-phenyl-2,3,4,5-tetrahydro-1,5-benzoxazepin-3-yl]carbamate (69a) (80 mg, 0.202 mmol) was dissolved in 5:1 (v/v) dichloromethane:trifluoroacetic acid (3 mL) and kept at ambient temperature for 30 min. The solution was evaporated and the residue was dissolved in ethyl acetate and extracted with saturated aqueous sodium bicarbonate. The organic solution was dried and evaporated to afford the title compound (59 mg, 99%) as a white solid. MS APCI, m/z=297 (M+1). LC/MS: 1.79 min

Example 70

Methyl [(2R,3S)-3-(N-[(3,5-difluorophenyl)acetyl]-L-alanylamino)-4-oxo-2-phenyl-3,4dihydro-1,5-benzoxazepin-5(2H)-yl]-acetate (70)

To a stirred solution of methyl [(2R,3S)-3-amino-4-oxo-2-phenyl-3,4-dihydro-1,5-benzoxazepin-5(2H)-yl]acetate (70b) (130 mg, 0.398 mmol) in dichloromethane (4 mL) was added N-[(3,5-difluorophenyl)acetyl]-L-alanine (1e) (125 mg, 0.514 mmol), HOBt (71 mg, 0.525 mmol), NMM (53 mg, 0.525 mmol) and EDAC-HCl (100 mg, 0.522 mmol). After stirring at ambient temperature under nitrogen for 48 h the solvent was evaporated and the residue partitioned between ethyl acetate and saturated aqueous sodium bicarbonate. The organic solution was separated, washed with 1N aqueous HCl then dried, filtered and evaporated. The residue was purified by flash chromatography on silica gel eluting with 1:1 (v/v) hexane:ethyl acetate to afford the title compound (185 mg, 82%) as a white solid. TLC $R_f$=0.13 (1:1 hexane:ethyl acetate). $^1$H NMR (300 MHz, CDCl$_3$) δ1.21 (d, 3H, J=7.0 Hz), 3.46 (s, 2H), 3.80 (s, 3H), 4.23 (m, 1H), 4.55 and 4.68 (AB quartet, 2H, J=17.1 Hz), 5.16 (t, 1H, J=7.2 Hz), 5.72 (d, 1H, J=7.4 Hz), 5.87 (br d, 1H, J=7.0 Hz), 6.17 (br d, 1H, J=6.6 Hz), 6.66-6.87 (m, 3H), 7.19-7.33 (m, 4H), 7.37 (s, 5H). MS APCI, m/z=552 (M+1). LC/MS: 2.52 min.

The precursor methyl [(2R,3S)-3-amino-4-oxo-2-phenyl-3,4-dihydro-1,5-benzoxazepin-5(2H)-yl]acetate (70b) was prepared as follows:

a. Methyl [(2R,3S)-3-[(tert-butoxycarbonyl)amino]-4-oxo-2-phenyl-3,4dihydro-1,5-benzoxazepin-5(2H)-yl]acetate (70a)

To a stirred solution of tert-butyl [(2R,3S)-4-oxo-2-phenyl-2,3,4,5-tetrahydro-1,5-benzoxazepin-3-yl]carbamate (67a) (150 mg, 0.423 mmol) in dry DMF (4 mL) under nitrogen was added methyl bromoacetate (97 mg, 0.634 mmol) and powdered cesium carbonate (207 mg, 0.635 mmol). The mixture was stirred overnight at ambient temperature then diluted with water and extracted with ethyl acetate three times. The residue from the organic extract was purified by flash chromatography on silica gel eluting with 4:1 (v/v) hexane:ethyl acetate to afford the title compound (175 mg, 97%) as a white solid. TLC $R_f$=0.20 (4:1 hexane:ethyl acetate). $^1$H NMR (300 MHz, CDCl$_3$) δ1.38 (s, 9H), 3.80 (s, 3H), 4.54 and 4.69 (AB quartet, 2H, J=17.1 Hz), 4.93 (m, 1H), 5.02 (m, 1H), 5.70 (d, 1H, J=7.0 Hz), 7.19-7.29 (m, 4H), 7.35-7.48 (m, 5H). MS APCI, m/z=327 (M-BOC). LC/MS: 2.76 min.

b. Methyl [(2R,3S)-3-amino-4-oxo-2-phenyl-3,4-dihydro-1,5-benzoxazepin-5(2H)-yl]acetate (70b)

Methyl [(2R,3S)-3-[(tert-butoxycarbonyl)amino]-4-oxo-2-phenyl-3,4-dihydro-1,5-benzoxazepin-5(2H)yl]acetate (70a) (175 mg, 0.410 mmol) was dissolved in 5:1 (v/v) dichloromethane:trifluoroacetic acid (4 mL) and kept at ambient temperature for 30 min. The solution was evaporated and the residue was dissolved in ethyl acetate and extracted with saturated aqueous sodium bicarbonate. The organic solution was dried and evaporated and the residue used immediately in the next step.

Example 71

[(2R,3S)-3-(N-[(3,5-Difluorophenyl)acetyl]-L-alanylamino)-4-oxo-2-phenyl-3,4-dihydro-1,5benzoxazepin-5(2H)yl]acetic acid (71)

To a stirred solution of methyl [(2R,3S)-3-({N-[(3,5-difluorophenyl)acetyl]-L-alanyl}amino)-4-oxo-2-phenyl-3,4-dihydro-1,5-benzoxazepin-5(2H)-yl]acetate (70) (133 mg, 0.241 mmol) in THF (4 mL) was added a solution of lithium hydroxide (11 mg, 0.262 mmol) in water (1 mL). Several small drops of methanol were then added until a clear homogeneous solution was achieved. The mixture was stirred for 1 h at ambient temperature then acidified with 1N aqueous HCl and extracted with ethyl acetate. The organic solution was dried, filtered and evaporated. The glass-like solid residue was dissolved in dichloromethane (2 mL) then precipitated by addition of hexanes to afford the title compound (124 mg, 96%) as a white solid. $^1$H NMR (300 MHz, DMSO-d6) δ1.08 (d, 3H, J=7.0 Hz), 3.41 and 3.48 (AB quartet, 2H, J=14.5 Hz), 4.21 (m, 1H), 4.58 (s, 2H), 5.02 (t, 1H, J=7.0 Hz), 5.55 (d, 1H, J=7.0 Hz), 6.94 (m, 2H), 7.08 (m, 1H), 7.24-7.49 (m, 10H), 8.33 (d, 1H, J=7.0 Hz), 12.94 (br, 1H). MS APCI, m/z=538 (M+1). LC/MS: 2.27 min.

Example 72

$N^1$-[(2R,3S)-5-(Cyclopropylmethyl)-4-oxo-2-phenyl-2,3,4,5-tetrahydro-1,5-benzoxazepin-3-yl]-$N^2$-[(3,5-difluorophenyl)acetyl]-L-alaninamide (72)

To a stirred solution of (2R,3S)-3-amino-5-(cyclopropylmethyl)-2-phenyl-2,3-dihydro-1,5-benzoxazepin-4(5H)-one (72b) (150 mg, 0.486 mmol) in dichloromethane (4 mL) was added N-[(3,5-difluorophenyl)acetyl]-L-alanine (1e) (130 mg, 0.534 mmol), HOBt (75 mg, 0.555 mmol), NMM (60 mg, 0.594 mmol) and EDAC-HCl (103 mg, 0.537 mmol). After stirring at ambient temperature under nitrogen overnight the solvent was evaporated and the residue partitioned between ethyl acetate and saturated aqueous sodium bicarbonate. The organic solution was separated, washed with 1N aqueous HCl then dried, filtered and evaporated. The residue was purified by flash chromatography on silica gel eluting with 5:1 (v/v) dichloromethane:ethyl acetate to afford the title compound (230 mg, 88%) as a white solid. TLC $R_f$=0.22 (5:1 dichloromethane:ethyl acetate). $^1$H NMR (300 MHz, CDCl$_3$) δ0.20 (m, 1H), 0.36-0.64 (m, 3 h), 1.14 (m, 1H), 1.21 (d, 3H, J=7.0 Hz), 3.47 (s, 2H), 3.52 (m, 1H), 4.10-4.29 (m, 2H), 5.05 (t, 1H, J=7.0 Hz), 5.68 (d, 1H, J=7.4 Hz), 5.90 (d, 1H), 6.24 (d, 1H), 6.68-6.85 (m, 3H), 7.28 (s, 4H), 7.36, s, 5H). MS APCI, m/z=534 (M+1). LC/MS: 2.78 min.

The precursor (2R,3S)-3-amino-5-(cyclopropylmethyl)-2-phenyl-2,3-dihydro-1,5-benzoxazepin-4(5H)-one (72b) was prepared as follows:

a. tert-Butyl [(2R,3S)-5-(cyclopropylmethyl)-4-oxo-2-phenyl-2,3,4,5-tetrahydro-1,5-benzoxazepin-3-yl]carbamate (72a)

To a stirred solution of tert-butyl [(2R,3S)-4-oxo-2-phenyl-2,3,4,5-tetrahydro-1,5-benzoxazepin-3-yl]carbamate (67a) (190 mg, 0.536 mmol) in dry DMF (2 mL) under nitrogen was added (bromomethyl)cyclopropane (108 mg, 0.800 mmol) and powdered cesium carbonate (264 mg, 0.810 mmol). The mixture was stirred overnight at ambient temperature then diluted with ewater and extracted with ethyl acetate three times. The residue from the combined organic extracts was purified by flash chromatography on silica gel eluting with 6:1 (v/v) hexane:ethyl acetate to afford the title compound (201 mg, 92%) as a white solid. TLC $R_f$=0.31 (6:1 hexane:ethyl acetate). $^1$H NMR (300 MHz, CDCl$_3$) δ0.19 (m, 1H), 0.35-0.62 (m, 3H), 1.15 (m, 1H), 1.37 (s, 9H), 3.50 and 3.55 (dd, 1H, J=7.0 Hz), 4.12 and 4.17 (dd, 1H, J=7.0 Hz), 4.93 (m, 2H), 5.65 (d, 1H, J=7.0 Hz), 7.29 (m, 4H), 7.41 (m, 5H). MS APCI, m/z=309 (M-BOC). LC/MS: 3.08 min.

b. (2R,3S)-3-Amino-5-(cyclopropylmethyl)-2-phenyl-2,3-dihydro-1,5-benzoxazepin-4(5H)-one (72b)

tert-Butyl [(2R,3S)-5-(cyclopropylmethyl)-4-oxo-2-phenyl-2,3,4,5-tetrahydro-1,5-benzoxazepin-3-yl]carbamate (72a) (201 mg, 0.492 mmol) was dissolved in 5:1 (v/v) dichloromethane:trifluoroacetic acid (5 mL) and kept at ambient temperature for 1 h. The solution was evaporated and the residue was dissolved in ethyl acetate and extracted with saturated aqueous sodium bicarbonate. The organic solution was dried and evaporated and the residue used immediately in the next step. MS APCI, m/z=309 (M+1). LC/MS: 1.82 min.

Example 73

$N^1$-[(2R,3S)-5-(Cyclopropylmethyl)-7-methoxy-4-oxo-2-phenyl-2,3,4,5-tetrahydro-1,5-benzoxazepin-3-yl]-$N^2$-[(3,5-difluorophenyl)acetyl]-L-alaninamide (73)

To a stirred solution of $N^2$-[(3,5-difluorophenyl)acetyl]-$N^1$-[(2,3-cis)-7-methoxy-4-oxo-2-phenyl-2,3,4,5-tetrahydro-1,5-benzoxazepin-3-yl]-L-alaninamide (68) (95 mg, 0.186 mmol) in DMF (1 mL) under nitrogen was added (bromomethyl)cyclopropane (70 mg, 0.518 mmol) and powdered cesium carbonate (170 mg, 0.521 mmol). The mixture was stirred overnight at ambient temperature then diluted with water and extracted with ethyl acetate. The residue obtained from the organic extract was purified by flash chromatography on silica gel eluting with diethyl ether to afford the title compound in a 1:1 mixture with the 2S,3R diastereomer (65 mg, 62%) as a white solid. TLC $R_f$=0.26 (diethyl ether). $^1$H NMR (300 MHz, CDCl$_3$) δ0.23 (m, 1H), 0.37-0.65 (m, 3H), 1.07 (d 1.5H, J=7.0 Hz), 1.21)d, 1.5H, J=7.0 Hz), 3.43 (s, 1H), 3.47 (s, 1H), 3.83 (s, 3H), 4.09 (m, 1H), 4.25 (m, 1H), 5.05 (m, 1H), 5.61 (m, 1H), 5.89 (br d, 1H), 5.99 (br d, 1H), 6.20 (br t, 1H), 6.66-6.85 (m, 5H), 7.19 (d, 1H), 8.3 Hz), 7.30-7.42 (m, 6H). MS APCI, m/z=564 (M+1). LC/MS: 2.77 min.

Example 74

$N^1$-[(2R,3)-5-(2-Azetidin-1-yl-2-oxoethyl)-4-oxo-2-phenyl-2,3,4,5-tetrahydro-1,5-benzoxazepin-3-yl]-$N^2$-[(3,5difluorophenyl)acetyl]-L-alaninamide (74)

To a stirred solution of [(2R,3S)-3-(N-[(3,5-difluorophenyl)acetyl]-L-alanylamino)-4-oxo-2-phenyl-3,4-dihydro-1,5-benzoxazepin-5(2H)-yl]acetic acid (71) (56 mg, 0.098 mmol) in dichloromethane (2 mL) under nitrogen was added HOBt (20 mg, 0.148 mmol), NMM (21 mg, 0.207 mmol), azetidine (20 mg, 0.351 mmol) and EDAC-HCl (29 mg, 0.151 mmol). The mixture was stirred at ambient temperature for 48 h. The reaction was diluted with ethyl acetate and extracted in succession with saturated aqueous sodium bicarbonate and 1N aqueous HCl. The residue obtained from the organic solution was purified by recrystallization from ethyl acetate/hexanes to afford the title compound (46 mg, 81%) as a white solid. TLC R$_f$=0.09 (ethyl acetate). $^1$H NMR (300 MHz, CDCl$_3$) δ1.21 (d, 3H, J=7.0 Hz), 2.36 (m, 2H), 3.46 (s, 2H), 4.02-4.45 (m, 5H), 4.38 (m, 1H), 4.71 (d, 1H, J=16.2 Hz), 5.14 (t, 1H, J=7.2 Hz), 5.74 (d, 1H, J=7.0 Hz), 5.96 (br d, 1H, J=7.0 Hz), 6.21 (br d, 1H, J=7.0 Hz), 6.67-6.85 (m, 3H), 7.22-7.51 (m, 9H). MS APCI, m/z=577 (M+1). LC/MS: 2.30 min.

Example 75

N$^2$-[(3,5-Difluorophenyl)acetyl]-N$^1$-[(2R,3S)-7-fluoro-4oxo-2-phenyl-2,3,4,5-tetrahydro-1,5-benzoxazepin-3-yl]-L-alaninamide (75)

To a solution of (2,3-cis)-3-amino-7-fluoro-2-phenyl-2,3-dihydro-1,5-benzoxazepin-4(5H)-one (75 h) (75 mg), N-[(3,5-difluorophenyl)acetyl]-L-alanine, HOBt (56 mg), and NMM (28 mg) in dichloromethane (8 ml) was added EDAC-HCl (79 mg). The mixture was stirred at RT under nitrogen for 2 h. The reaction was diluted with 1 N hydrochloric acid and extracted with dichloromethane (3×). The organic extracts were combined and washed with 1 N potassium carbonate. The organic layer was dried, filtered and evaporated. The crude product was purified by flash chromatography (2% methanol/dichloromethane) to afford the off-white solid title compound (110 mg) as a 1:1 mixture with the 2S,3R diastereomer. $^1$H NMR (300 MHz, d6-DMSO) δ 1.03-1.12 (m, 3H), 3.41-3.45 (m, 2H), 4.21-4.35 (m, 1H), 5.58-5.62 (m, 1H), 6.91-7.11 (m, 3H), 7.28-7.50 (m, 9H), 8.22-8.33 (m, 1H), 10.38-10.42 (m, 1H). MS APCI, m/z=498 (M+1). LC/MS: 2.38 min.

The starting (2,3-cis)-3-amino-7-fluoro-2-phenyl-2,3-dihydro-1,5-benzoxazepin-4(5H)-one (75 h) was prepared in the following manner:

a. Ethyl (2R, S3RS)-3-(4fluoro-2-nitrophenoxy)-2-hydroxy-3-phenylpropanoate (75a)

The title compound was prepared according to the published procedure of Carlo Banzatti, Franco Heidempergher, and Piero Melloni; J. Heterocyclic Chem. 20, 259 (1983).

b. Ethyl (2SR,3RS)-2-azido-3-(4-fluoro-2-nitrophenoxy)-3-phenylpropanoate (75b)

To a solution of ethyl (2RS,3RS)-3-(4-fluoro-2-nitrophenoxy)-2-hydroxy-3-phenylpropanoate (75a) (3.00 g) and trifluoromethane sulfonic anhydride (3.63 g) in dichloromethane (125 ml) was added via syringe 2,6-lutidine under nitrogen at 0° C. The mixture was kept at 0° C. for 1 hour. Additional trifluoromethane sulfonic anhydride (987 mg) and 2,6-lutidine (375 mg) was added and the mixture kept at 0° C. for 30 minutes. The reaction was concentrated in vacuo without heating, and the resulting residue immediately dissolved in DMF (90 ml). Sodium azide (838 mg) was added to the solution and the mixture was heated to 45° C. overnight. The DMF was removed in vacuo with heating. The residue was purified by flash chromatography (10:1 hexane:Ethyl acetate) to afford the title compound (2.82 g). $^1$H NMR (300 MHz, d6-DMSO) δ 1.09 (t, 3H, J=7 Hz), 4.16 (m, 2H), 4.73 (d, 1H, J=4 Hz), 6.16 (d, 1H, 4 Hz), 7.20-7.48 (m, 7H), 7.87 (dd, 1H, J=3 Hz, J=8 Hz). MS APCI, m/z=347 (M+1−N$_2$) LC/MS: 2.81 min.

c. Ethyl (2SR,3RS)-2-amino-3-(4-fluoro-2-nitrophenoxy)-3-phenylpropanoate (75c)

To a solution of ethyl (2SR,3RS)-2-azido-3-(4-fluoro-2-nitrophenoxy)-3-phenylpropanoate (75b) (2.60 g) and triphenylphosphine (2.01 g) in THF (100 ml) was added water (2 ml) and the mixture was refluxed for 1 h then stirred at RT overnight. The reaction was concentrated in vacuo and the resulting residue was purified by flash chromatography (5:2 hexane:ethyl acetate) to afford the title compound (1.55 g) as a yellow oil. $^1$H NMR (300 MHz, d6-DMSO) δ 1.01 (t, 3H, J=7 Hz), 1.85 (s, 2H), 3.76 (d, 1H, J=5 Hz), 3.99 (1, 2H, J=7 Hz), 5.75 (d, 1H, J=5 Hz), 6.89-7.44 (m, 7H), 7.85 (dd, 1H, J=3 Hz, J=9 Hz). MS APCI, m/z=349 (M+1). LC/MS: 1.82 min.

d. Ethyl (2SR,3RS)-N-(tert-butoxycarbonyl)-3-(4-fluoro-2-nitrophenoxy)-3-phenylpropanoate (75d)

To a solution of ethyl (2SR,3RS)-2-amino-3-(4-fluoro-2-nitrophenoxy)-3-phenylpropanoate 75c (1.72 g) in THF (55 ml) was added di-tert-butyl dicarbonate (1.19 g) in THF (12 ml) and the mixture was stirred at RT for 70 h. The reaction was concentrated in vacuo and the resulting residue was purified by flash chromatography (5:1 hexane:ethyl acetate) to afford the title compound (2.21 g). $^1$H NMR (300 MHz, d6-DMSO) δ 0.95 (t, 3H, J=7 Hz), 1.32 (s, 9H), 3.95 (q, 2H, J=7 Hz), 4.53 (m, 1H), 5.86 (d, 1H, J=5.85 Hz), 7.09-7.20 (m, 2H), 7.31-7.43 (m, 6H), 7.83 (dd, 1H, J=3 Hz, J=8 Hz). MS APCI, m/z=349 (M+1-Boc).

LC/MS: 2.96 min.

e. Ethyl (2SR,3RS)-3-amino-4-fluorophenoxy)-N-(tert-butoxycarbonyl)-3-phenylpropanoate (75e)

To a solution of ethyl (2SR,3RS)—N-(tert-butoxycarbonyl)-3-(4-fluoro2-nitrophenoxy)-3-phenylpropanoate (75d) (2.16 g) in ethanol (80 ml) was added 5% palladium on carbon (500 mg) and the mixture hydrogenated on a Parr apparatus at 35 psi. The mixture was filtered through diatomaceous earth and the filtrate was evaporated and purified by flash chromatography (10:3 hexane:ethyl acetate) to afford the title compound (1.55 g) as a tan solid. $^1$H NMR (300 MHz, d6-DMSO) δ 1.07-1.13 (m, 3H), 1.27 (s, 9H), 4.06-4.16 (m, 2H), 4.54-4.61 (m, 1H), 5.75-6.04 (m, 1H), 6.24-6.32 (m, 0.5H), 6.46-6.54 (m, 1H), 6.63-6.67 (m, 0.5H), 7.22-7.49 (m, 6H), 7.82 (d, 1H, J=10 Hz), 8.53 (s, 0.5H), 8.81 (s, 0.5H). MS APCI m/z=418 (M+1). LC/MS: 2.74 min.

f. (2SR,3RS)-3-(2-Amino-4-fluorophenoxy)-N-(tert-butoxycarbonyl)-3-phenylpropanoic acid (75f)

To a solution of ethyl (2SR,3RS)-3-(2-amino-4-fluorophenoxy)-N-(tert-butoxycarbonyl)-3-phenylpropanoate (75e) (1.52 g) in THF (50 ml) was added a solution of lithium hydroxide (168 mg) in water (25 ml) under nitrogen at 0° C. The mixture was stirred at 0° C. for 1.5 H, then at RT for 1 H. The reaction was diluted with water and extracted with EtAOc. To the aqueous layer was added 1 N HCl until the pH=1 and this mixture was extracted with Ethyl acetate. The ethyl acetate layers were combined, washed with brine, dried, filtered and evacuated to give the title compound (1.68 g) as a crude tacky solid. No filter analysis or purification was performed.

g. tert-Butyl [(2,3-cis)-7-fluoro-4-oxo-2-phenyl-2,3, 4,5-tetrahydro-1,5-benzoxazepin-3-yl]carbamate (75 g)

To a solution of crude (2SR,3RS)-3-(2-amino-4-fluorophenoxy)-N-(tert-butoxycarbonyl)-3-phenylpropanoic acid (75f) (580 mg), HOBt (251 mg), and NMM (150 mg) in dichloromethane (60 ml) was added EDAC.HCl (353 mg). The mixture was stirred at RT for 2 h. The reaction was then evaporated and purified with flash chromatography (5:1 hexane:ethyl acetate) to give the title compound (242 mg) as an off white solid. $^1$H NMR (300 MHz, d6-DMSO) δ 1.32 (s, 9H), 4.74 (t, 1H, J=7 Hz), 5.33 (d, 1H, J=8 Hz0, 5.64 (d, 1H, J=6 Hz), 6.94-7.06 (m, 2H), 7.26-7.45 (m, 5H), 10.39 (s, 1H). MS APCI, m/z=373 (M+1)

LC/MS: 2.63 min.

h. (2,3-cis)-3-Amino-7-fluoro-2-phenyl-2,3-dihydro-1,5-benzoxazepin-4(5H)-one (75h)

To a solution of tert-butyl [(2,3-cis)-7-fluoro-4-oxo-2-phenyl-2,3,4,5-tetrahydro-1,5-benzoxazepin-3-yl]carbamate (75 g) in dichloromethane was added trifluoroacetic acid (5 ml). The mixture was stirred at RT for 1 h. The solvent was removed in vacuo and the residue dissolved in dichloromethane. The solution was washed with 1 N potassium chloride, dried, filtered, and evaporated to afford the title compound (362 mg) as a yellow solid. $^1$H NMR (300 MHz, d6-DMSO) δ 1.46 (s, 2H), 3.81 (d, 1H, J=6 Hz), 5.45 (d, 1H, J=7 Hz), 6.88-7.01 (m, 2H), 7.19-7.25 (m, 1H), 7.35-7.42 (m, 5H), 10.07 (s, 1H). MS APCI, m/z=273 (M+1)

LC/MS:1.50 min.

Example 76

(2S)—N-((1S)-2-[(2R,3S)-7-Fluoro-4-oxo-2-phenyl-2,3,4,5-tetrahydro-1,5-benzoxazepin-3-yl]amino-2-oxo-1-phenylethyl)-2-hydroxy-4-methylpentanamide (76)

To a solution of (2,3-cis)-3-amino-7-fluoro-2-phenyl-2,3-dihydro-1,5-benzoxazepin-4(5H)-one (75 h) (75 mg), (2S)-{[(2S)-2-hydroxy4-methylpentanoyl]amino}(phenyl)acetic acid (76b) (73 mg), HOBt (56 mg), and NMM (28 mg) in dichloromethane (8 ml) was added EDAC-HCl (79 mg). The mixture was stirred at RT under nitrogen for 2 h. The reaction was diluted with 1 N hydrochloric acid and extracted with dichloromethane (3×). The organic extracts were combined and washed with 1 N potassium carbonate. This organic layer was dried, filtered and evaporated. The crude product was purified by flash chromatography (2% methanol/dichloromethane) to afford the off-white solid title compound (110 mg) as a 1:1 mixture with the 2S,3R diastereomer. $^1$H NMR (300 MHz, d6-DMSO) δ 0.81-0.94 (m, 8H), 1.27-1.46 (m, 1H), 1.56-1.80 (m, 1H), 3.84-3.95 (m, 1H), 4.97-5.15 (m, 1H), 5.33-5.35 (m, 1H), 5.47-5.75 (m, 3H), 6.89-7.06 (m, 4H), 7.12-7.43 (m, 8H), 7.97-8.22 (m, 2H), 10.32-10.39 (m, 1H). MS APCI, m/z=520 (M+1). LC/MS: 2.51 min.

The (2S)-{[(2S)-2-hydroxy-4-methylpentanoyl]amino}(phenyl)acetic acid (76b) was prepared in the following manner:

a. Methyl (2S)-{[(2S)-2-hydroxy-4-methylpentanoyl]amino}(phenyl)acetate (76a)

To a cooled (0° C.) solution of methyl (2S)-amino(phenyl)acetate (3.06 g), (2S)-2-hydroxy-4-methylpentanoic acid hydrochloride, NMM (1.85 ml), and HOBt (6.15 g) in dichloromethane (50 ml) was added EDAC-HCl (5.81 g). Additional NMM (2.31 ml) was then added. The mixture was stirred for 2h at 0° C., then overnight at RT. The reaction was concentrated and the residue was taken up in Ethyl acetate washed with 0.1N hydrochloric acid, saturated sodium bicarbonate, brine, dried, filtered and evaporated to afford the title compound (4.20 g). $^1$H NMR (300 MHz, CDCl$_3$) δ 0.92-0.95 (m, 6H), 1.47-1.67 (m, 2H), 1.76-2.04 (m, 1H), 2.63 (bs, 1H), 3.74 (s, 3H), 4.21 (d, 1H, J=9 Hz), 5.58 (d, 1H, J=8 Hz), 7.26-7.42 (m, 5H). MS APCI, m/z=280 (M+1). LC/MS: 1.95 min.

b. (2S)-{[(2S)-2-Hydroxy-4-methylpentanoyl]amino}(phenyl)acetic acid (76b)

To a solution of methyl (2S)-{[(2S)-2-hydroxy-4-methylpentanoyl]amino}(phenyl)acetate (76a) (4.185 g) in THF (30 ml) and water (15 ml) cooled to 0° C. was added lithium hydroxide (1.45 g) portion wise. The mixture was stirred at RT overnight. The reaction was acidified with 1N hydrochloric acid until pH=1. The mixture was concentrated to remove THF and extracted with Ethyl acetate (3×). The organic layers were washed with water, brine, dried, filtered and evaporated to afford the title compound as a tacky white solid. Trituration with dichloromethane/diethyl ether yielded a free flowing solid (3.85 g). $^1$H NMR (300 MHz, CDCl$_3$) δ 0.89-0.94 (m, 6H), 1.45-1.63 (m, 2H), 1.76-1.83 (m, 1H), 3.25 (bs, 2H), 4.20-4.25 (m, 1H), 5.56 (d, 1H, J=7 Hz), 7.35-7.39 (m, 5H), 7.53 (d, 1H, J=7 Hz). MS APCI, m/z=266 (M+1). LC/MS: 1.68 min.

Example 77

$N^2$-[(2R)-2-(3,5-Difluorophenyl)-2-hydroxyacetyl]-$N^1$-[(2R,3S)-4-oxo-2-phenyl-2,3,4,5-tetrahydro-1,5-benzoxazepin-3-yl]-L-alaninamide (77)

To a solution of (2,3-cis)-3-amino-2-phenyl-2,3-dihydro-1,5-benzoxazepin-4(5H)-one hydrochloride (6e) (54 mg, 0.185 mmol) in dichloromethane (10 mL) under nitrogen was added N-[((2R)-2-(3,5-difluorophenyl)-2-hydroxylacetyl]-L-alaninate acid (77d) (48 mg, 0.185 mmol), HOBt (32 mg, 0.237 mmol), triethylamine (75 µL, 0.538 mmol) and EDAC-HCl (50 mg, 0.261 mmol). The mixture was stirred overnight at ambient temperature, diluted with dichloromethane (40 mL), then extracted with 1N aqueous HCl, 20% K$_2$CO$_3$, and brine. The organic solution was dried (MgSO$_4$), filtered and evaporated. The residue was purified by flash chromatography on silica gel eluting with dichloromethane, then 100:1 and 50:1 (v/v) dichloromethane:methanol to afford the title compound as a 1:1 mixture with the 2S,3R diastereomer (40 mg, 43%) as a white solid. $^1$H NMR (300 MHz, DMSO-d$_6$) δ 1.00-1.20 (m, 3H), 4.25-4.42 (m, 1H), 4.90-5.07 (m, 2H), 5.59 (s, 0.5H), 5.61 (s, 0.5H), 6.44 (d, J=5 Hz, 0.5H), 6.47 (d, J=5 Hz, 0.5H), 7.00-7.45 (m, 12H), 7.61-7.78 (m, 1H), 7.92-8.15 (m, 1H), 10.27 (s, 0.5H), 10.31 (s, 0.5H). MS APCI, m/z=496 (M+1). LC/MS: 2.12 min.

The requisite acids were prepared as follows:

a. Methyl N-[((2S)-2-(3,5-difluorophenyl)-2-hydroxylacetyl]-L-alaninate (77a)

b. Methyl N-[((2R)-2-(3,5-difluorophenyl)-2-hydroxylacetyl]-L-alaninate (77b)

To a solution of 3,5-difluoromandelic acid (2.50 g, 13.3 mmol) in dichloromethane (60 mL) under nitrogen was added L-alanine methyl ester hydrochloride (1.86 g, 13.3 mmol), HOBt (3.6 g, 26.6 mmol), EDAC-HCl (4.2 g, 21.9 mmol) and NMM (3.84 mL, 34.9 mmol). The mixture was stirred overnight at ambient temperature then evaporated. The residue was dissolved in ethyl acetate and extracted in succession with saturated sodium bicarbonate, 1N aqueous HCl, and brine. The organic solvent was dried, filtered and evaporated. The residue was purified by flash chromatography on silica gel eluting with 100:1 (v/v) chloroform:methanol to afford the title compound as a 1:1 mixture of diastereomers (2.0 g, 56%) as a white solid. The diastereomers was separated using the chiral HPLC at the following conditions:elute (hexane:isopropanol)=90:10, Column Chiralpak AD Methyl N-[((2S)-2-(3,5-difluorophenyl)-2-hydroxylacetyl]-L-alaninate (77a) as a white solid.

$^1$H NMR (300 MHz, CD$_3$OD) δ 1.23 (d, 3H), 3.64 (s, 3H), 4.43 (q, 1H), 5.33 (d, 1H), 6.85 (m, 3H). MS m/z=274 (M+1). LC/MS: 1.48 min.

Methyl N-[((2R)-2-(3,5-difluorophenyl)-2-hydroxylacetyl]-L-alaninate (77b) as a white solid.

$^1$H NMR (300 MHz, CD$_3$OD) δ 1.23 (d, 3H), 3.64 (s, 3H), 4.43 (q, 1H), 5.33 (d, 1H), 6.85 (m, 3H). MS m/z=274 (M+1). LC/MS: 1.40 min c. N-[((2S)-2-(3,5-Difluorophenyl)-2-hydroxylacetyl]-L-alaninate (77c)

To a solution of methyl N-[((2S)-2-(3,5-difluorophenyl)-2-hydroxylacetyl]-L-alaninate (77a) (500 mg, 1.93 mmol) in dichloromethane (5 mL) was added dropwise a solution of LiOH (100 mg, 4.18 mmol) in water (4 mL). The mixture was stirred overnight under nitrogen and the solution was acidified with 1N HCl until pH~1. The mixture was extracted with ethyl acetate. The organic phase was washed with brine, dried, filtered and evaporated. The title compound was obtained as a white solid (470 mg, 99%). $^1$H NMR (300 MHz, CD$_3$OD) δ 1.37 (d, 3H), 4.63 (q, 1H), 5.33 (d, 1H), 6.85 (m, 3H). MS m/z=260 (M+1).

LC/MS: 1.20 min.

d. N-[(2R)-2-(3,5-Difluorophenyl)-2-hydroxylacetyl]-L-alaninate (77d)

To a solution of methyl N-[((2R)-2-(3,5-difluorophenyl)-2-hydroxylacetyl]-L-alaninate (77b) (500 mg, 1.93 mmol) in dichloromethane (5 mL) was added dropwise a solution of LiOH (100 mg, 4.18 mmol) in water (4 mL). The mixture was stirred overnight under nitrogen and the solution was acidified with 1N HCl until pH~1. The mixture was extracted with ethyl acetate. The organic phase was washed with brine and dried, filtered and evaporated. The title compound was obtained as a white solid (470 mg, 99%). $^1$H NMR (300 MHz, CD$_3$OD) δ 1.37 (d, 3H), 4.63 (q, 1H), 5.33 (d, 1H), 6.85 (m, 3H). MS m/z=260 (M+1).

LC/MS: 1.21 min.

Example 78

$N^2$-[(2S)-2-(3,5-Difluorophenyl)-2-hydroxyacetyl]-$N^1$-[(2R,3S)-4 oxo-2-phenyl-2,3,4,5-tetrahydro-1,5-benzoxazepin-3-yl]-L-alaninamide (78)

To a solution of (2,3-cis)-3-amino-2-phenyl-2,3-dihydro-1,5-benzoxazepin-4(5H)-one hydrochloride (6e) (76 mg, 0.263 mmol) in dichloromethane (10 mL) under nitrogen was added N-[((2S)-2-(3,5-difluorophenyl)-2-hydroxylacetyl]-L-alaninate acid (77c) (68 mg, 0.263 mmol), HOBt (45 mg, 0.333 mmol), triethylamine (100 μL, 0.717 mmol) and EDAC-HCl (71 mg, 0.370 mmol). The mixture was stirred overnight at ambient temperature, diluted with dichloromethane (40 mL), then extracted with 1N aqueous HCl, 20% K$_2$CO$_3$, and brine. The organic solution was dried (MgSO$_4$), filtered and evaporated. The residue was purified by flash chromatography on silica gel eluting with dichloromethane, then 100:1 to 50:1 (v/v) dichloromethane:methanol to afford the title compound in a 1:1 mixture with the 2S,3R diastereomer (60 mg, 46%) as a white solid. $^1$H NMR (300 MHz, DMSO-d$_6$) δ 1.00-1.20 (m, 3H), 4.25-4.42 (m, 1H), 4.90-5.07 (m, 21H), 5.59 (s, 0.5H), 5.61 (s, 0.5H), 6.44 (d, J=5 Hz, 0.5H), 6.48 (d, J=5 Hz, 0.5H), 7.00-7.45 (m, 12H), 7.61-7.78 (m, 1), 7.92-8.15 (m, 1H), 10.27 (s, 0.5H), 10.31 (s, 0.5H). MS APCI, m/z 496 (M+1). LC/MS: 2.12 min.

Example 79

$N^2$-[(3,5-Difluorophenyl)acetyl]-$N^1$-[(3S,4R)-2-oxo-4-phenyl-2,3,4,5-tetrahydro-1H-1-benzazepin-3-yl]-L-alaninamide (79)

To a solution of (3,4-cis)-3-amino-4-phenyl-1,3,4,5-tetrahydro-2H-1-benzazepin-2-one hydrochloride (79 g) (50 mg, 0.172 mmol) in dichloromethane (5 mL) under nitrogen was added N-[(3,5-difluorophenyl)acetyl]-L-alanine (1e) (50 mg, 0.205 mmol), HOBt (35 mg, 0.260 mmol), triethylamine (95 μL, 0.682 mmol) and EDAC-HCl (50 mg, 0.261 mmol). The mixture was stirred overnight at ambient temperature, diluted with dichloromethane (40 mL), then extracted with 1N aqueous HCl, 20% K$_2$CO$_3$, and brine. The organic solution was dried (MgSO$_4$), filtered and evaporated. The residue was purified by flash chromatography on silica gel eluting with dichloromethane, then 100:1 to 50:1 (v/v) dichloromethane:methanol to afford the title compound as a 1:1 mixture with the 3R,4S diastereomer (50 mg, 61% ) as a white solid. $^1$H NMR (300 MHz, DMSO-d$_6$) δ 0.78 (d, J=7 Hz, 1.5H), 0.94 (d, J=7 Hz, 1.5H), 2.90-3.03 (m, 2H), 3.22-3.47 (m, 2H), 3.82-3.94 (m, 1H), 4.02 (quin, J=7 Hz, 0.5H), 4.14 (quin, J=7 Hz, 0.5H), 4.40 (t, J=8 Hz, 0.5H), 4.48 (t, J=8 Hz, 0.5H), 6.82-7.36 (m, 12H), 7.41 (d, J=7 Hz, 1H), 8.12 (d, J=8 Hz, 0.5H), 8.21 (d, J=7 Hz, 0.5H), 10.24 (s, 0.5H), 10.25 (s, 0.5H). MS APCI, m/z=478 (M+1). LC/MS: 2.40 min.

The required (3,4-cis)-3-amino-4-phenyl-1,3,4,5-tetrahydro-2H-1-benzazepin-2-one hydrochloride (79 g) was prepared as follows:

a. 1-(3,3-Diethoxy-2-phenylpropyl)-2-nitrobenzene (79a)

A suspension of sodium hydride (6.0 g, 0.15 mol, 60% oil dispersion) in DMP (375 mL) was treated with diethyl benzalmalonate (24.8 g, 0.099 mol) followed by a solution of 2-nitrotoluene (15.1 g, 0.110 mol) in DMF (25 mL) and the resulting reaction mixture was stirred for 16 h. At the end of this period the reaction mixture was treated with a solution of acetic acid (20 mL) in methanol (50 mL), followed by water (1 L) and extracted with ethyl acetate (3×250 mL). The organic layer was washed with 1N HCl, sodium bicarbonate solution, brine, dried over anhydrous magnesium sulfate and concentrated under reduced pressure. The material thus obtained was purified by column chromatography over silica gel. Elution with 9:1 hexane: ethyl acetate afforded the title compound (11.74 g). $^1$H NMR (300 MHz, CDCl$_3$) δ 0.91 (t, 3H, J=7 Hz), 1.30 (t, 3H, J=7 Hz), 3.27 (dd, 1H, J=10 Hz, J=14 Hz), 4.48 (dd, 1H, J=4 Hz, J=10 Hz), 3.87 (m, 3H), 4.23 (q, 1H, J=7 Hz), 6.99-7.60 (m, 8H), 7.74 (d,1H, J=1 Hz).

b. [2-(3,3-Diethoxy-2-phenylpropyl)phenyl]amine-acetate (79b)

A solution of 1-(3,3-diethoxy-2-phenylpropyl)-2-nitrobenzene (11.74 g, 30.5 mmol) (79a) in acetic acid (30 mL) was hydrogenated under hydrogen atmosphere (40 psi) in the presence of Pd/C (100 mg) for 16 h. At the end of this period the reaction mixture was filtered through a pad of diatomaceous earth and the pad was washed with acetic acid. Upon concentration under reduced pressure the title compound was obtained (11.36 g). $^1$H NMR (300 MHz, CDCl$_3$) δ 0.86 (t, 3H, J=10 Hz), 1.30 (t, 3H, J=7 Hz), 2.27 (dd, 1H, J=11 Hz, J=14 Hz), 3.08 (dd, 1H, J=3 Hz, J=14 Hz), 3.62 (dt, 1H, J=11, 15 Hz), 3.84 (m, 3H), 4.27 (q, 1H, J=7 Hz), 6.36 (m, 2H), 6.61 (d, 1H, J=8 Hz), 6.87-7.26 (m, 5H). MS APCI, m/z=356 (M+1). LC/MS: 2.11 min.

c. Ethyl 2-oxo-4-phenyl-2,3,4,5-tetrahydro-1H-1-benzazepin-3-carboxylate (79c)

A solution of [2-(3,3-diethoxy-2-phenylpropyl)phenyl]amine-acetate (11.36 g, 31.9 mmol) (79b) was dissolved in dichloromethane (100 mL), washed with solution of sodium carbonate (2×50 mL) and concentrated under reduced pressure upon drying over anhydrous potassium carbonate. The resulting product was dissolved in o-xylene (150 mL), treated with pTSA monohydrate (190 mg, 1.02 mmol) and heated to reflux for 3 h. At the end of this period the reaction mixture was allowed to cool and then cooled in ice. The solid precipitate was filtered to afford the title compound (6.9 g): $^1$H NMR (300 MHz, CDCl$_3$) δ 1.04 (t, 3H, J=7 Hz), 2.81 (dd, 1H, J=4 Hz, J=14 Hz), 3.58 (dd, 1H, J=7 Hz, 14Hz), 3.76 (d, 1H, J=9 Hz), 4.00 (m, 3H), 4.21 (m, 1H), 6.91-7.33 (m, 9H), 7.58 (s, 1H). MS APCI, m/z=310 (M+1). LC/MS: 2.21 min.

d. 4(RS)-Phenyl-1,3,4,5-tetrahydro-2H-1-benzazepin-2-one (79d)

A stirred slurry of ethyl 2-oxo-4-phenyl-2,3,4,5-tetrahydro-1H-1-benzazepine-3-carboxylate (79c) (5.14 g, 16.6 mmol), 4-aminothiophenol (4.49 g, 35.9 mmol) and LiBr (8.66 g, 99.7 mmol) in 50 mL N,N'-dimethylformamide was heated to 160° C. for 24 h. The cooled mixture was diluted with 200 mL 1N HCl and extracted with ethyl acetate (3×100 mL). The combined extracts were washed with 1N HCl, 20% K$_2$CO$_3$, and brine. The organic solution was dried (MgSO$_4$), filtered, and evaporated. The crude product was triturated (EtOH/EtOAc) to give a white powder (2.96 g, 75%). $^1$H NMR (300 MHz, CDCl$_3$) δ 2.55-2.72 (m, 2H), 2.90 (dd, 1H, J=7 Hz, J=14 Hz), 3.19 (dd, 1H, J=7 Hz, J=14 Hz, 1H), 3.70 (quin, J=7 Hz, 1H), 7.03 (d, J=7 Hz, 1H), 7.10-7.40 (m, 8H), 7.71 (br s, 1H). MS APCI, m/z=238 (M+1).

LC/MS: 2.24 min.

e. (3,4-trans)-3-Iodo-4-phenyl-1,3,4,5-tetrahydro-2H-1-benzazepin-2-one (79e)

To a stirred solution of 4(RS)-phenyl-1,3,4,5-tetrahydro-2H-1-benzazepin-2-one (79d) (3.54 g, 14.9 mmol) and triethylamine (10.5 mL, 75.0 mmol) in 80 mL dichloromethane cooled to −20° C. was slowly added iodotrimethylsilane (6.0 g, 30 mmol). When addition was complete, the mixture was stirred for 10 min, and then iodine was added (7.61 g, 30.0 mmol) all in one portion. The mixture was stirred for 1.5 h at −20° C., diluted with 800 mL dichloromethane, and extracted with 10% aqueous sodium bisulfite, water, and brine. The organic solution was dried (MgSO$_4$), filtered, and evaporated to give a light yellow solid (4.07 g, 75%). $^1$H NMR (300 MHz, DMSO-d$_6$) δ 2.75 (dd, J=5 Hz, J=14 Hz, 1H), 3.20 (dd, J=7 Hz, J=14 Hz, 1H), 3.70 (dd, J=7 Hz, J=14 Hz, 1H), 4.57 (d, J=8 Hz, 1H), 7.00-7.20 (m, 5H), 7.21-7.42 (m, 4H), 10.07 (br s, 1H). MS APCI, m/z=364 (M+1). LC/MS: 2.49 min.

f. (3,4cis)-3-Azido-4-phenyl-1,3,4,5-tetrahydro-2H-1-benzazepin-2one (79f)

To a stirred solution of (3,4-trans)-3-iodo-4-phenyl-1,3,4,5-tetrahydro-2H-1-benzazepin-2-one (79e) (4.07 g, 11.2 mmol) in DMF (200 mL) was added sodium azide (5.6 g, 86 mmol). The mixture was stirred for 18 h, the DMF was removed under reduced pressure, and residue was dissolved in 500 mL chloroform. The solution was extracted with water, saturated aqueous sodium bicarbonate, and brine. The organic solution was dried (MgSO$_4$), filtered, and evaporated to give 3.24 g (quantitative) of an off-white solid. $^1$H NMR (300 MHz, CDCl$_3$) δ 2.99 (dd, J=7 Hz, J=14 Hz, 1H), 3.22 (t, J=13 Hz, 1H), 3.81 (dd, J=7 Hz, J=13 Hz, 1H), 4.18 (d, J=8 Hz, 1H), 7.04-7.09 (m, 1H), 7.15-7.43 (m, 8H), 7.93 (br s, 1H). MS APCI, m/z=251 (M+1−N$_2$). LC/MS: 2.40 min.

g. (3,4cis)-3-Amino-4-phenyl-1,3,4,5-tetrahydro-2H-1-benzazepin-2-one hydrochloride (79 g)

To a Parr hydrogen flask was added 10% Pd/C (120 mg) followed by 150 mL absolute ethanol. To this was then added (3,4-cis)-3-azido-4-phenyl-1,3,4,5-tetrahydro-2H-1-benzazepin-2-one (79f) (1.70 g, 6.06 mmol). The mixture was gently warmed with a heat gun to dissolve the azide. Aqueous 1N HCl was added (20 mL), the flask was placed on the Parr® shaker, and evacuated/backfilled with hydrogen (4 cycles). The mixture was shaken under 50 psi hydrogen for 24 h, filtered through diatomaceous earth, and the ethanol was evaporated. The residue was stirred with 200 mL Et$_2$O for 30 min and the precipitated product was filtered off, washed with ether, and dried under vacuum for 18 h. to yield the title compound as a white powder (1.61 g, 92%) which contained residual ether. $^1$H NMR (300 MHz, DMSO-d$_6$) δ 2.94 (t, J=13 Hz, 1H), 3.04 (dd, J=7 Hz, J=14 Hz, 1H), 3.89 (d, J=8 Hz, 1H), 3.97 (dd, J=7 Hz, J=12 Hz, 1H), 7.13 (d, J=7 Hz, 1H), 7.22 (d, J=8 Hz, 1H), 7.32-7.46 (m, 7H), 8.04 (br s, 3H), 10.60 (s, 1H). MS APCI, m/z=253 (M+1−HCl). LC/MS: 1.48 min.

Example 80

N²-[(3,5-Difluorophenyl)acetyl]-N-[(3S,4R)-8-fluoro-1-methyl-2-oxo-4-phenyl-2,3,4,5-tetrahydro-1H-1-benzazepin-3-yl]-L-alaninamide (80)

Using a procedure similar to that described in Example 1, except using (3,4-cis)-3-amino-8-fluoro-1-methyl-4-phenyl-1,3,4,5-tetrahydro-2H-1-benzazepin-2-one (80c) (51.1 mg) as the amine component, the title compound (80) was obtained in a 1:1 mixture with the 3R,4S diastereomer (37 mg, 65%) as a white solid. ¹H NMR (300 MHz, CD₃OD) δ 0.89 (d 1.5H), 0.97 (d, 1.5H), 2.90 (m, 1H), 3.47 (s, 3H), 3.52 (m, 2H), 3.80 (s, 2H), 3.80 (s, 2H), 4.67 (m, 1H), 4.79 (q, 1H), 6.76-6.72 (m, 11H). MS APCI, m/z=510 (M+1), 532 (M+Na). LC/MS: 2.54 min.

The starting amine, (3,4-cis)-3-amino-8-fluoro-1-methyl-4-phenyl-1,3,4,5-tetrahydro-2H-1-benzazepin-2-one (80c) was prepared in the following manner:

a. tert-Butyl-[(3,4-cis)-8-fluoro-2-oxo-4-phenyl-2,3,4,5-tetrahydro-1H-1-benzazepin-3-yl]-carbamate (80a)

To a solution of (3,4-cis)-3-amino-8-fluoro-4-phenyl-1,3,4,5-tetrahydro-2H-1-benzazepin-2-one (8k) (50 mg) in THF (10 mL) at 0° C. under nitrogen was added (Boc)₂O (61 mg). After the solid was completely dissolved, triethylamine (0.044 mL) was added and the mixture was stirred at 0° C. for 1 h, then at RT for 1 h. The mixture was concentrated in vacuo and then partitioned between H₂O (10 mL) and ethyl acetate (20 mL). The organic phase was separated and consecutively washed with 0.1 N HCl (2×10 mL), saturated NaHCO₃, and brine, dried, filtered and evaporated to yield the title compound (68 mg, 99%) as a viscous oil.

¹H NMR (300 MHz, CD₃OD) δ 1.42 (s 9H), 3.04 (m, 1H), 3.11 (m, 2H), 3.46 (m, 2H), 6.54-7.70 (m, 8H). MS APCI, m/z=371 (M+1), 532 (M+Na). LC/MS: 2.88 min.

b. tert-Butyl-[(3,4cis -8-fluoro-1-methyl-2-oxo-4-phenyl-2,3,4,5-tetrahydro-1H-1-benzazepin-3-yl]-carbamate (80b)

To a mixture of tert-butyl-[(3,4-cis)-8-fluoro-2-oxo-4-phenyl-2,3,4,5-tetrahydro-1H-1-benzazepin-3-yl]-carbamate (80a) (68.5 mg) and KOH (13.4 mg) in THF (10 mL) at 25° C. under nitrogen was added Bu₄NBr (6.0 mg). MeI (11.0 µL) was then added dropwise. The mixture was stirred at RT for 18 h, concentrated in vacuo and then partitioned between H₂O (10 mL) and ethyl acetate (20 mL). The organic phase was washed with brine, dried, filtered and evaporated to yield the title compound (65 mg, 92%) as a tan solid. ¹H NMR (300 MHz, CD₃OD) δ 1.42 (s 9H), 3.04 (m, 1H), 3.11 (m, 2H), 3.18 (s, 3H), 3.46 (m, 2H), 6.54-7.70 (m, 8H). MS APCI, m/z=285 (M+1-Boc). LC/MS: 2.98 min.

c. (3,4cis)-3-Amino-8-fluoro-1-methyl-4-phenyl-1,3,4,5-tetrahydro-2H-1-benzazepin-2-one (80c)

To a solution of tert-butyl [(3,4-cis)-8-fluoro-1-methyl-2-oxo-4-phenyl-2,3,4,5-tetrahydro-1H-1-benzazepin-3-yl]carbamate (80b) (65.0 mg) in dichloromethane (3.0 mL) at RT under nitrogen was added TFA (0.2 mL). The mixture was stirred at RT for 1 h. The mixture was concentrated in vacuo, redissolved in dichloromethane (10 mL), washed with saturated NaHCO₃ (2×) and brine, dried, filtered and evaporated to yield the title compound (42.0 mg, 87.5%) as yellow gum.

¹H NMR (300 MHz, CD₃OD) δ 2.42 (d, 2H), 2.77 (m, 2H), 2.97 (m, 1H), 3.17 (m, 1H), 3.88 (m, 1H), 6.54-7.47 (m, 8H). MS APCI, m/z=285 (M+1).

LC/MS: 1.60 min.

Example 81

(2S)—N-((1S)-2-{[(3S,4R)-8-Fluoro-2-oxo-4-phenyl-2,3,4,5-tetrahydro-1H-1-benzazepin-3-yl]amino}-2-oxo-1-phenylethyl)-2-hydro-4-methylpentanamide (81)

Using a procedure similar to that described in Example 1, except using (3,4-cis)-3-amino-8-fluoro-4-phenyl-1,3,4,5-tetrahydro-2H-1-benzazepin-2-one (8k) (27 mg) as the amine component, and (2S)-{[(2S-2-hydroxy-4-methylpentanoyl]amino}(phenyl)acetic acid (27 mg) as the acid component, the title compound (81) was obtained as a 1:1 mixture with the 3R, 4S diastereomer (45 mg, 87%) as a white solid. ¹H NMR (300 MHz, CD₃OD) δ 0.76 (m, 1H), 0.87 (m, 6H), 1.55 (m, 1H), 1.96 (m, 1H), 2.15 (m, 2H), 3.05 (m, 1H), 3.92 (m, 1H), 4.47 (m, 1H), 5.30 (s, 1H), 6.62-7.36 (m, 13H). MS APCI, m/z=518 (M+1), 540 (M+Na).

LC/MS: 2.46 min.

Example 82

(2S)-2-Hydroxy-4-methyl-N-((1S)-2oxo-2-{[(3S,4R)-2-oxo-4phenyl-2,3,4,5-tetrahydro-1H-1-benzazepin-3-yl]amino}-1-phenylethyl)pentanamide (82)

Using a procedure similar to that described in Example 1, except using (3,4-cis)-3-amino-4-phenyl-1,3,4,5-tetrahydro-2H-1-benzazepin-2-one (50 mg) as the amine component, and (2S)-{[(2S)-2-hydroxy-4-methylpentanoyl]amino}(phenyl)acetic acid (46 mg) as the acid component, the title compound (82) was obtained in a 1:1 mixture with the 3R,4S diastereomer (80 mg, 93%) as a white solid. ¹H NMR (300 MHz, CD₃OD) δ 0.76 (m, 1H), 0.87 (m, 6H), 1.55 (m, 1H), 1.96 (m, 1H), 2.15 (m, 2H), 3.04 (m, 1H), 3.95 (m, 1H), 4.48 (m, 1H), 5.30 (s, 1H), 6.61-7.49 (m, 14H). MS APCI, m/z 500 (M+1). LC/MS: 2.43 min.

Example 83

N²-[(3,5-Difluorophenyl)acetyl]-N¹-[(3S4R)-2-oxo-4-phenyl-1-prop-2-yn-1-yl-2,3,4,5-tetrahydro-1H-1-benzazepin-3-yl]-L-alaninamide (83)

Using a procedure similar to that described in Example 1, except using (3,4-cis)-3-amino-4-phenyl-1-prop-2-yn-1-yl-1,3,4,5-tetrahydro-2H-1-benzazepin-2-one (83c) (77 mg) as the amine component, the white solid title compound (8) was obtained as a 1:1 mixture with the 3R,4S diastereomer (110 mg, 79%). ¹H NMR (400 MHz, CD₃OD) δ 0.80 (d 1.5H), 1.12 (d, 1.5H), 2.28 (d, 1H), 2.90 (m, 1H), 3.46 (m, 2H), 3.60 (s, 2H), 4.37 (m, 2H), 4.73 (q, 1H), 6.58-6.78 (m, 3H), 6.99 (m, 4H), 7.17-7.39 (m, 5H). MS APCI, m/z =516 (M+1), 538 (M+Na). LC/MS: 2.56 min.

The starting amine, (3,4-cis)-3-amino-4-phenyl-1-prop-2-yn-1-yl-1,3,4,5-tetrahydro-2H-1-benzazepin-2-one (83c), was prepared in the following manner:

a. tert-Butyl-[(3,4cis)-2-oxo4phenyl-2,3,4,5-tetrahydro-1H-1-benzazepin-3-yl]-carbamate (83a)

To a solution of (3,4-cis)-3-amino-4-phenyl-1,3,4,5-tetrahydro-2H-1-benzazepin-2-one (300 mg) in dioxane (20 mL) and H₂O (5 mL) at 0° C. under nitrogen was added (Boc)₂O (229 mg). After the solid was completely dissolved, TEA (0.42 mL) was added and the mixture was stirred at 0° C. for 1 h. The mixture was concentrated in vacuo and then partitioned between H₂O (10 mL) and Ethyl acetate (20 mL). The organic phase was separated and consecutively washed with 0.1 N HCl (2×10 mL), saturated NaHCO₃, and brine, dried, filtered and evaporated to yield the title compound (360 mg, 98%) as a tan solid. ¹H NMR (300 MHz, CD₃OD) δ 1.42 (s 9H), 2.15 (m, 21H), 2.95 (m, 1H), 3.16 (m, 1H), 6.60-7.80 (m, 9H). MS APCI, m/z=253 (M+1-Boc). LC/MS: 2.55 min.

b. tert-Butyl-[(3,4-cis)-2-oxo-4-phenyl-1-prop-2-yn-1-yl-2,3,4,5-tetrahydro-1H-1-benzazepin-3-yl]-carbamate (83b)

To a mixture of tert-butyl-[(3,4-cis)-2-oxo-4-phenyl-2,3,4,5-tetrahydro-1H-1-benzazepin-3-yl]-carbamate (83a) (100 mg) and Cs₂CO₃ (184 mg) in DMF (5 mL) at 25° C. under nitrogen was added propargyl bromide (35 µL, 80% wt in toluene). The mixture was stirred at RT for 18 h, concentrated in vacuo and then partitioned between 0.5 N HCl (10 mL) and Ethyl acetate (20 mL). The organic phase was washed with saturated NaHCO₃, and brine, dried, filtered and evaporated to yield the title compound (105 mg, 96%) as a yellow gum. ¹H NMR (300 MHz, CD₃OD) δ 1.42 (s 9H), 2.28 (s, 1H), 3.09 (m, 1H), 3.16 (m, 1H), 3.46 (m, 2H), 4.47 (s, 2H), 7.72-7.71 (m, 9H). MS APCI, m/z=291 (M+1-Boc). LC/MS: 2.82 min.

c. (3,4cis)-3-Amino-4-phenyl-1-prop-2-yn-1-yl-1,3,4,5-tetrahydro-2H-1-benzazepin-2-one (83c)

To a solution of tert-butyl [(3,4-cis)-2-oxo-4-phenyl-1-prop-2-yn-1-yl-2,3,4,5-tetrahydro-1H-1-benzazepin-3-yl] carbamate (83b) (110 mg) in dichloromethane (5 mL) at RT under nitrogen was added TFA (0.3 mL). The mixture was stirring at RT for 30 min. The mixture was concentrated in vacuo, redissolved in dichloromethane (10 mL), washed with saturated NaHCO₃ (2×) and brine, dried, filtered and evaporated to yield the title compound (77 mg, 95%) as a yellow gum. ¹H NMR (300 MHz, CD₃OD) δ 2.27 (s, 1H), 2.77 (m, 2H), 2.99 (m, 1H), 3.91(d, 1H), 4.40 (s, 2H), 7.25-7.39 (m, 9H). MS APCI, m/z=291 (M+1). LC/MS: 1.68 min.

Example 84

N¹-[(3S,4R)-1-(Cyclopropylmethyl)-2-oxo-4-phenyl-2,3,45-tetrahydro-1H-1-benzazepin-3-yl]-N²-[(3,5-difluorophenyl)acetyl]-L-alaninamide (84)

Using a procedure similar to that described in Example 1, except using (3,4-cis)-3-amino-1-(cyclopropylmethyl)-4-phenyl-1,3,4,5-tetrahydro-2H-1-benzazepin-2-one (84b) (50 mg) as the amine component, the title compound (84) was obtained in a 1:1 mixture with the 3R,4S diastereomer (72 mg, 85%) as a white solid. ¹H NMR (300 MHz, CD₃OD) δ 0.50 (m, 2H), 0.67 (m, 2H), 1.21(m, 1H), 1.29 (d, 3H), 3.05 (m, 1H), 3.46 (d, 2H), 3.53 (m, 2H), 3.80 (s, 2H), 4.70 (q, 1H), 4.78 (d, 1H), 6.53-7.52 (m, 12H). MS APCI, m/z =532 (M+1), 554 (M+Na). LC/MS: 2.74 mm.

The starting amine, (3,4-cis)-3-amino-1-(cyclopropylmethyl)-4-phenyl-1,3,4,5-tetrahydro-2H-1-benzazepin-2-one (b), was prepared in the following manner:

a. tert-Butyl-[(3,4-cis)-1-(cycloproylmethyl)-2-oxo-4-phenyl-2,3,4,5-tetrahydro-1H-1-benzazepin-3-yl]-carbamate (84a)

Using a procedure similar to that described in Example 83b, except using cyclopropylmethyl bromide, the title compound (84a) was obtained as a yellow gum (81%). ¹H NMR (300 MHz, CD₃OD) δ 0.50 (m, 2H), 0.69 (m, 2H), 1.19 (m, 1H), 1.42 (s 9H), 3.09 (m, 1H), 3.16 (m, 1H), 3.46 (m, 2H), 4.47 (s, 2H), 7.72-7.71 (m, 9H). MS APCI, m/z=307 (M+1-Boc). LC/MS: 3.01 min.

b. (3,4-cis)-3-Amino-1-(cycloproylmethyl)iphenyl-1,3,4,-tetrahydro-2H-1-benzazepin-2-one (84b)

Using a procedure similar to that described in Example 83c, the title compound (84b) was obtained as a yellow gum (78%). ¹H NMR (300 MHz, CD₃OD) δ 0.50 (m, 2H), 0.69 (m, 2H), 1.19 (m, 1H), 3.09 (m, 1H), 3.16 (m, 1H), 3.46 (m, 2H), 4.47 (s, 2H), 7.72-7.71 (m, 9H). MS APCI, m/z=307 (M+1). LC/MS: 1.90 min.

Example 85

N²-[(3,5-Difluorophenyl)acetyl]-N¹-[(3S,4R)-1-isopropyl-2-oxo-4-phenyl-2,3,4,5-tetrahydro-1H-1-benzazepin-3-yl]-L-alaninamide (85)

Using a procedure similar to that described in Example 1, except using (3,4-cis)-3-amino-1-isopropyl-4-phenyl-1,3,4,5-tetrahydro-2H-1-benzazepin-2-one (85b) (47 mg) as the amine component, the white solid title compound (5) was obtained as a 1:1 mixture with the 3R,4S diastereomer (65 mg, 78%). ¹H NMR (300 MHz, CD₃OD) δ 1.17 (d, 6H), 1.29 (d, 3H), 3.16(m, 1H), 3.50 (m, 2H), 3.80 (s, 2H), 4.70 (q, 1H), 4.88 (m, 1H), 4.95 (m, 1H), 6.58-7.56 (m, 12H). MS APCI, m/z=520 (M+1), 542 (M+Na). LC/MS: 2.71 min.

The starting amine, (3,4-cis)-3-amino-1-isopropyl-4-phenyl-1,3,4,5-tetrahydro-2H-1-benzazepin-2-one (85b), was prepared in the following manner:

a. tert-Butyl-[(3,4-cis)-1-isopropyl-2-oxo-4-phenyl-2,3,4,5-tetrahydro-1H-1-benzazepin-3-yl]-carbamate (85a)

Using a procedure similar to that described in Example 83b, except using 2-iodopropane, the title compound (85) was obtained as yellow gum (96%). ¹H NMR (300 MHz, CD₃OD) δ 1.17 (d, 6H), 1.42 (s 9H), 3.09 (m, 1H), 3.16 (m, 1H), 3.46 (m, 2H), 4.95 (m, 1H), 7.72-7.71 (m, 9H). MS APCI, m/z=295 (M+1-Boc). LC/MS: 2.99 min.

b. (3,4-cis)-3-Amino-1-isopropyl-4-phenyl-1,3,4,5-tetrahydro-2H-1-benzazepin-2-one (85b)

Using a procedure similar to that described in Example 83c, the title compound (85b) was obtained as yellow gum (61%). ¹H NMR (300 MHz, CD₃OD) δ 1.17 (d, 6H), 2.83 (m, 2H), 3.12 (m, 1H), 4.08 (m, 1H), 5.02 (m, 1H), 6.58-7.65 (m, 9H). MS APCI, m/z=295 (M+1). LC/MS: 1.81 min.

Example 86

N²-[(2S )-2-Hydroxy-4-methyl-1-oxopentyl]-N¹-[(2R,3R)-2-(4-methoxyphenyl)-4oxo-2,3,4,5-tetrahydro-1,5-benzothiazepin-3-yl]-L-alaninamide (86)

Using a procedure similar to that described in Example 1, except with (2,3-cis)-3-amino-2-(4-methoxyphenyl)-2,3-dihydro-1,5-benzothiazepin-4(5H)-one (41d) (70 mg, 0.184 mmol) as the amine component, N-(2S)-2-hydroxy-4-methyl-1-oxopentyl-L-alanine (37.5 mg, 0.185 mmol) as the acid component and dichloromethane/DMF as solvent gave after aqueous workup and column chromatography (1:1 hexane/ethyl acetate) the solid title compound as a 1:1 mixture with the (2S,3S) diastereomer (52 mg, 58%). $^1$H NMR (300 MHz, CDCl$_3$) δ0.93 (m, 6H), 1.10 (d, 1.5H, J=7.0 Hz), 1.22 (d, 1.5H, J=7.0 Hz), 1.4-1.65 (m, 4H), 3.81 (s, 3H), 3.9-74.03 (m, 1H), 4.24-4.36 (m, 1H), 4.84-4.91 (m, 1H), 5.20-5.26 (m, 1H), 6.43 (d, 0.5H), 6.64 (d, 1H), 6.80 (d, 0.5H), 6.88 (d, 2H, J=8.3 Hz), 7.14 (d, 1H, J=7.5 Hz), 7.24-7.28 (m, 1H), 7.36 (d, 2H, J=8.8 Hz), 7.37-7.44 (m, 1H), 7.70 (d, 1H, J=7.9 Hz), 7.74 (s, 0.5H), 7.83 (s, 0.5H). MS APCI, m/z=508(M+Na). LC/MS: 2.23 min.

Example 87

N¹-[(2R,3R)-2-(2-Chlorophenyl)-4-oxo-2,3,4,5-tetrahydro-1,5-benzothiazepin-3-yl]-N²-[(2S)-2-hydroxy-4-methyl-1-oxopentyl]-L-alaninamide (82)

Using a procedure similar to that described in Example 1, except with (2,3-cis)-3-amino-2-(2-chlorophenyl)-2,3-dihydro-1,5-benzothiazepin-4(5H)-one (87d) (70mg, 0.181 mmol) as the amine component, N-(2S)-2-hydroxy-4-methyl-1-oxopentyl-L-alanine (36.7 mg, 0.181 mmol) as the acid component and dichloromethane/DMF as solvent gave after aqueous workup and column chromatography (hexane/ethyl acetate gradient) the solid title compound as a 1:1 mixture with the (2S,3S) diastereomer (42 mg, 47%). $^1$H NMR (300 MHz, CDCl$_3$) δ0.92 (m, 6H), 1.09 (d, 1.5H, J=7.0 Hz), 1.24 (d, 1.5H, J=7.0 Hz), 1.4-1.6 (m, 2H), 1.75-1.86 (m, 1H), 2.64 (t, 1H), 3.99-4.05 (m, 1H), 4.32-4.45 (m, 1H), 4.96-5.06 (m, 1H), 5.93-5.99 (m, 1H), 6.52 (d, 0.5H), 6.68 (d, 0.5H), 6.77 (d, 0.5H), 6.85 (d, 0.5H), 7.16 (d, 1H), 720-7.47 (m, 5H), 7.74 (t, 1H), 7.86-7.93 (m, 1.5H), 7.99 (s, 0.5H). MS APCI, m/z=512(M+Na). LC/MS: 2.33 min.

The starting amine, (2,3-cis)-3-amino-2-(2-chlorophenyl)-2,3-dihydro-1,5-benzothiazepin-4(5B)-one hydrobromide (87d), was prepared in the following manner:

a. Methyl (2Z)-2-{[(benzyloxy)carbonyl]amino}-3-(2-chlorophenyl)acrylate(87a)

Using a procedure similar to that described in example 1 part a, except using 2-chlorobenzaldehyde (1.82 g, 13.0 mmol) as the aldehyde component, the title compound (87a) was obtained as an oil (3.0 g, 67%) contaminated with 30% (2E)-isomer. MS APCI, m/z=346 (M+1).

b. Methyl β-[(2-aminophenyl)thio]-N-[(benzyloxy)carbonyl]-2-chlorophenylalaninate (87b)

Using a procedure similar to that described in example 10, part b, (stirred 40 h) except using methyl (2Z)-2-{[(benzyloxy)carbonyl]amino}-3-(2-chlorophenyl)acrylate (87a) (2.0 g, 5.8 mmol), gave the title compound (87b) (2.5 g, 91%) as a clear oil (70:30 mixture (erythro:threo)). MS APCI, m/z=471(M+1).

c. Benzyl [(2,3-cis)-2-(2-chlorophenyl)-4-oxo-2,3,4,5-tetrahydro-1,5-benzothiazepin-3-yl]carbamate (87c)

Using a procedure similar to that described in example 41, part b, except using methyl β-[(2-aminophenyl)thio]-N-[(benzyloxy)carbonyl]-2-chlorophenylalaninate (87b) (2.0 g, 4.2 mmol) as the aniline component, afforded the title compound (1.65 g) containing 10% of the 2,3 trans product. Recrystallization from hot ethyl acetate (75 mL) gave pure title compound (87c) (1.3 g, 65%) as a white solid. MS APCI, m/z=439(M+1). LC/MS: 2.77 Min d. (2,3-cis)-3-Amino-2-(2-chlorophenyl)-5-methyl-2,3-dihydro-1,5-benzothiazepin-4(5H)-one hydrobromide(87d)

Using a procedure similar to that described in example 41, part c, except using benzyl [(2,3-cis)-2-(2-chlorophenyl)-4-oxo-2,3,4,5-tetrahydro-1,5-benzothiazepin-3-yl]carbamate (87c (1.2 g, 2.7 mmol) as the protected amine component, the title compound (87d) (930 mg, 88%) as a white solid. $^1$H NMR (300 MHz, d6-DMSO) δ4.41 (d, 1H, J=7.4 Hz), 5.78 (d, 1H, J=7.4 Hz), 7.31 (m, 2H), 7.4-7.6 (m, 6H), 7.72 (d, 1H, J=7.4 Hz), 7.87 (d, 2H, J=7.4 Hz), 8.15 (bs, 3H), 10.95 (s, 1H). MS APCI, m/z=305(M+1). LC/MS: 1.62 min

Example 88

N¹-[(2R,3R)-2-(2-Chlorophenyl)-4-oxo-2.3,4,5-tetrahydro-1,5-benzothiazepin-3-yl]-N²-[(3,5-difluorophenyl)acetyl]-L-alaninamide (88)

Using a procedure similar to that described in Example 1, except with (2,3-cis)-3-amino-2-(2-chlorophenyl)-2,3-dihydro-1,5-benzothiazepin-4(5H)-one (87d) (70 mg, 0.181 mmol) as the amine component and dichloromethane/DMF as solvent gave after aqueous workup and column chromatography (hexane/ethyl acetate gradient) the solid title compound as a 1:1 mixture with the (2S,3S) diastereomer (64 mg, 67%). $^1$H NMR (300 MHz, CDCl$_3$) δ0.99 (d, 1.5H, J=7.0 Hz), 1.21 (d, 1.5H, J=6.6 Hz), 3.45 (d, 2H, J=7.5 Hz), 4.28-4.39 (m, 0.5H), 4.52-4.60 (m, 0.5H), 4.91 (t, 0.5H, J=7.5 Hz), 4.99 (t, 0.5H, J=7.0 Hz), 5.93 (d, 0.5H, J=7.0 Hz), 5.99 (d, 0.5H, J=7.5 Hz), 6.05 (d, 0.5H, J=7.5 Hz), 6.22 (d, 0.5H, J=7.5 Hz), 6.50 (d, 0.5H, J=7.9 Hz), 6.66-6.79 (m, 2.5H), 7.07 (d, 0.5H, J=7.9 Hz), 7.15 (d, 0.5H, J=7.5 Hz), 7.23-7.46 (m, 6H), 7.73 (d, 1H, J=7.9 Hz), 7.84 (s, 0.5H), 7.84-7.89 (m, 1H), 8.42 (s, 0.5H). MS APCI, m/z=552(M+Na). LC/MS: 2.53 min.

Example 89

N¹-[(2R,3R)-7-Chloro-5-methyl-4-oxo-2-phenyl-2,3,4,5-tetrahydro-1,5-benzothiazepin-3-yl]-N²-[(3,5-difluorophenyl)acetyl]-L-alaninamide (89)

Using a procedure similar to that described in Example 1, except with (2,3-cis)-3-amino-7-chloro-5-methyl-2-phenyl-2,3-dihydro-1,5-benzothiazepin-4(5H)-one hydrobromide (89b) (70 mg, 0.175 mmol) as the amine component and dichloromethane/DMF as solvent gave after aqueous workup and column chromatography (30:1 methanol/chloroform) the title compound as a 1:1 mixture with the (2S,3S) diastereomer; solid (54 mg, 57%). $^1$H NMR (300 MHz, CDCl$_3$) δ0.92 (d, 1.5H, J=7.0 Hz), 1.15 (d, 1.5H, J=7.0 Hz), 3.42 (s, 1H), 3.50 (s, 3H), 4.11-4.22 (m, 1H), 4.72-4.78 (m, 1H), 5.11 (d, 1H, J=7.5 Hz), 5.75 (d, 0.5H, J=7.9 Hz), 5.94 (d, 0.5H, J=7.9 Hz), 6.30 (t, 1H), 6.67-6.78 (m, 2H), 7.27-7.36 (8H), 7.66 (d, 1H, J=8.3 Hz). MS APCI, m/z=566 (M+Na). LC/MS: 2.78 min.

The starting amine, (2,3-cis)-3-amino-7-chloro-5-methyl-2-phenyl-2,3-dihydro-1,5-benzothiazepin -4(5H)-one hydrobromide (89b), was prepared in the following manner:

a. Benzyl [(2,3-cis)-7-chloro-5-methyl-4-oxo-2-phenyl-2,3,4,5-tetrahydro-1,5-benzothiazepin -3-yl]carbamate (89a)

Using a procedure similar to that described in example 5 part a, substituting benzyl [(2,3-cis)-7-chloro-4-oxo-2-phenyl-2,3,4,5-tetrahydro-1,5-benzothiazepin-3-yl]carbamate (13b) (1.1 g, 2.51 mmol) as the amide component, the title compound (89a) (970 mg, 85%)was obtained as a white solid. MS APCI, m/z=453(M+Na). LC/MS: 3.04 min.

b. (2,3-cis)-3-Amino-7-chloro-5-methyl-2-phenyl-2,3-dihydro-1,5-benzothiazepin-4(5H)-one hydrobromide (89b)

Using a procedure similar to that described in example 41, part c, substituting benzyl [(2,3-cis)-7-chloro-5-methyl-4-oxo-2-phenyl-2,3,4,5-tetrahydro-1,5-benzothiazepin-3-yl]carbamate (89a) (700 mg, 1.59 mmol) as the protected amine component, the title compound (89b) (500 mg, 78%) as a white solid. $^1$H NMR (300 MHz, d6-DMSO) δ3.48 (s, 3H), 4.36 (d, 1H, J=7.0 Hz), 5.09 (d, 1H, J=7.0 Hz), 7.48 (m, 6H), 7.75 (d, 1H), 7.86 (s, 1H), 8.04 (bs, 3H). MS APCI, m/z=319(M+H). LC/MS: 1.82 min

Example 90

N$^1$-[(3,5-Difluorophenyl)acetyl]-N$^1$-[(2R,3R)-2-(2-fluorophenyl)-4-oxo-2,3,4,5-tetrahydro-1,5-benzothiazepin-3-yl]-L-alaninamide (90)

Using a procedure similar to that described in Example 1, except with (2,3-cis)-3-amino-2-(2-fluorophenyl)-2,3-dihydro-1,5-benzothiazepin-4(5H)-one hydrobromide (90d) (70 mg, 0.189 mmol) as the amine component and dichloromethane/DMF as solvent gave after aqueous workup the title compound as a 1:1 mixture with the (2S,3S) diastereomer; solid (96 mg, 99%). $^1$H NMR (300 MHz, CDCl$_3$) δ1.03 (d, 1.5H, J=6.6 Hz), 1.21 (d, 1.5H, J=7.0 Hz), 3.43 (s, 1H), 3.47 (s, 1H), 4.31-4.44 (m, 0.5H), 4.501-4.59 (m, 0.5H), 4.86-4.97 (m, 1H), 5.75 (q, 1H), 6.01 (d, 0.5H, J=7.5H), 6.20 (d, 0.5H, J=7.9 Hz), 6.54 (d, 0.5H, J=7.9 Hz), 6.65-6.80 (m, 3.5H), 6.92-7.46 (m, 6H), 7.72 (d, 1H, J=7.5 Hz), 7.80 (s, 0.5H), 7.82 (d, 1H, J=8.3 Hz), 8.31 (s, 05H). MS APCI, m/z=514(M+1). LC/MS: 2.43 min.

The starting amine, (2,3-cis)-3-amino-2-(2-fluorophenyl)-2,3-dihydro-1,5-benzothiazepin-4(5H)-one hydrobromide (90d), was prepared in the following manner:

a. Methyl (2Z)-2-{[(benzyloxy)carbonyl]amino}-3-(2-fluorophenyl)acrylate(90a)

Using a procedure similar to that described in example 1 part a, except using 2-fluorobenzaldehyde (596 μL, 5.50 mmol) as the aldehyde component, the title compound (90a) was obtained as an oil (1.8 g, 98%) contaminated with 15% (2E)-isomer. MS APCI, m/z=330(M+1).

b. Methyl β-[(2-aminophenyl)thio]-N-[(benzyloxy)carbonyl]-2-fluorophenylalaninate (90b)

Using a procedure similar to that described in example 10, part b, (stirred 40 h) except using methyl (2Z)-2-{[(benzyloxy)carbonyl]amino}-3-(2-fluorophenyl)acrylate (90a) (1.8 g, 5.5 mmol), to afford crude title compound. After recrystallization from methanol-ether the title compound (90b) was obtained (1.2 g, 49%) as a white solid (95:5 mixture (erythro:threo)). MS APCI, m/z=455(M+1). LC/MS: 2.69 min.

c. Benzyl [(2,3-cis)-2-(2-fluorophenyl)-4oxo-2,3,4,5-tetrahydro-1,5-benzothiazepin-3-yl]carbamate (90c)

Using a procedure similar to that described in example 41, part b, substituting methyl β-[(2-aminophenyl)thio]-N-[(benzyloxy)carbonyl]-2-fluorophenylalaninate (90b) (1.2 g, 2.6 mmol) as the aniline component, the title compound (90c) (650 mg, 58%) was obtained as a white solid. MS APCI, m/z=445(M+Na). LC/MS: 2.77 min.

d. (2R,3R)-3-Amino-2-(2-fluorophenyl)-5-methyl-2,3-dihydro-1,5-benzothiazepin-4(5H)-one hydrobromide (90d)

Using a procedure similar to that described in example 41, part c, substituting benzyl [(2,3-cis)-2-(2-fluorophenyl)-4-oxo-2,3,4,5-tetrahydro-1,5-benzothiazepin-3-yl]carbamate (90c) (580 mg, 1.37 mmol) as the protected amine component, the title compound (90d) (480 mg, 94%) was obtained as a white solid. $^1$H NMR (300 MHz, d6-DMSO) δ4.37 (d, 1H, J7.0 Hz), 5.61 (d, 1H, J 7.0 Hz), 7.26-7.36 (m, 4H), 7.46-7.59 (m, 2H), 7.75 (m, 2H), 8.19 (bs, 3H), 10.95 (s, 1H). MS APCI, m/z=289(M+1). LC/MS: 1.51 min.

Example 91

N$^2$-[(35-Difluorophenyl)acetyl]-N$^1$-[(2R,3R)-2-(4-fluorophenyl)-4-oxo-2,3,4,5-tetrahydro-1,5-benzothiazepin-3-yl]-L-alaninamide (91)

Using a procedure similar to that described in Example 1, except with (2,3-cis)-3-amino-2-(4-fluorophenyl)-2,3-dihydro-1,5-benzothiazepin-4(5H)-one hydrobromide (91d) (70 mg, 0.189 mmol) as the amine component and dichloromethane/DMF as solvent gave after aqueous workup the title compound as a 1:1 mixture with the (2S,3S) diastereomer; solid (64 mg, 66%). $^1$H NMR (300 MHz, CDCl$_3$) δ0.98 (d, 1.5H, J=6.6 Hz), 1.18 (d, 1.5H, J=7.0 Hz), 3.43 (s, 1H), 3.45 (s, 1H), 4.17-4.27 (m, 0.5H), 4.45-4.54 (m, 0.5H), 4.83 (q, 1H), 5.28 (q, 1H), 5.82 (d, 0.5H, J=6.6 Hz), 6.06 (d, 0.5H, J=7.0 Hz), 6.41 (d, 0.5, J=7.0 Hz), 6.65 (d, 0.5H, J=7.0 Hz), 6.72-6.79 (m, 3H), 6.98-7.16 (m, 3H), 7.20-7.31 (m, 1H), 7.37-7.44 (m, 3H), 7.70 (d, 1.5H, J=7.5 Hz), 8.17 (s, 0.5H). MS APCI, m/z=536(M+Na). LC/MS: 2.51 min.

The starting amine, (2,3-cis)-3-amino-2-(4-fluorophenyl)-2,3-dihydro-1,5-benzothiazepin-4(5B)-one hydrobromide (91d), was prepared in the following manner:

a. Methyl (2Z)-2-{[(benzyloxy)carbonyl]amino}-3-(4-fluorophenyl)acrylate (91a)

Using a procedure similar to that described in example 1 part a, except using 4-fluorobenzaldehyde (600 µL, 5.50 mmol) as the aldehyde component, the title compound (91a) was obtained as an oil (1.8 g, 98%) contaminated with 15% (2E) isomer. MS APCI, m/z=330(M+1).

b. Methyl β-[(2-aminophenyl)thio]-N-[(benzyloxy)carbonyl]-4-fluorophenylalaninate (91b)

Using a procedure similar to that described in example 10, part b, (stirred 40 h) except using methyl (2Z)-2-{[(benzyloxy)carbonyl]amino}-3-(4-fluorophenyl)acrylate (91a) (1.8 g, 5.5 mmol) as reactant, to afford crude title compound. After recrystallization from ethyl acetate-hexanes the title compound (91b) (1.3 g, 52%) was obtained as a white solid (97:3 mixture (erythro:threo)). MS APCI, m/z=455(M+1). LC/MS: 2.69 min.

c. Benzyl [(2,3-cis)-2-(4-fluorophenyl)-4-oxo-2,3,4,5-tetrahydro-1,5-benzothiazepin-3-yl]carbamate (91c)

Using a procedure similar to that described in example 41, part b, substituting methyl β-[(2-aminophenyl)thio]-N-[(benzyloxy)carbonyl]-4-fluorophenylalaninate (91b) (1.3 g, 2.86 mmol) as the aniline component, the title compound (91c) (900 mg, 73%) was obtained as a white solid. MS APCI, m/z=445(M+Na). LC/MS: 2.77 min.

d. (2,3-cis)-3-Amino-2-(4-fluorophenyl)-5-methyl-2,3-dihydro-1,5-benzothiazepin-4(5H)-one hydrobromide (91d)

Using a procedure similar to that described in example 41, part c, substituting benzyl [(2,3-cis)-2-(4-fluorophenyl)-4-oxo-2,3,4,5-tetrahydro-1,5-benzothiazepin-3-yl]carbamate (91c (850 mg, 2.01 mmol) as the protected amine component, the title compound (91d) (700 mg, 94%) as a white solid. MS APCI, m/z=313(M+Na). LC/MS: 1.57 min. $^1$H NMR (300 MHz, d6-DMSO) δ4.29 (d, 1H, J 7.0 Hz), 5.28 (d, 1H, J 7.0 Hz), 7.26-7.36 (m, 4H), 7.55 (m, 3H), 7.69 (d, 1H, J=7.9 Hz), 8.06 (bs, 3H), 10.89 (s, 1H).

Example 92

$N^1$-[(2R,3R)-7-chloro-2-(2,5-difluorophenyl)-4-oxo-2,3,4,5-tetrahydro-1,5-benzothiazepin-3-yl]-$N^2$-[(3,5-difluorophenyl)acetyl]-L-alaninamide (92)

A stirred slurry of (2,3-cis)-3-amino-7-chloro-2-(2,5-difluorophenyl)-2,3-dihydro-1,5-benzothiazepin-4(5H)-one hydrobromide (92c (0.127 g, 0.30 mmol) in dichloromethane (12 mL), under $N^2$, was treated with NMM (0.05 mL, 0.45 mmol) and the clear solution cooled in an ice-bath. N-[(3,5-difluorophenyl)acetyl]-L-alanine (1e) (0.080 g, 0.33 mmol), EDAC HCl (0.0863 g, 0.45 mmol) and NMM (0.05 mL, 0.45 mmol) were added successively and the mixture stirred for 2 h. The solvent was removed in vacuo and the residue portioned between ethyl acetate (50 mL) and water (50 mL). The material from the washed (sat. $NaHCO_3$ and brine) ethyl acetate solution was a mixture of two diastereomers and was partially purified by column chromatography (eluent: 3:1, 2:1 and 1:1 hexane :ethyl acetate) to yield the white title compound as a 9:1 mixture with the 2R,3R diastereomer (0.041 g, 24%). $^1$H NMR (300 MHz, CDCl$_3$) δ1.08 (d, 0.3H, J=7.0 Hz, 2R,3R diastereomer), 1.21 (d, 3H, J=7.0 Hz), 3.44 (s, 0.2H, 2R,3R diastereomer), 3.48 (s, 2H), 4.32 (m, 1H), 4.91 (t, 1H), 5.66 (d, 1H, J=8.3 Hz), 5.99 (d, 1H, J=7.0 Hz), 6.54 (d, 1H, J=7.5 Hz), 6.79 (d, 1H, J=7.9 Hz), 6.9-7.0 (m, 2H), 7.16 (s, 1H), 7.50-7.56 (m, 1H), 7.65 (d, 1H, J=7.9 Hz), 7.85 (m, 5H). MS APCI, m/z=566(M+1). HPLC Method A: 3.34 min.

The required 3-amino-7-chloro-2-(2,5-difluorophenyl)-2,3-dihydro-1,5-benzothiazepin-4(5H)-one hydrobromide was prepared in the following manner:

a. Methyl β-[(2-amino-4chlorophenyl)thio]-N-[(benzyloxy)carbonyl]-2,5-difluorophenylalaninate (92a)

The title compound was obtained from 2-amino-4-chlorobenzenethiol (5.0 g, 31.3 mmol) and (1a) (2.17 g, 6.26 mmol) as a yellow foam (2.68 g, 85%) following Method B. The Z:E ratio of the material was 85:15 as determined by $^1$H-NMR (methyl integration). $^1$H NMR (300 MHz, CDCl$_3$) δ3.55 (s, 3H, Z isomer), 3.72 (s, 0.5H, E isomer), 4.37 (br. s, 2H), 4.85-4.9 (m, 2H), 5.0-5.15 (m, 2H), 5.73(d, 1H, J=9.7 Hz), 6.54 (dd, 1H, J=8.3, 2.0 Hz), 6.67 (d, 1H, J=2.0 Hz), 6.9-7.0 (m, 2H), 7.07 (d, 1H, J=8.3 Hz), 7.13-7.17 (m, 1H), 7.3-7.4 (m, 5H), MS APCI, ml/z=507(M+1). HPLC Method A: 3.62 min.

b. Benzyl [(2,3-cis)-7-chloro-2-(2,5-difluorophenyl)-oxo-2,3,4,5-tetrahydro-1,5-benzothiazepin -3-yl]carbamate (92b)

A solution of (91a) (2.68 g, 5.29 mmol) and pTSA (0.1 g) in xylenes (75 mL) was stirred in an oil bath at 150° for 3 h, 170° for 2 h, allowed to stand overnight and the precipitated white solid (2.0 g) collected. The material was dissolved in hot methyl ethyl ketone (150 mL), treated with ethyl ether (150 mL), refrigerated and the pure title compound obtained as a white solid (1.52 g, 76%), mp 233-5°. $^1$H NMR (300 MHz, d6-DMSO) δ 4.64 (t, 1 H), 4.96 (s, 2H), 5.49 (d, 1H, J=7.0 Hz), 7.10 (d, 1H, J=7.9 Hz), 7.24-7.38 (m, 9H), 7.72 (d, 1H, J=7.9 Hz), 10.65 (s, 1H). MS APCI, m/z=507(M+1). HPLC Method A: 3.62 min.

c. (2,3-cis)-3-Amino-7-chloro-2-(2,5-difluorophenyl)-2,3-dihydro-1,5-benzothiazepin-4(5H)-one hydrobromide (92c)

A mixture of (92b) (1.0 g, 2.1 mmol), acetic acid (5 mL) and 30% HBr/acetic acid (10 mL) was stirred in a 60° oil bath for 1 h, cooled, treated with ethyl ether (75 mL) and the white solid collected (0.86 g, 97%), mp 254-6° dec. The material contained 1 mole of acetic acid. after drying at 50°/0.1 torr overnight. $^1$H NMR (300 MHz d6-DMSO) δ1.91 (s, 31H), 4.49 (d, 1H, J=7.0 Hz), 5.57 (d, 1H, J=7.0 Hz), 7.3-7.5 (m, 5H), 7.75 (d, 1H, J=8.3 Hz), 8.27 (br. S, 3H), 11.06 (s, 1H). MS APCI, m/z=341(M+1). HPLC Method A: 2.22 min.

Example 93

$N^2$-[(2S)-2-Hydroxy-4-methyl-1-oxopentyl]-$N^1$-[(6R,7R)-5-oxo-7-phenyl-1,4-thiazepan-6-yl]-L-alaninamide (93)

Using a procedure similar to that described in Example 1, except with (6,7-cis)-6-amino-7-phenyl-1,4-thiazepan-5-one (7d) (84.3 mg, 0.38 mmol) as the amine component, N-(2S)-2-hydroxy-4-methyl-1-oxopentyl-L-alanine (85.4 mg, 0.42 mmol) as the acid component and DMF (3 mL) as solvent gave after aqueous workup and column chromatography (2% methanol/chloroform) the title compound as a 1:1 mixture with the (6S,7S) diastereomer; white solid (0.12 g, 78%), mp 93-9°. ¹HNMR (300 MHz, CDCl₃) δ0.94 (d, 6H, J=6.1 Hz), 1.20 (d, 1.5H, J=7.5 Hz), 1.31 (d, 1.5H, J=7.0 Hz), 1.4-1.65 (m, 2H), 1.75-1.9 (m, 1H), 2.77-2.94 (m, 2H), 3.0-3.1 (m, 1H), 3.7-3.9 (m, 2H), 4.04-4.11 (m, 1H), 4.34 (d, 1H, J=3.9 Hz), 4.4-4.5 (m, 1H), 5.29-5.36 (m, 1H), 6.32-6.43 (m,1H), 6.90 (d, 0.5H), 6.99 (d, 0.5H), 7.08 (d, 0.5H), 7.22 (d, 0.5H), 7.28 (s, 5H). MS APCI, m/z=408(M+1). HPLC Method A: twined peak at 2.26 and 2.31 min.

Example 94

N²-[(3,5-Difluorophenyl)acetyl]-N¹-[(2S,3R2-(3-methyl-2-thienyl)-4-oxo-2,3,4,5-tetrahydro-1,5-benzothiazepin-3-yl]-L-alaninamide (94)

To a solution of (2,3-cis)-3-amino-2-(3-methyl-2-thienyl)-2,3-dihydro-1,5-benzothiazepin-4(5H)-one hydrobromide (94d) (0.501 g, 1.35 mmol), HOBt (0.237 g, 1.76 mmol), N-[(3,5-difluorophenyl)acetyl]-L-alanine (1e) (0.352 g, 1.45 mmol), and N,N-diisopropylethylamine (0.401 g, 3.10 mmol) in dry dichloromethane (7 mL) was added EDAC-HCl (0.336 g, 1.75 mmol). The mixture was stirred at ambient temperature under nitrogen for 4 h then loaded directly onto a silica gel flash column, eluting with 100 mL each of 9:1, 8:2, and 7:3 (v/v) dichloromethane/ethyl acetate to afford the title compound as an oil, which crystallized from 10:1 petroleum ether/ether as a 1:1 mixture with the 2R,3S diastereomer as a white solid (285 mg, 41%). ¹H NMR (300 MHz, d6-DMSO) δ0.97 (d, 1.5H, J=7 Hz), 1.04 (d, 1.5H, J=7 Hz), 1.98 (s, 1.5H), 2.05 (s, 1.5H), 3.40 (m, 2H), 4.29 (m, 1H), 4.71 (m, 1H), 5.55 (d, 0.5H, J=6.6 Hz), 5.59 (d, 0.5H, J=7.0 Hz), 6.81-7.29 9M, 6H), 7.46-7.67 (m, 4H), 8.25 (t, 1H, J=7.9 Hz), 10.50 (d, 1H, J=5.7 Hz). MS APCI, m/z=516 (M+1). LC/MS: 2.27 min.

The starting amine, (2,3-cis)-3-amino-2-(3-methyl-2-thienyl)-2,3-dihydro-1,5-benzothiazepin-4(5H)-one hydrobromide (94d) was prepared in the following manner:

a. Methyl (2Z)-2-{[(benzyloxy)carbonyl]amino}-3-(3-methyl-2-thienyl)acrylate (94a)

A stirred solution of N-(benzyloxycarbonyl)-α-phosphonoglycine trimethyl ester (5.01 g, 15.1 mmol) and 3-methylthiophene-2-carbaldehyde (7.5:1 mixture with 4-methylthiophene-2-carbaldehyde, 2.48 g, 19.6 mmol) in dry dichloromethane (100 mL), was cooled to 0° C. and treated dropwise with DBU (2.76 g, 18.1 mmol). The mixture was warmed to ambient temperature and stirred overnight. The solution was concentrated, taken up in ethyl acetate (150 mL) and washed with 5% hydrochloric acid (2×75 mL). The organic extract was washed with saturated aqueous sodium bicarbonate (2×75 mL), water (75 mL), dried (magnesium sulfate), filtered and evaporated. The residue was purified by flash chromatography (20-40% ethyl acetate/hexanes gradient) to afford the title compound (4.07 g, 81%) as an orange oil. The product is a mixture of 3- and 4-methylthiophene isomers (6.8:1). ¹H NMR major isomer: (300 MHz, d₆-DMSO) δ2.33 (s, 3H), 3.72, (s, 3H), 5.13 (bs, 2H), 7.01 (d, 1H, J=5.3 Hz), 7.18-7.52 (m, 5H), 7.60-7.85 (m, 2H), 8.83 (s, 1H). MS APCI, m/z=354(M+Na). LC/MS: 2.43 min.

b. Methyl β-[(2-aminophenyl)thio]-N-[(benzyloxy)carbonyl]-3-(3-methyl-2-thienyl)alaninate (94b)

To a degassed solution of methyl (2Z)-2-{[(benzyloxy)carbonyl]amino})-3-(3-methyl-2-thienyl)acrylate (94a) (4.07 g, 12.3 mmol) and triethylamine (0.871 g, 8.61 mmol) in anhydrous methanol (50 mL) was added 2-aminothiophenol (6.14 g, 49.1 mmol) under N². The reaction mixture was heated at reflux overnight then cooled to ambient temperature and evaporated under reduced pressure. The mixture was partitioned between 20% aqueous potassium carbonate (100 mL) and ethyl acetate (100 mL). The organic phase was separated and washed with 20% aqueous potassium carbonate, dried, filtered and evaporated to yield 5.62 g of orange oil. The crude product was passed through a flash column eluting with a 20-40% ethyl acetate/hexanes solvent gradient affording the title compound as a mixture with the 4-methylthiophene isomer (4.31 g, 77%). The mixture was used directly in the next step without further purification. MS APCI, m/z=457 (M+1). LC/MS: 2.74 min.

c. Benzyl [(2,3-cis)-2-(3-methyl-2-thienyl)-4-oxo-2,3,4,5-tetrahydro-1,5-benzothiazepin-3-yl]carbamate (94c)

To a suspension of methyl β-[(2-aminophenyl)thio]-N-[(benzyloxy)carbonyl]-3-(3-methyl-2-thienyl)alaninate (94b) (4.31 g, 9.44 mmol) in o-xylene (95 mL) was added a catalytic amount of p-toluenesulfonic acid hydrate (0.107 g, 0.565 mmol). The mixture was heated at 170° C. for 2 h then cooled to ambient temperature. The mixture was filtered, the filtrate was concentrated under reduced pressure and partitioned between ethyl acetate (150 mL) and 5% hydrochloric acid (100 mL). The organic phase was separated, washed with aqueous saturated sodium bicarbonate, brine, dried (magnesium sulfate), filtered and concentrated leaving an orange oil. Purification by flash chromatography on silica gel eluting with a 20-80% ethyl acetate/hexane solvent gradient afforded the title compound in a 9:1 mixture with the 4-methylthiophene isomer (1.42 g, 35%) as a pale yellow solid. ¹H NMR major isomer (300 MHz, d₆-DMSO) δ2.01 (s, 3H), 4.56 (t, 1H, J=7.5 Hz), 4.98 (s, 2H), 5.58 (d, 1H, J=7.0 Hz), 6.22 (d, 1H, J=7.9 Hz), 6.86 (d, 1H, J=5.3 Hz), 7.19-7.52 (m, 9H), 7.66 (d, 1H, J=7.5 Hz), 10.49 (s, 1H). MS APCI, m/z=425 (M+1). LC/MS: 2.52 min.

d. (2,3-cis)-3-Amino-2-(3-methyl-2-thienyl)-2,3-dihydro-1,5-benzothiazepin-4(5H)-one hydrobromide (94d)

To benzyl [(2,3-cis)-2-(3-methyl-2-thienyl)-4-oxo-2,3,4,5-tetrahydro-1,5-benzothiazepin-3-yl]carbamate (94c) (1.37 g, 3.22 mmol) was added 4.1M HBr in acetic acid (10 mL). The stirred suspension became a homogeneous solution over 20 min. The reaction stirred at ambient temperature for an additional 2 h and was diluted with ether to afford the hydrobromide salt of the title compound in a 9.3:1 mixture with the 4-methylthiophene isomer (0.919 g, 77%) as a white solid. ¹H NMR major product (300 MHz, d₆-DMSO) δ2.23 (s, 3H), 4.24 (d, 1H, J=6.6 Hz), 5.69 (d, 1H, J=6.6 Hz), 6.91 (d, 1H, J=4.8 Hz), 7.23-7.33 (m, 2H), 7.54 (t, 1H), 7.61 (d, 1H, J=4.8 Hz), 7.67 (d, 1H, J=7.5 Hz), 8.09 (bs, 2H), 10.87 (s, 1H). MS APCI, m/z=291 (M+1). LC/MS: 1.55 min.

131

Example 95

N²-[(3,5-Difluorophenyl)acetyl]-N¹-[(2S,3R)-2-(4-methyl-2-thienyl)-4-oxo-2,3,4,5-tetrahydro-1,5-benzothiazepin-3-yl]-L-alaninamide (95)

The title compound was synthesized according to the method of Example 94, employing (2,3-cis)-3-amino-2-(4-methyl-2-thienyl)-2,3-dihydro-1,5-benzothiazepin-4(5H)-one hydrobromide (95e) (97.0 mg, 0.261 mmol), HOBt (51.0 mg, 0.377 mmol), N-[(3,5-difluorophenyl)acetyl]-L-alanine 1e (69.0 mg, 0.284 mmol), diisopropylethylamine (77.8 mg, 0.602 mmol), and EDAC-HCl (64.5 mg, 0.336 mmol) in dry dichloromethane (2 mL). Purification by flash chromatography on silica gel eluting with a 10-50% ethyl acetate/dichloromethane solvent gradient afforded the title compound as a 1:1 mixture with the 2R,3S diastereomer (87 mg, 64%) as a pale yellow solid. ¹H NMR (300 MHz, d₆-DMSO) δ1.05 (d, 1.5H, J=7 Hz), 1.09 (d, 1.5H, J=7 Hz), 2.15 (s, 1.5H), 2.17 (s, 1.5H), 3.42 (m, 2H), 4.29 (m, 1H), 4.64 (m, 1H), 5.34 (m, 1H), 6.89-7.29 (m, 7H), 7.47-7.75 (m, 3H), 8.27 (d, 0.5H, J=7.5 Hz), 8.37 (d, 0.5H, J=7.5 Hz), 10.50 (s, 0.5H), 10.54 (s, 0.5H). MS APCI, m/z=516 (M+1). LC/MS: 2.35 min.

The starting amine, (2,3-cis)-3-amino-2-(4-methyl-2-thienyl)-2,3-dihydro-1,5-benzothiazepin-4(5B)-one hydrobromide (95e), was prepared in the following manner:

a. 4-Methylthiophene-2-carbaldehyde (95a)

The title compound was prepared as a 4:1 mixture of the desired isomer and 3-methylthiophene-2-carbaldehyde, according to the published procedure of Jean Sicé; *J. Org. Chem.* 19. 70 (1954).

b. Methyl (2Z)-2-{[(benzyloxy)carbonyl]amino}-3-(4-methyl-2-thienyl)acrylate (95b)

A stirred solution of N-(benzyloxycarbonyl)-α-phosphonoglycine trimethyl ester (5.01 g, 15.1 mmol) and 4-methylthiophene-2-carbaldehyde (95a) (2.50 g, 19.8 mmol) in dry dichloromethane (100 mL) was cooled to 0° C. and treated dropwise with DBU (2.76 g, 18.1 mmol). The mixture was warmed to ambient temperature and stirred overnight. The solution was concentrated, taken up in ethyl acetate (150 mL) and washed with 5% hydrochloric acid (2×100 mL). The organic extract was washed with saturated aqueous sodium bicarbonate (2×150 mL), water (200 mL), dried (magnesium sulfate), filtered and evaporated. The residue was purified by crystallization from 4:1 (v/v) ethyl acetate/hexanes to afford the title compound (3.38 g, 67%) as the sole product. ¹H NMR (300 MHz, d₆-DMSO) δ2.20 (s, 3H), 3.70, (s, 3H), 5.12 (s, 2H), 7.20-7.52 (m, 7H), 7.69 (s, 1H), 8.82 (s, 1H). MS APCI, m/z=354 (M+Na). LC/MS: 2.43 min.

c. Methyl β-[(2-aminophenyl)thio]-N-[(benzyloxy)carbonyl]-3-(4-methyl-2-thienyl)alaninate (95c)

The title compound was prepared according to the method of Example 94b, employing methyl (2Z)-2-{[(benzyloxy)carbonyl]amino}-3-(4-methyl-2-thienyl)acrylate (95b) (3.38 g, 10.2 mmol), triethylamine (0.722 g, 7.14 mmol), and 2-aminothiophenol (6.43 g, 51.4 mmol) in anhydrous methanol (41 mL). The crude product was crystallized from 4:1 (v/v) petroleum ether/ether affording the title compound (2.74 g, 59%) as a pale yellow solid. ¹H NMR (300 MHz, d₆-DMSO) δ2.04 (s, 3H), 3.38 (s, 3H), 4.56 (t, 1H, J=8.3 Hz), 4.85 (d, 1H, J=7.9 Hz), 5.09 (m, 2H), 5.42 (bs, 2H), 6.36 (t, 1H, J=7.5 Hz), 6.56 (s, 1H), 6.65 (d, 1H, J=7.9 Hz), 6.94-7.02 (m, 3H), 7.30-7.42 (m, 5H), 8.21 (d, 1H, J=9.3 Hz). MS APCI, m/z=457 (M+1). LC/MS: 2.64 min.

d. Benzyl [(2,3-cis)-2-(4-methyl-2-thienyl)-4oxo-2,3,4,5-tetrahydro-1,5-benzothiazepin-3-yl]carbamate (95d)

The title compound was prepared according to the method of Example 94c, employing methyl β-[(2-aminophenyl)thio]-N-[(benzyloxy)carbonyl]-3-(4-methyl-2-thienyl)alaninate (95c) (2.71 g, 5.93 mmol), p-toluenesulfonic acid hydrate (0.0882 g, 0.464 mmol), and o-xylene (60 mL). The reaction was heated at reflux overnight. Upon treatment of the crude product with ethanol/ether/petroleum ether, a solid impurity precipitated and was filtered off. The filtrate was concentrated and crystallized from ethyl acetate/hexane affording a yellow solid (189 mg, 7%). ¹H NMR (300 MHz, d₆-DMSO) δ2.17 (s, 3H), 4.49 (dd, 1H, J=7.5, J3 6.6 Mz), 4.99 (m, 2H), 5.42 (d, 1H, J=6.6 Hz), 6.23 (m, 1H), 6.92 (s, 1H), 7.12 (s, 1H), 7.20-7.52 (m, 8H), 7.65 (d, 1H, J=7.5 Hz), 10.48 (s, 1H). MS APCI, m/z=447 (M+Na). LC/MS: 2.66 min.

e. (2,3cis)-3-Amino-2-4methyl-2-thienyl)-2,3-dihydro-1,5benzothiazepin-4(5 H)-one hydrobromide (95e)

The title compound was prepared according to the method of Example 94d, employing benzyl [(2,3-cis)-2-(4-methyl-2-thienyl)-4-oxo-2,3,4,5-tetrahydro-1,5-benzothiazepin-3-yl]carbamate (95d) (189 mg, 0.444 mmol) and 4.1M HBr in acetic acid (4.0 mL). The title compound was isolated as the hydrobromide salt (97 mg, 59%). ¹H NMR (300 MHz, d₆-DMSO) δ2.22 (s, 3H), 4.25 (d, 1H), 5.50 (d, 1H), 7.09 (s, 1H), 7.20-7.70 (m, 5H). 8.15 (bs, 2H), 10.85 (s, 1H). MS APCI, m/z=291 (M+1). LC/MS: 1.43 min.

Example 96

Methyl 5-[(2S3R)-3-(N-[(3,5difluorophenyl)acetyl]-L-alanylamino)-4-oxo-2,3,4,5tetrahydro-1,5benzothiazepin-2-yl]thiophene-3-carboxylate (96)

The title compound was synthesized according to the method of Example 94, employing methyl 5-[(2,3-cis)-3-amino-4-oxo-2,3,4,5-tetrahydro-1,5-benzothiazepin-2-yl]thiophene-3-carboxylate hydrobromide (96e) (200 mg, 0.482 mmol), HOBt (93.4 mg, 0.691 mmol), N-[(3,5-difluorophenyl)acetyl]-L-alanine 1e (128 mg, 0.526 mmol), diisopropylethylamine (143 mg, 1.11 mmol), and EDAC-HCl (127 mg, 0.665 mmol) in dry dichloromethane (5 mL). Purification by flash chromatography on silica gel (20-80% ethyl acetate/hexane solvent gradient) afforded the title compound in a 1:1 mixture with the 2R,3S diastereomer (151 mg, 56%) as a white solid. ¹H NMR (300 MHz, d₆-DMSO) δ1.05 (d, 1.5H, J=7 Hz), 1.09 (d, 1.5H, J=7.1 Hz), 3.35-3.51 (m, 2H), 3.78 (s, 1.5H), 3.79 (s, 1.5H), 4.20-4.36 (m, 1H), 4.66-4.74 (m, 1H), 5.43 (m, 1H), 6.90-7.31 (m, 5H), 7.43-7.69 (m, 4H), 7.84 (d, 0.5H, J=7 Hz), 8.22 (d, 0.5H, J=7 Hz), 8.32 (s, 111), 10.56 (s, 0.5H), 10.57 (s, 0.5H). MS APCI, m/z=516 (M+1). LC/MS: 2.35 min.

The starting amine, methyl 5-[(2S,3R)-3-amino-4-oxo-2,3,4,5-tetrahydro-1,5-benzothiazepin-2-yl]thiophene-3-carboxylate hydrobromide (96e), was prepared in the following manner:

a. Methyl (2Z)-2-{[(benzyloxy)carbonyl]amino}-3-(4-bromo-2-thienyl)acrylate (96a)

The title compound was prepared according to the method of Example 94a, employing N-(benzyloxycarbonyl)-α-phosphonoglycine trimethyl ester (10.0 g, 30.2 mmol), 4-bromothiophene-2-carbaldehyde (7.52 g, 39.4 mmol), and DBU (5.34 g, 35.1 mmol) in dry dichloromethane (200 mL). Recrystallization from 4:1 (v/v) hexane/ethyl acetate afforded the title compound (8.13 g, 20.5 mmol, 68%) as a white solid. $^1$H NMR (300 MHz, $d_6$-DMSO) δ3.71 (s, 3H), 5.12 (bs, 2H), 7.10-7.51 (bm, 5H), 7.59 (s, 1H), 7.71 (s, 1H), 7.87 (s, 1H), 8.98 (bs, 1H). MS APCI, m/z=354, 352. LC/MS: 2.53 min.

b. Methyl β-[(2-aminophenyl)thio]-N-[(benzyloxy)carbonyl]-3-(4-bromo-2-thienyl)alaninate (96b)

The title compound was prepared according to the method of Example 94b, employing methyl (2Z)-2-{[(benzyloxy)carbonyl]amino}-3-(4-bromo-2-thienyl)acrylate (96a) (8.13 g, 20.5 mmol), triethylamine (1.43 g, 14.1 mmol), and 2-aminothiophenol (14.0 g, 112 mmol) in anhydrous methanol (80 mL). Purification by flash chromatography on silica gel eluting with 4:1 (v/v) hexane/ethyl acetate yielded a solid, which was recrystallized from 6:1 (v/v) hexane/ethyl acetate to afford the title compound (4.90 g, 46%) as a white solid. $^1$H NMR (300 MHz, $d_6$-DMSO) δ3.44 (s, 3H), 4.63 (t, 1H, J=8.1 Hz), 4.92 (d, 1H, J=7.4 Hz), 5.09 (m, 21H), 5.46 (bs, 2H), 6.38 (t, 1H, J=7.5 Hz), 6.66 (d, 1H, J=8.3 Hz), 6.80 (s, 1H), 6.99-7.03 (m, 2H), 7.32-7.39 (m, 5H), 7.52 (s, 1H), 8.28 (d, 1H, J=9.2 Hz). MS APCI, m/z=521, 523. LC/MS: 2.71 min.

c. Benzyl [(2,3-cis-)-2-(4-bromo-2-thienyl)-4-oxo-2,3,4,5-tetrahydro-1,5-benzothiazepin-3-yl]carbamate (96c)

The title compound was prepared according to the method of Example 94c, employing methyl β-[(2-aminophenyl)thio]-N-[(benzyloxy)carbonyl]-3-(4-bromo-2-thienyl)alaninate (96b) (4.79 g, 9.19 mmol), p-toluenesulfonic acid hydrate (0.101 g, 0.532 mmol), and o-xylene (90 mL). The reaction was heated at 170° C. for 2 h, then at ambient temperature for 2 days. The resulting precipitate was filtered, washed with o-xylene and ether affording the title compound (3.99 g, 89%) as a white solid. $^1$H NMR (300 MHz, $d_6$-DMSO) δ4.52-4.56 (m, 1H), 4.99 (s, 2H), 5.46 (d, 1H, J=6.6 Hz), 6.76 (d, 1H, J=7.4 Hz), 7.09 (s, 1H), 7.20-7.36 (m, 7H), 7.51 (t, 1H, J=7.6 Hz), 7.66 (d, 1H, J=7.5 Hz), 7.69 (s, 1H), 10.52 (s, 1H). MS APCI, m/z=489, 491. LC/MS: 2.76 min.

d. Methyl 5-((2,3-cis)-3-{[(benzyloxy)carbonyl]amino}-4-oxo-2,3,4,5-tetrahydro-1,5-benzothiazepin-2-yl)thiophene-3-carboxylate (96d)

To a degassed solution of benzyl [(2,3-cis)-2-(4-bromo-2-thienyl)-4-oxo-2,3,4,5-tetrahydro-1,5-benzothiazepin-3-yl]carbamate (96c) (0.502 g, 1.02 mmol) and triethylamine (0.145 g, 1.43 mmol) in anhydrous 1:1 (v/v) methanol/DMSO (19 mL) was added 1,3-bis(diphenylphosphino)propane (42.4 mg, 0.103 mmol) and palladium (II) acetate (21.8 mg, 0.0972 mmol). The reaction mixture was purged with CO and heated at 75° C. under a CO atmosphere for 2d. After cooling methanol (20 mL) was added, and the reaction mixture was filtered through diatomaceous earth. The filtrate was partitioned between water (100 mL) and ethyl acetate (100 mL). The organic phase was washed with water(4×200 mL), dried, filtered and evaporated to a reddish-brown oil. Purification by flash chromatography on silica gel (20-60% ethyl acetate/hexane solvent gradient) afforded the title compound (201 mg, 42%) as a white solid. $^1$H NMR (300 MHz, $d_6$-DMSO) δ3.80 (s, 3H), 4.53-4.57 (m, 1H), 4.99 (s, 2H), 5.50 (d, 1H, J=6.6 Hz), 6.66 (d, 1H, J=7.0 Hz), 7.09-7.31 (m, 7H), 7.49-7.54 (m, 2H), 7.66 (d, 1H, J=7.4 Hz), 8.33 (s, 1H), 10.52 (s, 1H). MS APCI, m/z=469 (M+1). LC/MS: 2.58 min.

e. Methyl 5-[(2,3-cis)-3-amino-4oxo-2,3,4,5-tetrahydro-1,5-benzothiazepin-2-yl]thiophene-3-carboxylate hydrobromide (96e)

The title compound was prepared according to the method of Example 94d, employing methyl 5-((2,3-cis)-3-{[(benzyloxy)carbonyl]amino}-4oxo-2,3,4,5-tetrahydro-1,5-benzothiazepin-2-yl)thiophene-3-carboxylate (96d) (245 mg, 0.523 mmol) and 4.1M HBr in acetic acid (5.0 mL). The title compound was isolated as the hydrobromide salt (200 mg, 0.481 mmol, 92%). $^1$H NMR (300 MHz, $d_6$-DMSO) δ3.82 (s, 3H), 4.32 (d, 1H, J=6.1 Hz), 5.63 (d, 1H, J=6.2 Hz), 7.25-7.36 (m, 2H), 7.53-7.73 (m, 3H), 8.21 (bs, 2H), 8.44 (s, 1H), 10.92 (s, 1H). MS APCI, m/z=291 (M+1). LC/MS: 1.43 min.

Example 97

$N^1$-[(2R,3R)-4Oxo-2-phenyl-2,3,4,5-tetrahydro-1,5-benzothiazepin-3-yl]-$N^2$-(phenylacetyl)-L-alaninamide (97)

To a solution of $N^1$-[(2,3-cis)-4-oxo-2-phenyl-2,3,4,5-tetrahydro-1,5-benzothiazepin-3-yl]-L-alaninamide 97b (162 mg), HOBt (74 mg), phenylacetic acid (75 mg) and EDAC-HCl (105 mg) in dichloromethane (10 mL) was added triethylamine (202 mg). The mixture was stirred at RT under nitrogen for 16 h and purified by flash chromatography (1:1 hexane:ethyl acetate) to afford the title compound as a 1:1 mixture with the 2S,3R diastereomer, white solid (117 mg), m.p. 114-124° C. $^1$H NMR (300 MHz, d6-DMSO) δ 0.913 (d, 1.5H, J=7 Hz), 1.01 (d, 1.5H, J=7 Hz), 4.12 (m, 1H), 4.66 (m, 1H), 5.13 (m, 1H), 7.15-7.52 (m, 14H), 8.08 (d, 0.5H, J=7 Hz), 8.22 (d, 0.5H, J=7 Hz), 10.53 (br, 1H). MS APCI, m/z=460 (M+1) LC/MS: 2.17 mm.

The starting amine $N^1$-[(2S,3S)-4-oxo-2-phenyl-2,3,4,5-tetrahydro-1,5-benzothiazepin-3-yl]-L-alaninamide(97b) was prepared in the following manner:

a. $N^2$-[tert-Butoxycarbonyl]-$N^1$-[(2,3-cis)-4-oxo-2-phenyl-2,3,4,5-tetrahydro-1,5-benzothiazepin-3-yl]-L-alaninamide (97a)

To a solution of (2,3-cis)-3-amino-2-phenyl-2,3-dihydro-1,5-benzothiazepin-4(5H)-one hydrobromide (9d (303 mg), HOBt (216 mg), N-(tert-butoxycarbonyl)-L-alanine (284 mg), 4-dimethylaminopyridine (2 mg) and EDAC-HCl (288 mg) in dichloromethane (10 mL) was added triethylamine (404 mg). The mixture was stirred at RT under nitrogen for 16 h and purified by flash chromatography (1:1 hexane:ethyl acetate) to afford the title compound (440 mg). $^1$H NMR (300 MHz, d6-DMSO) δ0.88 (d, 1.5H, J=7 Hz), 0.95 (d, 1.5H, J=7 Hz), 1.30 (two peaks, 9H), 3.73 (t, 0.5H J=7 Hz), 3.90 (t, 0.5H, J=7 Hz), 4.66 (m, 1H), 5.14(t, 1H, J=6 Hz), 6.61-7.53 (m, 10H), 7.7 (d, 1H, J=6 Hz),10.55 (d, 1H, J=5 Hz). MS APCI, m/z=324 (M−99). LC/MS: 2.31 min.

b. $N^1$-[(2,3-cis)-4-Oxo-2-phenyl-2,3,4,5-tetrahydro-1,5-benzothiazepin-3-yl]-L-alaninamide (97b)

A solution of $N^2$-[tert-butoxycarbonyl]-$N^1$-[(2,3-cis)-4-oxo-2-phenyl-2,3,4,5-tetrahydro-1,5-benzothiazepin-3-yl]-L-alaninamide (97a) (440 mg) in trifluoroacetic acid (10 mL) was stirred for 10 min. and concentrated under reduced pressure. The resulting material was diluted with 15% solution of potassium carbonate (20 mL) and extracted twice with dichloromethane (150 mL). The dichloromethane layer was dried over anhydrous potassium carbonate and concentrated under reduce pressure to afford the desired material (325 mg). $^1$H NMR (300 MHz, d6-DMSO) δ0.90 (d, 1.5H, J=7 Hz), 0.98 (d, 1.5H, J=7 Hz), 3.11 (h, 1H J=7 Hz), 4.66 (m, 1H), 5.15(t, 1H, J=6 Hz), 7.13-7.76 (m, 11H),10.5 (br., 1H). MS APCI, m/z=342 (M+1). LC/MS: 1.59 min.

Example 98

$N^1$-[(2R,3R)-4-Oxo-2-Phenyl-2,3,4,5-tetrahydro-1,5-benzothiazepin-3-yl]-$N^2$-(2-phenylethyl)-L-alaninamide (98)

A solution of $N^1$-[(2,3cis)-4-oxo-2-phenyl-2,3,4,5-tetrahydro-1,5-benzothiazepin-3-yl]-L-alaninamide (97b) (618 mg) in 20 mL of methanol was treated with phenylacetaldehyde (220 mg), acetic acid (0.6 mL) followed by sodium cyanoborohydride (200 mg) and the resulting reaction mixture was stirred at RT for 16 h. At the end of this period, the reaction mixture was treated with 2M HCl (1 mL), stirred for 30 min., concentrated under reduced pressure and diluted with dichloromethane. Upon washing with 20% sodium carbonate solution the dichloromethane layer was dried over anhydrous potassium carbonated and concentrated under reduce pressure to afford the crude product that was purified by column chromatography on silica gel. Elution with 2:1 dichloromethane:ethyl acetate afforded purified product which was dissolved in methanol (2 mL) and treated with HCl in ether. Upon diluting with ether (150 mL) and stirring for 1 h the solid was collected by filtration to afford the title compound hydrochloride as a 1:1 mixture with the 2S,3S diastereomer (435 mg), white solid, m.p. 184-195° C. $^1$H NMR (300 MHz, d6-DMSO) δ 0.99 (d, 1.5H, J=7 Hz), 1.25 (d, 1.5H, J=7 Hz), 2.9 (m, 4H), 4.66 (m, 1H), 3.91 (m, 1H), 4.77 (m, 1H), 5.20 (m, 1H), 7.04-7.54 (m, 12H), 7.70 (m, 1H), 8.42 (m, 1H), 8.86 (br, 1H), 9.50 (br., 1H), 10.60(m, 1H). MS APCI, m/z=446(M+1). LC/MS: 2.17 min.

Example 99

$N^2$-[(3,5-Difluorophenyl)acetyl]-$N^1$-[(2S,31)-4oxo-2-(2-thienyl)-2,3,4,5-tetrahydro-1,5-benzothiazepin-3-yl]-L-alaninamide. (99)

A method similar to the one described for 97 was used except that (2, 3-cis)-3-amino-2-(2-thienyl)-2,3-dihydro-1,5-benzothiazepin-4(5H)-one hydrobromide (99c) (52 mg) was used as the amine component and N-[(3,5-difluorophenyl)acetyl]-L-alanine (1e) was used as the acid component to afford the title compound as a 1:1 mixture with the (2R,3R) diastereomer, white solid (79 mg), m.p. 117-119° C. $^1$H NMR (300 MHz, d6-DMSO) δ 1.087 (m, 3H), 3.42 (m, 2H), 4.24 (m, 1H), 4.66 (m, 1H), 5.44(d, 1H, J=7 Hz), 6.89-7.22 (m, 8H), 7.45 (m, 2H), 7.65(d,1H, J=8 Hz), 8.22 (two d, 1H, J=7 Hz), 10.43(m,1H). MS APCI, m/z=524 (M+Na). LC/MS: 2.20 min.

The starting amine (2R, 3S)-3-amino-2-(2-thienyl)-2,3-dihydro-1,5-benzothiazepin-4(5H)-one hydrobromide9 was prepared in the following manner:

a. Methyl (2Z)-2-{[(benzyloxy)carbonyl]amino}-3-(2-thienyl)acrylate (99a)

In a dry reaction vessel 2-thiophenecarboxaldehyde (336 mg) was treated with a solution of N-(benzyloxycarbonyl)-α-phosphonoglycine trimethylester (762 mg) in dichloromethane (2 mL) followed by a solution of DBU (304 mg) in dichloromethane (2 mL). The reaction mixture was stirred for 2 h and the desired product was purified by column chromatography over silica gel. Elution with 20:1 dichloromethane:ethyl acetate afforded the desired product (530 mg): $^1$H NMR (300 MHz, CDCl$_3$) δ 3.795 (s, 3H), 5.19 (s, 2H), 5.99 (br., 1H), 7.07 (m, 1H), 7.34 (m, 7H), 7.49 (d, 1H, J=5 Hz), 7.77 (s, 1H). LC/MS: 2.32 min.

b. Benzyl [(2,3-cis)-4-oxo-2-(2-thienyl)-2,3,4,5-tetrahydro-1,5-benzothiazepin-3-yl]carbamate (99b)

A solution of triethylamine (101 mg) and 2-aminothiophenol (375 mg) in MeOH (2 mL) was added to a solution of methyl (2Z)-2-{[(benzyloxy)carbonyl]amino}-3-(2-thienyl)acrylate (99a) in MeOH (5 mL). The reaction mixture was heated to 60° C. for 16 h and the solid product was filtered and dissolved in xylene (10 mL). Upon treating pTSA (10 mg) the reaction mixture was heated to reflux for 2 h. At the end of this period the reaction mixture was cooled to RT and the solid was filtered, washed with hexane to afford the title compound as a white solid (142 mg), m.p.184-195° C. $^1$H NMR (300 MHz, d6-DMSO) δ 4.518 (t, 1H, J=7 Hz), 4.99 (s, 2H), 5.52 (d,1H, J=7 Hz), 6.89-7.29 (m, 9H), 7.53 (m, 2H), 6.65 (d,1H, J=8 Hz), 10.49 (s, 1H). LC/MS: 2.47 min.

c. (2,3-cis)-3-Amino-2-(2-thienyl)-2,3-dihydro-1,5-benzothiazepin-4(5H)-one hydrobromide (99c)

A solution of benzyl [(2R,3S)-4-oxo-2-(2-thienyl)-2,3,4,5-tetrahydro-1,5-benzothiazepin-3-yl]carbamate (9b) (142 mg) in 30% hydrobromic acid in acetic acid (1 mL) was stirred for 1 h and diluted with ether (35 mL). The precipitate was collected, washed with ether, suspended in 20% sodium carbonate solution and extracted with dichloromethane and ethyl acetate. Drying the organic layers with anhydrous potassium carbonate and concentration under reduced pressure afforded the title compound (52 mg). This material was used without further characterization.

Example 100

$N^2$-[(3,5-Difluorophenyl)acetyl]-$N^1$-[(2R,3R)-4-oxo-2-(3-thienyl)-2,3,4,5-tetrahydro-1,5-benzothiazepin-3-yl]-L-alaninamide. (100)

A method similar to the one described for 97 was used except that (2,3-cis)-3-amino-2-(3-thienyl)-2,3-dihydro-1,5-benzothiazepin-4(5H)-one hydrobromide (100c) (147 mg) was used as the amine component and N-[(3,5-difluorophenyl)acetyl]-L-alanine (1e) was used as the acid component to afford the title compound as a 1:1 mixture with the 2S,3S diastereomer, white solid (212 mg), m.p. 117-122° C. $^1$H NMR (300 MHz, d6-DMSO) δ 1.03 (m, 3H), 3.40 (m, 2H), 4.20 (m, 1H), 4.61 (m, 1H), 5.26 (m, 1H), 6:90-7.36 (m, 7H), 7.52 (m, 4H), 7.65 (d,1H, J=9 Hz), 8.28 (two d, 1H, J=7 Hz), 10.51 (d, 1H, J=12 Hz). MS APCI, m/z=501 (M+1). LC/MS: 2.20 min.

The starting amine (2,3-cis)-3-amino-2-(3-thienyl)-2,3-dihydro-1,5-benzothiazepin-4(5H)-one hydrobromide (100c) was prepared in the following manner:

a. Methyl (2Z)-2-{[(benzyloxy)carbonyl]amino}-3-(3-thienyl)acrylate (100a)

A method similar to that used for the preparation of (99a) was used except that 3-thiophenecarboxaldehyde (762 mg) was used as the aldehyde component to afforded the desired product (549 mg). $^1$H NMR (300 MHz, CDCl$_3$) δ 3.795 (s, 3H), 5.19 (s, 2H), 5.99 (br., 1H), 7.07 (m, 1H), 7.34(m, 7H), 7.49(d, 1H, J=5 Hz), 7.77(s, 1H). LC/MS: 2.32 min.

b. Benzyl [(2,3-cis)-4-oxo-2-(3-thienyl)-2,3,4,5-tetrahydro-1,5-benzothiazepin-3-yl]carbamate (100b)

A method similar to that used for the preparation of (99b) was used except that methyl (2Z)-2-{[(benzyloxy)carbonyl]amino}-3-(3-thienyl)acrylate (100a) (549 mg) was used as starting material to afford the title compound as a white solid. $^1$H NMR (300 MHz, d6-DMSO) δ 4.5 (t, 1H, J=7 Hz), 4.96 (s, 2H), 5.33 (d, 1H, J=7 Hz), 6.10 (d, 1H, J=7 Hz), 7.14-7.30 (m, 8H), 7.50 (m, 3H), 6.65 (d,1H, J=8 Hz), 10.47 (s, 1H). LC/MS: 2.56 min.

c. (2,3-cis)-3-Amino-2-(3-thienyl)-2,3-dihydro-1.5-benzothiazepin-4(56H)-one hydrobromide (100c)

A method similar to that used for the preparation of (99c) was used except that benzyl [(2,3-cis)-4oxo-2-(3-thienyl)-2,3,4,5-tetrahydro-1,5-benzothiazepin-3-yl]carbamate (100b) was used as starting material to afford the title compound (147 mg). This material was used without further characterization.

Example 101

N$^2$-[(3,5-Difluorophenyl)acetyl]-N$^1$-[(2S,3R)-2-(2-furyl)-4-oxo-2,3,4,5-tetrahydro-1,5-benzothiazepin-3-yl]-L-alaninamide (101)

A method similar to the one described for (97) was used except that (2,3-cis)-3-amino-2-(2-furyl)-2,3-dihydro-1,5-benzothiazepin-4(5H)-one (101c) (56 mg) was used as the amine component and N-[(3,5-difluorophenyl)acetyl]-L-alanine (1e) was used as the acid component to afford the title compound as a 1:1 mixture with the 2R,3S diastereomer, white solid (44 mg), m.p.125-130° C. $^1$H NMR (300 MHz, d6-DMSO) δ 1.01 (m, 3H), 3.45 (m, 2H), 4.30 (m, 1H), 4.70 (m, 1H), 5.30 (m, 1H), 6.5 (m, 2H), 7.0 (m, 3H), 7.5 (m, 2H), 7.75 (m, 3H), 8.25 (two d, 1H, J=7 Hz),10.45 (d, 1H, J=12 Hz). MS APCI, m/z=508 (M+Na). LC/MS: 2.20 min.

The starting amine (2,3-cis)-3-amino-2-(2-furyl)-2,3-dihydro-1,5-benzothiazepin-4(5H)-one hydrobromide (101c) was prepared in the following manner:

a. Methyl (2Z)-2-{[(benzyloxy)carbonyl]amino}-3-(2-furyl)acrylate (101a)

A method similar to that used for the preparation of (99a) was used except that 2-furylcarboxaldehyde (288 mg) was used as the aldehyde component to afforded the desired product (530 mg). $^1$H NMR (300 MHz, CDCl$_3$) δ 3.788 (s, 3H), 5.17 (s, 2H), 6.29 (m, 1H), 6.46 (m, 1H), 6.73 (br., 1H), 6.94 (s, 1H), 7.37 (m, 6H). LC/MS: 2.27 min.

b. Benzyl [(2,3-cis)-4-oxo-2-(2-furyl)-2,3,4,5-tetrahydro-1,5-benzothiazepin-3-yl]carbamate 101b)

A method similar to that used for the preparation of (99b) was used except that methyl (2Z)-2-{[(benzyloxy)carbonyl]amino}-3-(2-furyl)acrylate 101a (530 mg) was used as starting material to afford the title compound as a white solid (94 mg). $^1$H NMR (300 MHz, d6-DMSO) δ 4.51 (t, 1H, J=7 Hz), 4.98 (s, 2H), 5.32 (d,1H, J=7 Hz), 6.52 (m, 2H), 6.90-7.66 (m, 11H), 10.43 (s, 1H). LC/MS: 2.31 min.

c. (2,3-cis)-3-Amino-2-(2-furyl)-2,3-dihydro-1,5-benzothiazepin-4(5H)-one hydrobromide (101c)

A method similar to that used for the preparation of (99c) was used except that benzyl [(2,3-cis)-4-oxo-2-(2-furyl)-2,3,4,5-tetrahydro-1,5-benzothiazepin-3-yl]carbamate (101b) was used as starting material to afford the title compound (56 mg). This material was used in the next step without further characterization.

Example 102

N$^2$-[(3,5-Difluorophenyl)acetyl]-N$^1$-[(2S,3R)-2-(3-furyl)-4-oxo-2,3,4,5-tetrahydro-5-benzothiazepin-3-yl]-L-alaninamide (102)

A method similar to the one described for 97 was used except that (2,3-cis)-3-amino-2-(3-furyl)-2,3-dihydro-1,5-benzothiazepin-4(5H)-one (102c) (80 mg) was used as the amine component and N-[(3,5-difluorophenyl)acetyl]-L-alanine (1e) was used as the acid component to afford the title compound as a 1:1 mixture with the 2R,3S diastereomer, white foam (144 mg), m.p.115-120° C. $^1$H NMR (300 MHz, d6-DMSO) δ 0.93 (m, 3H), 3.29 (m, 2H), 4.32 (m, 1H), 4.64 (m, 1H), 5.04 (m, 1H), 6.54 (m, 1H), 6.95 (m, 3H), 7.08 (m, 2H), 7.46 (m, 2H), 7.59 (m,3H), 8.29 (two d, 1H, J=7 Hz),10.42 (d,1H, J 13 Hz). MS APCI, m/z=508 (M+Na) LC/MS: 2.31 min.

The starting amine (2,3-cis)-3-amino-2-(3-furyl)-2,3-dihydro-1,5-benzothiazepin-4(5H)-one hydrobromide (102c) was prepared in the following manner:

a. Methyl (2Z)-2-{[(benzyloxy)carbonyl]amino}-3-(3-furyl)acrylate (102a)

A method similar to that used for the preparation of (99a) was used except that 3-furylcarboxaldehyde (288 mg) was used as the aldehyde component to afforded the desired product (531 mg). $^1$H NMR (300 MHz, CDCl$_3$) δ 3.79 (s, 3H), 5.16 (s, 2H), 6.12 (br., 1H), 6.57 (s, 1H), 7.36(m, 7H), 7.68(s, 1H). LC/MS: 2.24 min.

b. Benzyl [(2R,3S)-4-oxo-2-(3-furyl)-2,3,4,5-tetrahydro-1,5-benzothiazepin-3-yl]carbamate (102b)

A method similar to that used for the preparation of (99b) was used except that methyl (2Z)-2-{[(benzyloxy)carbonyl]amino}-3-(3-furyl)acrylate (102a) (530 mg) was used as starting material to afford the title compound as a white solid (235 mg). $^1$H NMR (300 MHz, d6-DMSO) δ 4.66 (t, 1H, J=4 Hz), 4.97 (s, 2H), 5.20(d, 1H, J=6 Hz), 6.38 (d, 2H, J=7 Hz), 6.5(s, 1H), 7.07-7.75 (m, 11H), 10.44 (s, 1H). LC/MS: 2.32 min.

c. (2,3-cis)-3-Amino-2-(3-furyl)-2,3-dihydro-1,5-benzothiazepin-4(5H)-one hydrobromide (102c)

A method similar to that used for the preparation of (99c) was used except that benzyl [(2R,3S)-4oxo-2-(3-furyl)-2,3,4,5-tetrahydro-1,5-benzothiazepin-3-yl]carbamate (102b) was used as starting material to afford the title compound (80 mg). This material was used without further characterization.

Example 103

N$^1$-[(2S,3R)-2-(5-Bromo-2-thienyl)-4-oxo-2,3,4,5-tetrahydro-1,5-benzothiazepin-3-yl]-N$^2$-[(3,5-difluorophenyl)acetyl]-L-alaninamide (103)

A method similar to the one described for (97) was used except that (2,3-cis)-3-amino-2-(5-bromo-2-thienyl)-2,3-dihydro-1,5-benzothiazepin-4(5H)-one (103c) (460 mg) was used as the amine component and N-[(3,5-difluorophenyl)acetyl]-L-alanine (1e) was used as the acid component to afford the title compound as a 1:1 mixture with the 2R,3S diastereomer (357 mg), white solid, m.p.139-140° C. $^1$H NMR (300 MHz, d6-DMSO) δ 1.09 (m, 3H), 3.45 (m, 2H), 4.30 (m, 1H), 4.66 (m, 1H), 5.36 (m, 1H), 6.87-7.25 (m, 6H), 7.42 (t, 1H, J=11 Hz), 7.64-7.83 (m, 2H), 8.31 (two d, 2H, J=7 Hz), 10.55 (d, 1H, J=8 Hz). MS APCI, m/z=582 (M+1). LC/MS: 2.41 min.

The starting amine (2,3-cis)-3-amino-2-(5-bromo-2-thienyl)-2,3-dihydro-1,5-benzothiazepin-4(5H)-one hydrobromide (103c) was prepared in the following manner:

a. Methyl (2Z)-2-{[(benzyloxy)carbonyl]amino}-3-(5-bromo-2-thienyl)acrylate (103a)

A method similar to that used for the preparation of (99a) was used except that the reaction product was passed through a Dowex ion exchange resin 50×2-200 and 5-bromo-2-thiphenecarboxaldehyde (955 mg) was used as the aldehyde component to afforded the desired product (1.80 g). $^1$H NMR (300 MHz, CDCl$_3$) δ 3.79 (s, 3H), 5.20 (s, 2H), 5.93 (br., 1H), 6.95 (m, 1H), 7.36 (m, 5H), 7.70 (s, 1H). LC/MS: 2.36 min.

b. Benzyl [(2,3-cis)-4-oxo-2-(5-bromo-2-thienyl)-2,3,4,5-tetrahydro-1,5-benzothiazepin-3-yl]carbamate (103b)

A method similar to that used for the preparation of (99b) was used except that methyl (2Z)-2-{[(benzyloxy)carbonyl]amino}-3-(5-bromo-2-thienyl)acrylate (103a) (1.8 g) was used as the starting material to afford the title compound (651 mg). $^1$H NMR (300 MHz, d6-DMSO) δ 4.93 (m, 1H), 4.98 (s, 2H), 5.11 (br., 1H), 5.46 (d, 1H, J=6 Hz), 6.55 (d, 1H, J=7 Hz), 7.11 (d, 1H, J=4 Hz), 7.13-7.74 (m, 10H), 10.51(s, 1H). LC/MS: 2.66 min.

c. (2,3-cis)-3-Amino-2-(5-bromo-2-thienyl)-2,3-dihydro-1,5-benzothiazepin-4(5H)-one hydrobromide (103c)

A method similar to that used for the preparation of (99c) was used except that benzyl [(2,3-cis)-4-oxo-2-(5-bromo-2-thienyl)-2,3,4,5-tetrahydro-1,5-benzothiazepin-3-yl]carbamate (103b) was used as the starting material to afford the title compound (460 mg). This material was used without further purification.

Example 104

N$^1$-[(2S,3R)-(4Bromo-2-thienyl)-4oxo-2,3,4,5-tetrahydro-1,5-benzothiazepin-3-yl]-N$^2$-[(3,5-difluorophenyl)acetyl]-L-alaninamide (104)

A method similar to the one described for (97) was used except that (2,3-cis)-3-amino-2-(4bromo-2-thienyl)-2,3-dihydro-1,5-benzothiazepin-4(5H)-one (104c) (320 mg) was used as the amine component and N-[(3,5-difluorophenyl)acetyl]-L-alanine (1e) was used as the acid component to afford the title compound in 1:1 mixture with the 2R,3S diastereomer (357 mg), white solid, m.p.145-155° C. $^1$H NMR (300 MHz, d6-DMSO) δ 1.09 (m, 3H), 3.42 (m, 2H), 4.31 (m, 1H), 4.69 (m, 1H), 5.38 (m, 1H), 6.90-7.30 (m, 6H), 7.50 (t, 1H, J=7.5 Hz), 7.657 (m, 2H), 7.88 (d, 1H, J=7.5 Hz), 8.31(two d, 2H, J=7 Hz), 10.55(d, 1H, J=5 Hz). MS APCI, m/z=582 (M+1) LC/MS: 2.37 min.

The starting amine (2,3-cis)-3-amino-2-(4-bromo-2-thienyl)-2,3-dihydro-1,5-benzothiazepin-4(5H)-one hydrobromide (104c) was prepared in the following manner:

a. Methyl (2Z)-2-{[(benzyloxy)carbonyl]amino}-3-(4-bromo-2-thienyl)acrylate (104a)

A method similar to that used for the preparation of (99a) was used except that the reaction product was passed through a Dowex ion exchange resin 50×2-200 and 4-bromo-2-thiphenecarboxaldehyde (955 mg) was used as the aldehyde component to afford the desired product (1.52 g). $^1$H NMR (300 MHz, CDCl$_3$) δ 3.79 (s, 3H), 5.24 (s, 2H), 5.99 (br., 1H), 7.20-7.37 (m, 7H), 7.67 (s, 1H). LC/MS: 2.37 min.

b. Benzyl [(2,3-cis)-oxo-2-(4-bromo-2-thienyl)-2,3,4,5-tetrahydro-1,5-benzothiazepin-3-yl]carbamate (104b)

A method similar to that used for the preparation of (99b) was used except that methyl (2Z)-2-{[(benzyloxy)carbonyl]amino}-3-(4-bromo-2-thienyl)acrylate (104a) (1.8 g) was used as starting material to afford the title compound (528 mg). $^1$H NMR (300 MHz, d6-DMSO) δ 4.51 (m, 1H), 4.98 (s, 2H), 5.47 (d, 1H, J=6 Hz), 6.74 (d, 1H, J=7 Hz), 7.09 (s, 1H), 7.32 (m, 7H), 7.51 (t,1H, J=5 Hz), 7.689 (m, 2H), 10.51 (s, 1H). LC/MS: 2.63 min.

c. (2,3-cis)-3-Amino-2-(4-bromo-2-thienyl)-2,3-dihydro-1,5-benzothiazepin-4(5H)-one hydrobromide 104c A method similar to that used for the preparation of (99c) was used except that benzyl [(2,3-cis)-4-oxo-2-(4-bromo-2- thienyl)-2,3,4,5-tetrahydro-1,5-benzothiazepin-3-yl]carbamate (104b) was used as starting material to afford the title compound (460 mg). This material was used without further purification.

Example 105

N-[(3,5-Difluorophenyl)acetyl]-N-[(2R,3R)-4-oxo-2-phenyl-2,3,4,5-tetrahydro-1,5-benzothiazepin-3-yl]-L-phenylalaninamide (105)

A method similar to the one described for (97) was used except that N-[(2,3-cis)-4-oxo-2-phenyl-2,3,4,5-tetrahydro-1,5-benzothiazepin-3-yl]-L-phenylalaninamide (105a) was used as the amine component and 3,5-difluorophenylacetic acid was used as the acid component to afford the title compound as a 1:1 mixture with the 2S,3S diastereomer (58 mg), white solid, m.p.115-120° C. $^1$H NMR (300 MHz, d6-DMSO) δ 4.45 (m, 1H), 4.75 (m, 1H), 5.10 (m, 1H), 6.70 (m, 2H), 6.95-7.90 (m, 16H), 8.25 (two d, 1H, J=8 Hz),10.5 (m 1H). MS APCI, m/z=572 (M+1). LC/MS: 2.68 min.

The starting amine N-[(2,3-cis)-4oxo-2-phenyl-2,3,4,5-tetrahydro-1,5-benzothiazepin-3-yl]-L-phenylalaninamide (105a) was prepared in the following manner:

a. N-[(2S,3S)-4-Oxo-2-phenyl-2,3,4,5-tetrahydro-1,5-benzothiazepin-3-yl]-L-phenylalaninamide (105a)

To a solution of (2S,3S)-3-amino-2-phenyl-2,3-dihydro-1,5-benzothiazepin-4(5H)-one hydrobromide (9d) (91 mg) in 10 mL of THF was added Fmoc-Phe-Opfp (185 mg) followed by DIEA (58 μL). The reaction mixture was stirred for 30 min and treated with DBU (0.1 mL) and stirred for 10 min. The material thus produced was used in the next step without purification or characterization.

Example 106

N$^2$-[(3,5-Difluorophenyl)acetyl]-N$^1$-[(2R,3R)-4-oxo-2-phenyl-2,3,4,5-tetrahydro-1,5-benzothiazepin-3-yl]glycinamide (106)

A method similar to the one described for (97) was used except that N-[(2,3-cis)-4-oxo-2-phenyl-2,3,4,5-tetrahydro-1,5-benzothiazepin-3-yl]glycinamide (106a) was used as the amine component and 3,5-difluorophenylacetic acid was used as the acid component to afford the title compound as a 1:1 mixture with the 2S,3S diastereomer (80 mg),white solid, m.p.125-130° C. $^1$H NMR (300 MHz, d6-DMSO) δ 4.76 (t, 1H, J=7 Hz), 5.12 (d, 1H, J=7 Hz), 6.91-7.49 (m, 12H), 7.67 (d, 1H, J 7 Hz), 8.25 (s, 1H), 10.49 (s, 1H). MS APCI, m/z=482(M+1). LC/MS: 2.27 min.

The starting amine N-[(2,3-cis)-4-oxo-2-phenyl-2,3,4,5-tetrahydro-1,5-benzothiazepin-3-yl]-L-phenylalaninamide (106a) was prepared in the following manner:

a. N-[(2,3-cis)-4-Oxo-2-phenyl-2,3,4,5-tetrahydro-1,5-benzothiazepin-3-yl]glycinamide (106a)

A method similar to the preparation of (105a) was used except that Fmoc-Gly-Opfp (153 mg) was used in place of Fmoc-Phe-Opfp. The material thus produced was used in the next step without purification or characterization.

Example 107

N$^2$-[(3,5-Difluorophenyl)acetyl]-N$^1$-[(2R,3R)-4oxo-2-phenyl-2,3,4,5-tetrahydro-1,5-benzothiazepin-3-yl]-L-valinamide (107)

A method similar to the one described for (97) was used except that (2,3-cis)-3-amino-2-phenyl-2,3-dihydro-1,5-benzothiazepin-4(5H)-one hydrobromide (9d) (105 mg) was used as the amine component and N-[(3,5-difluorophenyl)acetyl]-L-valine (81 mg) 107b was used as the acid component to afford the title compound in 1:1 mixture with the (2S,3S) diastereomer (91 mg), white solid, m.p. 110-115° C. $^1$H NMR (300 MHz, d6-DMSO) δ 4.76 (t, 1H, J=7 Hz), 5.12(d, 1H, J=7 Hz), 6.91-7.49 (m, 12H), 7.67 (d, 1H, J=7 Hz), 8.25 (s, 1H),10.49 (s, 1H). MS APCI, m/z=524(M+1). LC/MS: 2.54 min.

The starting acid N-[(3,5-difluorophenyl)acetyl]-L-valine (107b) was prepared in the following manner:

a. Methyl N-[(3,5-difluorophenyl)acetyl]-L-valinate (107a)

To a solution of methyl-L-valinate hydrochloride (168 mg) in dichloromethane (6 mL) was added HOBt (135 mg), 3,5-difluorophenylacetic acid (172 mg), EDCI (191 mg) and DIEA (0.522 mL). The reaction mixture was stirred for 16 h, diluted with dichloromethane (50 mL), washed with 5% hydrochloric acid (10 mL) and 10% potassium carbonate (10 mL). The organic layer after drying over anhydrous magnesium sulfate and concentration under reduced pressure afforded the title compound (272 mg). $^1$H NMR (300 MHz, CDCl$_3$) δ 0.87 (d, 1.5H, J=7 Hz), 0.89 (d, 1.5H, J=7 Hz), 2.01 (m, 1H), 3.58 (s, 2H), 3.63 (s, 3H),4.18 (d,d, 1H, J=6 Hz, J=8 Hz), 7.0 (m, 3H), 8.45 (d, 1H, J=8 Hz). MS APCI, m/z=244(M+1). LC/MS: 1.97 min.

b. N-[(3,5-Difluorophenyl)acetyl]-L-valine (107b)

A solution of methyl N-[(3,5-difluorophenyl)acetyl]-L-valinate (107a) in methanol (10 mL) was treated with 1N sodium hydroxide solution (2 mL) and stirred for 2 h. At the end of this period the reaction mixture was acidified with 1N hydrochloric acid solution, diluted with saturated sodium chloride and extracted with dichloromethane (100 mL). After drying over anhydrous magnesium sulfate and concentration under reduced pressure the organic layer afforded the title compound (210 mg). $^1$H NMR (300 MHz, CDCl$_3$)) δ 0.87 (m, 3H), 2.05 (m, 1H), 3.58 (m, 2H), 4.15 (t, 1H, J=8 Hz), 7.07 (m, 3H), 8.30 (m, 1H), 12.61 (s, 1H). MS APCI, m/z=226(M+1) LC/MS: 1.84 min.

Example 108

N$^2$-[(3,5-Difluorophenyl)acetyl]-N$^1$-[(2R,3R)-4-oxo-2-phenyl-2,3,4,5-tetrahydro-1,5-benzothiazepin-3-yl]-L-valinamide (108)

A method similar to the one described for (97) was used except that (2,3-cis)-3-amino-2-phenyl-2,3-dihydro-1,5-benzothiazepin-4(5H)-one hydrobromide (9d) (105 mg) was used as the amine component and N-[(3,5-difluorophenyl)acetyl]-L-leucine (108b) (85 mg) was used as the acid component to afford the title compound as a 1:1 mixture with the 2S,3S diastereomer (107 mg), white solid, m.p.180-190° C. $^1$H NMR (300 MHz, d6-DMSO) δ 4.76 (t, 1H, J=7

Hz), 5.12 (d, 1H, J=7 Hz), 6.91-7.49(m, 12H), 7.67 (d, 1H, J=7 Hz), 8.25 (s, 1H),10.49 (s, 1H). MS APCI, m/z=538 (M+1). LC/MS: 2.65 min.

The starting acid N-[(3,5-difluorophenyl)acetyl]-L-leucine (108b) was prepared in the following manner:

a. Methyl N-[(3,5-difluorophenyl)acetyl]-L-leucinate (108a)

A method similar to that used for the preparation of (107a) was used except that methyl-L-leucinate hydrochloride (182 mg) was used instead of methyl-L-valinate hydrochloride to afford the desired product (280 mg ). $^1$H NMR (300 MHz, CDCl$_3$) δ 0.69 (d, 3H, J=6 Hz), 0.81(d, 3H, J=6 Hz), 1.48 (m, 3H), 3.47 (s, 2H), 3.61 (s, 3H). 4.26 (m, 1H), 7.07 (m, 3H), 8.54 (d, 1H, J=8 Hz). MS APCI, m/z=300(M+1). LC/MS: 2.15 min.

b. N-[(3,5-Difluorophenyl)acetyl]-L-leucine (108b)

A method similar to that used for the preparation of (107b) was used except that methyl N-[(3,5-difluorophenyl)acetyl]-L-leucinate (108a) (280 mg) was used instead of methyl N-[(3,5-difluorophenyl)acetyl]-L-valinate to afford the desired product (216 mg ). $^1$H NMR (300 MHz, CDCl$_3$) δ 0.83 (d, 3, J=6 Hz), 0.89 (d, 3H, J=6 Hz), 1.51(m, 3H),3.52 (s, 2H), 4.22 (m, 1H), 7.07 (m, 3H), 8.41 (d, 1H, J=8 Hz), 12.54 (s, 1H).

Example 109

N$^2$-[(3,5-Difluorophenyl)acetyl]-N$^1$-[(2R,3R)-4-oxo-2-phenyl-2,3,4,5-tetrahydro-1,5-benzothiazepin-3-yl]-L-methioninamide (109)

A method similar to the one described for (97) was used except that (2,3-cis)-3-amino-2-phenyl-2,3-dihydro-1,5-benzothiazepin-4(5H)-one hydrobromide (9d) (105 mg) was used as the amine component and N-[(3,5-difluorophenyl)acetyl]-L-methionine (109b) (91 mg) was used as the acid component to afford the title compound as a 1:1 mixture with the (2S,3S) diastereomer (63 mg), white solid, m.p.85-90° C. $^1$H NMR (300 MHz, d6-DMSO) δ 1.55 (m, 4H), 2.20 (s, 3H), 2.40 (m,2H), 3.03 (m,4H), 4.26 (m,1H), 4.72 (m,1H), 5.17 (d, 1H, J=7 Hz), 5.829 (d, 1H, j=6 Hz), 6.89-7.79 (m, 12H), 8.21(m, 1H),10.53 (m, 1H). MS APCI, m/z=556(M+1). LC/MS: 2.55 min.

The starting acid N-[(3,5-difluorophenyl)acetyl]-L-methionine (109b) was prepared in the following manner:

a. Methyl N-[(3,5-difluorophenyl)acetyl]-L-methioninate (109a)

A method similar to that used for the preparation of (107a) was used except that methyl-L-methionine hydrochloride (214 mg) was used instead of methyl-L-valinate hydrochloride to afford the desired product (300 mg). $^1$H NMR (300 MHz, CDCl$_3$) δ 1.178 (t, 3H, J=7 Hz), 1.93 (m, 2H), 2.02 (s, 3H), 2.51 (m, 2H), 3.53 (s, 2H), 4.38 (m, 1H), 7.07 (m, 3H), 8.54 (d, 1H, J=8 Hz). LC/MS: 2.28 min.

b. N-[(3.Difluorophenyl)acetyl]-L-methionine (109b)

A method similar to that used for the preparation of (107b) was used except that methyl N-[(3,5-difluorophenyl)acetyl]-L-methioninate (109a) (300 mg) was used instead of methyl N-[(3,5-difluorophenyl)acetyl]-L-valinate to afford the desired product (237 mg). This material was not further characterized but used in the next step.

Example 110

N$^2$-[(3,5Difluorophenyl)acetyl]-3-(1H-indol-2-yl)-N$^1$-[(2R,3R)-4oxo-2-phenyl-2,3,4,5-tetrahydro-1,5-benzothiazepin-3-yl]-L-alaninamide (110)

A method similar to the one described for (97) was used except that (2,3-cisS)-3-amino-2-phenyl-2,3-dihydro-1,5-benzothiazepin-4(5H)-one hydrobromide (9d) (105 mg) was used as the amine component and N-[(3,5-difluorophenyl)acetyl]-3-(1H-indol-2-yl)-L-alanine (110b) (119 mg) was used as the acid component to afford the title compound as a 1:1 mixture with the 2S,3S diastereomer (173 mg), white solid, m.p.85-90° C. $^1$H NMR (300 MHz, d6-DMSO) δ 2.40 (m, 2H), 3.03 (m, 4H), 4.26 (m, 1H), 4.72 (m, 1H), 5.17(d, 1H, J=7 Hz), 5.82(d, 1H, J=6 Hz), 6.89-7.79 (m, 12H), 8.21(m, 1H), 10.53 (m, 1H). MS APCI, m/z=611(M+1). LC/MS: 2.66.min.

The starting acid N-[(3,5-difluorophenyl)acetyl]-3-(1H-indol-2-yl)-L-alanine (110b) was prepared in the following manner:

a. Methyl N-[(3,5-difluorophenyl)acetyl]-3-(1H-indol-2-yl)-L-alaninate (110a)

A method similar to that used for the preparation of (107a) was used except that methyl-L-methionine hydrochloride (214 mg) was used instead of methyl-L-valinate hydrochloride to afford the desired product (365 mg). $^1$H NMR (300 MHz, CDCl$_3$) δ 3.17 (m, 2H), 3.43 (s, 2H), 4.90 (m, 1H), 5.94(d, 1H, J=7 Hz), 6.62 (m, 2H), 6.71 (m, 1H), 7.12(m, 1H), 7.17 (m, 1H), 7.36 (d, 1H, J=8 Hz), 7.39 (d, 1H, J=8 Hz), 8.09 (s, 1H). MS APCI, m/z=373(M+1). LC/MS: 2.28 min.

b. N-[(3,5-Difluorophenyl)acetyl]-3-(1H-indol-2-yl)-L-alanine (110b)

A method similar to that used for the preparation of (107b) was used except that methyl N-[(3,5-difluorophenyl)acetyl]-L-methioninate (110a) (300 mg) was used instead of methyl N-[(3,5-difluorophenyl)acetyl]-L-valinate to afford the desired product (341 mg). This material was not further characterized but used in the next step.

Example 111

N$^2$-[(3,5-Difluorophenyl)acetyl]-N$^1$-[(2R,3R)-4-oxo-2-phenyl-2,3,4,5-tetrahydro-1,5benzothiazepin-3-yl]-L-α-aspartic acid (111)

A method similar to the one described for (97) was used except that (2,3-cis)-3-amino-2-phenyl-2,3-dihydro-1,5-benzothiazepin-4(5H)-one hydrobromide (9d) (105 mg) was used as the amine component and 4-tert-butyl N-[(3,5-difluorophenyl)acetyl]-L-aspartate (110b) (115 mg) was used as the acid component to afford a product which was treated with trifluoroacetic acid (2 mL) and stirred for 5 min. At the end of this period the reaction mixture was concentrated under reduced pressure, diluted with ethyl acetate and hexanes and the solid was filtered to afford the title compound as a 1:1 mixture with the (2S,3S) diastereomer (118 mg), white solid, m.p.65-80° C. ¹H NMR (300 MHz, d6-DMSO) δ 4.44 (m, 1H), 4.72 (m, 1H), 5.13 (d, 1H, J=7 Hz), 6.03 (s, 11), 6.87-7.73 (m, 11H), 8.41 (m,1H), 9.38 (s, 1H), 10.51(m,1H). MS APCI, m/z=540(M+1). LC/MS: 2.66 min.

The starting acid 4tert-butyl N-[(3,5-difluorophenyl) acetyl]-L-aspartate (110b) was prepared in the following manner:

a. 4tert-Butyl 1-methyl N-[(3,5-difluorophenyl)acetyl]-L-aspartate (111 a)

A method similar to that used for the preparation of (107a ) was used except that 4-tert-butyl 1-methyl-L-aspartate hydrochloride (239 mg) was used instead of methyl-L-valinate hydrochloride to afford the desired product (350 mg). ¹H NMR (300 MHz, CDCl₃) δ 2.69 (d,d, 1H, J=5 Hz, J=5 Hz), 2.95(dd, 1H, J=5 Hz, J=5 Hz), 3.56 (s, 2H), 3.74 (s, 3H), 4.82 (m,1H), 6.50 (d, 1H, J=7 Hz), 6.79 (m, 3H).

b. 4tert-Butyl N-[(3,5-difluorophenyl)acetyl]-L-aspartate (111b)

A method similar to that used for the preparation of (107b) was used except that 4-tert-butyl 1-methyl N-[(3,5-difluorophenyl)acetyl]-L-aspartate (111a) (350 mg) was used instead of methyl N-[(3,5-difluorophenyl)acetyl]-L-valinate to afford the desired product (292 mg ). This material was not further characterized but used in the next step Example 112

N-[(3,5-Difluorophenyl)acetyl]-N¹-[(2R,3R)-4-oxo-2-phenyl-2,3,4,5, -tetrahydro-1,5-benzothiazepin-3-yl]-L-α-glutamic acid (112c)

A method similar to the one described for (97) was used except that (2,3-cis)-3-amino-2-phenyl-2,3-dihydro-1,5-benzothiazepin-4(5H)-one hydrobromide (9d) (105 mg) was used as the amine component and 4-tert-butyl N-[(3,5-difluorophenyl)acetyl]-L-glutamate (112b) (119 mg) was used as the acid component to afford a product which was treated with trifluoroacetic acid (2 mL) and stirred for 5 min. At the end of this period the reaction mixture was concentrated under reduced pressure, diluted with ethyl acetate and hexanes and the solid was filtered to afford the title compound in 1:1 mixture with the (2S,3S) diastereomer (160 mg), white solid, m.p.65-80° C. ¹H NMR (300 MHz, d6-DMSO) δ 4.20 (m, 1H), 4.72 (m, 1H), 5.15 (d, 1H, J=7 Hz), 6.03 (s, 1H), 6.89-7.73 (m, 11H), 8.41 (m,1H), 9.39 (s,1H), 10.52 (m,1H). MS APCI, m/z=554(M+1). LC/MS: 2.27 min.

The starting acid 4-tert-butyl N-[(3,5-difluorophenyl) acetyl]-L-glutamate (112b) was prepared in the following manner:

a. 4tert-Butyl 1-methyl N-[(3,5difluorophenyl)acetyl]-L-glutamate (112a)

A method similar to that used for the preparation of (107a) was used except that 4-tert-butyl 1-methyl-L-glutamate hydrochloride (253 mg) was used instead of methyl-L-valinate hydrochloride to afford the desired product (360 mg). ¹H NMR (300 MHz, CDCl₃) δ 1.95-2.34 (m, 4H), 3.47 (s, 2H), 3.79 (s, 3H), 4.59 (m,1H), 6.3 (d, 1H, J=7 Hz), 6.79 (m, 3H).

b. 4-tert-Butyl N-[(3,5-difluorophenyl)acetyl]-L-glutamate (112b)

A method similar to that used for the preparation of (107b) was used except that 4-tert-butyl 1-methyl N-[(3,5-difluorophenyl)acetyl]-L-glutamate (111a) (360 mg) was used instead of methyl N-[(3,5-difluorophenyl)acetyl]-L-valinate to afford the desired product (325 mg). This material was not further characterized but used in the next step Example 113

N¹-[(2R,3S)-4-Oxo-2-phenyl-2,3,4,5-tetrahydro-1,5-benzoxazepin-3-yl]-N²-(phenylacetyl)-L-alaninamide (113)

To a solution of N¹-[(2,3-cis)-4-oxo-2-phenyl-2,3,4,5-tetrahydro-1,5-benzoxazepin-3-yl]-L-alaninamide (113a) (130 mg), HOBt (81 mg), phenylacetic acid (68 mg), and EDAC-HCl (115mg) in dichloromethane (10 mL) was added triethylamine (126 mg). The mixture was stirred at RT under nitrogen for 16 h and purified by flash chromatography (2:1 dichloromethane:ethyl acetate) to afford the title compound in 1:1 mixture with the 2S,3R diastereomer (135 mg), white solid, m.p.122-136° C. ¹H NMR (300 MHz, CDCl₃) δ 0.97 (d, 1.5H, J=5 Hz), 1.05 (d, 1.5H, J=5 Hz), 3.47 (two peaks, 2H), 4.53 (p, 0.5H, J=7 Hz), 4.60 (p, 0.5H, J=7 Hz), 4.89 (t, 1H, J=6 Hz), 5.11(t, 1H, J=6 Hz), 5.78 (d, d, 1H, J=7 Hz, J=10 Hz), 6.08 (d, 0.5H, J=8 Hz), 6.2(d, 0.5 Hz, J=8 Hz), 6.61(d, 0.5H, J=6 Hz), 6.80 (d, 0.5H, J=7 Hz), 6.91-7.34 (m, 14H), 7.997 (s, 1H). MS APCI, m/z=466 (M+Na). LC/MS: 2.04 min.

The starting amine N-[(2,3-cis)-4-oxo-2-phenyl-2,3,4,5-tetrahydro-1,5-benzoxazepin-3-yl]-L-alaninamide (113a) was prepared in the following manner:

a. N¹-[(2,3-cis)-4-Oxo-2-Phenyl-2,3,4-tetrahydro-1, 5-benzoxazepin-3-yl]-L-alaninamide (113a)

A solution of N²-[tert-Butoxycarbonyl]-N¹-[(2,3-cis)-4-oxo-2-phenyl-2,3,4,5-tetrahydro-1,5-benzoxazepin-3-yl]-L-alaninamide (6f) (1.94 g) in trifluoroacetic acid (10 mL) was stirred for 10 min. and concentrated under reduced pressure. The resulting material was diluted with 15% solution of sodium carbonate (50 mL) and extracted twice with dichloromethane (100 mL). The dichloromethane layer was dried over anhydrous potassium carbonate and concentrated under reduce pressure to afford the desired material (1.33 g). ¹H NMR (300 MHz, CDCl₃) δ 1.18 (m, 3H), 3.37 (m, 1H), 5.21 (m, 1H), 5.80 (d, 1H, J=7 Hz), 6.91-7.54 (m, 9H), 7.70 (s, 1H). MS APCI, m/z=326 (M+1). LC/MS: 1.24 min.

Example 114

N²-[(2-Fluorophenyl)acetyl]-N-[(2R,3S)-4-oxo-2-phenyl-2,3,4,5-tetrahydro-1,5-benzoxazepin-3-yl]-L-alaninamide (114)

A method similar to the one described for (113) was used except that 2-fluorophenylacetic acid (77 mg) was used instead of phenylacetic acid to afford the title compound as a 1:1 mixture with the 2S,3R diastereomer (150 mg), white solid, m.p. 115-135° C. ¹H NMR (300 MHz, CDCl₃) δ 0.97 (d, 1.5H, J=5 Hz), 1.25 (d, 1.5H, J=5 Hz), 3.49 (m, 2H), 4.63 (p, 0.5H, J=7 Hz), 4.75 (p, 0.5H, J=7 Hz), 4.85 (t, 1H, J=6 Hz), 5.11 (t, 1H, J=6 Hz), 5.80 (dd, 1H, J=7 Hz, J=10 Hz), 6.08 (d, 0.5H, J=8 Hz), 6.27 (d, 0.5 Hz, J=8 Hz), 6.38 (d, 0.5 h, J=6 Hz), 6.66 (d, 0.5H, J=7 Hz), 6.78-7.34 (m, 13H), 8.02 (s, 1H). MS APCI, m/z=484 (M+Na). LC/MS: 2.09 min.

Example 115

N²-[(3-Fluorophenyl)acetyl]-N¹-[(2R,3S)-4-oxo-2-phenyl-2,3,4,5-tetrahydro-1,5-benzoxazepin-3-yl]-L-alaninamide (115)

A method similar to the one described for (113) was used except that 3-fluorophenylacetic acid (77 mg) was used in place of phenylacetic acid to afford the title compound as a 1:1 mixture with the (2S,3R) diastereomer (140 mg), white solid, m.p.130-140° C. ¹H NMR (300 MHz, CDCl₃) δ 0.97 (d, 1.5H, J=5 Hz), 1.27 (d, 1.5H, J=5 Hz), 3.45 (two peaks, 2H), 4.52 (m, 0.5H), 4.67 (m, 0.5H), 4.91 (t, 1H, J=6 Hz), 5.12 (t, 1H, J=6 Hz), 5.79 (dd, 1H, J=7 Hz, J=10 Hz), 6.15 (d, 0.5H, J=8 Hz), 6.28 (d, 0.5 Hz, J=8 Hz), 6.63 (d, 0.5 h, J=6 Hz), 6.70 (d, 0.5H, J=7 Hz), 6.86-7.70 (m, 13H), 7.96 (s, 1H). MS APCI, m/z=484 (M+Na). LC/MS: 2.09 min.

Example 116

N²-[(4-Fluorophenyl)acetyl]-N¹-[(2R,3S)-4-oxo-2-phenyl-2,3,4,5-tetrahydro-1,5-benzoxazepin-3-yl]-L-alaninamide (116)

A method similar to the one described for (113) was used except that 4-fluorophenylacetic acid (77 mg) was used instead of phenylacetic acid to afford the title compound as a 1:1 mixture with the 2S,3R diastereomer (134 mg), white solid, m.p. 130-140° C. ¹H NMR (300 MHz, CDCl₃) δ 0.97 (d, 1.5H, J=5 Hz), 1.07 (d, 1.5H, J=5Hz), 3.43 (two peaks, 2H), 4.52 (m, 0.5H), 4.57(m, 0.5H), 4.93 (t, 1H, J=6 Hz), 5.11 (t, 1H, J=6 Hz), 5.78(dd, 1H, J=7 Hz, J=10 Hz), 6.05 (d, 0.5H, J=8 Hz), 6.21(d, 0.5 Hz, J=8 Hz), 6.33 (d, 0.5 h, J=6 Hz), 6.66 (d, 0.5H, J=7 Hz), 6.88-7.60 (m, 13H), 7.96 (s, 1H). MS APCI, m/z=484 (M+Na). LC/MS: 2.10 min.

Example 117

N¹-[(2R,3S,5aS,9aS)-5-(Cyclopropylmethyl)-4-oxo-2-phenyldecahydro-1,5-benzoxazepin-3-yl]-N²-[(3,5-difluorophenyl)acetyl]alaninamide (117)

Using a procedure similar to that described in Example 1, except using (2R,3S,5aS,9aS)-3-amino-5-(cyclopropylmethyl)-2-phenyloctahydro-1,5-benzoxazepin-4(5H)-one (117e) (16 mg, 0.05 mmol) as the amine component, the title compound (117) was obtained as a white solid (10 mg, 37%). ¹H NMR (300 MHz, CDCl₃) δ0.36 (m, 2H), 0.64 (m, 2H), 1.20 (m, 1H), 1.29 (d, 3H), 1.5 (m, 4H), 1.87 (m, 2H), 2.17 (m, 2H), 2.87 (dd, 1H, J=6.8, 14.0 Hz), 3.39 (t, 1H), 3.49, (s, 2H), 3.80 (dd, 1H), 4.23 (m, 1H), 4.30 (q, 1H), 5.26 (d, 1H, J=6.46), 5.43 (t, 1H, J=6.46), 6.01, (d, 1H), 6.47 (d, 1H), 6.72, (m, 1H), 6.83 (d, 2H), 7.26 (m, 5H). MS APCI, m/z=540(M+1). LC/MS: 2.71 min.

The amine component, (2R,3S,5aS,9aS)-3-amino-5-(cyclopropylmethyl)-2-phenyloctahydro-1,5-benzoxazepin-4 (5H)-one (117e) was prepared in the following manner:

a. (1,2-trans)-2-[(Cyclopropylmethyl)amino]cyclohexanol (117a)

To a stirred, cooled (5-10° C.) slurry of trans-2-aminocyclohexanol hydrochloride (9.86 g, 65 mmol) in toluene (30 mL) was added consecutively magnesium sulfate (0.79 g, 6.5 mmol), triethylamine (13.6 mL, 97.5 mmol) and cyclopropanecarboxaldehyde (4.9 g, 70 mmol) and the mixture stirred in the ice bath overnight, rising to RT overnight as the ice melted. The mixture was filtered, the salt cake washed with a little toluene and the filtrate stripped in vacuo. The resulting residue, dissolved in methanol (30 mL), was cooled in an ice bath as sodium borohydride (2.70 g, 71.3 mmol) was added portionwise with stirring. The mixture was stirred in the bath as the ice melted for 2.5 h, re-cooled in an ice bath and treated cautiously with acetone (6.5 mL). After stirring for 15 min the solvent was stripped, the residue treated with ether, the solids filtered off, washed with ether and the filtrate stripped in vacuo. The resulting material was kugelrohred and the title compound was collected at 170-210°/2 torr (bulb temperature), soft white solid (2.90 g, 26%). The material was used in the next step without further purification. ¹H NMR (300 MHz, CDCl₃) δ0.06-0.17 (m, 2H), 0.42-0.53 (m, 2H), 0.87-1.00 (m, 2H), 1.14-1.35 (m, 4H), 1.71-1.73 (m, 2H), 2.02-2.07 (m, 3H), 2.18-2.27 (m, 1H), 2.44-2.56 (m, 2H), 3.13-3.21 (m, 1H).

b. (2R,3S)-N-(Cyclopropylmethyl)-N-[(1R,2R)-2-hydroxycyclohexyl]-3-phenylpropane2-carboxamide (117b)

To a stirred solution of (1,2-trans)-2-[(cyclopropylmethyl)amino]cyclohexanol (117a) (4.34 g, 25.6 mmol) in THF (100 mL) was added potassium (2R,3S)-3-phenylpropane-2-carboxylate (64a) (5.06 g, 25.0 mmol), HOBt (4.20 g, 27.4 mmol), NMM (8.25 mL, 75.0 mmol) and EDAC-HCl (5.94 g, 31.0 mmol). The mixture was stirred at ambient temperature under nitrogen overnight. The solvent was evaporated and the residue was purified by flash chromatography on silica gel eluting with dichloromethane ethyl acetate (3:1 then 1:1) followed by 10% methanol/dichloromethane to afford the title compound as a sticky white gum (5.22 g, 66%). The foam when dissolved in a little ether gave, on standing at RT overnight, a white solid (1.65 g, 21%), mp 110-120° C. TLC R$_f$~0.50 (4:1 hexane:ether). ¹H NMR (300 MHz, CDCl₃) δ0.19-0.41 (m, 2H), 0.53-0.59 (m, 2H), 0.80-1.37 (m, 4H), 1.45-1.60 (m, 1H), 1.65-1.86 (m, 3H), 2.03-2.18 (m, 2H), 3.10-3.82 (m, 4H), 3.99-4.13 (m, 1H), 7.36 (m, 5H). HPLC (Method B): 3.67 min. On standing in the HPLC vial the 3.67 min peak diminished and a peak at 4.57 min (117c) increased.

A sample of the title compound (~2 mg) in an NMR tube containing CD₃CN (0.75 mL) was treated with TFA (2 μL) and the spectra showed complete conversion to 117c. ¹H NMR (300 MHz, CD₃CN) δ0.34-0.38 (m, 2H), 0.49-0.57 (m, 2H), 1.02-1.13 (m, 1H), 1.22-1.43 (m, 31), 1.67-1.83 (m, 3H), 1.92-1.98 (m, 1H), 2.06-2.11 (m, 1H), 3.32 (dd 1H, J=7 Hz, J=14 Hz), 3.60-3.68 (m, 1H), 3.78 (dd, 1H, J=7 Hz, J=14 Hz), 3.75-3.88 (m, 1H),4.33 (d, 1H, J=8.8 Hz), 4.64 (d, 1H, J=8.8 Hz), 7.27-7.40 (m, 5H).

c. (2S,3R,5aR,9aR)-5-(Cyclopropylmethyl)-3-hydroxy-2-Phenyloctahydro-1,5-benzoxazepin-4(5H)-one (117c)

A solution of (2R,3S)-N-(cyclopropylmethyl)-N-[(1R,2R)-2-hydroxycyclohexyl]-3-phenylpropane-2-carboxamide (117b) (1.05 g, 3.33 mmol) in 125 mL acetonitrile/TFA (0.4%) was stirred for 6 hours. After evaporation the crude oil was purified by chromatography (CHCl₃) to afford the title compound (850 mg, 81%). HPLC: 4.54 min (Method B). ¹H NMR (300 MHz, CDCl₃) δ0.37-0.44 (m, 2H), 0.49-0.57 (m, 2H), 0.85 (m, 1H), 1.03 (m, 1H), 1.14-1.50

(m, 2H), 1.66-1.80 (m, 2H), 1.83-2.02 (m, 1H), 2.03-2.16 (m, 2H), 3.32 (dd, 1H, J=7 Hz, J=14 Hz), 3.60 (m 1H), 3.74 (m, 1H), 3.85 (dd, 1H, J=7 Hz, J=14 Hz), 4.34 (m, 1H), 4.60 (m, 1H), 7.27-7.40 (m, 5H).

d. (2R,3S,5aS,9aS)-3-Azido-5-(cycloproplmethyl)-2-phenyloctahydro-1,5-benzoxazepin-4(5)-one (117d)

Using a procedure similar to Example 31 part c, except using (2S,3R,5aR,9aR)-5-(cyclopropylmethyl)-3-hydroxy-2-phenyloctahydro-1,5-benzoxazepin-4(5H)-one (117c) (450 mg, 1.42 mmol), slightly impure title compound (30c) (112 mg, 23%) was obtained as an off white solid. $^1$H NMR (300 MHz, CDCl$_3$) δ0.28-0.34 (m, 2H), 0.49-0.57 (m, 2H), 1.02-1.13 (m, 1H), 1.22-1.50 (m, 4H), 1.80 (m, 2H), 2.16 (m, 2H), 3.25 (dd, 1H, J=7 Hz, J=14 Hz), 3.40 (m 1H), 3.57 (dd, 1H, J=7 Hz,=14 Hz), 4.06 (m, 1H), 4.38 (d, 1H, J=1.7 Hz), 5.41 (d, 1H, J=1.7 Hz), 7.23-7.36 (m, 3H), 7.42-7.50, (m, 2H).

e. (2R,3S,5aS,9aS)-3-Amino-5-(cycloproplmethyl)-2-phenyloctahydro-1,5-benzoxazepin-4(5H)-one (117e)

Using a procedure similar to that described in example 30, part d, except using (2R,3S,5aS,9aS)-3-azido-5-(cyclopropylmethyl)-2-phenyloctahydro-1,5-benzoxazepin-4(5H)-one (117d) (110 mg, 0.325 mmol) as the azido component, the product was obtained as a slightly crude yellow solid (35 mg). The crude salt was partitioned between saturated sodium bicarbonate and ethyl acetate. The organic phase was separated and washed consecutively with water and brine, dried, filtered and evaporated and column chromatographed (5% methanol/chloroform) to yield the title compound (117e) (16 mg, 16%) as an off white solid. MS APCI, m/z=315(M+I). LC/MS: 1.80 min.

Utility

The compounds of the present invention have utility for the prevention and treatment of Alzheimer's disease by inhibiting amyloid β production. Methods of treatment target formation of amyloid β production through enzymes involved in the proteolytic processing of β amyloid precursor protein. Compounds that inhibit β and γ secretase activity, either directly or indirectly, controls the production of amyloid β. The inhibitions of β and γ secretases reduce the production of amyloid β and are thought to reduce or prevent the neurological disorders such as Alzheimer's disease. The compounds of the present invention have utility for the prevention and treatment of disorders involving amyloid β production, such as cerebrovascular disorders.

Compounds of the present invention have been shown to inhibit amyloid β production, as determined by the gamma secretase detergent extract assay and gamma secretase whole cell described below.

Compounds provided by this invention should also be useful as standards and reagents in determining the ability of a potential pharmaceutical to inhibit amyloid β production. These would be provided in commercial kits comprising a compound of this invention.

As used herein "ug" denotes microgram, "mg" denotes milligram, "g" denotes gram, "uL" denotes microliter, "mL" denotes milliliter, "L" denotes liter, "nM" denotes nanomolar, "uM" denotes micromolar, "mM" denotes millimolar, "M" denotes molar, "nm" denotes nanometer, "DMSO" denotes dimethyl sulfoxide, "DTT" denotes dithiothreitol, "DPBS" denotes Dulbecco's phosphate buffer saline, "EDTA" denotes ethylenediaminetetraacetate.

Gamma Secretase Detergent Extract Assay

The gamma secretase enzyme assay measures the amount of amyloid β (Aβ)40 product generated by the cleavage of C100, a truncated form of amyloid precursor protein (APP). The C100 substrate is a recombinant protein purified from *E. coli* inclusion bodies. The γsecretase enzyme complex is prepared by detergent extraction of HeLa 8A8 cell membranes. The enzyme reaction contains 10 μl of inhibitor at a defined concentration, diluted from a DMSO stock into 96-well microplates (final concentration of DMSO is maintained at 5%). 20 ul of the C100 substrate (600 nM final concentration), in reaction buffer, (50 mM MES, pH 6.5, containing 100 mM NaCl, 1 mM EDTA, 1 mM DTT, 1 mg/mL BSA, 0.25% Chapso, 0.01% PE, 0.01% PC and a protease cocktail), is added to the plates. The reactions are initiated by addition of l Oul enzyme at a 20-fold dilution from stock. An Aβ340 standard curve diluted in the reaction buffer plus C100 is included in each assay. Plates are incubated for 3 hours at 37 degrees. After the incubation period, 50 μl of an antibody mixture is added: rabbit anti-Aβ40 antibody (Biosource #44-3481) at 0.16 ug/ml and biotinylated 4G8 (Senetek #240-10) at 0.25 ug/ml in DPBS (Fisher #MT21031CV) containing 0.5% bovine serum albumin, 0.5% Tween 20. Plates are then incubated overnight at 4 degrees. The following morning, a 50ul mixture of 0.0625 mg/ml Ruthenium labeled goat anti-rabbit IgG (labeled in-house) and 125 ug/ml of Streptavadin beads (Igen #M280), diluted in the same DPBS buffer, is added to detect the cleaved product. After a one hour incubation period at room temperature, an Igen M Series instrument is utilized to quantitate the results by electrochemiluminescence.

Gamma Secretase Whole Cell Assay (GSWC)

Preparation of Cells for Assay

Human Embryonic Kidney (HEK) cells stably expressing human Amyloid Precursor protein (APP) and Presenelin I were grown in DMEM media (Fisher MT10013CV) containing 10% fetal calf serum (Fisher #MT135011CV), 0.2 mg/mL G418 (Fisher #MT30234CR) and 1× concentration of antibiotic/antimycotic mixture (Fisher #MT30004CI). Cells were grown in tissue culture flasks and passaged every week at a ratio of 1:30.

Thirty minutes prior to incubation with test compounds, cells were harvested by treating the monolayer with DPBS (Fisher #MT21031 CV) containing 3 mM EDTA. Cells were resuspended at a density of 2 million cells/mL in complete growth medium. Aβ 40 assay Test compounds were solubilized in DMSO at a concentration of 3.3 mM. From this stock solution a dilution series was prepared in complete growth medium of cells. Dilution series were then transferred to 96 well assay plate (Costar #3595) with 100 μL in each well. Cells (100 μL) were added to each well containing test compound. Two controls, one containing only cells (Total) and one containing only growth medium (Background) were also included. Cells were incubated with compounds for 14-16 hours in cell culture incubator.

At the end of 14-16 hour incubation, 100 μL of supernatant was transferred from each well in to a polypropylene 96 well plate. This supernatant was mixed with 100 μL of DPBS (Fisher #MT21031CV) containing 0.5% bovine serum albumin, 0.5% Tween 20, 0.25 μg/mL of biotinylated 4G8 (Senetek #240-10), 0.18 μg/mL rabbit anti-Aβ40 antibody (Biosource #44-3481), 0.045 μg/mL Ruthenium labeled goat anti-rabbit IgG (labeled in-house) and 60 μg/mL of Streptavadin beads (Igen #M280). The mixture was incubated for 4-6 hours at 4° C. on a plate shaker.

At the completion of 4-6 hour incubation, plate was brought to room temperature and the generated Aβ40 was detected using the Igen M8 analyzer. Raw data was imported into Microsoft Excel software. $IC_{50}$ values for inhibition of Aβ40 generation by test compounds were calculated using Excel-Fit.

In the claims:
1. A compound of formula (I):

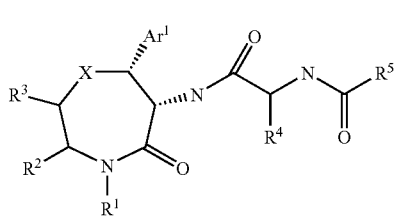

wherein:
X is $CH_2$, O, $NR^1$, $SO_2$ or S;
$Ar^1$ is a 5- or 6-membered aromatic or heterocyclic ring optionally substituted with 0, 1, 2, or 3 $R^e$ moieties, said ring having 0, 1, 2 or 3 nitrogen, oxygen or sulfur atoms, but no more than 2 oxygen atoms or 2 sulfur atoms or 1 oxygen and 1 sulfur atom;
$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$, $C_{1-4}$alkylC(=O)R$^d$; or $C_{1-3}$alkylphenyl substituted with 0, 1, 2 or 3 $R^e$;
$R^a$ and $R^b$ are at each occurrence independently selected from H, $C_{1-4}$alkyl or $C_{3-6}$cycloalkyl, or $R^a$ and $R^b$ and the N to which they are attached in combination form a 5 or 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;
$R^c$ is, at each occurrence independently selected from H, $C_{1-3}$alkyl, or substituted phenyl with 0, 1, 2, or 3 $R^e$;
$R^d$ is, at each occurrence independently selected from $C_{1-3}$alkyl, hydroxy, $C_{1-3}$alkoxy, or NR$^a$R$^b$;
$R^e$ is, at each occurrence independently selected from H, OH, F, Cl, Br, I, CN, $NO_2$, $CF_3$, $C_{1-6}$alkyl, or $C_{1-6}$alkoxy;
$R^2$ and $R^3$ are at each occurrence independently selected from H, $C_{1-6}$alkyl, $C_{4-6}$ cycloalkyl, aryl, or heteroaryl, or $R^2$ and $R^3$ in combination form a fused phenyl or cyclohexyl moiety that may be substituted with 0, 1 or 2 $R^f$ moieties,
$R^f$ is $NO_2$, F, Cl, Br, I, $CF_3$, CN, $C_{1-6}$alkyl, or $C_{1-6}$alkoxy;
$R^4$ is H, CHR$^7$R$^8$, 5- or 6- membered cycloalkyl, 5- or 6-membered heterocyclic, 5 or 6-membered aromatic ring optionally substituted with 0, 1, or 2 $R^f$ moities, said heterocycic ring having 0, 1, 2 or 3 nitrogen, oxygen or sulfur atoms, but no more than 2 oxygen atoms or 2 sulfur atoms or 1 oxygen and 1 sulfur atom;
$R^5$ is $C_{1-3}$alkylR$^9$ or CH(OH)R$^{10}$;
$R^7$ and $R^8$ are, at each occurrence are independently selected from H, $C_{1-4}$alkyl, OH, SH, $CH_2SCH_3$, $CONH_2$, $CH_2CONH_2$, $CO_2H$, $CH_2CO_2H$, $(CH_2)_3$NHCH(NH$_2$)$_2$$C_{1-4}$alkylamino, indolyl, imidazolyl, phenyl or hydroxyphenyl $R^7$ and $R^8$ in combination form a 6-membered aromatic or heterocyclic ring optionally substituted with 0, 1 or 2 $R^f$ moieties said heterocyclic ring having 0, 1, 2 or 3 nitrogen, oxygen or sulfur atoms, but no more than 2 oxygen atoms or 2 sulfur atoms or 1 oxygen and 1 sulfur atom;
$R^9$ is phenyl substituted with 0, 1, 2 or 3 $R^e$;
$R^{10}$ is alkyl or $R^9$;
or a pharmaceutically acceptable salt thereof.

2. A compound of claim 1, wherein:
X is $CH_2$, O, $NR^1$, $SO_2$ or S; $Ar^1$ is a 5- or 6-membered aromatic or heterocyclic ring optionally substituted with 0, 1, 2, or 3 $R^0$ moieties, said ring having 0, 1, or 2 nitrogen, oxygen or sulfur atoms, but no more than 2 oxygen atoms or 1 oxygen and 1 sulfur atom;
$R^1$ is H, $C_{1-3}$alkyl$C_{3-6}$cycloalkyl, $C_{1-6}$alkyl, $C_{3-6}$alkenyl, $C_{3-6}$alkynyl, $C_{3-6}$cycloalkyl, $C_{2-4}$alkylNR$^a$R$^b$, $C_{1-4}$alkylC(=O)R$^d$; or $C_{1-3}$alkylphenyl substituted with 0, 1, or 2 $R^e$;
$R^a$ and $R^b$ are, at each occurrence independently selected from H, $C_{1-4}$alkyl or $C_{3-6}$cycloalkyl, or $R^a$ and $R^b$ and the N to which they are attached in combination form a 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;
$R^c$ is, at each occurrence independently selected from H, $C_{1-3}$alkyl, or phenyl;
$R^d$ is, at each occurrence independently selected from $C_{1-3}$alkyl, or NR$^a$R$^b$;
$R^e$ is, at each occurrence independently selected from H, OH, F, Cl, Br, I, CN, $NO_2$, $CF_3$, $C_{1-3}$alkyl, or $C_{1-3}$alkoxy;
$R^2$ and $R^3$ are at each occurrence independently selected from H, $C_{1-6}$alkyl, $C_{4-6}$cycloalkyl, or aryl, or $R^2$ and $R^3$ in combination form a fused phenyl moiety that may be substituted with 0, 1 or 2 $R^f$ moieties;
$R^f$ is $NO_2$, F, Cl, Br, I, $CF_3$, CN, $C_1$-3alkoxy;
$R^4$ is H, CHR$^7$R$^8$, 6-membered cycloalkyl, or 6-membered heterocyolic, or 6-membered aromatic ring optionally substituted with 0, 1, or 2 moities, said heterocyclis ring having 0, 1, 2 or 3 nitrogen, oxygen or sulfur atoms, but no more than 2 oxygen atoms or 2 sulfur atoms or 1 oxygen and 1 sulfur atom;
$R^5$ is $C_{1-3}$alkylR$^9$ or CH(OH)R$^{10}$;
$R^7$ and $R^8$ are, at each occurrence independently selected from H, $C_{1-4}$alkyl, OH, $CONH_2$, $CH_2CONH_2$, $CO_2H$, $CH_2CO_2H$, $(CH_2)_3$NHCH(NH$_2$)$_2$, $C_{1-4}$alkylamino, indolyl, imidazolyl, phenyl or hydroxyphenyl or $R^7$ and $R^8$ in combination form a 6-membered aromatic or heterocyclic ring optionally substituted with 0, 1 or 2 $R^f$ moieties said heterocyclic ring having 0, 1, 2 or 3 nitrogen, oxygen or sulfur atoms, but no more than 2 oxygen atoms or 2 sulfur atoms or 1 oxygen and 1 sulfur atom;
$R^9$ is phenyl substituted with 0, 1, or 2 $R^e$; and
$R^{10}$ is alkyl or $R^9$.

3. A compound of claim 1, wherein:
X is $CH_2$, O, $NR^1$, $SO_2$ or S;
$Ar^1$ is a 5- or 6-membered aromatic or heterocyclic ring optionally substituted with 0, 1, 2, or 3 $R^e$ moieties, said ring having 0, 1, or 2 nitrogen, oxygen or sulfur atoms, but no more than 2 oxygen atoms or 1 oxygen and 1 sulfur atom;
$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$, $C_{1-4}$alkylC(=O)R$^d$; or $C_{1-3}$alkylphenyl substituted with 0, 1, or 2 $R^e$;

153

$R^a$ and $R^b$ are, at each occurrence independently selected from H, $C_{1-4}$alkyl or $C_{3-6}$cycloalkyl, or $R^a$ and $R^b$ and the N to which they are attached in combination form a 5-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^c$ is, at each occurrence independently selected from H, $C_{1-3}$alkyl, phenyl;

$R^d$ is, at each occurrence independently selected from $C_{1-3}$alkyl or $NR^aR^b$;

$R^e$ is, at each occurrence independently selected from H, OH, F, Cl, Br, I, CN, $NO_2$, $CF_3$, $C_{1-6}$alkyl, or $C_{1-6}$alkoxy;

$R^2$ and $R^3$ are at each occurrence independently selected from H, $C_{1-6}$alkyl, $C_{4-6}$cycloalkyl or aryl or $R^2$ and $R^3$ in combination form a fused phenyl moiety that may be substituted with 0, 1 or 2 $R^f$ moieties, $R^f$ is H, $NO_2$, F, Cl, Br, I, $CF_3$, $C_{1-6}$alkyl, or $C_{1-6}$alkoxy;

$R^4$ is H, $CHR^7R^8$, or 6-membered heterocyclic, or 6-membered aromatic ring optionally substituted with 0, 1, or 2 $R^f$ moities, said heterocyclic ring having 0, 1, 2 or 3 nitrogen, oxygen or sulfur atoms, but no more than 2 oxygen atoms or 2 sulfur atoms or 1 oxygen and 1 sulfur atom;

$R_4$ is H or $CHR^7R^8$;

$R^5$ is $C_{1-3}$alkyl $R^9$ or $CH(OH)R^{10}$;

n is 0, 1 or 2;

$R^7$ and $R^8$ are, at each occurrence independently selected from H, $C_{1-4}$alkyl, OH, $CONR_2$, $CH_2CONH_2$, $CO_2H$, $CH_2CO_2H$, $(CH_2)_3NHCH(NH_2)_2$, $C_{1-4}$alkyl amino, indolyl, imidazolyl, phenyl or hydroxyphenyl or $R^7$ and $R^8$ in combination form a 6-membered aromatic or heterocyclic ring optionally substituted with 0, 1 or 2 $R^f$ moieties said heterocyclic ring having 0, 1, or 2 nitrogen, oxygen or sulfur atoms;

$R^9$ is phenyl substituted with 1, or 2 $R^e$; and $R^{10}$ is alkyl or phenyl substituted with 1, or 2 $R^e$.

4. A compound of claim 1, wherein:

X is $CH_2$, O, $NR^1$, $SO_2$ or S;

$Ar^1$ is a 5- or 6-membered aromatic or heterocyclic ring optionally substituted with 0, 1, 2, or 3 $R^e$ moieties, said ring having 0, 1, or 2 nitrogen, oxygen or sulfur atoms, but no more than 1 oxygen and 1 sulfur atom;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkyl$NR^aR^b$, $C_{1-4}$alkyl$C(=O)R^d$; or $C_{1-3}$alkylphenyl substituted with 0, or 1 $R^e$;

$R^a$ and $R^b$ are, at each occurrence independently selected from H, $C_{1-4}$alkyl or $C_{5-6}$cycloalkyl, or $R^a$ and $R^b$ and the N to which they are attached in combination form a 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^c$ is, at each occurrence independently selected from H, $C_{1-3}$alkyl;

$R^d$ is, at each occurrence independently selected from $C_{1-3}$alkyl;

$R^e$ is, at each occurrence independently selected from H, OH, F, Cl, Br, I, CN, $NO_2$, $CF_3$, $C_{1-6}$alkyl;

$R^2$ and $R^3$ are at each occurrence independently selected from H, $C_{1-6}$alkyl, or $R^2$ and $R^3$ in combination form a fused phenyl moiety that may be substituted with 0, 1 or 2 $R^f$ moieties, $R^f$ is H, F, Cl, Br, I, $CF_3$, $C_{1-6}$alkyl;

154

$R^4$ is H, $CHR^7R^8$, or 6-membered heterocyclic, or 6-membered aromatic ring optionally substituted with 0, 1, or 2 $R^f$ moieties, said heterocyclic ring having 0, 1, or 2 nitrogen, oxygen or sulfur atoms;

$R^5$ is $C_{1-3}$alkyl$R^9$ or $CH(OH)R^{10}$;

n is 0, 1 or 2;

$R^7$ and $R^8$ are, at each occurrence independently selected from H, $C_{1-4}$alkyl, OH, $CONH_2$, $CH_2CONH_2$, $CO_2H$, $CH_2CO_2H$, $(CH_2)_3NHCH(NH_2)_2$, $C_{1-4}$alkylamino, indolyl, imidazolyl, phenyl or hydroxyphenyl or $R^7$ and $R^8$ in combination form a 6-membered aromatic or heterocyclic ring optionally substituted with 0, 1 or 2 $R^f$ moieties said heterocyclic ring having 0, 1, or 2 nitrogen, or oxygen atoms;

$R^9$ is phenyl substituted with 1, or 2 $R^e$; and $R^{10}$ is alkyl or $R^9$.

5. A compound of claim 1, wherein:

X is $CH_2$, O, $SO_2$ or S;

$Ar^1$ is a 5- or 6-membered aromatic or heterocyclic ring optionally substituted with 0, 1, or 2 $R^e$ moieties, said ring having 0, 1, or 2 nitrogen, oxygen or sulfur atoms;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkyl$NR^aR^b$, $C_{1-4}$alkyl$C(=O)R^d$;

$R^a$ and $R^b$ are, at each occurrence independently selected from H, $C_{1-4}$alkyl or $C_{5-6}$cycloalkyl, or $R^a$ and $R^b$ and the N to which they are attached in combination form a 6-membered N-linked heterocycle having 2 nitrogen atoms, wherein the non-linked nitrogen is substituted with $R^c$ or 1 nitrogen and 1 oxygen, ring atoms wherein there is no non-linked nitrogen;

$R^d$ is, at each occurrence independently selected from $C_{1-3}$alkyl;

$R^e$ is, at each occurrence independently selected from H, OH, F, Cl, Br, I, $NO_2$, $CF_3$, or $C_{1-6}$alkyl;

$R^2$ and $R^3$ are at each occurrence independently selected from $C_{1-6}$alkyl or $R^2$ and $R^3$ in combination form a fused phenyl moiety that may be substituted with 0, 1 or 2 $R^f$ moieties, $R^f$ is H, F, Cl, Br, I, $CF_3$;

$R^4$ is H, $CHR^7R^8$, or 6-membered heterocyclic, or 6-membered aromatic ring optionally substituted with 0, 1, or 2 $R^f$ moities, said heterocyclic ring having 0, 1, or 2 nitrogen, or oxygen atoms;

$R^5$ is $C_{1-3}$alkyl$R^9$ or $CH(OH)R^{10}$;

$R^7$ and $R^8$ are, at each occurrence independently selected from H, $C_{1-4}$alkyl, OH, $CONH_2$, $CH_2CONH_2$, $CO_2H$, $C_{1-4}$alkylamino, phenyl or hydroxyphenyl or $R^7$ and $R^8$ in combination form a 6-membered aromatic or heterocyclic ring optionally substituted with 0, 1 or $R^f$ moieties said heterocyclic ring having 0, 1, or 2 nitrogen, or oxygen atoms;

$R^9$ is phenyl substituted with 1, or 2 $R^e$; and $R^{10}$ is alkyl or $R^9$.

6. A compound of claim 1, wherein:

X is $CH_2$, O, $SO_2$ or S;

$Ar^1$ is a 6-membered aromatic or heterocyclic ring optionally substituted with 0, 1, or 2 $R^e$ moieties, said ring having 0, or 1 nitrogen, oxygen or sulfur atoms;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkyl$NR^aR^b$, $C_{1-4}$alkyl$C(=O)R^d$;

$R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen;

$R^d$ is, at each occurrence independently selected from $C_{1-3}$alkyl;

$R^e$ is, at each occurrence independently selected from H, OH, F, Cl, Br, I, $CF_3$;

$R^2$ and $R^3$ are combined to form a fused phenyl moiety substituted with 0, 1 or 2 $R^f$ moieties, $R^f$ is H, F, Cl, Br, I, or $CF_3$;

$R^4$ is H, $CHR^7R^8$, or 6-membered heterocyclic, or 6-membered aromatic ring optionally substituted with 0, 1, or 2 $R^f$ moieties, said heterocyclic ring having 0, or 1, nitrogen, or oxygen atoms;

$R^5$ is $C_{1-3}$alkyl$R^9$ or $CH(OH)R^{10}$;

$R^7$ and $R^8$ are, at each occurrence independently selected from H, OH, or $R^7$ and $R^8$ in combination form a 6-membered aromatic or heterocyclic ring optionally substituted with 0, 1 or 2 $R^f$ moieties said heterocyclic ring having 0, or 1, nitrogen, or oxygen atoms;

$R^9$ is phenyl substituted with 2 $R^e$; and $R^{10}$ is phenyl substituted with 2 $R^e$.

7. A compound of claim 1, wherein:

X is $CH_2$, O, or S;

$Ar^1$ is a 6-membered aromatic or heterocyclic ring optionally substituted with 0, 1, or 2 $R^e$ moieties, said ring having having 0, or 1 nitrogen, or oxygen atoms;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$;

$R^a$ and $R^b$ are, at each occurrence independently selected from H, $C_{1-4}$alkyl or $C_{5-6}$cycloalkyl or $R^a$ and R1 and the N to which they are attached in combination form a 6-membered N-linked heterocycle having 1 nitrogen and 1 oxygen, ring atom, wherein there is no non-linked nitrogen;

$R^2$ and $R^3$ are combined to form a fused phenyl moiety substituted with 0, 1 or 2 $R^f$;

$R^2$ is, at each occurrence independently selected from H, OH, F, Cl, Br, I, $CF_3$;

$R^f$ is F or Cl;

$R^4$ is H, $CHR^7R^8$, or 6-membered aromatic ring optionally substituted with 0, 1, or 2 $R^f$ moieties;

$R^5$ is $C_{1-3}$alkyl$R^9$ or $CH(OH)R^{10}$;

$R^7$ and $R^8$ are, at each occurrence independently selected from H, OH, or $R^7$ and $R^8$ in combination form a 6-membered aromatic ring optionally substituted with 0, 1 or 2 $R^f$ moieties $R^7$ and $R^8$ are, at each occurrence independently selected from H or OH;

$R^9$ is phenyl substituted with 2 $R^e$; and $R^{10}$ is phenyl substituted with 2 $R^e$.

8. A compound of claim 1, wherein:

X is O or $CH_2$ or S;

$Ar^1$ is a 6-membered aromatic or heterocyclic ring optionally substituted with 0, 1, or 2 $R^e$ moieties, said ring having having 0, or 1 nitrogen atom;

$R^1$ is H, $C_{1-3}$alkyl$C_{3-6}$cycloalkyl, $C_{1-6}$alkyl, $C_{3-6}$alkenyl, $C_{3-6}$alkynyl $C_{3-6}$cycloalkyl, $C_{2-4}$alkylNR$^a$R$^b$;

$R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen;

$R^2$ and $R^3$ are combined to form a fused phenyl moiety substituted with 0, 1 or 2 $R^f$ wherein $R^f$ is F or Cl;

$R^4$ is H, $CH_3$, or a 6-membered aromatic ring optionally substituted with 0, 1, or 2 $R^f$ moieties;

$R^5$ is $C_{1-3}$alkyl$R^9$;

$R^e$ is, at each occurrence independently selected from H, OH, F, Cl, Br, I, $CF_3$; and $R^9$ is phenyl substituted with 2 $R^e$.

9. A compound of claim 1, wherein:

X is O or $CH_2$;

$Ar^1$ is a 6-membered aromatic ring optionally substituted with 0, 1, or 2 $R^e$ moieties;

$R^1$ is H, $C_{1-3}$alkyl$C_{3-6}$cycloalkyl, $C_{1-6}$alkyl, $C_{3-6}$alkenyl, $C_{3-6}$alkenyl $C_{3-6}$cycloalkyl, $C_{2-4}$alkylNR$^a$R$^b$;

$R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen;

$R^2$ and $R^3$ are combined to form a fused phenyl moiety substituted with 0, 1 or 2 $R^f$ wherein $R^f$ is F or Cl;

$R^4$ is H, $CH_3$, or a 6-membered aromatic ring optionally substituted with 0, 1, or 2 $R^f$ moieties;

$R^5$ is $C_{1-3}$alkyl$R^9$;

$R^e$ is, at each occurrence independently selected from H, OH, F, Cl, Br, I, $CF_3$; and $R^9$ is phenyl substituted with 2 $R^e$.

10. A compound of claim 1, wherein:

X is O;

$Ar^1$ is a 6-membered aromatic ring optionally substituted with 0, 1, or 2 $R^e$ moieties;

$R^1$ is $C_{1-3}$alkyl$C_{3-6}$cycloalkyl, $C_{1-6}$alkyl, $C_{3-6}$alkenyl, $C_{3-6}$alkynyl;

$R^2$ and $R^3$ are combined to form a fused phenyl moiety substituted with 0, 1 or 2 $R^f$ wherein $R^f$ is F or Cl;

$R^4$ is H, $CH_3$, or a 6-membered aromatic ring optionally substituted with 0, 1, or 2 $R^f$ moieties;

$R^5$ is $C_{1-3}$alkyl$R^9$;

$R^e$ is, at each occurrence independently selected from H, OH, F, Cl, Br, I, $CF_3$; and $R^9$ is phenyl substituted with 2 $R^e$.

11. A compound of claim 1, wherein X is $CH_2$, O, $SO_2$ or S.

12. A compound of claim 1, wherein:

$Ar^1$ is a 5-or 6-membered aromatic or heterocyclic ring optionally substituted with 0 or 1 $R^e$.

13. A compound of claim 1, wherein:

$R^1$ is $C_{1-3}$alkyl$C_{3-6}$cycloalkyl, $C_{1-6}$alkyl, $C_{3-6}$alkenyl, $C_{3-6}$alkynyl.

14. A compound of claim 1, wherein:

$R^a$ and $R^b$ are, at each occurrence independently selected from H, $C_{1-4}$alkyl or $C_{5-6}$cycloalkyl or $R^a$ and $R^b$ and the N to which they are attached in combination form a 6-membered N-linked heterocycle having 1 nitrogen and 1 oxygen, ring atom, wherein there is no non-linked nitrogen.

15. A compound of claim 1, wherein:

$R^2$ and $R^3$ are combined to form a fused phenyl moiety substituted with 0, 1 or 2 $R^f$.

16. A compound of claim 1, wherein $R^e$ is, at each occurrence independently selected from F or Cl.

17. A compound of claim 1, wherein $R^f$ is F or Cl.

18. A compound of claim 1, wherein $R^4$ is H or $CHR^7R^8$ or a 6-membered aromatic ring optionally substituted with 0, 1, or 2 $R^f$ moieties wherein $R^7$ and $R^8$ are, at each occurrence independently selected from H or OH.

19. A compound of claim 1, wherein $R^4$ is a 6-membered aromatic ring optionally substituted with 0, 1, or 2 $R^f$ moieties wherein $R^f$ is halo.

20. A compound of claim 1, wherein $R^5$ is $C_{1-3}$alkyl$R^9$ or CH(OH)$R^{10}$.

21. A compound of claim 1, wherein $R^7$ and $R^8$ are, at each occurrence independently selected from H or OH.

22. A compound of claim 1, wherein $R^9$ is phenyl substituted with 2 $R^e$.

23. A compound of claim 1, wherein $R^{10}$ is phenyl substituted with 2 $R^e$.

24. A compound of formula (I) selected from:

$N^2$-[(3,5-difluorophenyl)acetyl]-$N^1$-[(2R,3R)-2-(2,5-difluorophenyl)-4-oxo-2,3,4,5-tetrahydro-1,5-benzothiazepin-3-yl]-L-alaninamide;

$N^1$-[(2R,3R)-5-cyclohexyl-2-(2,5-difluorophenyl)-4-oxo-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-{(2R,3R)-2-(2,5-difluorophenyl)-5-[2-(dimethylamino)ethyl]-4-oxo-2,3,4,5-tetrahydro-1,5-benzothiazepin-3-yl}-L-alaninamide;

$N^2$-[(3,5-difluorophenyl)acetyl]-$N^1$-[(2R,3R)-2-(2,5-difluorophenyl)-4-oxo-2,3,4,5-tetrahydro-1,5-benzothiazepin-3-yl]-L-serinamide;

$N^2$-[(3,5-difluorophenyl)acetyl]-$N^1$-[(2R,3R)-2-(2,5-difluorophenyl)-5-methyl-4-oxo-2,3,4,5-tetrahydro-1,5-benzothiazepin-3-yl]-L-alaninamide;

$N^2$-[(3,5-difluorophenyl)acetyl]-$N^1$-[(2R,3S)-4-oxo-2-phenyl-2,3,4,5-tetrahydro-1,5-benzoxazepin-3-yl]-L-alaninamide;

$N^2$-[(3,5-difluorophenyl)acetyl]-$N^1$-[(6R,7R)-5-oxo-7-phenyl-1,4-thiazepan-6-yl]-L-alaninamide;

$N^2$-[(3,5-difluorophenyl)acetyl]-$N^1$-[(3S,4R)-8-fluoro-2-oxo-4-phenyl-2,3,4,5-tetrahydro-1H-1-benzazepin-3-yl]-L-alaninamide;

$N^2$-[(3,5-difluorophenyl)acetyl]-$N^1$-[(2R,3R)-4-oxo-2-phenyl-2,3,4,5-tetrahydro-1,5-benzothiazepin-3-yl]-L-alaninamide;

$N^1$-[(2R,3R)-2-(3,4-dichlorophenyl)-4-oxo-2,3,4,5-tetrahydro-1,5-benzothiazepin-3-yl]-$N^2$-[(3,5-difluorophenyl)acetyl]-L-alaninamide;

$N^1$-[(2R,3R)-2-(4-chlorophenyl)-4-oxo-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-[(2R,3R)-2-(4-methylphenyl)-4-oxo-2,3,4,5-tetrahydro-1,5-benzothiazepin-3-yl]-L-alaninamide;

$N^1$-[(2R,3R)-7-chloro-4-oxo-2-phenyl-2,3,4,5-tetrahydro-1,5-benzothiazepin-3-yl]-$N^2$-[(3,5-difluorophenyl)acetyl]-L-alaninamide;

$N^1$-{(2R,3R)-7-chloro-5-[2-(dimethylamino)ethyl]-4-oxo-2-phenyl-2,3,4,5-tetrahydro-1,5-benzothiazepin-3-yl}-$N^2$-[(3,5-difluorophenyl)acetyl]-L-alaninamide;

$N^1$-[(2R,3R)-2-(3-chlorophenyl)-4-oxo-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-[(2R,3R)-2-(3,5-difluorophenyl)-4-oxo-2,3,4,5-tetrahydro-1,5-benzothiazepin-3-yl]-L-alaninamide;

$N^2$-[(3,5-difluorophenyl)acetyl]-$N^1$-[(2R,3R)-2-(3,5-difluorophenyl)-5-methyl-4-oxo-2,3,4,5-tetrahydro-1,5-benzothiazepin-3-yl]-L-alaninamide;

$N^2$-[(3,5-difluorophenyl)acetyl]-$N^1$-[(2R,3R)-2-(2-fluorophenyl)-5-methyl-4-oxo-2,3,4,5-tetrahydro-1,5-benzothiazepin-3-yl]-L-alaninamide;

$N^1$-{(2R,3R)-2-(3-chlorophenyl)-5-[2-(dimethylamino)ethyl]-4-oxo-2,3,4,5-tetrahydro-1,5-benzothiazepin-3-yl}-$N^2$-[(3,5-difluorophenyl)acetyl]-L-alaninamide;

$N^2$-[(3,5-difluorophenyl)acetyl]-$N^1$-[(2R,3R)-2-(2,5-difluorophenyl)-4-oxo-2,3,4,5-tetrahydro-1,5-benzothiazepin-3-yl]-D-serinamide;

$N^1$-[(2R,3R)-2-(3-chlorophenyl)-5-methyl-4-oxo-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-[(2R,3R)-5-methyl-4-oxo-2-phenyl-2,3,4,5-tetrahydro-1,5-benzothiazepin-3-yl]-L-alaninamide;

$N^1$-[(2R,3R)-5-cyclohexyl-4-oxo-2-phenyl-2,3,4,5-tetrahydro-1,5-benzothiazepin-3-yl]-$N^2$-[(3,5-difluorophenyl)acetyl]-L-alaninamide;

$N^1$-[(2R,3R)-7-chloro-5-cyclohexyl-4-oxo-2-phenyl-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-[(6R,7R)-7-(1-naphthyl)-5-oxo-1,4-thiazepan-6-yl]-L-alaninamide;

(2S)-2-{[(3,5-difluorophenyl)acetyl]amino}-N-[(6R,7R)-7-(1-naphthyl)-5-oxo-1,4-thiazepan-6-yl]-2-phenylacetamide;

(2S)-2-hydroxy-4-methyl-N-((1S)-2-{[(6R,7R)-7-(1-naphthyl)-5-oxo-1,4-thiazepan-6-yl]amino}-2-oxo-1-phenylethyl)pentanamide;

(2S)-2-hydroxy-4-methyl-N-((1S)-2-oxo-2-{[(2R,3S)-4-oxo-2-phenyl-2,3,4,5-tetrahydro-1,5-benzoxazepin-3-yl]amino}-1-phenylethyl)pentanamide;

$N^2$-[(2S)-2-hydroxy-4-methylpentanoyl]-$N^1$-[(2R,3S)-4-oxo-2-phenyl-2,3,4,5-tetrahydro-1,5-benzoxazepin-3-yl]-L-leucinamide;

$N^2$-[(3,5-difluorophenyl)acetyl]-$N^1$-[(6S,7R)-4-methyl-5-oxo-7-phenyl-1,4-oxazepan-6-yl]-L-alaninamide;

$N^2$-[(3,5-difluorophenyl)acetyl]-$N^1$-[(2S,6S,7R)-4-methyl-5-oxo-2,7-diphenyl-1,4-oxazepan-6-yl]-L-alaninamide;

$N^2$-[(3,5-difluorophenyl)acetyl]-$N^1$-[(6R,7R)-4-methyl-5-oxo-7-phenyl-1,4-thiazepan-6-yl]-L-alaninamide;

$N^2$-[(3,5-difluorophenyl)acetyl]-$N^1$-[(3R,6S,7R)-4-methyl-5-oxo-3,7-diphenyl-1,4-oxazepan-6-yl]-L-alaninamide;

(2S)-2-hydroxy-1,4-methyl-N-((1S)-2-{[(6S,7R)-4-methyl-5-oxo-7-phenyl -1,4-oxazepan-6-yl]amino}-2-oxo-1-phenylethyl)pentanamide;

(2S)-2-{[(3,5-difluorophenyl)acetyl]amino}-N-[(6S,7R)-4-methyl-5-oxo-7-phenyl-1,4-oxazepan-6-yl]-2-phenylacetamide;

(2S)-2-cyclohexyl-2-{[(3,5-difluorophenyl)acetyl]amino}-N-[(3R,6S,7R)-4-methyl-5-oxo-3,7-diphenyl-1,4-oxazepan-6-yl]acetamide;

(2S)-2-{[(3,5-difluorophenyl)acetyl]amino}-N-[(3R,6S,7R)-4-methyl-5-oxo-3,7-diphenyl-1,4-oxazepan-6-yl]-2-phenylacetamide;

$N^2$-[(3,5-difluorophenyl)acetyl]-$N^1$-[(6S,7R)-4-(4-methoxybenzyl)-5-oxo-7-phenyl-1,4-oxazepan-6-yl]-L-alaninamide;

$N^2$-[(3,5-difluorophenyl)acetyl]-$N^1$-[(2R,3S,5aR,9aR)-5-methyl-4-oxo-2-phenyldecahydro-1,5-benzoxazepin-3-yl]-L-alaninamide;

(2S)-2-{[(3,5-difluorophenyl)acetyl]amino}-N-[(6S,7R)-4-(4-methoxybenzyl)-5-oxo-7-phenyl-1,4-oxazepan-6-yl]-2-phenylacetamide;

$N^2$-[(3,5-difluorophenyl)acetyl]-$N^1$-[(2R,3R)-2-(4-methoxyphenyl)-4-oxo-2,3,4,5-tetrahydro-1,5-benzothiazepin-3-yl]-L-alaninamide;

$N^1$-[(2R,3R)-7-chloro-2-(2,5-difluorophenyl)-4-oxo-2,3,4,5-tetrahydro-1,5-benzothiazepin-3-yl]-$N^2$-(2S)-2-(3,5-difluorophenyl)-2-hydroxyacetyl]-L-alaninamide;

$N^2$-[(2S)-2-hydroxy-4-methyl-1-oxopentyl]-$N^1$-[(2R,3S)-4-oxo-2-phenyl-2,3,4,5-tetrahydro-1,5-benzoxazepin-3-yl]-L-alaninamide;

$N^2$-[(3,5-difluorophenyl)acetyl]-$N^1$-[(2R,3S)-5-methyl-4-oxo-2-phenyl-2,3,4,5-tetrahydro-1,5-benzoxazepin-3-yl]-L-alaninamide;

$N^1$-[(2R,3R)-7-chloro-2-(2,5-difluorophenyl)-5-methyl-4-oxo-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-{(2R,3S)-5-[2-(dimethylamino)ethyl]-4-oxo-2-phenyl-2,3,4,5-tetrahydro-1,5-benzoxazepin-3-yl}-L-alaninamide;

$N^1$-[(2R,3R)-7-chloro-2-(2,5-difluorophenyl)-4-oxo-5-phenyl-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-[(6R,7R)-5-oxo-7-phenyl-1,4-thiazepan-6-yl]-L-phenylalaninamide;

$N^2$-[(2S)-2-hydroxy-4-methylpentanoyl]-$N^1$-[(6R,7R)-5-oxo-7-phenyl-1,4-thiazepan-6-yl]-L-phenylalaninamide;

(2S)-2-{[(3,5-difluorophenyl)acetyl]amino}-N-[(6R,7R)-5-oxo-7-phenyl-1,4-thiazepan-6-yl]-2-phenylacetamide;

(2S)-2-hydroxy-4-methyl-N-((1S)-2-oxo-2-{[(6R,7R)-5-oxo-7-phenyl-1,4-thiazepan-6-yl]amino}-1-phenylethyl)pentanamide;

$N^2$-[(3,5-difluorophenyl)acetyl]-$N^1$-[(6R,7R)-5-oxo-7-phenyl-1,4-thiazepan-6-yl]-L-leucinamide;

$N^2$-[(2S)-2-hydroxy-4-methylpentanoyl]-$N^1$-[(6R,7R)-5-oxo-7-phenyl-1,4-thiazepan-6-yl]-L-leucinamide;

$N^2$-[(3,5-difluorophenyl)acetyl]-$N^1$-[(6R,7R)-5-oxo-7-phenyl-1,4-thiazepan-6-yl]-L-valinamide;

$N^2$-[(2S)-2-hydroxy-4methylpentanoyl]-$N^1$-[(6R,7R)-5-oxo-7-phenyl-1,4-thiazepan-6-yl]-L-valinamide;

$N^1$-[(2R,3S)-7-chloro-4-oxo-2-phenyl-2,3,4,5-tetrahydro-1,5-benzoxazepin-3-yl]-$N^2$-[(3,5-difluorophenyl)acetyl]-L-alaninamide;

(2S)-N-((1S)-2-{[(2R,3S)-7-chloro-4-oxo-2-phenyl-2,3,4,5-tetrahydro-1,5-benzoxazepin-3-yl]amino}-2-oxo-1-phenylethyl)-2-hydroxy-4-methylpentanamide;

(2S)-2-{[(3,5-difluorophenyl)acetyl]amino}-N-[(2R,3S)-4-oxo-2-phenyl-2,3,4,5-tetrahydro-1,5-benzoxazepin-3-yl]-2-phenylacetamide;

$N^2$-[(3,5-difluorophenyl)acetyl]-$N^1$-[(2R,3S)-4-oxo-2-phenyl-2,3,4,5-tetrahydro-1,5-benzoxazepin-3-yl]-L-serinamide;

(2S)-2-cyclohexyl-2-{[(3,5-difluorophenyl)acetyl]amino}-N-[(2R,3S)-4-oxo-2-phenyl-2,3,4,5-tetrahydro-1,5-benzoxazepin-3-yl]acetamide;

(2S)-N-((1S)-1-cyclohexyl-2-oxo-2-{[(2R,3S)-4-oxo-2-phenyl-2,3,4,5-tetrahydro-1,5-benzoxazepin-3-yl]amino}ethyl)-2-hydroxy-4-methylpentanamide;

3-cyclohexyl-$N^2$-[(3,5-difluorophenyl)acetyl]-$N^1$-[(6R,7R)-5-oxo-7-phenyl-1,4-thiazepan-6-yl]-L-alaninamide;

$N^2$-[(3,5-difluorophenyl)acetyl]-$N^1$-[(2R,3S)-5-(2-morpholin-4-ylethyl)-4-oxo-2-phenyl-2,3,4,5-tetrahydro-1,5-benzoxazepin-3-yl]-L-alaninamide;

$N^2$-[(3,5-difluorophenyl)acetyl]-$N^1$-[(2R,3S)-4-oxo-2-phenyl-2,3,4,5-tetrahydro-1,5-benzoxazepin-3-yl]-L-leucinamide;

(2S)-2-{[(3,5-difluorophenyl)acetyl]amino}-2-(4-fluorophenyl)-N-[(2R,3S)-4-oxo-2-phenyl-2,3,4,5-tetrahydro-1,5-benzoxazepin-3-yl]acetamide;

(2S)-2-[(cyclohexyloxy)amino]-2-(4-fluorophenyl)-N-[(2R,3S)-4-oxo-2-phenyl-2,3,4,5-tetrahydro-1,5-benzoxazepin-3-yl]acetamide;

$N^2$-[(3,5-difluorophenyl)acetyl]-$N^1$-[(2R,3S)-4-oxo-2-phenyl-5-prop-2-yn-1-yl-2,3,4,5-tetrahydro-1,5-benzoxazepin-3-yl]-L-alaninamide;

$N^2$-[(3,5-difluorophenyl)acetyl]-$N^1$-[(2R,3S)-7-methoxy-4-oxo-2-phenyl-2,3,4,5-tetrahydro-1,5-benzoxazepin-3-yl]-L-alaninamide;

$N^2$-[(3,5-difluorophenyl)acetyl]-$N^1$-[(2R,3S)-5-isopropyl-4-oxo-2-phenyl-2,3,4,5-tetrahydro-1,5-benzoxazepin-3-yl]-L-alaninamide;

methyl [(2R,3S)-3-({N-[(3,5-difluorophenyl)acetyl]-L-alanyl}amino)-4-oxo-2-phenyl-3,4-dihydro-1,5-benzoxazepin-5(2H)-yl]acetate;

[(2R,3S)-3-({N-[(3,5-difluorophenyl)acetyl]-L-alanyl}amino)-4-oxo-2-phenyl-3,4-dihydro-1,5-benzoxazepin-5(2H)-yl]acetic acid;

$N^1$-[(2R,3S)-5-(cyclopropylmethyl)-4-oxo-2-phenyl-2,3,4,5-tetrahydro-1,5-benzoxazepin-3-yl]-$N^2$-[(3,5-difluorophenyl)acetyl]-L-alaninamide;

$N^1$-[(2R,3S)-5-(cyclopropylmethyl)-7-methoxy-4-oxo-2-phenyl-2,3,4,5-tetrahydro-1,5-benzoxazepin-3-yl]-$N^2$-[(3,5-difluorophenyl)acetyl]-L-alaninamide;

$N^1$-[(2R,3S)-5-(2-azetidin-1-yl-2-oxoethyl)-4-oxo-2-phenyl-2,3,4,5-tetrahydro-1,5-benzoxazepin-3-yl]-L-alaninamide;

$N^2$-[(3,5-difluorophenyl)acetyl]-$N^1$-[(2R,3S)-7-fluoro-4-oxo-2-phenyl-2,3,4,5-tetrahydro-1,5-benzoxazepin-3-yl]-L-alaninamide;

(2S)-N-((1S)-2-{[(2R,3S)-7-fluoro-4-oxo-2-phenyl-2,3,4,5-tetrahydro-1,5-benzoxazepin-3-yl]amino}-2-oxo-1-phenylethyl)-2-hydroxy-4-methylpentanamide;

$N^2$-[(2R)-2-(3,5-difluorophenyl)-2-hydroxyacetyl]-$N^1$-[(2R,3S)-4-oxo-2-phenyl-2,3,4,5-tetrahydro-1,5-benzoxazepin-3-yl]-L-alaninamide;

$N^2$-[(2S)-2-(3,5-difluorophenyl)-2-hydroxyacetyl]-$N^1$-[(2R,3S)-4-oxo-2-phenyl-2,3,4,5-tetrahydro-1,5-benzoxazepin-3-yl]-L-alaninamide;

$N^2$-[(3,5-difluorophenyl)acetyl]-$N^1$-[(3S,4R)-2-oxo-4-phenyl-2,3,4,5-tetrahydro-1H-1-benzazepin-3-yl]-L-alaninamide;

$N^2$-[(3,5-difluorophenyl)acetyl]-$N^1$-[(3S,4R)-8-fluoro-1-methyl-2-oxo-4-phenyl -2,3,4,5-tetrahydro-1H-1-benzazepin-3-yl]-L-alaninamide;

(2S)-N-((1S)-2-{[(3S,4R)-8-fluoro-2-oxo-4-phenyl-2,3,4,5-tetrahydro-1H-1-benzazepin-3-yl]amino}-2-oxo-1-phenylethyl)-2-hydroxy-4-methylpentanamide;

(2S)-2-hydroxy-4-methyl-N-((1S)-2-oxo-2-{[(3S,4R)-2-oxo-4-phenyl-2,3,4,5-tetrahydro-1H-1-benzazepin-3-yl]amino}-1-phenylethyl)pentanamide;

$N^2$-[(3,5-difluorophenyl)acetyl]-$N^1$-[(3S,4R)-2-oxo-4-phenyl-1-prop-2-yn-1-yl-2,3,4,5-tetrahydro-1H-1-benzazepin-3-yl]-L-alaninamide;

$N^1$-[(3S,4R)-1-(cyclopropylmethyl)-2-oxo-4-phenyl-2,3,4,5-tetrahydro-1H-1-benzazepin-3-yl]-$N^2$-[(3,5-difluorophenyl)acetyl]-L-alaninamide;

$N^2$-[(3,5-difluorophenyl)acetyl]-$N^1$-[(3S,4R)-1-isopropyl-2-oxo-4-phenyl-2,3,4,5-tetrahydro-1H-1-benzazepin-3-yl]-L-alaninamide;

$N^2$-[(2S)-2-hydroxymethyl-1-oxopentyl]-$N^1$-[(2R,3R)-2-(4-methoxyphenyl)-4-oxo-2,3,4,5-tetrahydro-1,5-benzothiazepin-3-yl]-L-alaninamide;

$N^1$-[(2R,3R)-2-(2-chlorophenyl)-4-oxo-2,3,4,5-tetrahydro-1,5-benzothiazepin-3-yl]-$N^2$-[(2S)-2-hydroxy-4-methyl-1-oxopentyl]-L-alaninamide;

$N^1$-[(2R,3R)-2-(2-chlorophenyl)-4-oxo-2,3,4,5-tetrahydro-1,5-benzothiazepin-3-yl]-$N^2$-[(3,5-difluorophenyl)acetyl]-L-alaninamide;

$N^1$-[(2R,3R)-7-chloro-5-methyl-4-oxo-2-phenyl-2,3,4,5-tetrahydro-1,5-benzothiazepin-3-yl]-$N^2$-[(3,5-difluorophenyl)acetyl]-L-alaninamide;

$N^2$-[(3,5-difluorophenyl)acetyl]-$N^1$-[(2R,3R)-2-(2-fluorophenyl)-4-oxo-2,3,4,5-tetrahydro-1,5-benzothiazepin-3-yl]-L-alaninamide;

$N^1$-[(3,5-difluorophenyl)acetyl]-$N^1$-[(2R,3R)-2-(4-fluorophenyl)-4-oxo-2,3,4,5-tetrahydro-1,5-benzothiazepin-3-yl]-L-alaninamide;

$N^2$-[(2R,3R)-7-chloro-2-(2,5-difluorophenyl)-4-oxo-2,3,4,5-tetrahydro-1,5-benzothiazepin-3-yl]-$N^2$-[(3,5-difluorophenyl)acetyl]-L-alaninamide;

$N^2$-[(2S)-2-hydroxy-4-methyl-1-oxopentyl]-$N^1$-[(6R,7R)-5-oxo-7-phenyl-1,4-thiazepan-6-yl]-L-alaninamide;

$N^2$-[(3,5-difluorophenyl)acetyl]-$N^1$-[(2S,3R)-2-(3-methyl-2-thienyl)-4-oxo-2,3,4,5-tetrahydro-1,5-benzothiazepin-3-yl]-L-alaninamide;

$N^2$-[(3,5-difluorophenyl)acetyl]-$N^1$-[(2S,3R)-2-(4-methyl-2-thienyl)-4-oxo-2,3,4,5-tetrahydro-1,5-benzothiazepin-3-yl]-L-alaninamide;

Methyl 5-[(2S,3R)-3-({N-[(3,5-difluorophenyl)acetyl]-L-alanyl}amino)-4-oxo-2,3,4,5-tetrahydro-1,5-benzothiazepin-2-yl]thiophene-3-carboxylate;

$N^1$-[(2R,3R)-4-oxo-2-phenyl-2,3,4,5-tetrahydro-1,5-benzothiazepin-3-yl]-$N^2$-(phenylacetyl)-L-alaninamide;

$N^1$-[(2R,3R)-4-oxo-2-phenyl-2,3,4,5-tetrahydro-1,5-benzothiazepin-3-yl]-$N^2$-(2-phenylethyl)-L-alaninamide;

$N^2$-[(3,5-difluorophenyl)acetyl]-4]-$N^1$-[(2S,3R)-4-oxo-2-(2-thienyl)-2,3,4,5-tetrahydro-1,5-benzothiazepin-3-yl]-L-alaninamide;

$N^2$-[(3,5-difluorophenyl)acetyl]-$N^1$-[(2R,3R)-4-oxo-2-(3-thienyl)-2,3,4,5-tetrahydro-1,5-benzothiazepin-3-yl]-L-alaninamide;

$N^2$-[(3,5-difluorophenyl)acetyl]-$N^1$-[(2S,3R)-2-(2-furyl)-4-oxo-2,3,4,5-tetrahydro-1,5-benzothiazepin-3-yl]-L-alaninamide;

$N^2$-[(3,5-difluorophenyl)acetyl]-$N^1$-[(2R,3R)-2-(3-furyl)-4-oxo-2,3,4,5-tetrahydro-1,5-benzothiazepin-3-yl]-L-alaninamide;

$N^1$-[(2S,3R)-2-(5-bromo-2-thienyl)-4-oxo-2,3,4,5-tetrahydro-1,5-benzothiazepin-3-yl]-$N^2$-[(3,5-difluorophenyl)acetyl]-L-alaninamide;

$N^1$-[(2S,3R)-2-(4-bromo-2-thienyl)-4-oxo-2,3,4,5-tetrahydro-1,5-benzothiazepin-3-yl]-$N^2$-[(3,5-difluorophenyl)acetyl]-alaninamide;

N-[(3,5-difluorophenyl)acetyl]-N-[(2R,3R)-4-oxo-2-phenyl-2,3,4,5-tetrahydro-1,5-benzothiazepin-3-yl]-L-phenylalaninamide;

$N^2$-[(3,5-difluorophenyl)acetyl]-$N^1$-[(2R,3R)-4-oxo-2-phenyl-2,3,4,5-tetrahydro-1,5-benzothiazepin-3-yl] glycinamide;

$N^2$-[(3,5-difluorophenyl)acetyl]-$N^1$-[(2R,3R)-4-oxo-2-phenyl-2,3,4,5-tetrahydro-1,5-benzothiazepin-3-yl]-L-valinamide;

$N^2$-[(3,5-difluorophenyl)acetyl]-$N^1$-[(2R,3R)-4-oxo-2-phenyl-2,3,4,5-tetrahydro-1,5-benzothiazepin-3-yl]-L-leucinamide;

$N^2$-[(3,5-difluorophenyl)acetyl]-$N^1$-[(2R,3R)-4-oxo-2-phenyl-2,3,4,5-tetrahydro-1,5-benzothiazepin-3-yl]-L-methioninamide;

$N^2$-[(3,5-difluorophenyl)acetyl]-3-(1H-indol-2-yl)-$N^1$-[(2R,3R)-4-oxo-2-phenyl-2,3,4,5-tetrahydro-1,5-benzothiazepin-3-yl]-L-alaninamide;

$N^2$-[(3,5-difluorophenyl)acetyl]-$N^1$-[(2R,3R)-4-oxo-2-phenyl-2,3,4,5-tetrahydro-1,5-benzothiazepin-3-yl]-L-α-asparagine;

$N^2$-[(3,5-difluorophenyl)acetyl]-$N^1$-[(2R,3R)-4-oxo-2-phenyl-2,3,4,5-tetrahydro-1,5-benzothiazepin-3-yl]-L-α-glutamine;

$N^1$-[(2R,3S)-4-oxo-2-phenyl-2,3,4,5-tetrahydro-1,5-benzoxazepin-3-yl]-$N^2$-(phenylacetyl)-L-alaninamide;

$N^2$-[(2-fluorophenyl)acetyl]-$N^1$-[(2R,3S)-4-oxo-2-phenyl-2,3,4,5-tetrahydro-1,5-benzoxazepin-3-yl]-L-alaninamide;

$N^2$-[(3-fluorophenyl)acetyl]-$N^1$-[(2R,3S)-4oxo-2-phenyl-2,3,4,5-tetrahydro-1,5-benzoxazepin-3-yl]-L-alaninamide;

$N^2$-[(4-fluorophenyl)acetyl]-$N^1$-[(2R,3S)-4-oxo-2-phenyl-2,3,4,5-tetrahydro-1,5-benzoxazepin-3-yl]-L-alaninamide;

$N^1$-[(2R,3S,5aS,9aS)-5-(cyclopropylmethyl)-4oxo-2-phenyldecahydro-1,5-benzoxazepin-3-yl]-$N^2$-[(3,5-difluorophenyl)acetyl]-L-alaninamide;

or a pharmaceutical acceptable salt thereof.

25. A method for the treatment of Alzheimer's disease, comprising administering a therapeutically effective amount of a compound of formula (I) or a pharmaceutically acceptable salt thereof as claimed in any one of claims 1 to 24.

26. A pharmaceutical composition comprising a compound of formula (I), as defined in any one of claims 1 to 24, together with at least one pharmaceutically acceptable carrier, diluent or excipent.

\* \* \* \* \*

UNITED STATES PATENT AND TRADEMARK OFFICE
CERTIFICATE OF CORRECTION

PATENT NO. : 7,294,622 B2
APPLICATION NO. : 10/528640
DATED : November 13, 2007
INVENTOR(S) : Becker et al.

It is certified that error appears in the above-identified patent and that said Letters Patent is hereby corrected as shown below:

Column 152, line 5, claim 1, "$R^9$ is phenyl substituted with 0, 1, 2 or 3 $R^e$;" should read
-- $R^9$ is phenyl substituted with 0, 1, 2 or 3 $R^e$; and --.

Column 152, line 11, claim 2, "with 0, 1, 2, or 3 $R°$ moieties, said ring having 0, 1, or" should read
-- with 0, 1, 2, or 3 $R^e$ moieties, said ring having 0, 1, or --.

Column 152, line 36, claim 2, "$R^f$ is $NO_2$, F, Cl, Br, I, $CF_3$, CN, $C_1$-3alkoxy" should read
-- $R^f$ is $NO_2$, F, Cl, Br, I, $CF_3$, CN, $C_1$-3alkyl, or $C_1$-3alkoxy --.

Column 152, line 39, claim 2, "optionally substituted with 0, 1, or 2 moities, said" should read
-- optionally substituted with 0, 1, or 2 $R^f$ moities, said --.

Column 152, line 40, claim 2, "heterocyclis ring having 0, 1, 2 or 3 nitrogen, oxygen" should read
-- heterocyclic ring having 0, 1, 2 or 3 nitrogen, oxygen --.

Column 153, line 30, claim 3, "from H, $C_{1-4}$alkyl, OH, $CONR_2$, $CH_2CONH_2$, $CO_2H$," should read
-- from H, $C_{1-4}$alkyl, OH, $CONH_2$, $CH_2CONH_2$, $CO_2H$, --.

Column 154, line 63, claim 6, "$C_{3-6}$alkynyl $C_{3-6}$cycloalkyl, $C_{2-4}$alkyNR$^a$R$^b$," should read
-- $C_{3-6}$alkynyl $C_{3-6}$cycloalkyl, $C_{2-4}$alkylNR$^a$R$^b$ --.

Column 155, line 31, claim 7, "from H, $C_{1-4}$alkyl or $C_{5-6}$cycloalkyl or R$^a$ and R1 and" should read
-- from H, $C_{1-4}$alkyl or $C_{5-6}$cycloalkyl or R$^a$ and R$^b$ and --.

Column 155, line 38, claim 7, "$R^2$ is, at each occurrence independently selected from H," should read
-- $R^e$ is, at each occurrence independently selected from H, --.

Column 160, line 1, claim 24, "(2S)-2-[(cyclohexyloxy)amino]-2-(4-fluorophenyl)-N-" should read
-- (2S)-2-[(cyclohexylacetyl)amino]-2-(4-fluorophenyl)-N- --.

Column 160, line 26, claim 24, "nyl-2,3,4,5-tetrahydro-l,5-benzoxazepin-3-yl]-L-" should read
-- nyl-2,3,4,5-tetrahydro-l,5-benzoxazepin-3-yl]N$^2$-[(3,5-difluorophenyl)acetyl]-L- --.

Column 160, line 62, claim 24, "$N^2$-[(2S)-2-hydroxymethyl-1-oxopentyl]-$N^1$-[(2R,3R)-2-" should read
-- $N^2$-[(2S)-2-hydroxy-4-methyl-1-oxopentyl]-$N^1$-[(2R,3R)-2- --.

CERTIFICATE OF CORRECTION (continued)
U.S. Pat. No. 7,294,622 B2

Column 161, line 13, claim 24, "$N^2$-[(2R,3R)-7-chloro-2-(2,5-difluorophenyl)-4-oxo-2,3," should read -- $N^1$-[(2R,3R)-7-chloro-2-(2,5-difluorophenyl)-4-oxo-2,3, --.

Column 161, line 32, claim 24, "$N^2$-[(3,5-difluorophenyl)acetyl)-4]-$N^1$-[(2S,3R)-4-oxo-2-" should read -- $N^2$-[(3,5-difluorophenyl)acetyl]-$N^1$-[(2S,3R)-4-oxo-2- --.

Signed and Sealed this

Fifth Day of January, 2010

David J. Kappos
*Director of the United States Patent and Trademark Office*